US012563885B2

(12) United States Patent
Seo et al.

(10) Patent No.: US 12,563,885 B2
(45) **Date of Patent: *Feb. 24, 2026**

(54) LIGHT-EMITTING ELEMENT, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Satoshi Seo, Kanagawa (JP); Takeyoshi Watabe, Kanagawa (JP); Satomi Mitsumori, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/589,868

(22) Filed: Feb. 28, 2024

(65) Prior Publication Data

US 2024/0206209 A1 Jun. 20, 2024

Related U.S. Application Data

(63) Continuation of application No. 17/127,045, filed on Dec. 18, 2020, now Pat. No. 11,925,041, which is a continuation of application No. 15/278,750, filed on Sep. 28, 2016, now abandoned.

(30) Foreign Application Priority Data

Sep. 30, 2015 (JP) ................................ 2015-194796

(51) Int. Cl.

| | |
|---|---|
| ***H01L 51/54*** | (2006.01) |
| ***C07D 241/38*** | (2006.01) |
| ***C07D 403/12*** | (2006.01) |
| ***C07D 405/10*** | (2006.01) |
| ***C09K 11/02*** | (2006.01) |
| ***C09K 11/06*** | (2006.01) |
| ***H10K 50/11*** | (2023.01) |
| ***H10K 85/30*** | (2023.01) |
| ***H10K 85/60*** | (2023.01) |
| *H10K 50/13* | (2023.01) |
| *H10K 59/35* | (2023.01) |
| *H10K 101/00* | (2023.01) |
| *H10K 101/10* | (2023.01) |
| *H10K 101/30* | (2023.01) |
| *H10K 101/40* | (2023.01) |

(52) U.S. Cl.

CPC .......... *H10K 50/11* (2023.02); *C07D 241/38* (2013.01); *C07D 403/12* (2013.01); *C07D 405/10* (2013.01); *C09K 11/02* (2013.01); *C09K 11/06* (2013.01); *H10K 85/342* (2023.02); *H10K 85/633* (2023.02); *H10K 85/636* (2023.02); *H10K 85/6572* (2023.02); *H10K 85/6574* (2023.02); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1033* (2013.01); *C09K 2211/1044* (2013.01); *C09K 2211/1048* (2013.01); *C09K 2211/1051* (2013.01); *C09K 2211/1059* (2013.01); *C09K 2211/1088* (2013.01); *C09K 2211/1092* (2013.01); *C09K 2211/185* (2013.01); *C09K 2211/188* (2013.01); *H10K 50/131* (2023.02); *H10K 59/35* (2023.02); *H10K 85/615* (2023.02); *H10K 2101/10* (2023.02); *H10K 2101/27* (2023.02); *H10K 2101/30* (2023.02); *H10K 2101/40* (2023.02); *H10K 2101/90* (2023.02); *Y02P 20/582* (2015.11)

(58) Field of Classification Search

None

See application file for complete search history.

(56) References Cited

U.S. PATENT DOCUMENTS

| | | | |
|---|---|---|---|
| 7,175,922 | B2 | 2/2007 | Jarikov et al. |
| 7,183,010 | B2 | 2/2007 | Jarikov |
| 7,332,857 | B2 | 2/2008 | Seo et al. |
| 7,597,967 | B2 | 10/2009 | Kondakova et al. |
| 7,683,536 | B2 | 3/2010 | Forrest et al. |

(Continued)

FOREIGN PATENT DOCUMENTS

| | | | |
|---|---|---|---|
| CN | 102421772 | A | 4/2012 |
| CN | 102439004 | A | 5/2012 |

(Continued)

OTHER PUBLICATIONS

KR Patent No. 2015-0016507 CN Patent No. 104365180 TW Patent No. 201406547.

(Continued)

*Primary Examiner* — Andrew K Bohaty

(74) *Attorney, Agent, or Firm* — Husch Blackwell LLP

(57) ABSTRACT

To provide a light-emitting element with high emission efficiency and low driving voltage. The light-emitting element includes a guest material and a host material. A LUMO level of the guest material is lower than a LUMO level of the host material. An energy difference between the LUMO level and a HOMO level of the guest material is larger than an energy difference between the LUMO level and a HOMO level of the host material. The guest material has a function of converting triplet excitation energy into light emission. An energy difference between the LUMO level of the guest material and the HOMO level of the host material is larger than or equal to energy of light emission of the guest material.

21 Claims, 67 Drawing Sheets

(56) References Cited

U.S. PATENT DOCUMENTS

| | | | | |
|---|---|---|---|---|
| 7,906,226 | B2 | 3/2011 | Matsuura et al. | |
| 7,993,760 | B2 | 8/2011 | Komori et al. | |
| 8,034,465 | B2 | 10/2011 | Liao et al. | |
| 8,105,701 | B2 | 1/2012 | Matsuura et al. | |
| 8,274,214 | B2 | 9/2012 | Ikeda et al. | |
| 8,470,455 | B2 | 6/2013 | Matsuura et al. | |
| 8,652,654 | B2 | 2/2014 | Inoue et al. | |
| 8,853,680 | B2 | 10/2014 | Yamazaki et al. | |
| 8,865,323 | B2 | 10/2014 | Inoue et al. | |
| 8,877,352 | B2 | 11/2014 | Inoue et al. | |
| 8,940,414 | B2 | 1/2015 | Inoue et al. | |
| 8,963,127 | B2 | 2/2015 | Pieh et al. | |
| 8,981,355 | B2 | 3/2015 | Seo | |
| 8,993,129 | B2 | 3/2015 | Endo et al. | |
| 8,994,263 | B2 | 3/2015 | Shitagaki et al. | |
| 9,054,317 | B2 | 6/2015 | Monkman et al. | |
| 9,159,942 | B2 | 10/2015 | Seo et al. | |
| 9,175,213 | B2 | 11/2015 | Seo et al. | |
| 9,178,158 | B2 | 11/2015 | Kitano et al. | |
| 9,269,912 | B2 | 2/2016 | Graetzel et al. | |
| 9,356,250 | B2 | 5/2016 | Ohsawa et al. | |
| 9,368,741 | B2 | 6/2016 | Ishisone et al. | |
| 9,604,928 | B2 | 3/2017 | Shitagaki et al. | |
| 9,653,697 | B2 | 5/2017 | Ishisone et al. | |
| 10,193,077 | B2 | 1/2019 | Inoue et al. | |
| 10,454,054 | B2 | 10/2019 | Ishisone et al. | |
| 10,693,094 | B2 * | 6/2020 | Seo ........................ | C09K 11/02 |
| 11,925,041 | B2 * | 3/2024 | Seo ........................ | C09K 11/02 |
| 2003/0175553 | A1 | 9/2003 | Thompson et al. | |
| 2005/0048310 | A1 | 3/2005 | Cocchi et al. | |
| 2005/0221116 | A1 | 10/2005 | Cocchi et al. | |
| 2006/0134464 | A1 | 6/2006 | Nariyuki | |
| 2006/0251921 | A1 | 11/2006 | Forrest et al. | |
| 2007/0090756 | A1 | 4/2007 | Okada et al. | |
| 2008/0149923 | A1 | 6/2008 | Ohsawa et al. | |
| 2011/0279020 | A1 | 11/2011 | Inoue et al. | |
| 2012/0205632 | A1 | 8/2012 | Shitagaki et al. | |
| 2012/0217487 | A1 | 8/2012 | Yamazaki et al. | |
| 2012/0235131 | A1 | 9/2012 | Okamoto | |
| 2013/0134395 | A1 | 5/2013 | Kitano et al. | |
| 2014/0001457 | A1 | 1/2014 | Endo | |
| 2014/0005397 | A1 | 1/2014 | Graetzel et al. | |
| 2014/0217378 | A1 | 8/2014 | Nishimura et al. | |
| 2014/0340888 | A1 | 11/2014 | Ishisone et al. | |
| 2015/0069352 | A1 | 3/2015 | Kim et al. | |
| 2015/0188072 | A1 | 7/2015 | Seo | |
| 2015/0228912 | A1 | 8/2015 | Inoue et al. | |
| 2016/0049607 | A1 | 2/2016 | Seo et al. | |
| 2017/0012207 | A1 | 1/2017 | Seo et al. | |
| 2017/0025615 | A1 | 1/2017 | Seo et al. | |
| 2017/0040553 | A1 | 2/2017 | Watabe et al. | |
| 2017/0092890 | A1 | 3/2017 | Seo et al. | |

FOREIGN PATENT DOCUMENTS

| | | | |
|---|---|---|---|
| CN | 103137894 | A | 6/2013 |
| CN | 103339137 | A | 10/2013 |
| CN | 104167494 | A | 11/2014 |
| CN | 104365180 | A | 2/2015 |
| EP | 1202608 | A | 5/2002 |
| EP | 1718122 | A | 11/2006 |
| EP | 2415769 | A | 2/2012 |
| EP | 2423209 | A | 2/2012 |
| EP | 2688370 | A | 1/2014 |
| JP | 2008-288344 | A | 11/2008 |
| JP | 2010-182699 | A | 8/2010 |
| JP | 2011-199019 | A | 10/2011 |
| JP | 2012-195054 | A | 10/2012 |
| JP | 2012-212879 | A | 11/2012 |
| JP | 2013-048265 | A | 3/2013 |
| JP | 2013-545754 | | 12/2013 |
| JP | 2014-241405 | A | 12/2014 |
| JP | 2016-225498 | A | 12/2016 |
| KR | 2012-0057561 | A | 6/2012 |
| KR | 2013-0058620 | A | 6/2013 |
| KR | 2013-0143611 | A | 12/2013 |
| KR | 2014-0135628 | A | 11/2014 |
| KR | 2015-0016507 | A | 2/2015 |
| TW | 201141989 | | 12/2011 |
| TW | 201235354 | | 9/2012 |
| TW | 201406547 | | 2/2014 |
| WO | WO-2006/105387 | | 10/2006 |
| WO | WO-2007/108327 | | 9/2007 |
| WO | WO-2011/065138 | | 6/2011 |
| WO | WO-2011/132683 | | 10/2011 |
| WO | WO-2012/069170 | | 5/2012 |
| WO | WO-2012/124642 | | 9/2012 |
| WO | WO-2013/180036 | | 12/2013 |

OTHER PUBLICATIONS

US Patent Application Publication No. US 2014/0001457 A1 Ep Patent No. 2 688 370 A1 WO Patent No. 2012/124642 A1.

US Patent Application Publication No. US 2006/0251921 A1 U.S. Pat. No. 7,683,536 B2 * WO Patent No. 2006/105387 A1 *.

Yersin.H et al., Highly Efficient OLEDs with Phosphorescent Materials, 2008, pp. 1-97,283-309, Wiley-VCH Verlag GmbH & Co.

Tokito.S et al., "Improvement in performance by doping", Organic EL Display, Aug. 20, 2004, pp. 67-99, Ohmsha.

Jeon.W et al., "Ideal host and guest system in phosphorescent OLEDs", Organic Electronics, 2009, vol. 10, pp. 240-246, Elsevier.

Su.S et al., "RGB Phosphorescent Organic Light-Emitting Diodes by Using Host Materials with Heterocyclic Cores: Effect of Nitrogen Atom Orientations", Chem. Mater. (Chemistry of Materials), 2011, vol. 23, No. 2, pp. 274-284.

Rausch.A et al., "Matrix Effects on the Triplet State of the OLED Emitter Ir(4,6-dFppy)2(pic)(Flrpic): Investigations by High-Resolution Optical Spectroscopy", Inorg. Chem. (Inorganic Chemistry), 2009, vol. 48, No. 5, pp. 1928-1937.

Gong.X et al., "Phosphorescence from iridium complexes doped into polymer blends", J. Appl. Phys. (Journal of Applied Physics) , Feb. 1, 2004, vol. 95, No. 3, pp. 948-953.

Zhao.Q et al., "Synthesis and Photophysical, Electrochemical, and Electrophosphorescent Properties of a Series of Iridium(III) Complexes Based on Quinoline Derivatives and Different β-Diketonate Ligands", Organometallics, Jun. 14, 2006, vol. 25, No. 15, pp. 3631-3638.

Hino.Y et al., "Red Phosphorescent Organic Light-Emitting Diodes Using Mixture System of Small-Molecule and Polymer Host", Jpn. J. Appl. Phys. (Japanese Journal of Applied Physics) , Apr. 21, 2005, vol. 44, No. 4B, pp. 2790-2794, The Japan Society of Applied Physics.

Tsuboyama.A et al., "Homoleptic Cyclometalated Iridium Complexes with Highly Efficient Red Phosphorescence and Application to Organic Light-Emitting Diode", J. Am. Chem. Soc. (Journal of the American Chemical Society), 2003, vol. 125, No. 42, pp. 12971-12979.

Kondakova.M et al., "High-efficiency, low-voltage phosphorescent organic light-emitting diode devices with mixed host", J. Appl. Phys. (Journal of Applied Physics) , Nov. 4, 2008, vol. 104, pp. 094501-1-094501 17.

Chen.F et al., "Triplet Exciton Confinement in Phosphorescent Polymer Light-Emitting Diodes", Appl. Phys. Lett. (Applied Physics Letters) , Feb. 17, 2003, vol. 82, No. 7, pp. 1006-1008.

Lee.J et al., "Stabilizing the efficiency of phosphorescent organic light-emitting diodes", SPIE Newsroom, Apr. 21, 2008, pp. 1-3.

Tokito.S et al., "Confinement of Triplet Energy On Phosphorescent Molecules for Highly-Efficient Organic Blue-Light-Emitting Devices", Appl. Phys. Lett. (Applied Physics Letters) , Jul. 21, 2003, vol. 83, No. 3, pp. 569-571.

Endo.A et al., "Efficient Up-Conversion of Triplet Excitons Into a Singlet State and Its Application for Organic Light Emitting Diodes", Appl. Phys. Lett. (Applied Physics Letters) , Feb. 24, 2011, vol. 98, No. 8, pp. 083302-1-083302-3.

Itano.K et al., "Exciplex formation at the organic solid-state interface: Yellow emission in organic light-emitting diodes using green-fluorescent tris(8-quinolinolato)aluminum and hole-transporting molecu-

(56) References Cited

OTHER PUBLICATIONS lar materials with low ionization potentials", Appl. Phys. Lett. (Applied Physics Letters) , Feb. 9, 1998, vol. 72, No. 6, pp. 636-638.
Park.Y et al., "Efficient triplet harvesting by fluorescent molecules through exciplexes for high efficiency organic light-emitting diodes", Appl. Phys. Lett. (Applied Physics Letters) , Apr. 18, 2013, vol. 102, No. 15, pp. 153306-1-153306-5.
Endo.A et al., "Thermally Activated Delayed Fluorescence from Sn4+-Porphyrin Complexes and Their Application to Organic Light Emitting Diodes—A Novel Mechanism for Electroluminescence", Adv. Mater. (Advanced Materials), Aug. 12, 2009, vol. 21, No. 47, pp. 4802-4806.
Polikarpov.E et al., "Materials Design Concepts for Efficient Blue OLEDs: A Joint Theoretical and Experimental Study", Material Matters, Apr. 1, 2012, vol. 7, No. 1, pp. 2-8.
Kim.J et al., "Study of Sequential Dexter Energy Transfer in High Efficient Phosphorescent White Organic Light-Emitting Diodes with Single Emissive Layer", Sci. Rep. (Scientific Reports), Nov. 12, 2014, vol. 4, No. 7009, pp. 1-6, Nature.
Chinese Office Action (Application No. 201610872789.9) Dated Oct. 26, 2020.
Seo.S et al., "Exciplex-triplet energy transfer: A new method to achieve extremely efficient organic light-emitting diode with external quantum efficiency over 30% and drive voltage below 3V", Jpn. J. Appl. Phys. (Japanese Journal of Applied Physics) , Mar. 17, 2014, vol. 53, No. 4, pp. 042102-1-042102-8, The Japan Society of Applied Physics.
Nakanotani.H et al., "High-efficiency organic light-emitting diodes with fluorescent emitters", Nature Communications, May 30, 2014, vol. 5, pp. 4016-1-4016-7.
German Office Action (Application No. 102016218696.5) Dated Nov. 6, 2023.
Frey.J et al., "Structure-property relationships based on Hammett constants in cyclometalated iridium(III) complexes: their application to the design of a fluorine-free FlrPic-like emitter", Dalton Transactions, Dec. 2, 2013, vol. 43, No. 15, pp. 5667-5679, Royal Society of Chemistry.
D'Andrade.B et al., "Relationship Between the Ionization and Oxidation Potentials of Molecular Organic Semiconductors", Organic Electronics, 2005, vol. 6, No. 1, pp. 11-20.
Sworakowski.J, "How accurate are energies of HOMO and LUMO levels in small-molecule organic semiconductors determined from cyclic voltammetry or optical spectroscopy?", Synthetic Metals, Dec. 12, 2017, vol. 235, pp. 125-130.
Kolosov.D et al., "1,8-Naphtalimides in Phosphorescent Organic LEDs: The Interplay Between Dopant, Exciplex, and Host Emission", J. Am. Chem. Soc. (Journal of the American Chemical Society), Aug. 21, 2002, vol. 124, No. 33, pp. 9945-9954.

* cited by examiner

LIGHT-EMITTING ELEMENT, DISPLAY DEVICE, ELECTRONIC DEVICE, AND LIGHTING DEVICE

This application is a continuation of copending U.S. application Ser. No. 17/127,045, filed on Dec. 18, 2020 which is a continuation of U.S. application Ser. No. 15/278,750, filed on Sep. 28, 2016 (now abandoned), which are all incorporated herein by reference.

BACKGROUND OF THE INVENTION

1. Field of the Invention

One embodiment of the present invention relates to a light-emitting element, a display device including the light-emitting element, an electronic device including the light-emitting element, and a lighting device including the light-emitting element.

Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, a method for driving any of them, and a method for manufacturing any of them.

2. Description of the Related Art

In recent years, research and development have been extensively conducted on light-emitting elements using electroluminescence (EL). In a basic structure of such a light-emitting element, a layer containing a light-emitting material (an EL layer) is interposed between a pair of electrodes. By applying a voltage between the pair of electrodes of this element, light emission from the light-emitting material can be obtained.

Since the above light-emitting element is of a self-luminous type, a display device using this light-emitting element has advantages such as high visibility, no necessity of a backlight, low power consumption, and the like. Further, the display device also has advantages in that it can be formed to be thin and lightweight, and has high response speed.

In a light-emitting element (e.g., an organic EL element) whose EL layer contains an organic material as a light-emitting material and is provided between a pair of electrodes, application of a voltage between the pair of electrodes causes injection of electrons from a cathode and holes from an anode into the EL layer having a light-emitting property and thus a current flows. By recombination of the injected electrons and holes, the organic material having a light-emitting property is brought into an excited state to provide light emission.

Note that an excited state formed by an organic material can be a singlet excited state (S*) or a triplet excited state (T*). Light emission from the singlet excited state is referred to as fluorescence, and light emission from the triplet excited state is referred to as phosphorescence. The formation ratio of S* to T* in the light-emitting element is 1:3. In other words, a light-emitting element including a compound emitting phosphorescence (phosphorescent compound) has higher light emission efficiency than a light-emitting element including a compound emitting fluorescence (fluorescent compound). Therefore, light-emitting elements containing phosphorescent materials capable of converting energy of the triplet excited state into light emission have been actively developed in recent years (e.g., see Patent Document 1).

Energy for exciting an organic material depends on an energy difference between the LUMO level and the HOMO level of the organic material. The energy difference approximately corresponds to singlet excitation energy. In a light-emitting element containing a phosphorescent organic material, triplet excitation energy is converted into light emission energy. Thus, when the energy difference between the singlet excited state and the triplet excited state of an organic material is large, the energy needed for exciting the organic material is higher than the light emission energy by the amount corresponding to the energy difference. The difference between the energy for exciting the organic material and the light emission energy affects element characteristics of a light-emitting element: the driving voltage of the light-emitting element increases. Research and development are being conducted on techniques for reducing the driving voltage (see Patent Document 2).

Among light-emitting elements including phosphorescent materials, a light-emitting element that emits blue light in particular has not yet been put into practical use because it is difficult to develop a stable organic material having a high triplet excited energy level. This has motivated the research effort to develop highly reliable light-emitting elements that exhibit phosphorescence with high emission efficiency.

REFERENCES

Patent Documents

[Patent Document 1] Japanese Published Patent Application No. 2010-182699

[Patent Document 2] Japanese Published Patent Application No. 2012-212879

SUMMARY OF THE INVENTION

An iridium complex is known as a phosphorescent material with high emission efficiency. An iridium complex including a pyridine skeleton or a nitrogen-containing five-membered heterocyclic skeleton as a ligand is known as an iridium complex with high light emission energy. Although the pyridine skeleton and the nitrogen-containing five-membered heterocyclic skeleton have high triplet excitation energy, they have poor electron-accepting property. Accordingly, the HOMO level and LUMO level of the iridium complex having the skeletons as ligands are high, and hole carriers are easily injected thereto, while electron carriers are not. Thus, an iridium complex having a skeleton with high electron-accepting property as a ligand has been developed.

In contrast, the HOMO level and LUMO level of the iridium complex having a skeleton with high electron-accepting property as a ligand are low, and electron carriers tend to be injected thereto, while hole carriers do not. Thus, excitation by direct carrier recombination is sometimes difficult, which can hinder efficient light emission of a light-emitting element.

In view of the above, an object of one embodiment of the present invention is to provide a light-emitting element that has high emission efficiency and contains a phosphorescent material. Another object of one embodiment of the present invention is to provide a light-emitting element with low power consumption. Another object of one embodiment of the present invention is to provide a light-emitting element with high reliability. Another object of one embodiment of the present invention is to provide a novel light-emitting element. Another object of one embodiment of the present invention is to provide a novel light-emitting device. Another object of one embodiment of the present invention is to provide a novel display device.

Note that the description of the above object does not disturb the existence of other objects. In one embodiment of the present invention, there is no need to achieve all the objects. Other objects are apparent from and can be derived from the description of the specification and the like.

One embodiment of the present invention is a light-emitting element including a host material that can efficiently excite a phosphorescent material.

One embodiment of the present invention is a light-emitting element which includes a guest material and a host material and in which a LUMO level of the guest material is lower than a LUMO level of the host material, an energy difference between the LUMO level of the guest material and a HOMO level of the guest material is larger than an energy difference between the LUMO level of the host material and a HOMO level of the host material, and the guest material has a function of converting triplet excitation energy into light emission.

One embodiment of the present invention is a light-emitting element which includes a guest material and a host material and in which a LUMO level of the guest material is lower than a LUMO level of the host material, an energy difference between the LUMO level of the guest material and a HOMO level of the guest material is larger than an energy difference between the LUMO level of the host material and a HOMO level of the host material, the guest material has a function of converting triplet excitation energy into light emission, and an energy difference between the LUMO level of the guest material and the HOMO level of the host material is larger than or equal to transition energy calculated from an absorption edge of an absorption spectrum of the guest material.

One embodiment of the present invention is a light-emitting element which includes a guest material and a host material and in which a LUMO level of the guest material is lower than a LUMO level of the host material, an energy difference between the LUMO level of the guest material and a HOMO level of the guest material is larger than an energy difference between the LUMO level of the host material and a HOMO level of the host material, the guest material has a function of converting triplet excitation energy into light emission, and an energy difference between the LUMO level of the guest material and the HOMO level of the host material is larger than or equal to light emission energy of the guest material.

In each of the above structures, it is preferable that the energy difference between the LUMO level of the guest material and the HOMO level of the guest material be larger than the transition energy calculated from the absorption edge of the absorption spectrum of the guest material by 0.4 eV or more. It is preferable that the energy difference between the LUMO level of the guest material and the HOMO level of the guest material be larger than the light emission energy of the guest material by 0.4 eV or more.

In each of the above structures, it is preferable that the host material have a difference between a singlet excitation energy level and a triplet excitation energy level of larger than 0 eV and smaller than or equal to 0.2 eV. It is preferable that the host material have a function of exhibiting thermally activated delayed fluorescence.

In each of the above structures, it is preferable that the host material have a function of supplying excitation energy to the guest material. It is preferable that a light emission spectrum of the host material include a wavelength region overlapping with an absorption band on the lowest energy side in the absorption spectrum of the guest material.

In each of the above structures, it is preferable that the guest material include iridium. It is preferable that the guest material emit light.

In each of the above structures, it is preferable that the host material have a function of transporting an electron. It is preferable that the host material have a function of transporting a hole. It is preferable that the host material include a π-electron deficient heteroaromatic ring skeleton and include at least one of a π-electron rich heteroaromatic ring skeleton and an aromatic amine skeleton. It is preferable that the π-electron deficient heteroaromatic ring skeleton include at least one of a diazine skeleton and a triazine skeleton and the π-electron rich heteroaromatic ring skeleton include at least one of an acridine skeleton, a phenoxazine skeleton, a phenothiazine skeleton, a furan skeleton, a thiophene skeleton, and a pyrrole skeleton.

In the light-emitting element described in each of the above structures, it is preferable that the host material be a compound represented by any one of Structural Formulae (500) to (503) below:

[Chemical Formulae 1]

(500)

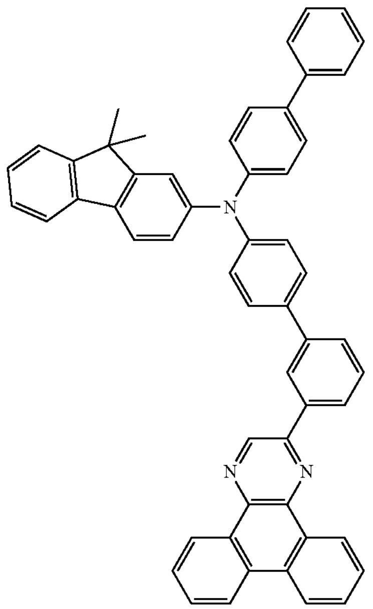

-continued
(501)
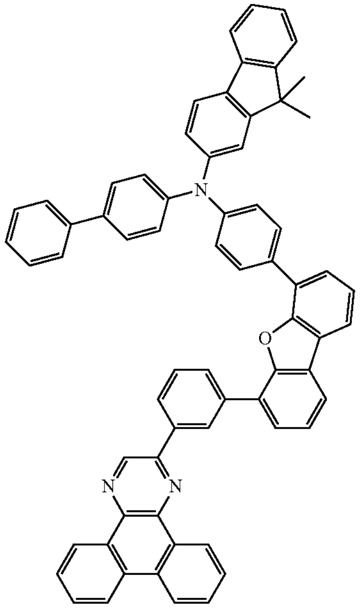
(502)
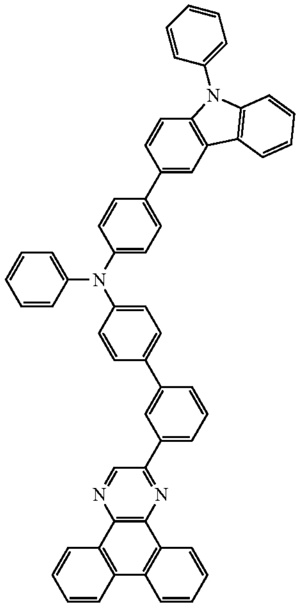
-continued
(503)
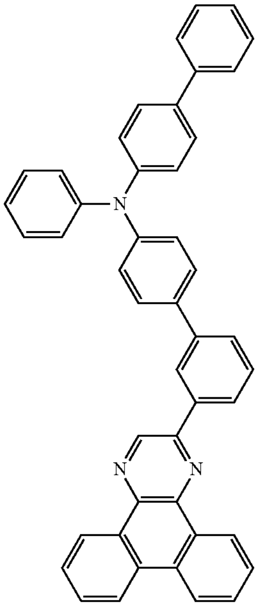
One embodiment of the present invention is a compound represented by any one of Structural Formulae (500) to (503) below:
[Chemical Formulae 2]
(500)
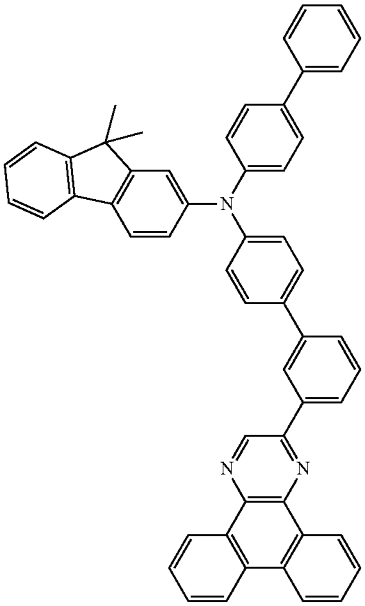

-continued (501)

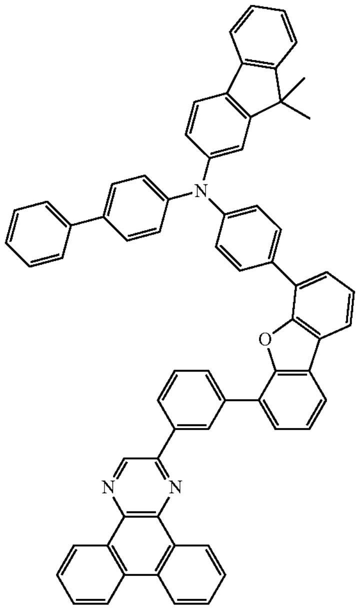

(502)

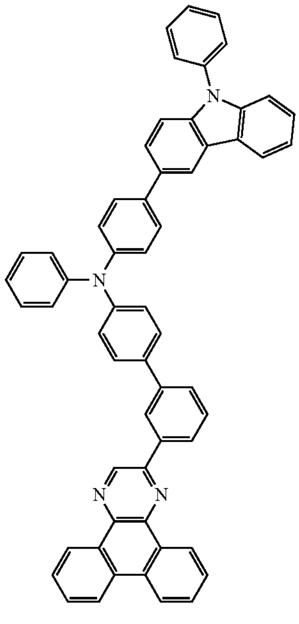

-continued (503)

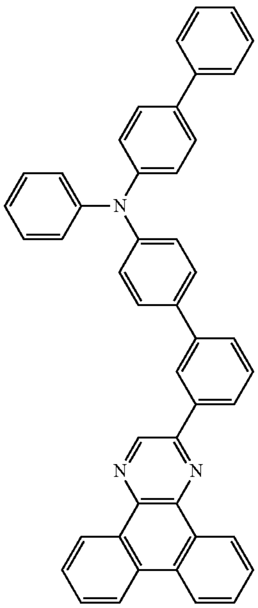

One embodiment of the present invention is a display device including the light-emitting element having any of the above structures, and at least one of a color filter and a transistor. One embodiment of the present invention is an electronic device 5 including the above-described display device and at least one of a housing and a touch sensor. One embodiment of the present invention is a lighting device including the light-emitting element having any of the above structures, and at least one of a housing and a touch sensor. The category of one embodiment of the present invention includes not only a light-emitting device including a light-emitting element but also an electronic device including a light-emitting device. Therefore, the light-emitting device in this specification refers to an image display device or a light source (e.g., a lighting device). A display module in which a connector such as a flexible printed circuit (FPC) or a tape carrier package (TCP) is connected to a light-emitting device, a display module in which a printed wiring board is provided on the tip of a TCP, and a display module in which an integrated circuit (IC) is directly mounted on a light-emitting element by a chip on glass (COG) method are also embodiments of the present invention.

With one embodiment of the present invention, a light-emitting element that has high emission efficiency and contains a phosphorescent material is provided. With one embodiment of the present invention, a light-emitting element with low power consumption is provided. With one embodiment of the present invention, a light-emitting element with high reliability is provided. With one embodiment of the present invention, a novel light-emitting element is provided. With one embodiment of the present invention, a novel light-emitting device is provided. With one embodiment of the present invention, a novel display device can be provided.

Note that the description of the above effects does not disturb the existence of other effects. In one embodiment of the present invention, there is no need to achieve all the effects. Other effects are apparent from and can be derived from the description of the specification, the drawings, the claims, and the like.

DETAILED DESCRIPTION OF THE INVENTION

Figure 1A:
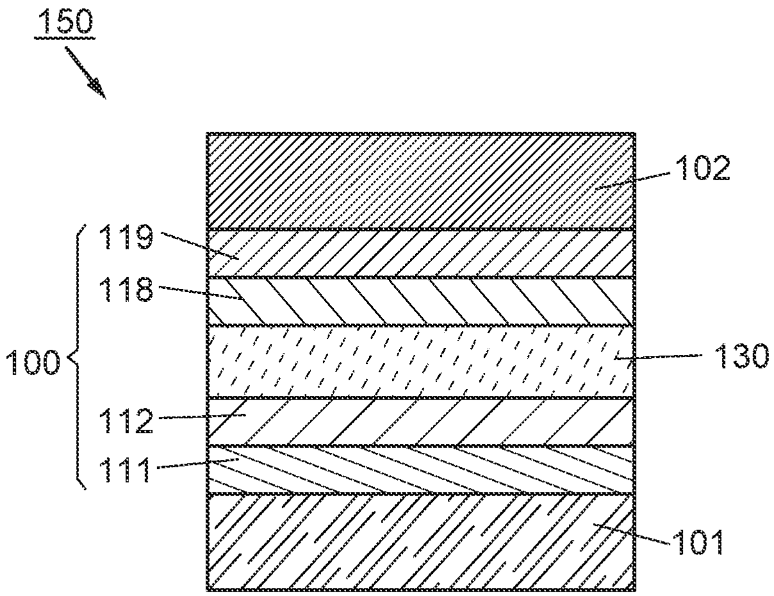
FIGS. 1A and 1B are schematic cross-sectional views of a light-emitting element of one embodiment of the present invention.

Embodiments of the present invention will be described in detail below with reference to the drawings. However, the present invention is not limited to description to be given below, and modes and details thereof can be variously modified without departing from the purpose and the scope of the present invention. Accordingly, the present invention should not be interpreted as being limited to the content of the embodiments below.

Note that the position, the size, the range, or the like of each structure illustrated in drawings and the like is not accurately represented in some cases for simplification. Therefore, the disclosed invention is not necessarily limited to the position, the size, the range, or the like disclosed in the drawings and the like.

Note that the ordinal numbers such as "first", "second", and the like in this specification and the like are used for convenience and do not denote the order of steps or the stacking order of layers. Therefore, for example, description can be made even when "first" is replaced with "second" or "third", as appropriate. In addition, the ordinal numbers in this specification and the like are not necessarily the same as those which specify one embodiment of the present invention.

In the description of modes of the present invention in this specification and the like with reference to the drawings, the same components in different diagrams are commonly denoted by the same reference numeral in some cases.

In this specification and the like, the terms "film" and "layer" can be interchanged with each other. For example, the term "conductive layer" can be changed into the term "conductive film" in some cases. Also, the term "insulating film" can be changed into the term "insulating layer" in some cases.

In this specification and the like, a singlet excited state ($S^*$) refers to a singlet state having excitation energy. An S1 level means the lowest level of the singlet excitation energy level, that is, the excitation energy level of the lowest singlet excited state. A triplet excited state ($T^*$) refers to a triplet state having excitation energy. A T1 level means the lowest level of the triplet excitation energy level, that is, the excitation energy level of the lowest triplet excited state. Note that in this specification and the like, a singlet excited state and a singlet excitation energy level mean the lowest singlet excited state and the S1 level, respectively, in some cases. A triplet excited state and a triplet excitation energy level mean the lowest triplet excited state and the T1 level, respectively, in some cases.

In this specification and the like, a fluorescent material refers to a material that emits light in the visible light region when the relaxation from the singlet excited state to the ground state occurs. A phosphorescent material refers to a material that emits light in the visible light region at room temperature when the relaxation from the triplet excited state to the ground state occurs. That is, a phosphorescent material refers to a material that can convert triplet excitation energy into visible light.

Phosphorescence emission energy or a triplet excitation energy can be obtained from a wavelength of an emission peak (including a shoulder) or a rising portion on the shortest wavelength side of phosphorescence emission. Note that the phosphorescence emission can be observed by time-resolved photoluminescence in a low-temperature (e.g., 10 K) environment. A thermally activated delayed fluorescence emission energy can be obtained from a wavelength of an emission peak (including a shoulder) or a rising portion on the shortest wavelength side of thermally activated delayed fluorescence.

Note that in this specification and the like, "room temperature" refers to a temperature higher than or equal to 0° C. and lower than or equal to 40° C.

In this specification and the like, a wavelength range of blue refers to a wavelength range of greater than or equal to 400 nm and less than 500 nm, and blue light has at least one peak in that range in an emission spectrum. A wavelength range of green refers to a wavelength range of greater than or equal to 500 nm and less than 580 nm, and green light has at least one peak in that range in an emission spectrum. A wavelength range of red refers to a wavelength range of greater than or equal to 580 nm and less than or equal to 680 nm, and red light has at least one peak in that range in an emission spectrum.

Embodiment 1

In this embodiment, a light-emitting element of one embodiment of the present invention will be described below with reference to FIGS. 1A and 1B, FIGS. 2A and 2B, FIGS. 3A and 3B, and FIGS. 4A and 4B.

<Structure Example 1 of Light-Emitting Element>

First, a structure of the light-emitting element of one embodiment of the present invention will be described below with reference to FIGS. 1A and 1B.

FIG. 1A is a schematic cross-sectional view of a light-emitting element 150 of one embodiment of the present invention.

The light-emitting element 150 includes a pair of electrodes (an electrode 101 and an electrode 102) and an EL layer 100 between the pair of electrodes. The EL layer 100 includes at least a light-emitting layer 130.

The EL layer 100 illustrated in FIG. 1A includes functional layers such as a hole-injection layer 111, a hole-transport layer 112, an electron-transport layer 118, and an electron-injection layer 119 in addition to the light-emitting layer 130.

In this embodiment, although description is given assuming that the electrode 101 and the electrode 102 of the pair of electrodes serve as an anode and a cathode, respectively, they are not limited thereto for the structure of the light-emitting element 150. That is, the electrode 101 may be a cathode, the electrode 102 may be an anode, and the stacking order of the layers between the electrodes may be reversed. In other words, the hole-injection layer 111, the hole-transport layer 112, the light-emitting layer 130, the electron-transport layer 118, and the electron-injection layer 119 may be stacked in this order from the anode side.

The structure of the EL layer 100 is not limited to the structure illustrated in FIG. 1A, and a structure including at least one layer selected from the hole-injection layer 111, the hole-transport layer 112, the electron-transport layer 118, and the electron-injection layer 119 may be employed. Alternatively, the EL layer 100 may include a functional layer which is capable of lowering a hole- or electron-injection barrier, improving a hole- or electron-transport property, diminishing a hole- or electron-transport property, or suppressing a quenching phenomenon by an electrode, for example. Note that the functional layers may each be a single layer or stacked layers.

Figure 1B:
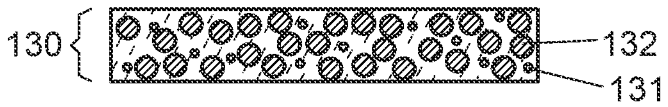

FIG. 1B is a schematic cross-sectional view illustrating an example of the light-emitting layer 130 in FIG. 1A. The light-emitting layer 130 in FIG. 1B includes a guest material 131 and a host material 132.

In the light-emitting layer 130, the host material 132 is present in the largest proportion by weight, and the guest material 131 is dispersed in the host material 132.

The guest material 131 is a light-emitting organic material. The light-emitting organic material preferably has a function of converting triplet excitation energy into light emission and is preferably a material capable of exhibiting phosphorescence (hereinafter also referred to as a phosphorescent material). In the description below, a phosphorescent material is used as the guest material 131. The guest material 131 may be rephrased as the phosphorescent material.

<Light Emission Mechanism 1 of Light-Emitting Element>

Next, the light emission mechanism of the light-emitting layer 130 is described below.

In the light-emitting element 150 of one embodiment of the present invention, voltage application between the pair of electrodes (the electrodes 101 and 102) causes electrons and holes to be injected from the cathode and the anode, respectively, into the EL layer 100 and thus current flows. By recombination of the injected electrons and holes, the guest material 131 in the light-emitting layer 130 of the EL layer 100 is brought into an excited state to provide light emission.

Note that light emission from the guest material 131 can be obtained through the following two processes:

(α) direct recombination process; and (β) energy transfer process.

<<(α) Direct Recombination Process>>

First, the direct recombination process in the guest material 131 will be described. Carriers (electrons and holes) are recombined in the guest material 131, and the guest material 131 is brought into an excited state. In this case, energy for exciting the guest material 131 by the direct carrier recombination process depends on the energy difference between the lowest unoccupied molecular orbital (LUMO) level and the highest occupied molecular orbital (HOMO) level of the guest material 131, and the energy difference approximately corresponds to singlet excitation energy. Since the guest material 131 is a phosphorescent material, triplet excitation energy is converted into light emission. Thus, when the energy difference between the singlet excited state and the triplet excited state of the guest material 131 is large, the energy for exciting the guest material 131 is higher than the light emission energy by the amount corresponding to the energy difference.

The energy difference between the energy for exciting the guest material 131 and the light emission energy affects element characteristics of a light-emitting element: the driving voltage of the light-emitting element varies. Thus, in (α) direct recombination process, the light emission start voltage of the light-emitting element is higher than the voltage corresponding to the light emission energy in the guest material 131.

In the case where the guest material 131 has high light emission energy, the guest material 131 has a high LUMO level. Thus, the injection of electrons as carriers into the guest material 131 is hampered, and the direct recombination of carriers (electrons and holes) is less likely to occur in the guest material 131. Accordingly, high emission efficiency is hardly obtained in the light-emitting element.

<<(β) Energy Transfer Process>>

Figure 2A:
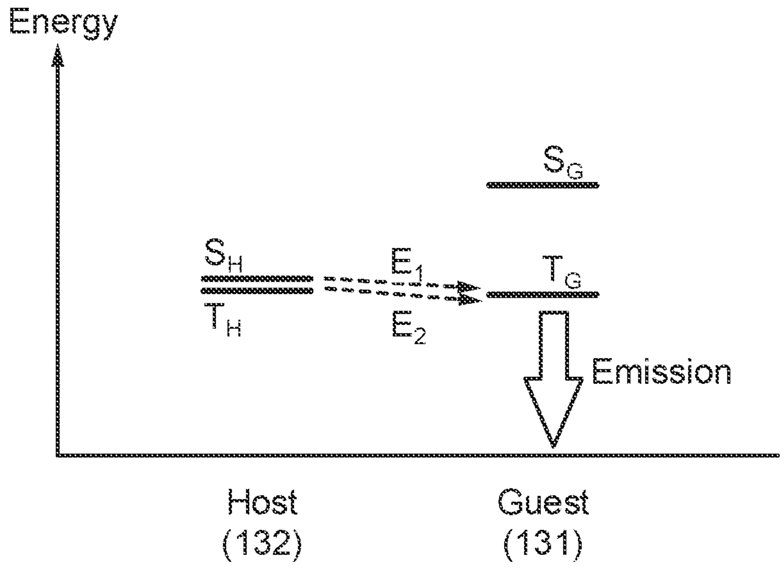
FIGS. 2A and 2B are schematic views showing a correlation of energy levels and a correlation between energy bands in a light-emitting layer of a light-emitting element of one embodiment of the present invention.

Next, in order to describe the energy transfer process of the host material 132 and the guest material 131, a schematic diagram illustrating the correlation of energy levels is shown in FIG. 2A. The following explains what terms and signs in FIG. 2A represent:

Guest (131): the guest material 131 (the phosphorescent material);

Host (132): the host material 132;

$S_G$: an S1 level of the guest material 131 (the phosphorescent material);

$T_G$: a T1 level of the guest material 131 (the phosphorescent material);

$S_H$: an S1 level of the host material 132; and $T_H$: a T1 level of the host material 132.

In the case where carriers are recombined in the host material 132 and the singlet excited state and the triplet excited state of the host material 132 are formed, as shown in Route $E_1$ and Route $E_2$ in FIG. 2A, both of the singlet excitation energy and the triplet excitation energy of the host material 132 are transferred from the singlet excitation energy level ($S_H$) and the triplet excitation energy level ($T_H$) of the host material 132 to the triplet excitation energy level ($T_G$) of the guest material 131, and the guest material 131 is brought into a triplet excited state. Phosphorescence is obtained from the guest material 131 in the triplet excited state.

Note that both of the singlet excitation energy level ($S_H$) and the triplet excitation energy level ($T_H$) of the host material 132 are preferably higher than or equal to the triplet excitation energy level ($T_G$) of the guest material 131. In that case, the singlet excitation energy and the triplet excitation energy of the formed host material 132 can be efficiently transferred from the singlet excitation energy level ($S_H$) and the triplet excitation energy level ($T_H$) of the host material 132 to the triplet excitation energy level ($T_G$) of the guest material 131.

In other words, in the light-emitting layer 130, excitation energy is transferred from the host material 132 to the guest material 131.

Note that in the case where the light-emitting layer 130 includes the host material 132, the guest material 131, and a material other than the host material 132 and the guest material 131, the material other than the host material 132 and the guest material 131 in the light-emitting layer 130 preferably has a triplet excitation energy level higher than the triplet excitation energy level ($T_H$) of the host material 132. Thus, quenching of the triplet excitation energy of the host material 132 is less likely to occur, which causes efficient energy transfer to the guest material 131.

In order to reduce energy loss caused when the singlet excitation energy of the host material 132 is transferred to the triplet excitation energy level ($T_G$) of the guest material 131, it is preferable that the energy difference between the singlet excitation energy level ($S_H$) and the triplet excitation energy level ($T_H$) of the host material 132 be small.

Figure 2B:
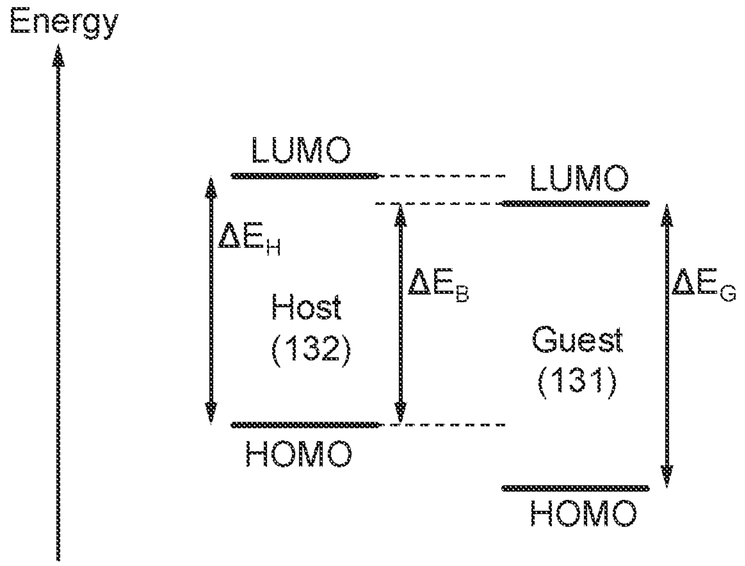

FIG. 2B is an energy band diagram of the guest material 131 and the host material 132. In FIG. 2B, "Guest (131)" represents the guest material 131, "Host (132)" represents the host material 132, $\Delta E_G$ represents the energy difference between the LUMO level and the HOMO level of the guest material 131, $\Delta E_H$ represents the energy difference between the LUMO level and the HOMO level of the host material 132, and $\Delta E_B$ represents the energy difference between the LUMO level of the guest material 131 and the HOMO level of the host material 132.

To make the guest material 131 emit light of a short wavelength and with high emission energy, the larger the energy difference ($\Delta E_G$) between the LUMO level and the HOMO level of the guest material 131 is, the better. However, excitation energy in the light-emitting element 150 is preferably as small as possible in order to reduce the driving voltage; thus, the smaller the excitation energy of an excited state formed by the host material 132 is, the better. Therefore, the energy difference ($\Delta E_H$) between the LUMO level and the HOMO level of the host material 132 is preferably small.

The guest material 131 is a phosphorescent material and thus has a function of converting triplet excitation energy into light emission. In addition, energy is more stable in a triplet excited state than in a singlet excited state. Thus, the guest material 131 emits light having energy smaller than the energy difference ($\Delta E_G$) between the LUMO level and the HOMO level of the guest material 131. The present inventors have found out that even in the case where the energy difference ($\Delta E_G$) between the LUMO level and the HOMO level of the guest material 131 is larger than the energy difference ($\Delta E_H$) between the LUMO level and the HOMO level of the host material 132, excitation energy transfer from an excited state of the host material 132 to the guest material 131 is possible and light emission can be obtained from the guest material 131 as long as light emission energy (abbreviation: $\Delta E_{Em}$) of the guest material 131 or transition energy (abbreviation: $\Delta E_{abs}$) calculated from an absorption edge of an absorption spectrum of the guest material 131 is equivalent to or lower than $\Delta E_H$. When $\Delta E_G$ of the guest material 131 is larger than the light emission energy ($\Delta E_{Em}$) of the guest material 131 or the transition energy ($\Delta E_{abs}$) calculated from the absorption edge of the absorption spectrum of the guest material 131, high electrical energy that corresponds to $\Delta E_G$ is necessary to directly cause electrical excitation of the guest material 131 and thus the driving voltage of the light-emitting element is increased. However, in one embodiment of the present invention, the host material 132 is electrically excited with electrical energy that corresponds to $\Delta E_H$ (that is smaller than $\Delta E_G$), and the guest material 131 is brought into an excited state by energy transfer therefrom, so that light emission of the guest material 131 can be obtained with low driving voltage and high efficiency. Therefore, the light emission start voltage (a voltage at the time when the luminance exceeds 1 cd/$m^2$) of the light-emitting element of one embodiment of the present invention can be lower than the voltage corresponding to the light emission energy ($\Delta E_{Em}$) of the guest material. That is, one embodiment of the present invention is useful particularly in the case where $\Delta E_G$ is significantly larger than the light emission energy ($\Delta E_{Em}$) of the guest material 131 or the transition energy ($\Delta E_{abs}$) calculated from the absorption edge of the absorption spectrum of the guest material 131 (for example, in the case where the guest material is a blue light-emitting material). Note that the light emission energy ($\Delta E_{Em}$) can be derived from a wavelength of an emission peak (the maximum value, or including a shoulder) on the shortest wavelength side or a wavelength of a rising portion of the emission spectrum.

Note that in the case where the guest material 131 includes a heavy metal, intersystem crossing between a singlet state and a triplet state is promoted by spin-orbit interaction (interaction between spin angular momentum and orbital angular momentum of an electron), and transition between a singlet ground state and a triplet excited state of the guest material 131 is allowed in some cases. Therefore, the emission efficiency and the absorption probability which relate to the transition between the singlet ground state and the triplet excited state of the guest material 131 can be increased. Accordingly, the guest material 131 preferably includes a metal element with large spin-orbit interaction, specifically a platinum group element (ruthenium (Ru), rhodium (Rh), palladium (Pd), osmium (Os), iridium (Ir), or platinum (Pt)). In particular, iridium is preferred because the absorption probability that relates to direct transition between a singlet ground state and a triplet excited state can be increased.

Note that the LUMO level of the guest material 131 is preferably low so that the guest material 131 can have stable and high reliability; thus, a ligand coordinated to a heavy metal atom in the guest material 131 preferably has a low LUMO level and a high electron-accepting property.

Such a guest material tends to have a molecular structure having a low LUMO level and a high electron-accepting property. When the guest material 131 has a molecular structure having a high electron-accepting property, the LUMO level of the guest material 131 is sometimes lower than that of the host material 132. In addition, when $\Delta E_G$ is larger than $\Delta E_H$, the HOMO level of the guest material 131 is lower than the HOMO level of the host material 132. Note that the energy difference between the HOMO level of the guest material 131 and the HOMO level of the host material 132 is larger than the energy difference between the LUMO level of the guest material 131 and the LUMO level of the host material 132.

Here, when the LUMO level of the guest material 131 is lower than that of the host material 132 and the HOMO level of the guest material 131 is lower than that of the host material 132, among carriers (holes and electrons) injected from the pair of electrodes (the electrode 101 and the electrode 102), holes injected from the anode are easily injected to the host material 132 and electrons injected from the cathode are easily injected to the guest material 131 in the light-emitting layer 130. Therefore, the guest material 131 and the host material 132 form an exciplex in some cases. Particularly when the energy difference ($\Delta E_B$) between the LUMO level of the guest material 131 and the HOMO level of the host material 132 becomes smaller than the emission energy of the guest material 131 ($\Delta E_{Em}$), generation of exciplexes formed by the guest material 131 and the host material 132 becomes predominant. In such a case, the guest material 131 itself is less likely to form an excited state, which decreases emission efficiency of the light-emitting element.

Note that the reactions described above can be expressed by General Formula (G11) or (G12).

$$H^+ + G^- \rightarrow (H\cdot G)^* \quad (G11)$$

$$H + G^* \rightarrow (H\cdot G)^* \quad (G12)$$

General Formula (G11) represents a reaction in which the host material 132 accepts a hole ($H^+$) and the guest material 131 accepts an electron ($G^-$), whereby the host material 132 and the guest material 131 form an exciplex ($(H\cdot G)^*$). General Formula (G12) represents a reaction in which the guest material 131 ($G^*$) in the excited state interacts with the host material 132 (H) in the ground state, whereby the host material 132 and the guest material 131 form an exciplex ($(H\cdot G)^*$). Formation of the exciplex ($(H\cdot G)^*$) by the host material 132 and the guest material 131 makes it difficult to form an excited state ($G^*$) of the guest material 131 alone.

An exciplex formed by the host material 132 and the guest material 131 has excitation energy that approximately corresponds to the energy difference ($\Delta E_B$) between the LUMO level of the guest material 131 and the HOMO level of the host material 132. The present inventors have found that when the energy difference ($\Delta E_B$) between the LUMO level of the guest material 131 and the HOMO level of the host material 132 is larger than or equal to an emission energy ($\Delta E_{Em}$) of the guest material 131 or a transition energy ($\Delta E_{abs}$) calculated from the absorption edge of the absorption spectrum of the guest material 131, the reaction for forming an exciplex by the host material 132 and the guest material 131 can be inhibited and thus light emission from the guest material 131 can be obtained efficiently. At this time, because $\Delta E_{abs}$ is smaller than $\Delta E_B$, the guest material 131 easily receives an excitation energy. Excitation of the guest material 131 by reception of the excitation energy needs lower energy and provides a more stable excitation state than formation of an exciplex by the host material 132 and the guest material 131.

As described above, even when the energy difference ($\Delta E_G$) between the LUMO level and the HOMO level of the guest material 131 is larger than the energy difference ($\Delta E_H$) between the LUMO level and the HOMO level of the host material 132, excitation energy transfers efficiently from the host material 132 in an excited state to the guest material 131 as long as transition energy ($\Delta E_{abs}$) calculated from the absorption edge of the absorption spectrum of the guest material 131 is equivalent to or smaller than $\Delta E_H$. As a result, a light-emitting element with high emission efficiency and low driving voltage can be obtained, which is a feature of one embodiment of the present invention. In this case, the formula $\Delta E_G > \Delta E_H > \Delta E_{abs}$ ($\Delta E_G$ is larger than $\Delta E_H$ and $\Delta E_H$ is larger than or equal to $\Delta E_{abs}$) is satisfied. Therefore, the mechanism of one embodiment of the present invention is suitable in the case where the energy difference ($\Delta E_G$) between the LUMO level and the HOMO level of the guest material 131 is larger than the transition energy ($\Delta E_{abs}$) calculated from the absorption edge of the absorption spectrum of the guest material 131. Specifically, the energy difference ($\Delta E_G$) between the LUMO level and the HOMO level of the guest material 131 is preferably larger than the transition energy ($\Delta E_{abs}$) calculated from the absorption edge of the absorption spectrum of the guest material 131 by 0.3 eV or more, more preferably larger than that by 0.4 eV or more. Since the light emission energy ($\Delta E_{Em}$) of the guest material 131 is equivalent to or smaller than $\Delta E_{abs}$, the energy difference ($\Delta E_G$) between the LUMO level and the HOMO level of the guest material 131 is preferably larger than the light emission energy ($\Delta E_{Em}$) of the guest material 131 by 0.3 eV or more, more preferably larger than that by 0.4 eV or more.

Furthermore, when the LUMO level of the guest material 131 is lower than the LUMO level of the host material 132, it is preferable that the formula $\Delta E_B \geq \Delta E_{abs}$ ($\Delta E_B$ is larger than or equal to $\Delta E_{abs}$) or $\Delta E_B \geq \Delta E_{Em}$ ($\Delta E_B$ is larger than or equal to $\Delta E_{Em}$) be satisfied. Therefore, it is preferable that the formula $\Delta E_G > \Delta E_H > \Delta E_B \geq \Delta E_{abs}$ ($\Delta E_G$ is larger than $\Delta E_H$, $\Delta E_H$ is larger than $\Delta E_B$, and $\Delta E_B$ is larger than or equal to $\Delta E_{abs}$) or the formula $\Delta E_G > \Delta E_H > \Delta E_B \geq \Delta E_{Em}$ ($\Delta E_G$ is larger than $\Delta E_H$, $\Delta E_H$ is larger than $\Delta E_B$, and $\Delta E_B$ is larger than or equal to $\Delta E_{Em}$) be satisfied. The above conditions are also important discoveries in one embodiment of the present invention.

The energy difference ($\Delta E_H$) between the LUMO level and the HOMO level of the host material 132 is equivalent to or slightly larger than the singlet excitation energy level ($S_H$) of the host material 132. The singlet excitation energy level ($S_H$) of the host material 132 is higher than the triplet excitation energy level ($T_H$) of the host material 132. The triplet excitation energy level ($T_H$) of the host material 132 is higher than or equal to the triplet excitation energy level ($T_G$) of the guest material 131. Therefore, the formula $\Delta E_G > \Delta E_H \geq S_H > T_H \geq T_G$ ($\Delta E_G$ is greater than $\Delta E_H$, $\Delta E_H$ is greater than or equal to $S_H$, $S_H$ is higher than $T_H$, and $T_H$ is higher than or equal to $T_G$) is satisfied. Note that $\Delta T_G$ is equivalent to or slightly smaller than $\Delta E_{abs}$ in the case where absorption that relates to the absorption edge of the absorption spectrum of the guest material 131 relates to transition between the singlet ground state and the triplet excited state of the guest material 131. Thus, in order to obtain $\Delta E_G$ larger than $\Delta E_{abs}$ by at least 0.3 eV, the energy difference between $S_H$ and $T_H$ is preferably smaller than the energy difference between $\Delta E_G$ and $\Delta E_{abs}$. Specifically, the energy difference between $S_H$ and $T_H$ is preferably greater than 0 eV and less than or equal to 0.2 eV, more preferably greater than 0 eV and less than or equal to 0.1 eV.

As an example of a material that has a small energy difference between the singlet excitation energy level and the triplet excitation energy level and is suitably used as the host material 132, a thermally activated delayed fluorescent (TADF) material can be given. The thermally activated delayed fluorescent material has a small energy difference between the singlet excitation energy level and the triplet excitation energy level and a function of converting triplet excitation energy into singlet excitation energy by reverse intersystem crossing. Note that the host material 132 of one embodiment of the present invention need not necessarily have high reverse intersystem crossing efficiency from $T_H$ to $S_H$ and high luminescence quantum yield from $S_H$, whereby materials can be selected from a wide range of options.

In order to have a small difference between the singlet excitation energy level and the triplet excitation energy level, the host material 132 preferably includes a skeleton having a function of transporting holes (a hole-transport property) and a skeleton having a function of transporting electrons (an electron-transport property). In this case, in the excited state of the host material 132, the skeleton having a hole-transport property includes the HOMO and the skeleton having an electron-transport property includes the LUMO; thus, an overlap between the HOMO and the LUMO is extremely small. That is, a donor-acceptor excited state in a single molecule is easily formed, and the difference between the singlet excitation energy level and the triplet excitation energy level is small. Note that in the host material 132, the difference between the singlet excitation energy level ($S_H$) and the triplet excitation energy level ($T_H$) is preferably greater than 0 eV and less than or equal to 0.2 eV.

Note that a molecular orbital refers to spatial distribution of electrons in a molecule, and can show the probability of finding of electrons. In addition, with the molecular orbital, electron configuration of the molecule (spatial distribution and energy of electrons) can be described in detail.

In the case where the host material 132 includes a skeleton having a strong donor property, a hole that has been injected to the light-emitting layer 130 is easily injected to the host material 132 and easily transported. In the case where the host material 132 includes a skeleton having a strong acceptor property, an electron that has been injected to the light-emitting layer 130 is easily injected to the host material 132 and easily transported. Both holes and electrons are preferably injected to the host material 132, in which case the excited state of the host material 132 is easily formed.

The shorter the emission wavelength of the guest material 131 is (the higher light emission energy $\Delta E_{Em}$ is), the larger the energy difference ($\Delta E_G$) between the LUMO level and the HOMO level of the guest material 131 is, and accordingly, larger energy is needed for directly and electrically exciting the guest material. However, in one embodiment of the present invention, when the transition energy ($\Delta E_{abs}$) calculated from the absorption edge of the absorption spectrum of the guest material 131 is equivalent to or smaller than $\Delta E_H$, the guest material 131 can be excited with energy as small as $\Delta E_H$, which is smaller than $\Delta E_G$, whereby the power consumption of the light-emitting element can be reduced. Therefore, the effect of the light emission mechanism of one embodiment of the present invention is brought to the fore in the case where the energy difference between the transition energy ($\Delta E_{abs}$) calculated from the absorption edge of the absorption spectrum of the guest material 131 and the energy difference ($\Delta E_G$) between the LUMO level and the HOMO level of the guest material 131 is large (i.e., particularly in the case where the guest material is a blue light-emitting material).

As the transition energy ($\Delta E_{abs}$) calculated from the absorption edge of the absorption spectrum of the guest material 131 decreases, the light emission energy ($\Delta E_{Em}$) of the guest material 131 also decreases. In that case, light emission that needs high energy, such as blue light emission, is difficult to obtain. That is, when a difference between $\Delta E_{abs}$ and $\Delta E_G$ is too large, high-energy light emission such as blue light emission is obtained with difficulty.

For these reasons, the energy difference ($\Delta E_G$) between the LUMO level and the HOMO level of the guest material 131 is preferably larger than the transition energy ($\Delta E_{abs}$) calculated from the absorption edge of the absorption spectrum of the guest material 131 by 0.3 eV to 0.8 eV inclusive, more preferably by 0.4 eV to 0.8 eV inclusive, much more preferably by 0.5 eV to 0.8 eV inclusive. Since the light emission energy ($\Delta E_{Em}$) of the guest material 131 is equivalent to or smaller than $\Delta E_{abs}$, the energy difference ($\Delta E_G$) between the LUMO level and the HOMO level of the guest material 131 is preferably larger than the light emission energy ($\Delta E_{Em}$) of the guest material 131 by 0.3 eV to 0.8 eV inclusive, more preferably larger than that by 0.4 eV to 0.8 eV inclusive, much more preferably larger than that by 0.5 eV to 0.8 eV inclusive.

In addition, the guest material 131 serves as an electron trap in the light-emitting layer 130 because of its LUMO level lower than the LUMO level of the host material 132. This is preferable because the carrier balance in the light-emitting layer can be easily controlled, leading to a longer lifetime. However, when the LUMO level of the guest material 131 is too low, the above-described $\Delta E_B$ becomes small. Therefore, the energy difference between the LUMO level of the guest material 131 and the LUMO level of the host material 132 is preferably greater than or equal to 0.05 eV and less than or equal to 0.4 eV. Furthermore, the energy difference between the HOMO level of the guest material 131 and the HOMO level of the host material 132 is preferably 0.05 eV or more, more preferably 0.1 eV or more, much more preferably 0.2 eV or more, which is suitable for easy injection of hole carriers to the host material 132.

Furthermore, since the energy difference ($\Delta E_H$) between the LUMO level and the HOMO level of the host material 132 is smaller than the energy difference ($\Delta E_G$) between the LUMO level and the HOMO level of the guest material 131, an excited state formed by the host material 132 is more energetically stable as an excited state formed by recombination of carriers (holes and electrons) injected to the light-emitting layer 130. Therefore, most of the excited states generated in the light-emitting layer 130 by direct combination of carriers exist as excited states formed by the host material 132. Accordingly, the structure of one embodiment of the present invention facilitates excitation energy transfer from the host material 132 to the guest material 131, leading to lower driving voltage of the light-emitting element and higher emission efficiency.

According to the above-described relation between the LUMO level and the HOMO level, a reduction potential of the guest material 131 is preferably higher than a reduction potential of the host material 132. Note that the oxidation potential and the reduction potential can be measured by cyclic voltammetry (CV).

When the light-emitting layer 130 has the above-described structure, light emission from the guest material 131 of the light-emitting layer 130 can be obtained efficiently.

<Energy Transfer Mechanism>

Next, factors controlling the processes of intermolecular energy transfer between the host material 132 and the guest material 131 will be described. As mechanisms of the intermolecular energy transfer, two mechanisms, i.e., Förster mechanism (dipole-dipole interaction) and Dexter mechanism (electron exchange interaction), have been proposed.

<<Förster Mechanism>>

In Förster mechanism, energy transfer does not require direct contact between molecules and energy is transferred through a resonant phenomenon of dipolar oscillation between the host material 132 and the guest material 131. By the resonant phenomenon of dipolar oscillation, the host material 132 provides energy to the guest material 131, and thus, the host material 132 in an excited state is brought to a ground state and the guest material 131 in a ground state is brought to an excited state. Note that the rate constant $k_{h^*\rightarrow g}$ of Förster mechanism is expressed by Formula (1).

$$k_{h^*\rightarrow g} = \frac{9000c^4K^2\phi \ln 10}{128\pi^5 n^4 N\tau R^6}\int\frac{f'_h(v)\varepsilon_g(v)}{v^4}dv \quad \text{[Formula 1]}$$

In Formula (1), ν denotes a frequency, $f'_h(\nu)$ denotes a normalized emission spectrum of the host material 132 (a fluorescence spectrum in energy transfer from a singlet excited state, and a phosphorescence spectrum in energy transfer from a triplet excited state), $\varepsilon_g(\nu)$ denotes a molar absorption coefficient of the guest material 131, N denotes Avogadro's number, n denotes a refractive index of a medium, R denotes an intermolecular distance between the host material 132 and the guest material 131, τ denotes a measured lifetime of an excited state (fluorescence lifetime or phosphorescence lifetime), c denotes the speed of light, ϕ denotes a luminescence quantum yield (a fluorescence quantum yield in energy transfer from a singlet excited state, and a phosphorescence quantum yield in energy transfer from a triplet excited state), and $K^2$ denotes a coefficient (0 to 4) of orientation of a transition dipole moment between the host material 132 and the guest material 131. Note that $K^2=2/3$ in random orientation.

<<Dexter Mechanism>>

In Dexter mechanism, the host material 132 and the guest material 131 are close to a contact effective range where their orbitals overlap, and the host material 132 in an excited state and the guest material 131 in a ground state exchange their electrons, which leads to energy transfer. Note that the rate constant $k_{h^*\rightarrow g}$ of Dexter mechanism is expressed by Formula (2).

$$k_{h^*\rightarrow g} = \left(\frac{2\pi}{h}\right)K^2\exp\left(-\frac{2R}{L}\right)\int f'_h(v)\varepsilon'_g(v)dv \quad \text{[Formula 2]}$$

In Formula (2), h denotes a Planck constant, K denotes a constant having an energy dimension, ν denotes a frequency, $f'_h(\nu)$ denotes a normalized emission spectrum of the host material 132 (a fluorescence spectrum in energy transfer from a singlet excited state, and a phosphorescence spectrum in energy transfer from a triplet excited state), $\varepsilon'_g(\nu)$ denotes a normalized absorption spectrum of the guest material 131, L denotes an effective molecular radius, and R denotes an intermolecular distance between the host material 132 and the guest material 131.

Here, the efficiency of energy transfer from the host material 132 to the guest material 131 (energy transfer efficiency $\phi_{ET}$) is expressed by Formula (3). In the formula, $k_r$ denotes a rate constant of a light-emission process (fluorescence in energy transfer from a singlet excited state, and phosphorescence in energy transfer from a triplet excited state) of the host material 132, $k_n$ denotes a rate constant of a non-light-emission process (thermal deactivation or intersystem crossing) of the host material 132, and τ denotes a measured lifetime of an excited state of the host material 132.

$$\phi_{ET} = \frac{k_{h^*\rightarrow g}}{k_r + k_n + k_{h^*\rightarrow g}} = \frac{k_{h^*\rightarrow g}}{\left(\frac{1}{\tau}\right) + k_{h^*\rightarrow g}} \quad \text{[Formula 3]}$$

According to Formula (3), it is found that the energy transfer efficiency $\phi_{ET}$ can be increased by increasing the rate constant $k_{h^*\rightarrow g}$ of energy transfer so that another competing rate constant $k_r+k_n$ (=1/τ) becomes relatively small.

<<Concept for Promoting Energy Transfer>>

In energy transfer by Förster mechanism, high energy transfer efficiency $\phi_{ET}$ is obtained when emission quantum yield ϕ (a fluorescence quantum yield in energy transfer from a singlet excited state, and a phosphorescence quantum yield in energy transfer from a triplet excited state) is high. Furthermore, it is preferable that the emission spectrum (the fluorescence spectrum in energy transfer from the singlet excited state) of the host material 132 largely overlap with the absorption spectrum (absorption corresponding to the transition from the singlet ground state to the triplet excited state) of the guest material 131. Moreover, it is preferable that the molar absorption coefficient of the guest material 131 be also high. This means that the emission spectrum of the host material 132 overlaps with the absorption band of the absorption spectrum of the guest material 131 that is on the longest wavelength side.

In energy transfer by Dexter mechanism, in order to make the rate constant $k_{h^*\rightarrow g}$ large, it is preferable that the emission spectrum (a fluorescence spectrum in energy transfer from a singlet excited state, and a phosphorescence spectrum in energy transfer from a triplet excited state) of the host material 132 largely overlap with the absorption spectrum (absorption corresponding to transition from a singlet ground state to a triplet excited state) of the guest material 131. Therefore, the energy transfer efficiency can be optimized by making the emission spectrum of the host material 132 overlap with the absorption band of the absorption spectrum of the guest material 131 that is on the longest wavelength side.

<Structure Example 2 of Light-Emitting Element>

Next, a light-emitting element having a structure different from the structure illustrated in FIGS. 1A and 1B will be described below with reference to FIGS. 3A and 3B.

Figure 3A:
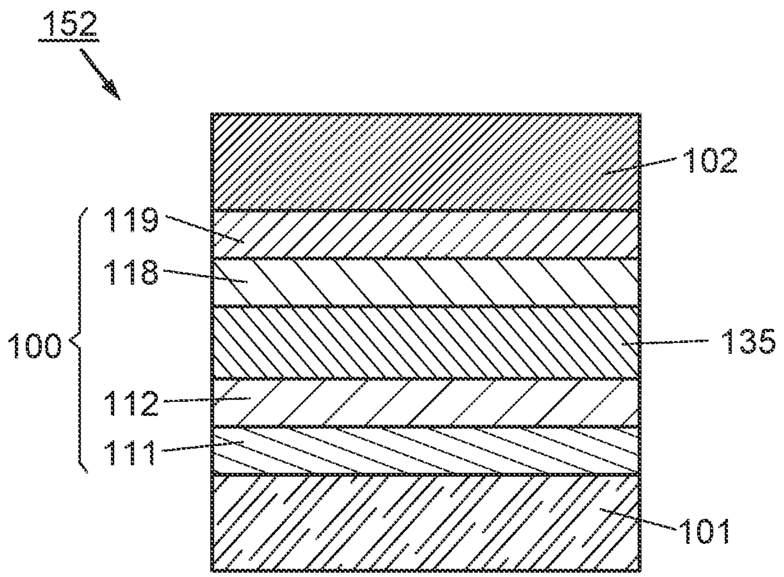
FIGS. 3A and 3B are schematic cross-sectional views of a light-emitting element of one embodiment of the present invention.

FIG. 3A is a schematic cross-sectional view of a light-emitting element 152 of one embodiment of the present invention. In FIG. 3A, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

The light-emitting element 152 includes the pair of electrodes (the electrode 101 and the electrode 102) and the EL layer 100 between the pair of electrodes. The EL layer 100 includes at least a light-emitting layer 135.

Figure 3B:
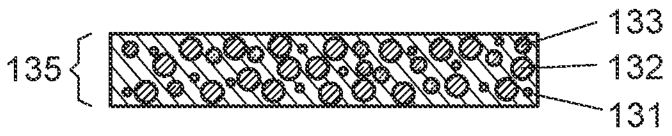

FIG. 3B is a schematic cross-sectional view illustrating an example of the light-emitting layer 135 in FIG. 3A. The light-emitting layer 135 in FIG. 3B includes at least the guest material 131, the host material 132, and a host material 133.

In the light-emitting layer 135, the host material 132 or the host material 133 is present in the largest proportion by weight, and the guest material 131 is dispersed in the host material 132 and the host material 133.

<Light Emission Mechanism 2 of Light-Emitting Element>

Next, the light emission mechanism of the light-emitting layer 135 is described.

Also in the light-emitting element 152 of one embodiment of the present invention, by recombination of electrons and holes injected from the pair of electrodes (the electrode 101 and the electrode 102), the guest material 131 in the light-emitting layer 135 of the EL layer 100 is brought into an excited state to provide light emission.

Note that light emission from the guest material 131 can be obtained through the following two processes:

(α) direct recombination process; and (β) energy transfer process.

Note that the direct recombination process (α) is not described here because it is similar to the direct recombination process in the description of the light emission mechanism of the light-emitting layer 130.

<<(β) Energy Transfer Process>>

Figure 4A:
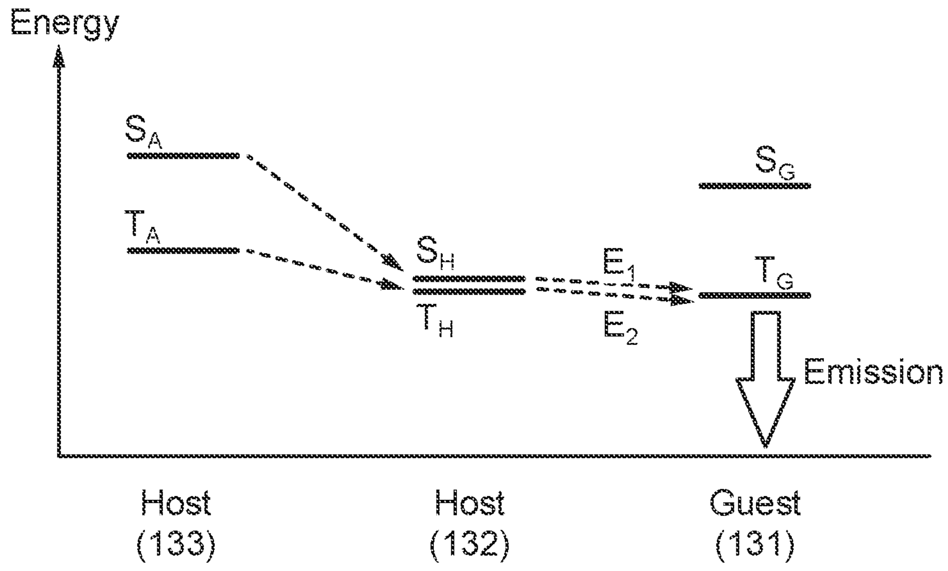
FIGS. 4A and 4B are schematic views showing a correlation between energy levels and a correlation between energy bands in a light-emitting layer of a light-emitting element of one embodiment of the present invention.

In order to describe the energy transfer process of the host material 132, the host material 133, and the guest material 131, a schematic diagram illustrating the correlation of energy levels is shown in FIG. 4A. The following explain what terms and signs in FIG. 4A represent, and the other terms and signs in FIG. 4A are similar to those in FIG. 2A.

Host (133): the host material 133;

$S_A$: an S1 level of the host material 133; and $T_A$: a T1 level of the host material 133.

In the case where carriers are recombined in the host material 132 and the singlet excited state and the triplet excited state of the host material 132 are formed, as shown in Route $E_1$ and Route $E_2$ in FIG. 4A, both of the singlet excitation energy and the triplet excitation energy of the host material 132 are transferred from the singlet excitation energy level ($S_H$) and the triplet excitation energy level ($T_H$) of the host material 132 to the triplet excitation energy level ($T_G$) of the guest material 131, and the guest material 131 is brought into a triplet excited state. Phosphorescence is obtained from the guest material 131 in the triplet excited state.

Note that in order to transfer excitation energy from the host material 132 to the guest material 131 efficiently, the triplet excitation energy level ($T_A$) of the host material 133 is preferably higher than the triplet excitation energy level ($T_H$) of the host material 132. Thus, quenching of the triplet excitation energy of the host material 132 is less likely to occur, which causes efficient energy transfer to the guest material 131.

Figure 4B:
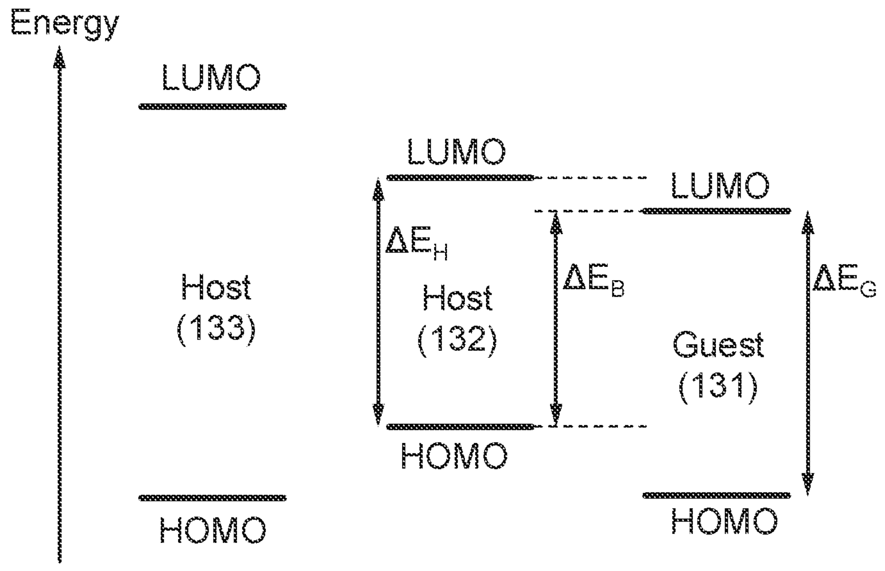

When the LUMO level of the guest material 131 is lower than the LUMO level of the host material 132 as shown in an energy band diagram in FIG. 4B, it is preferable that the energy difference ($\Delta E_G$) between the LUMO level and the HOMO level of the guest material 131 be larger than the energy difference ($\Delta E_H$) between the LUMO level and the HOMO level of the host material 132 and that $\Delta E_H$ be larger than the energy difference ($\Delta E_B$) between the LUMO level of the guest material 131 and the HOMO level of the host material 132, as described in Light emission mechanism 1 of light-emitting element.

It is preferable that the HOMO level of the host material 133 be lower than the HOMO level of the host material 132 and that the LUMO level of the host material 133 be higher than the LUMO level of the guest material 131. That is, the energy difference between the LUMO level and the HOMO level of the host material 133 is larger than the energy difference ($\Delta E_B$) between the LUMO level of the guest material 131 and the HOMO level of the host material 132. Thus, the reaction for forming an exciplex by the host material 133 and the host material 132 and the reaction for forming an exciplex by the host material 133 and the guest material 131 can be inhibited. In FIG. 4B, "Host (133)" represents the host material 133, and the other terms and signs are similar to those in FIG. 2B.

Note that the difference between the HOMO level of the host material 133 and the HOMO level of the host material 132 and the difference between the LUMO level of the host material 133 and the LUMO level of the guest material 131 are each preferably greater than or equal to 0.1 eV, more preferably greater than or equal to 0.2 eV. The energy difference is suitable because electron carriers and hole carriers injected from the pair of electrodes (the electrode 101 and the electrode 102) are easily injected to the guest material 131 and the host material 132, respectively.

Note that the HOMO level of the host material 133 may be either higher or lower than the HOMO level of the guest material 131, and the LUMO level of the host material 133 may be either higher or lower than the LUMO level of the host material 132.

Furthermore, the energy difference between the LUMO level and the HOMO level of the host material 133 is preferably larger than the energy difference ($\Delta E_H$) between the LUMO level and the HOMO level of the host material 132. In that case, since the energy difference ($\Delta E_H$) between the LUMO level and the HOMO level of the host material 132 is smaller than the energy difference ($\Delta E_G$) between the LUMO level and the HOMO level of the guest material 131, as an excited state formed by recombination of carriers (holes and electrons) injected to the light-emitting layer 135, an excited state formed by the host material 132 is more energetically stable than an excited state formed by the host material 133 and an excited state formed by the guest material 131. Therefore, most of the excited states generated in the light-emitting layer 135 by recombination of carriers exist as excited states formed by the host material 132. Thus, in the light-emitting layer 135, excitation energy transfer from an excited state of the host material 132 to the guest material 131 occurs easily as in the structure of the light-emitting layer 130, so that the light-emitting element 152 can be driven with low driving voltage and high emission efficiency.

Even in the case where holes and electrons are recombined in the host material 133 and an excited state is formed by the host material 133, excitation energy of the host material 133 can be immediately transferred to the host material 132 when the energy difference between the LUMO level and the HOMO level of the host material 133 is larger than the energy difference between the LUMO level and the HOMO level of the host material 132. Then, the excitation energy is transferred to the guest material 131 through a process similar to that in the description of the light emission mechanism of the light-emitting layer 130, whereby light emission from the guest material 131 can be obtained. Note that when the possibility that holes and electrons are recombined also in the host material 133 is taken into consideration, the host material 133 is preferably a material having a small energy difference between the singlet excitation energy level and the triplet excitation energy level, particularly preferably a thermally activated delayed fluorescent material, like the host material 132.

In order to obtain light emission from the guest material 131 efficiently, it is preferable that the singlet excitation energy level ($S_A$) of the host material 133 be higher than or equal to the singlet excitation energy level ($S_H$) of the host material 132 and that the triplet excitation energy level ($T_A$) of the host material 133 be higher than or equal to the triplet excitation energy level ($T_H$) of the host material 132.

According to the above-described relations between the LUMO levels and the HOMO levels, it is preferable that an oxidation potential of the host material 133 be higher than an oxidation potential of the host material 132 and that a reduction potential of the host material 133 be lower than the reduction potential of the guest material 131.

In the case where the combination of the host material 132 and the host material 133 is a combination of a material having a function of transporting holes and a material having a function of transporting electrons, the carrier balance can be easily controlled depending on the mixture ratio. Specifically, the ratio of the material having a function of transporting holes to the material having a function of transporting electrons is preferably within a range of 1:9 to 9:1 (weight ratio). Since the carrier balance can be easily controlled with the structure, a carrier recombination region can also be controlled easily. When the light-emitting layer 135 has the above-described structure, light emission from the guest material 131 of the light-emitting layer 135 can be obtained efficiently.

<Material>

Next, components of a light-emitting element of one embodiment of the present invention are described in detail below.

<<Light-Emitting Layer>>

In the light-emitting layer 130 and the light-emitting layer 135, the weight percentage of the host material 132 is higher than that of at least the guest material 131, and the guest material 131 (the phosphorescent material) is dispersed in the host material 132.

<<Host Material 132>>

The energy difference between the S1 level and the T1 level of the host material 132 is preferably small, and specifically, greater than 0 eV and less than or equal to 0.2 eV.

The host material 132 preferably includes a skeleton having a hole-transport property and a skeleton having an electron-transport property. Alternatively, the host material 132 preferably includes a π-electron deficient heteroaromatic ring skeleton and one of a π-electron rich heteroaromatic ring skeleton and an aromatic amine skeleton. Thus, a donor-acceptor excited state is easily formed in a molecule. Furthermore, to increase both the donor property and the acceptor property in the molecule of the host material 132, a structure where the skeleton having an electron-transport property and the skeleton having a hole-transport property are directly bonded to each other is preferably included. Alternatively, it is preferable that a structure where a π-electron deficient heteroaromatic ring skeleton is directly bonded to one of a π-electron rich heteroaromatic ring skeleton and an aromatic amine skeleton be included. By increasing both the donor property and the acceptor property in the molecule, an overlap between a region where the HOMO is distributed and a region where the LUMO is distributed in the host material 132 can be small, and the energy difference between the singlet excitation energy level and the triplet excitation energy level of the host material 132 can be small. Moreover, the triplet excitation energy level of the host material 132 can be kept high.

As an example of the material in which the energy difference between the triplet excitation energy level and the singlet excitation energy level is small, a thermally activated delayed fluorescent material can be given. Note that a thermally activated delayed fluorescent material has a function of converting triplet excited energy into singlet excited energy by reverse intersystem crossing because of having a small difference between the triplet excited energy level and the singlet excited energy level. Thus, the TADF material can up-convert a triplet excited state into a singlet excited state (i.e., reverse intersystem crossing is possible) using a little thermal energy and efficiently exhibit light emission (fluorescence) from the singlet excited state. The TADF material is efficiently obtained under the condition where the difference between the triplet excited energy level and the singlet excited energy level is preferably larger than 0 eV and smaller than or equal to 0.2 eV, more preferably larger than 0 eV and smaller than or equal to 0.1 eV.

In the case where the TADF material is composed of one kind of material, any of the following materials can be used, for example.

First, a fullerene, a derivative thereof, an acridine derivative such as proflavine, eosin, and the like can be given. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2OEP$).

[Chemical Formulae 3]

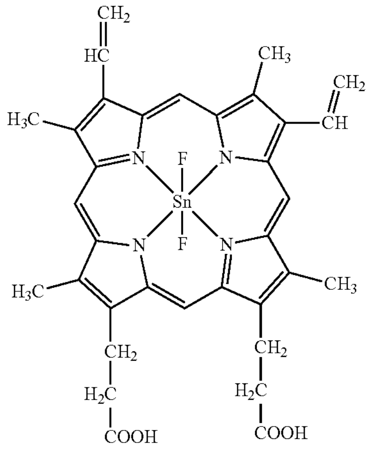

$SnF_2$(Proto IX)

-continued

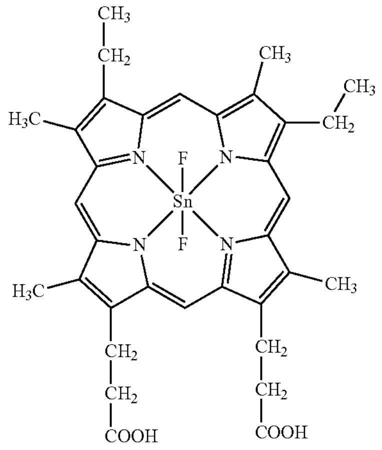

$SnF_2$(Meso IX)

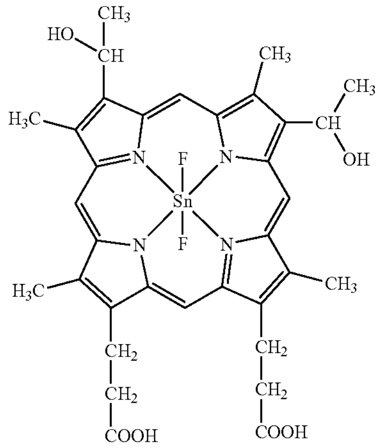

$SnF_2$(Hemato IX)

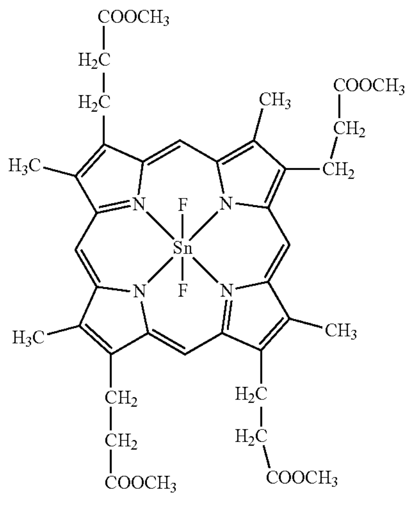

$SnF_2$(Copro III-4 Me)

-continued

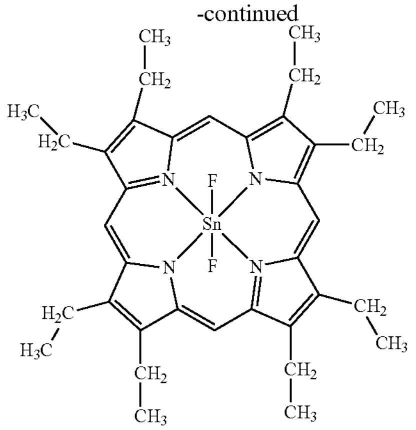

$SnF_2$(OEP)

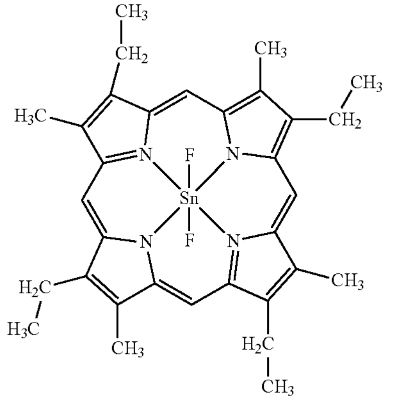

$SnF_2$(Etio I)

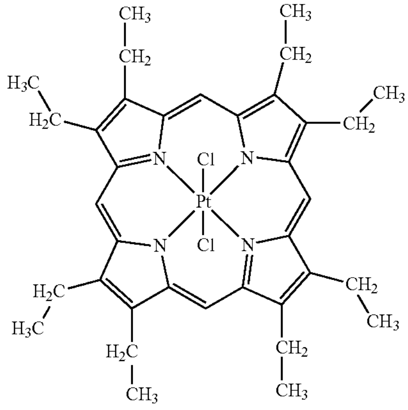

$PtCl_2OEP$

As the TADF material composed of one kind of material, a heterocyclic compound including a π-electron rich heteroaromatic ring and a π-electron deficient heteroaromatic ring can also be used. Specifically, 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H, 10'H-spiro[acridin-9,9'-anthracen]-10'-one (abbreviation: ACRSA) can be used. The heterocyclic compound is preferably used because of having the π-electron rich heteroaromatic ring and the π-electron deficient heteroaromatic ring, for which the electron-transport property and the hole-transport property are high. Among skeletons having the π-electron deficient heteroaromatic ring, a diazine skeleton (a pyrimidine skeleton, a pyrazine skeleton, or a pyridazine skeleton) and a triazine skeleton have high stability and high reliability and are particularly preferable. Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and high reliability; therefore, at least one of these skeletons are preferably included. As the furan skeleton, a dibenzofuran skeleton is preferable. As the thiophene skeleton, a dibenzothiophene skeleton is preferable. As the pyrrole skeleton, an indole skeleton, a carbazole skeleton, or a 9-phenyl-3,3'-bi-9H-carbazole skeleton is particularly preferred. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the difference between the level of the singlet excited state and the level of the triplet excited state becomes small. Note that an aromatic ring to which an electron-withdrawing group such as a cyano group is bonded may be used instead of the π-electron deficient heteroaromatic ring.

[Chemical Formulae 4]

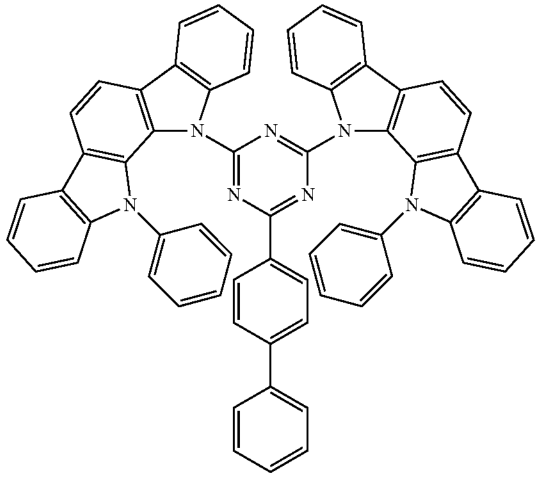

PIC-TRZ

-continued

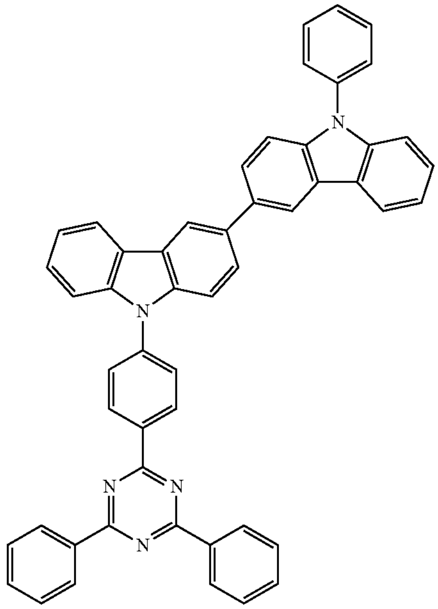

PCCzPTzn

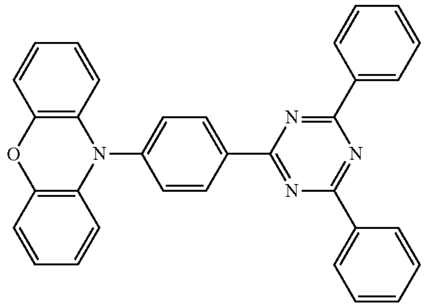

PXZ-TRZ

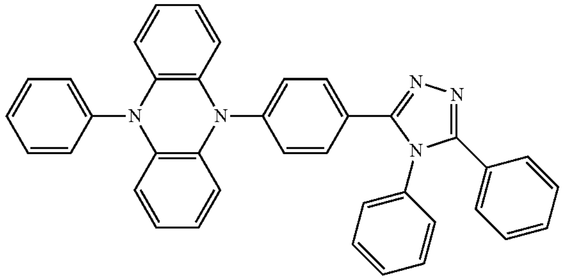

PPZ-3TPT

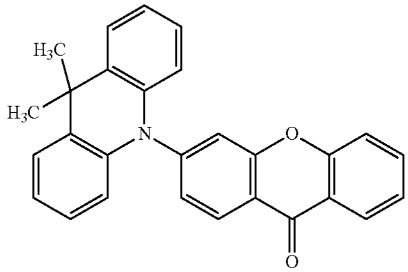

ACRXTN

-continued

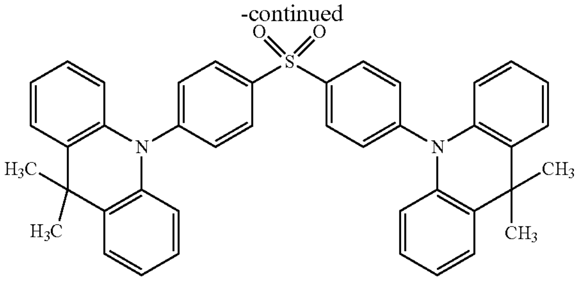

DMAC-DPS

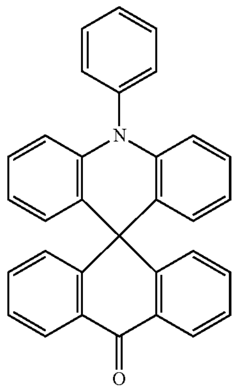

ACRSA

Among skeletons having the π-electron deficient heteroaromatic ring, a condensed heterocyclic skeleton having a diazine skeleton is preferable because of having higher stability and higher reliability, and a benzofuropyrimidine skeleton and a benzothienopyrimidine skeleton are particularly preferable because of having a higher acceptor property. As the benzofuropyrimidine skeleton, for example, a benzofuro[3,2-d]pyrimidine skeleton is given. As the benzothienopyrimidine skeleton, for example, a benzothieno[3,2-d]pyrimidine skeleton is given.

Among skeletons having the π-electron rich heteroaromatic ring, a bicarbazole skeleton is preferable because of having high excitation energy, high stability, and high reliability. As the bicarbazole skeleton, for example, a bicarbazole skeleton in which any of the 2- to 4-positions of a carbazolyl group is bonded to any of the 2- to 4-positions of another carbazolyl group is particularly preferable because of having a high donor property. As such a bicarbazole skeleton, for example, 2,2'-bi-9H-carbazole skeleton, 3,3'-bi-9H-carbazole skeleton, 4,4'-bi-9H-carbazole skeleton, 2,3'-bi-9H-carbazole skeleton, 2,4'-bi-9H-carbazole skeleton, 3,4'-bi-9H-carbazole skeleton, and the like are given.

In view of increasing a band gap and a triplet excitation energy, a compound in which the 9-position of one of the carbazolyl groups in the bicarbazole skeleton is directly bonded to the benzofuropyrimidine skeleton or the benzothienopyrimidine skeleton is preferable. In the case where the bicarbazole skeleton is directly bonded to the benzofuropyrimidine skeleton or the benzothienopyrimidine skeleton, a relatively low molecular compound is formed, and therefore, a structure that is suitable for vacuum evaporation (a structure that can be formed by vacuum evaporation at a relatively low temperature) is obtained, which is preferable. In general, a lower molecular weight tends to reduce heat resistance after film formation. However, because of high rigidity of the benzofuropyrimidine skeleton, the benzothienopyrimidine skeleton, and the bicarbazole skeleton, a compound including the skeleton can have sufficient heat resistance even with a relatively low molecular weight. The structure is preferable because a band gap and an excitation energy level are increased.

In the case where the bicarbazole skeleton is bonded to the benzofuropyrimidine skeleton or the benzothienopyrimidine skeleton through an arylene group having 6 to 25 carbon atoms, preferably 6 to 13 carbon atoms, the band gap is kept wide and the triplet excitation energy can be kept high. Moreover, a relatively low molecular compound is formed, and therefore, a structure that is suitable for vacuum evaporation (a structure that can be formed by vacuum evaporation at a relatively low temperature) is obtained.

In the case where a bicarbazole skeleton is bonded, directly or through an arylene group, to a benzofuro[3,2-d]pyrimidine skeleton or a benzothieno[3,2-d]pyrimidine skeleton, preferably the 4-position of the benzofuro[3,2-d]pyrimidine skeleton or the benzothieno[3,2-d]pyrimidine skeleton in a compound, the compound has a high carrier-transport property. Accordingly, a light-emitting element using the compound can be driven at a low voltage.

Compound Example 1

The above-described compound that is preferably used in a light-emitting element of one embodiment of the present invention is a compound represented by General Formula (G0).

[Chemical Formula 5]

(G0)

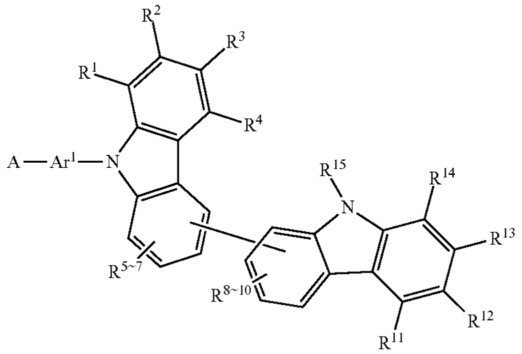

In General Formula (G0), A represents a substituted or unsubstituted benzofuropyrimidine skeleton or a substituted or unsubstituted benzothienopyrimidine skeleton. In the case where the benzofuropyrimidine skeleton or the benzothienopyrimidine skeleton has a substituent, as the substituent, an alkyl group having 1 to 6 carbon atoms, a cycloalkyl group having 3 to 7 carbon atoms, or a substituted or unsubstituted aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Further, each of $R^1$ to $R^{15}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Further, $Ar^1$ represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 25 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

In the compound represented by General Formula (G0), the benzofuropyrimidine skeleton is preferably a benzofuro[3,2-d]pyrimidine skeleton, and the benzothienopyrimidine skeleton is preferably a benzothieno[3,2-d]pyrimidine skeleton.

The compound represented by General Formula (G0) in which the 9-position of one of the carbazolyl groups in the bicarbazole skeleton is bonded, directly or through the arylene group, to the 4-position of the benzofuro[3,2-d]pyrimidine skeleton or the benzothieno[3,2-d]pyrimidine skeleton has a high donor property, a high acceptor property, and a wide band gap, and therefore can suitably be used in a light-emitting element that emits light with high energy such as blue light, which is preferable. The above-described compound is a compound represented by General Formula (G1).

[Chemical Formula 6]

(G1)

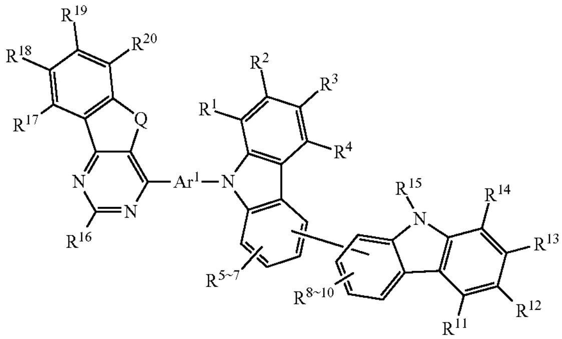

In General Formula (G1), Q represents oxygen or sulfur.

Further, each of $R^1$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Further, $Ar^1$ represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 25 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

The compound represented by General Formula (G1) in which the bicarbazole skeleton is a 3,3'-bi-9H-carbazole skeleton and the 9-position of one of the carbazolyl groups in the bicarbazole skeleton is bonded, directly or through the arylene group, to the 4-position of the benzofuro[3,2-d]pyrimidine skeleton or the benzothieno[3,2-d]pyrimidine skeleton has a high carrier-transport property and a light-emitting element including the compound can be driven at a low voltage, which is preferable. The above-described compound is a compound represented by General Formula (G2).

[Chemical Formula 7]

(G2)

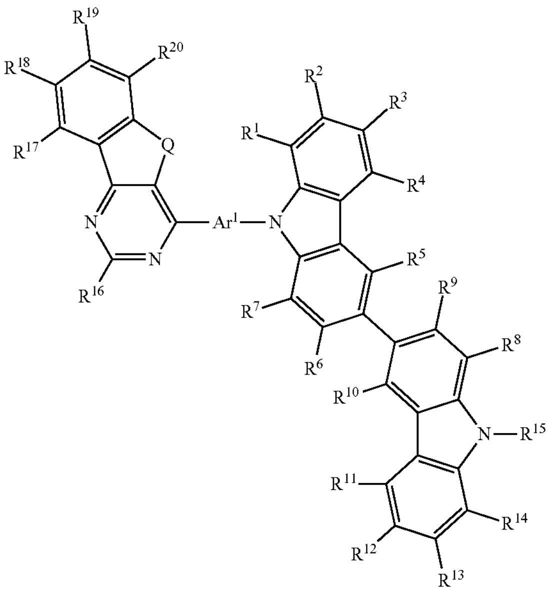

In General Formula (G2), Q represents oxygen or sulfur.

Further, each of $R^1$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Furthermore, $Ar^1$ represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 13 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

In the case where the bicarbazole skeleton is directly bonded to the benzofuropyrimidine skeleton or the benzothienopyrimidine skeleton in the compound represented by General Formula (G1) or (G2), the compound has a wider bandgap and can be synthesized with higher purity, which is preferable. Because the compound has an excellent carrier-transport property, a light-emitting element including the compound can be driven at a low voltage, which is preferable.

In the case where each of $R^1$ to $R^{14}$ and $R^{16}$ to $R^{20}$ represents hydrogen in General Formula (G1) or (G2), the compound is advantageous in terms of easiness of synthesis and material cost and has a relatively low molecular weight to be suitable for vacuum evaporation, which is particularly preferable. The compound is a compound represented by General Formula (G3) or (G4).

[Chemical Formula 8]

(G3)

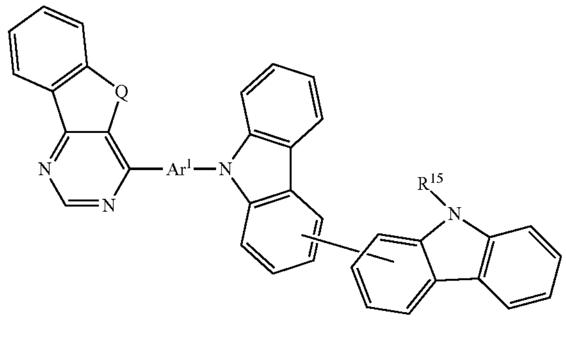

In General Formula (G3), Q represents oxygen or sulfur.

Further, $R^{15}$ represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Furthermore, $Ar^1$ represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 25 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

[Chemical Formula 9]

(G4)

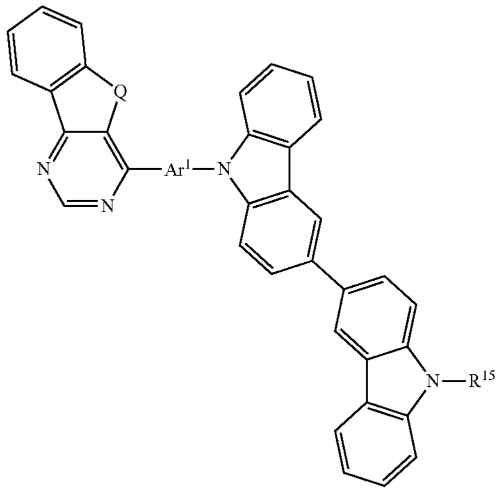

In General Formula (G4), Q represents oxygen or sulfur.

Further, $R^{15}$ represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Furthermore, $Ar^1$ represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 25 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

As the benzofuropyrimidine skeleton or the benzothienopyrimidine skeleton represented by A in General Formula (G0), any of structures represented by Structural Formulae (Ht-1) to (Ht-24) can be used, for example. Note that a structure that can be used as A is not limited to these.

[Chemical Formulae 10]

(Ht-1)

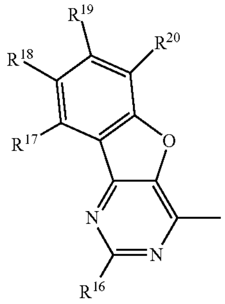

(Ht-2)

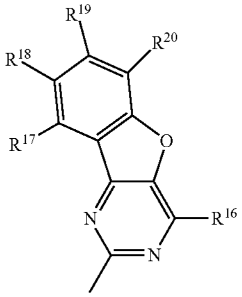

(Ht-3)

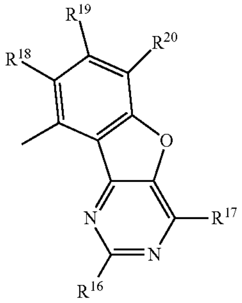

-continued (Ht-4)

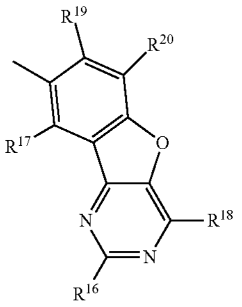

(Ht-5)

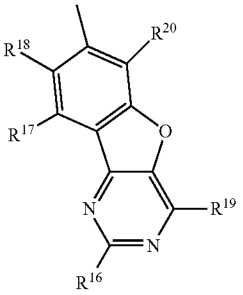

(Ht-6)

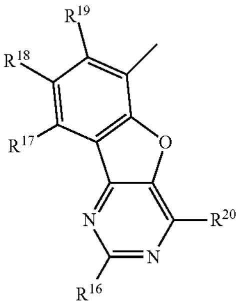

(Ht-7)

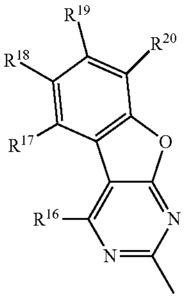

(Ht-8)

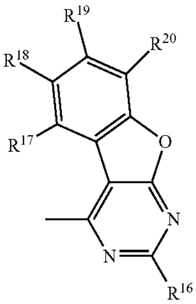

-continued
(Ht-9)
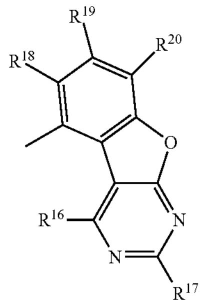
(Ht-10)
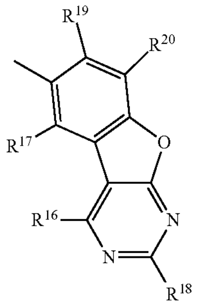
(Ht-11)
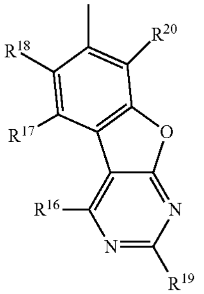
(Ht-12)
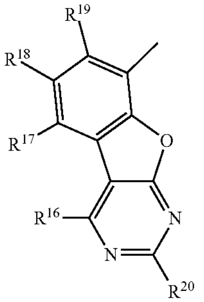
[Chemical Formulae 11]
(Ht-13)
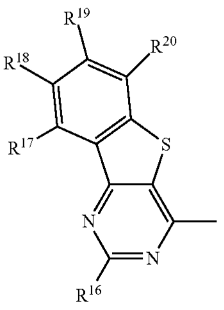
-continued
(Ht-14)
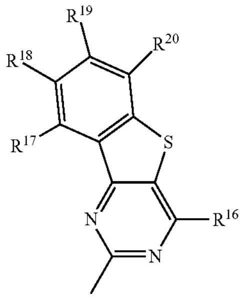
(Ht-15)
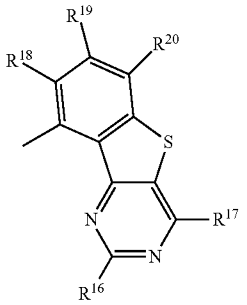
(Ht-16)
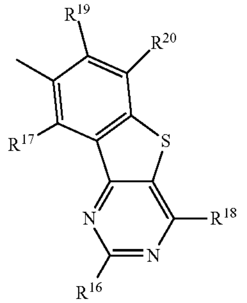
(Ht-17)
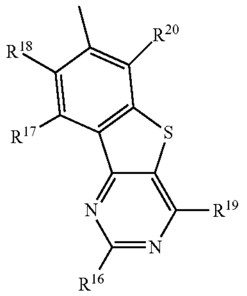
(Ht-18)
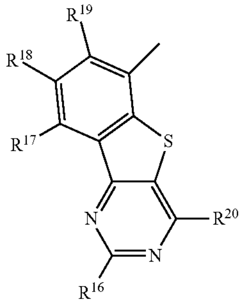

-continued (Ht-19)

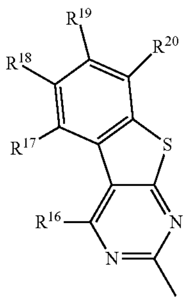

(Ht-20)

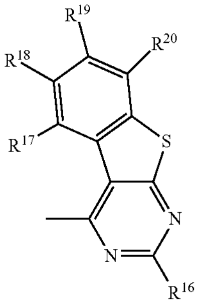

(Ht-21)

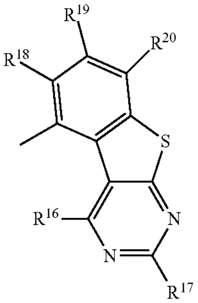

(Ht-22)

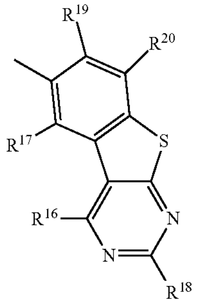

(Ht-23)

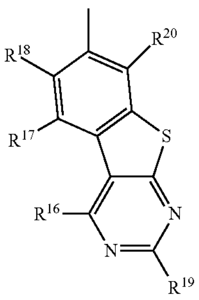

-continued (Ht-24)

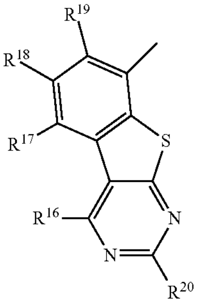

In Structural Formulae (Ht-1) to (Ht-24), each of $R^{16}$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

As a structure that can be used as the bicarbazole skeleton in General Formulae (G0) and (G1), any of structures represented by Structural Formulae (Cz-1) to (Cz-9) can be used, for example. Note that the structure that can be used as the bicarbazole skeleton is not limited to these.

[Chemical Formulae 12]
(Cz-1)
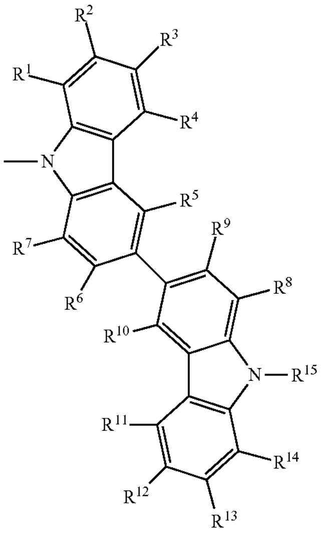
(Cz-2)
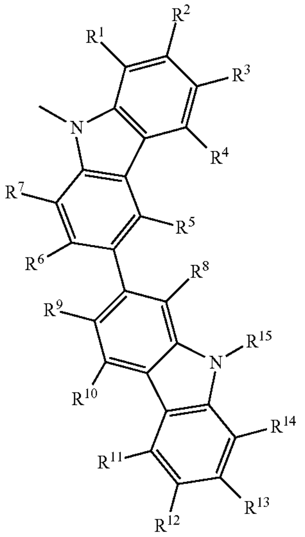
(Cz-3)
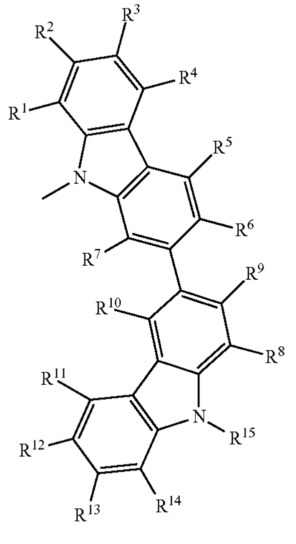
-continued
(Cz-4)
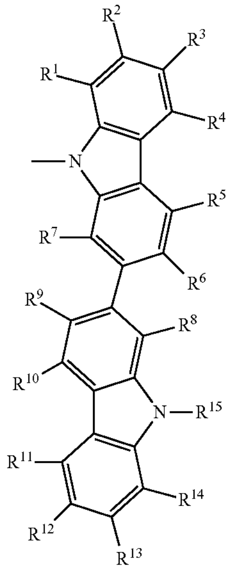
(Cz-5)
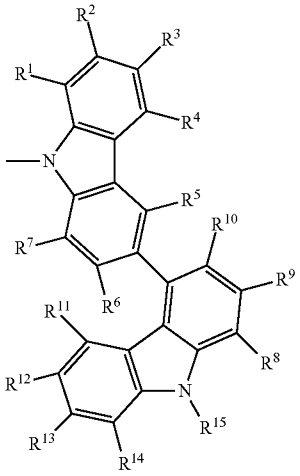
(Cz-6)
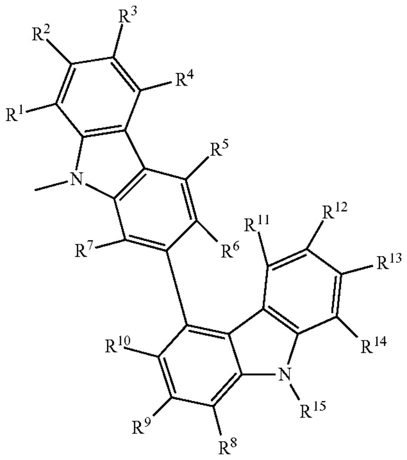

-continued

[Chemical Formulae 13]

(Cz-7)

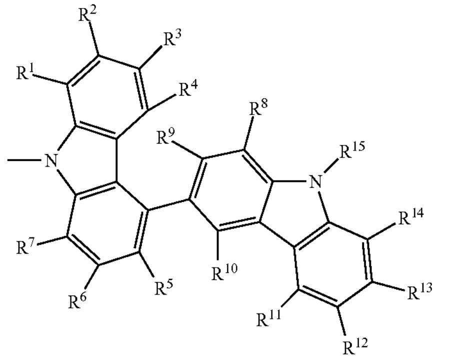

(Cz-8)

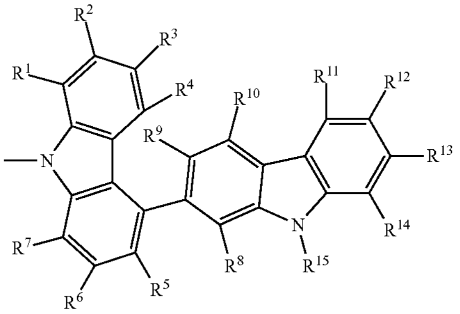

(Cz-9)

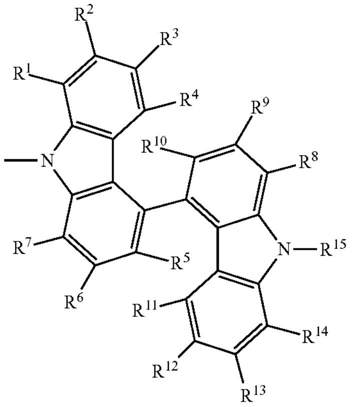

In Structural Formulae (Cz-1) to (Cz-9), each of $R^1$ to $R^{15}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

As the arylene group represented by $Ar^1$ in General Formulae (G0) to (G4), any of groups represented by Structure Formulae (Ar-1) to (Ar-27) can be used, for example. Note that the group that can be used for $Ar^1$ is not limited to these and may include a substituent.

[Chemical Formulae 14]

(Ar-1)

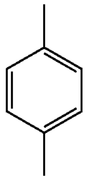

(Ar-2)

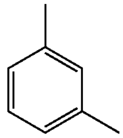

(Ar-3)

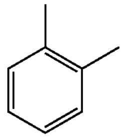

(Ar-4)

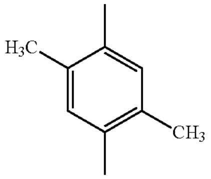

(Ar-5)

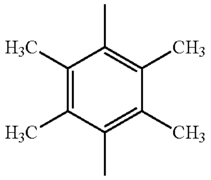

(Ar-6)

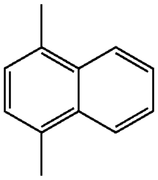

(Ar-7)

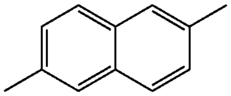

-continued
(Ar-8)
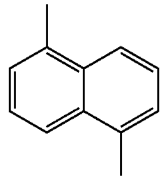
(Ar-9)
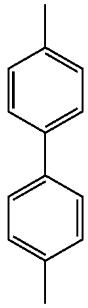
(Ar-10)
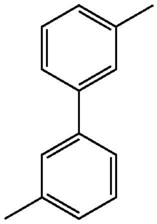
(Ar-11)
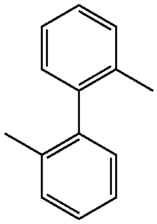
(Ar-12)
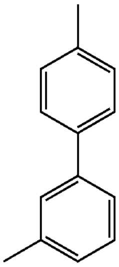
(Ar-13)
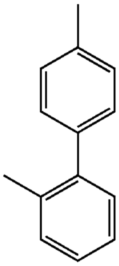
-continued
(Ar-14)
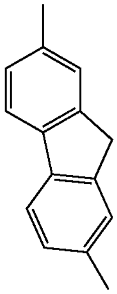
(Ar-15)
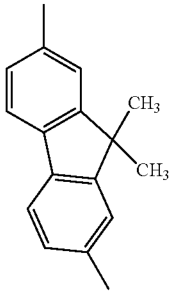
(Ar-16)
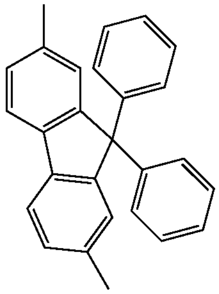
(Ar-17)
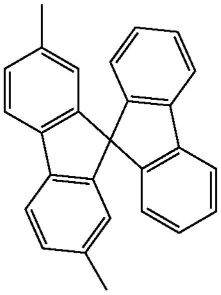
(Ar-18)
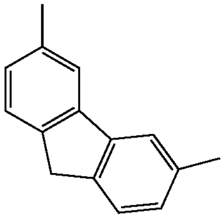

-continued

[Chemical Formulae 15]

(Ar-19)

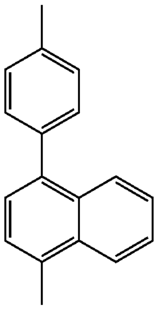

(Ar-20)

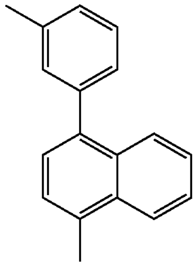

(Ar-21)

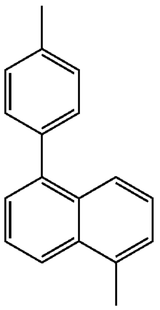

(Ar-22)

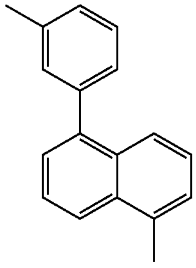

(Ar-23)

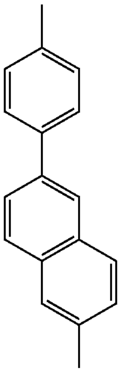

-continued (Ar-24)

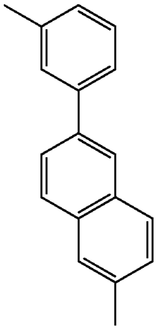

(Ar-25)

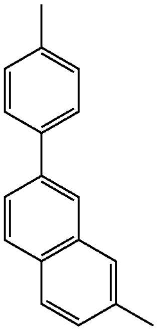

(Ar-26)

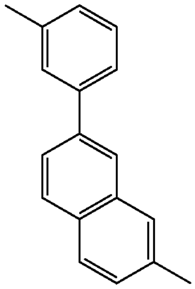

(Ar-27)

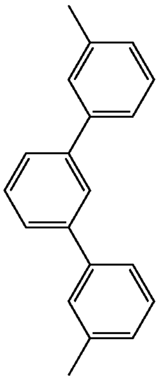

For example, any of groups represented by Structural Formulae (R-1) to (R-29) can be used for the alkyl group, the cycloalkyl group, or the aryl group represented by $R^1$ to $R^{20}$ in General Formulae (G1) and (G2), $R^1$ to $R^{15}$ in General Formula (G0), and $R^{15}$ represented by General Formulae (G3) and (G4). Note that the group that can be used as the alkyl group, the cycloalkyl group, or the aryl group is not limited to these and may include a substituent.

[Chemical Formulae 16]
(R-1)
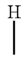
(R-2)
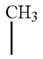
(R-3)
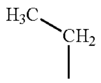
(R-4)
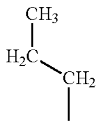
(R-5)
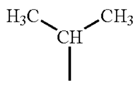
(R-6)
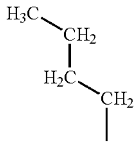
(R-7)
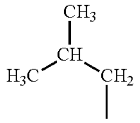
(R-8)
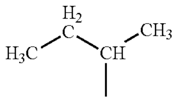
(R-9)
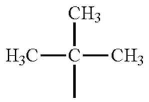
(R-10)
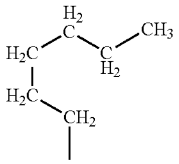
(R-11)
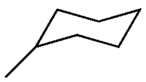
(R-12)
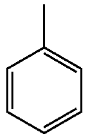
(R-13)
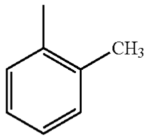
-continued
(R-14)
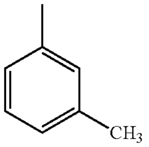
(R-15)
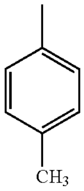
(R-16)
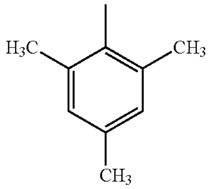
(R-17)
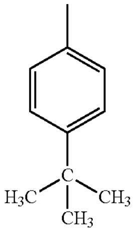
(R-18)
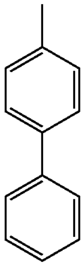
(R-19)
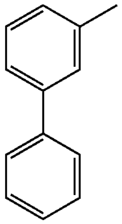
(R-20)
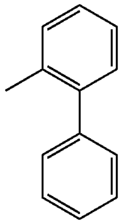

-continued
(R-21)
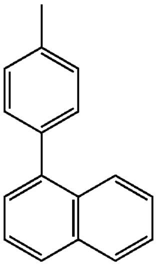
(R-22)
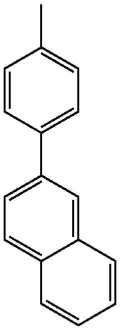
(R-23)
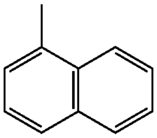
(R-24)
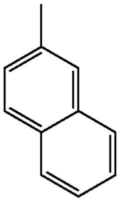
(R-25)
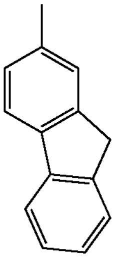
(R-26)
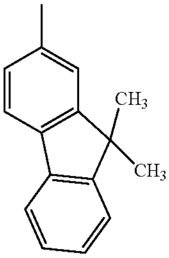
-continued
(R-27)
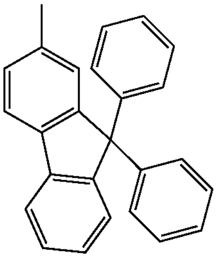
(R-28)
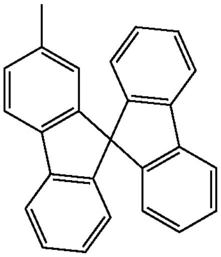
(R-29)
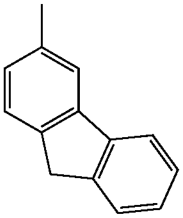
Specific Examples of Compounds
Specific examples of structures of the compounds represented by General Formulae (G0) to (G4) include compounds represented by Structural Formulae (100) to (147). Note that the compounds represented by General Formulae (G0) to (G4) are not limited to the following examples.
[Chemical Formulae 17]
(100)
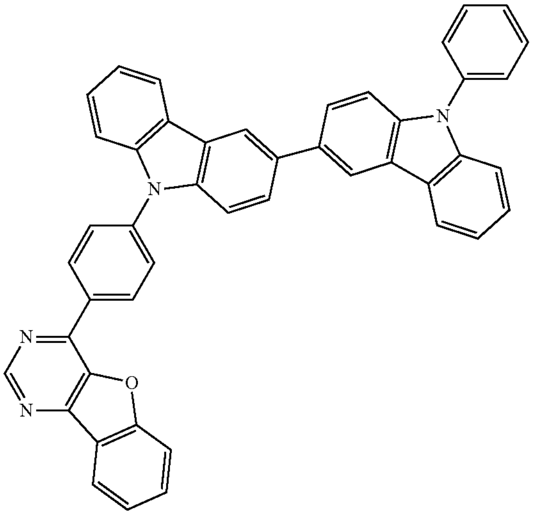

-continued
(101)
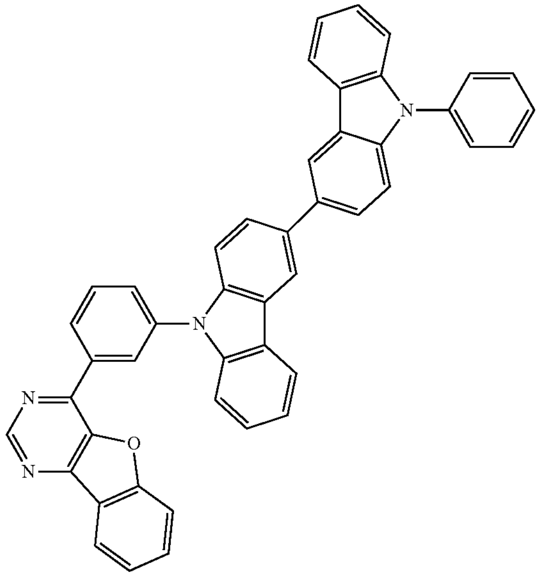
(102)
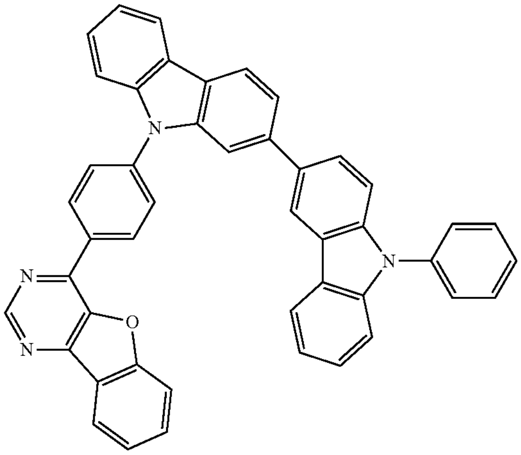
(103)
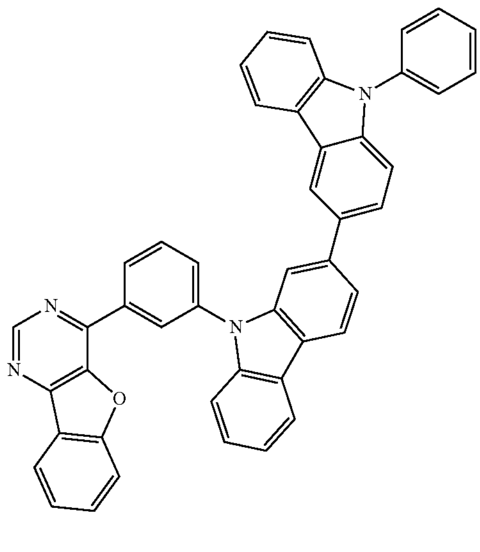
-continued
(104)
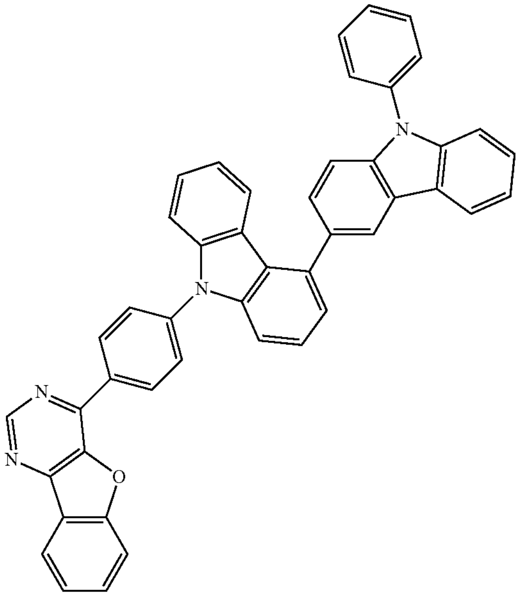
(105)
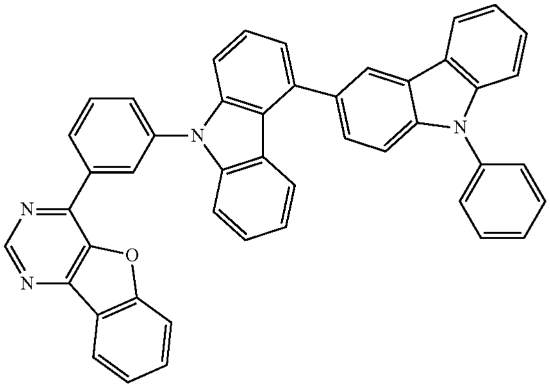
[Chemical Formulae 18]
(106)
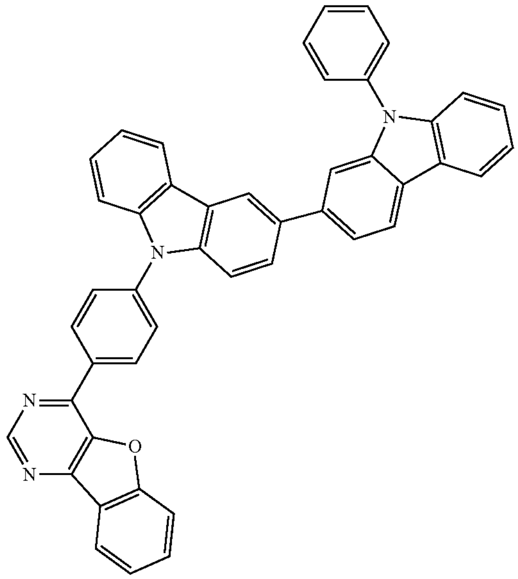

-continued
(107)
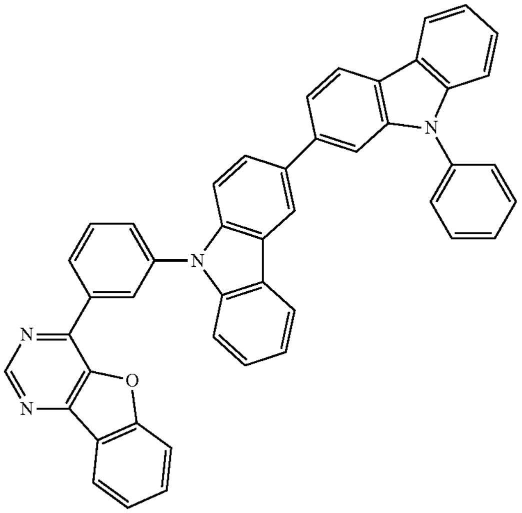
(108)
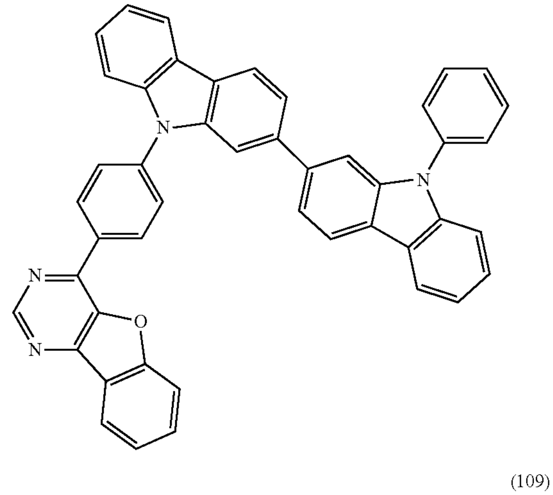
(109)
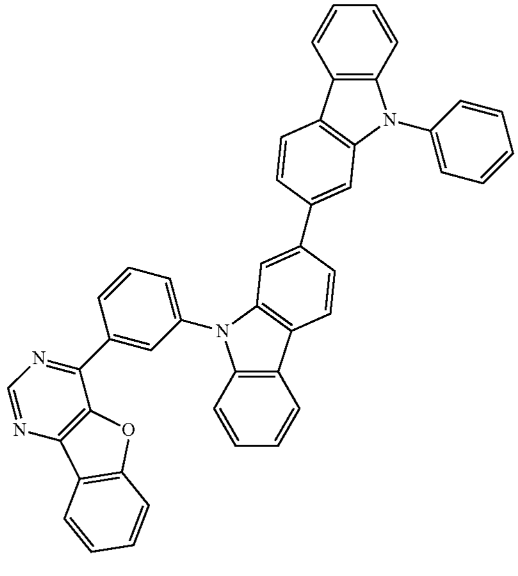
-continued
(110)
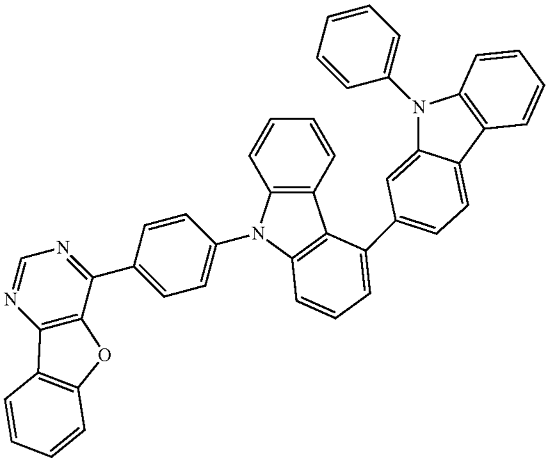
(111)
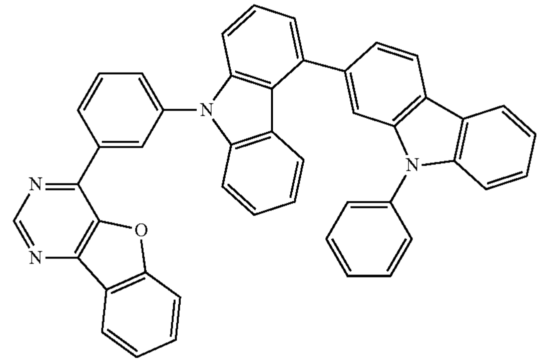
[Chemical Formulae 19]
(112)
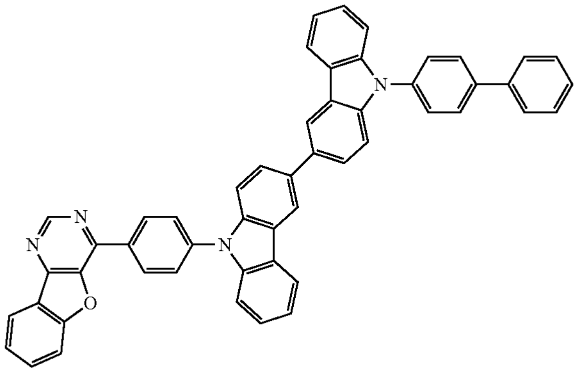

-continued
(113)
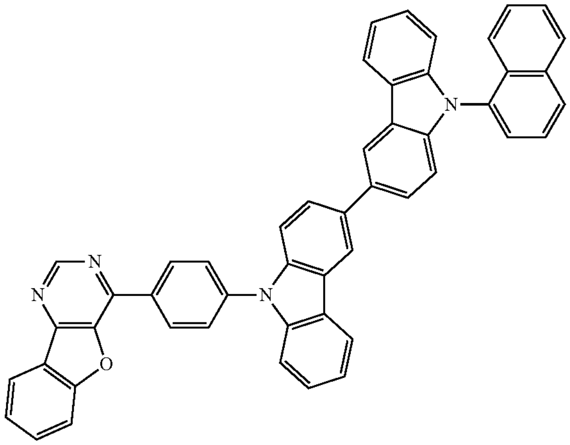
(114)
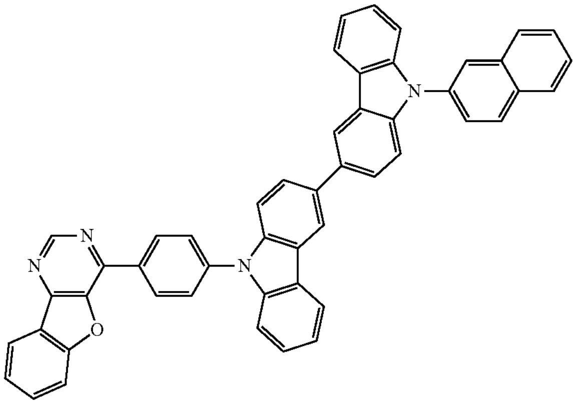
(115)
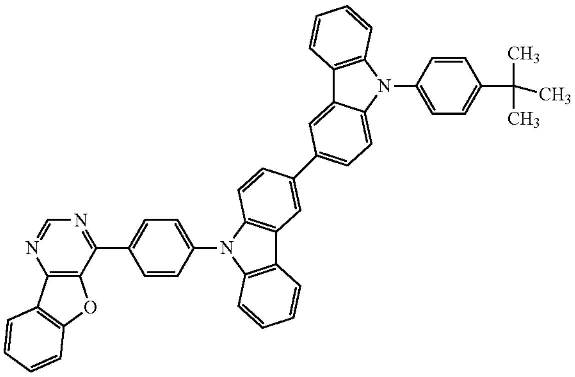
-continued
(116)
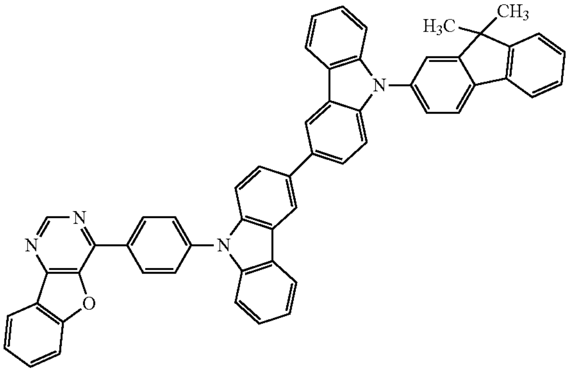
(117)
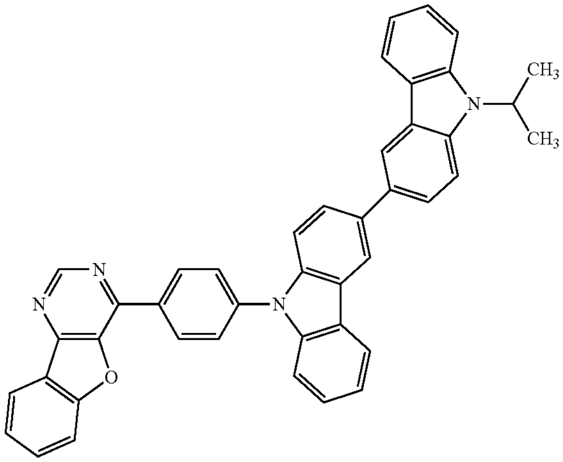
[Chemical Formulae 20]
(118)
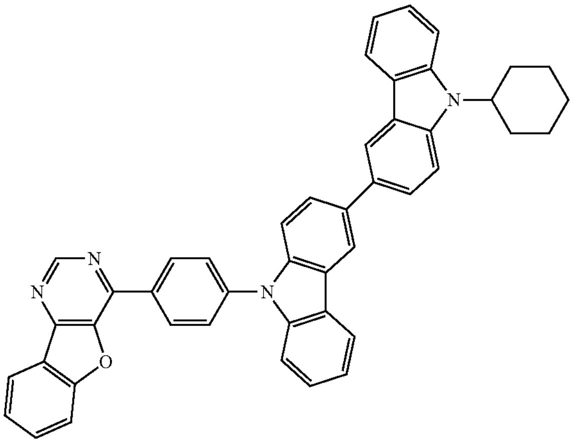

-continued
(119)
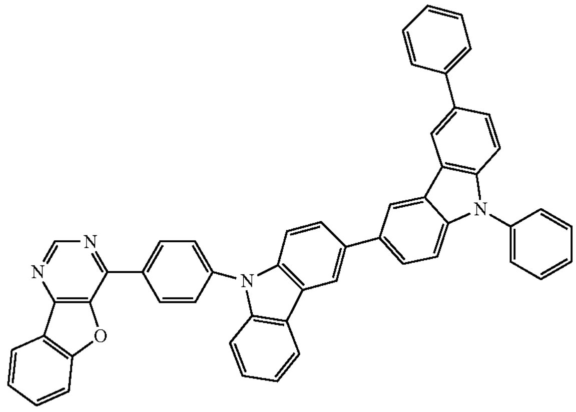
(120)
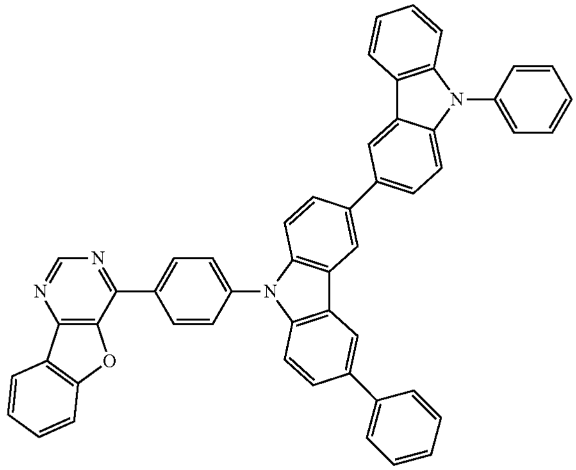
(121)
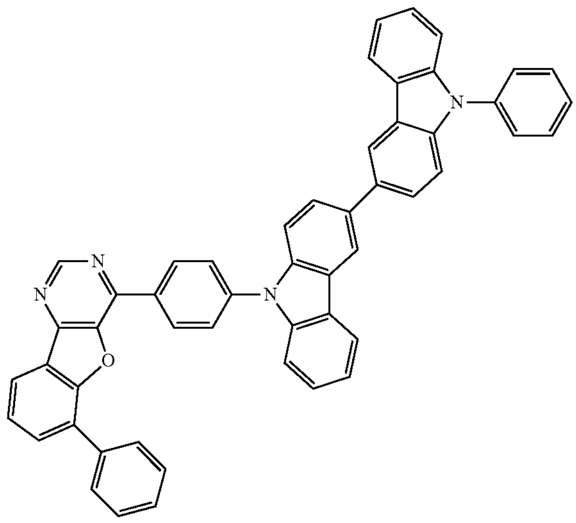
-continued
(122)
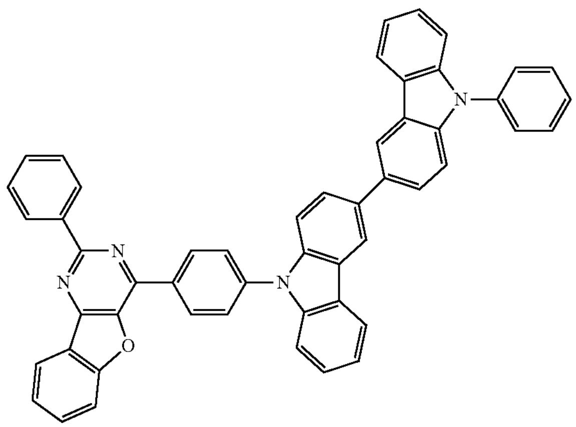
(123)
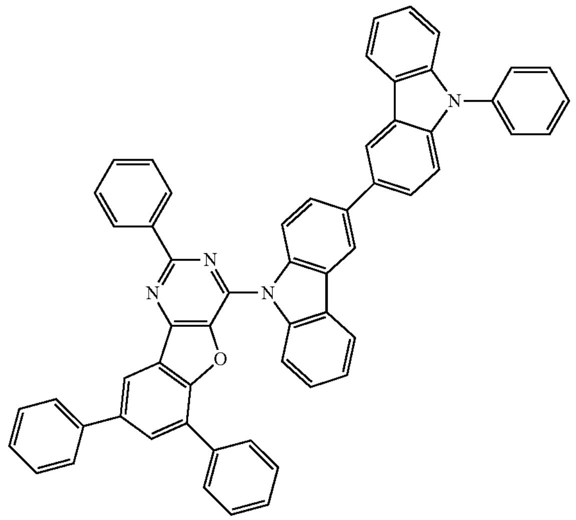
[Chemical Formulae 21]
(124)
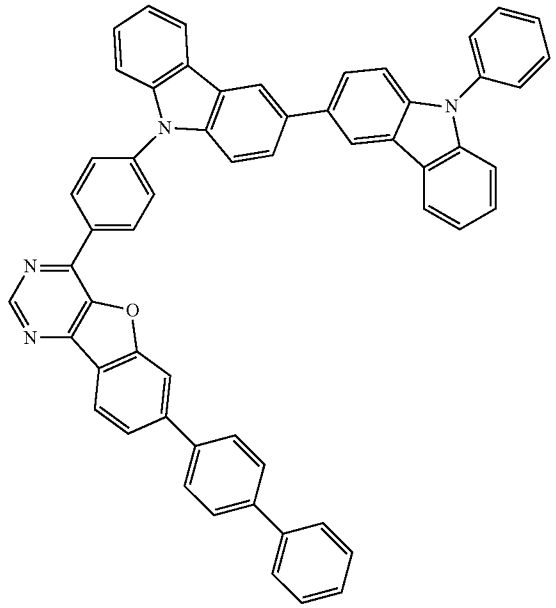

-continued
(125)
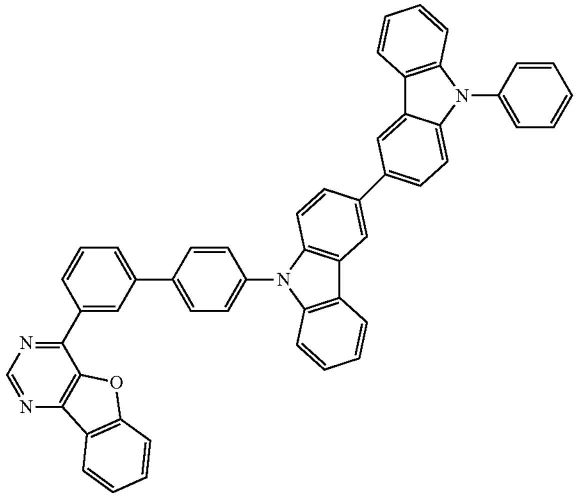
(126)
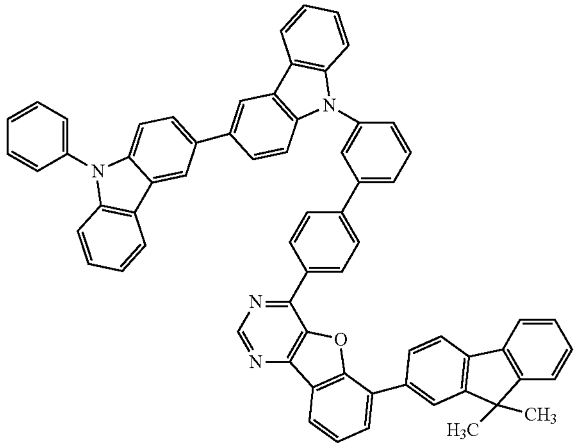
(127)
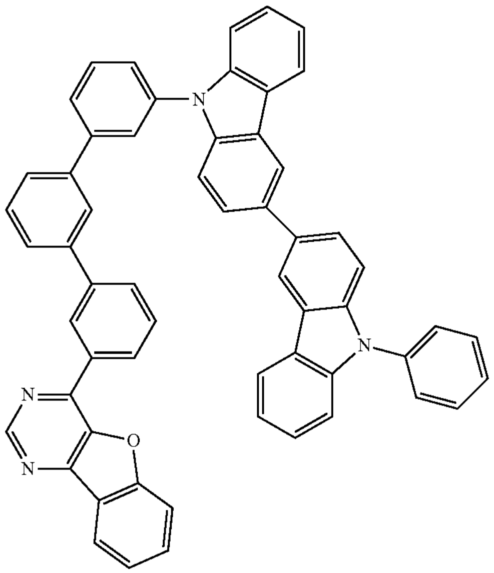
-continued
(128)
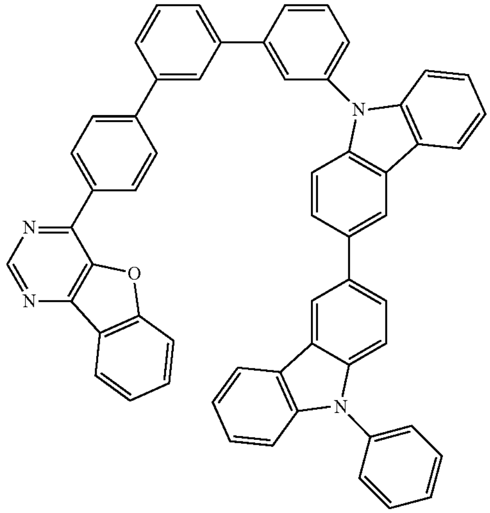
(129)
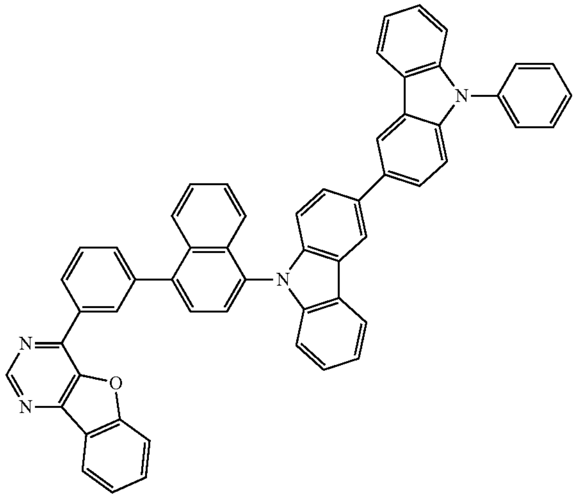

-continued
[Chemical Formulae 22]
(130)
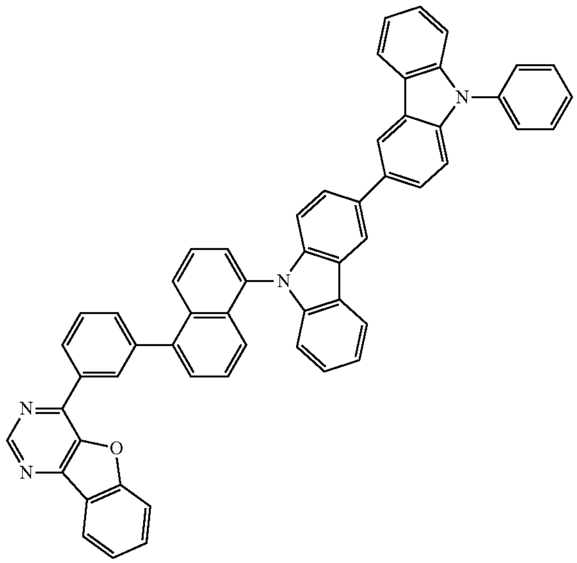
(131)
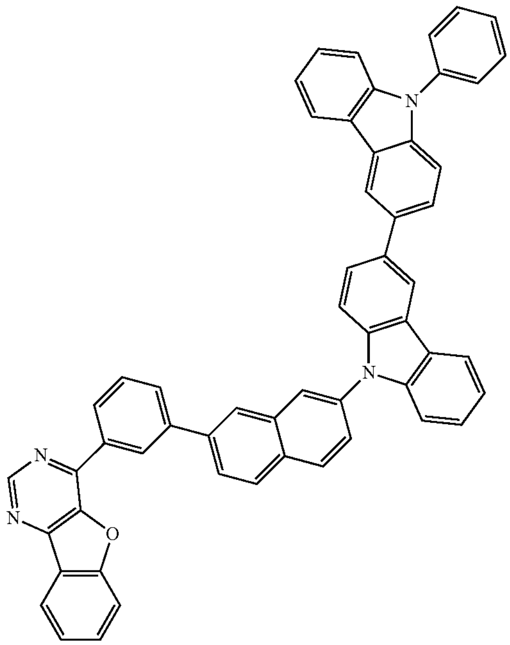
-continued
(132)
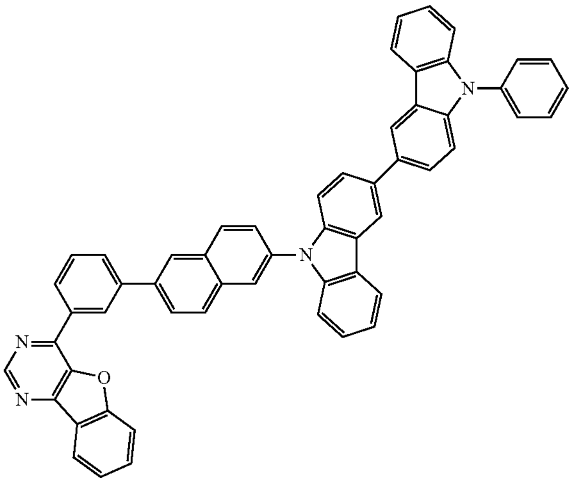
(133)
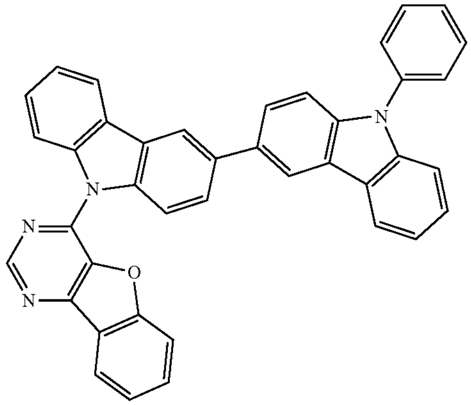
(134)
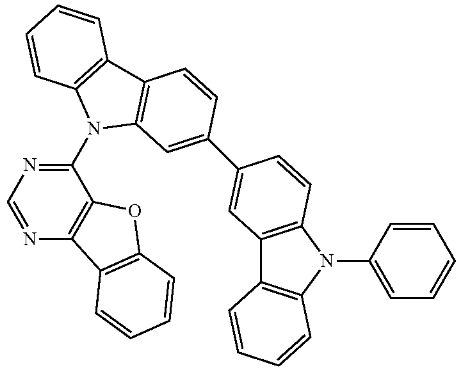
(135)
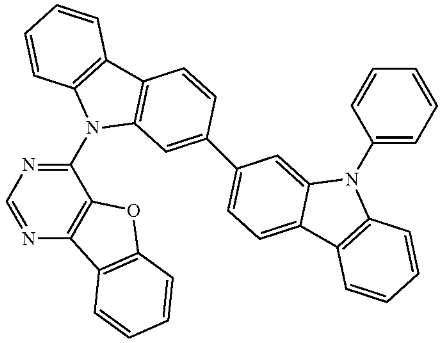

-continued
[Chemical Formulae 23]
(136)
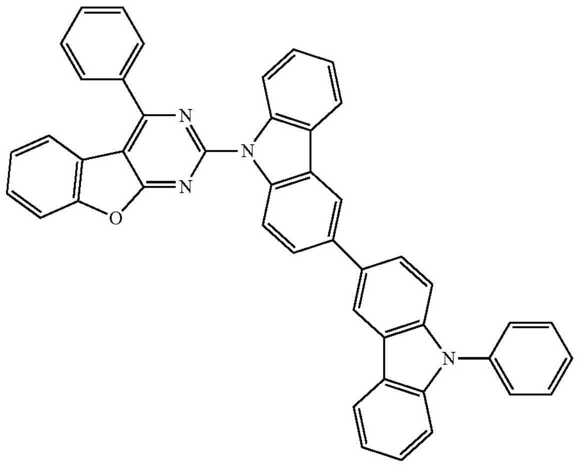
(137)
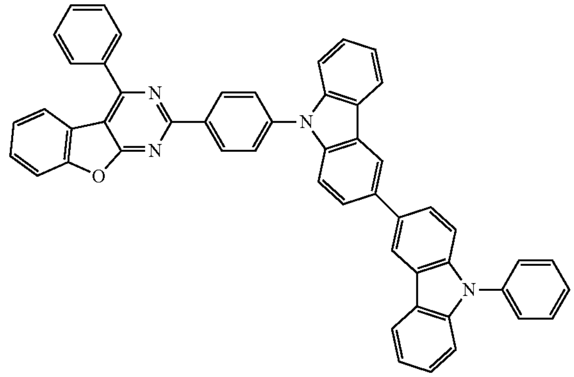
(138)
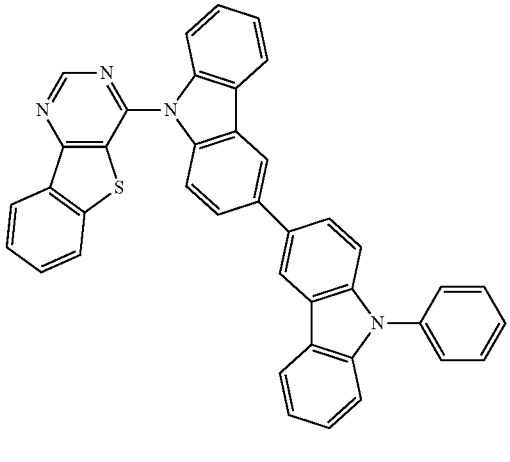
-continued
(139)
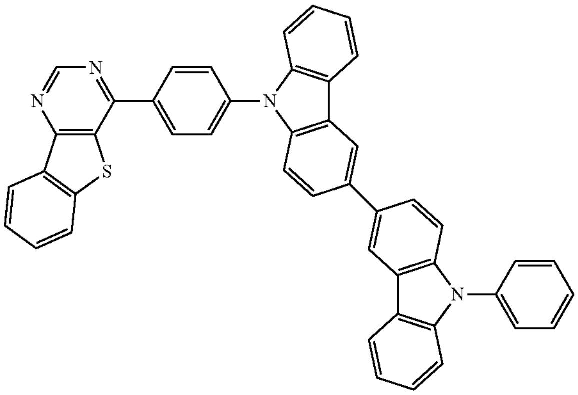
(140)
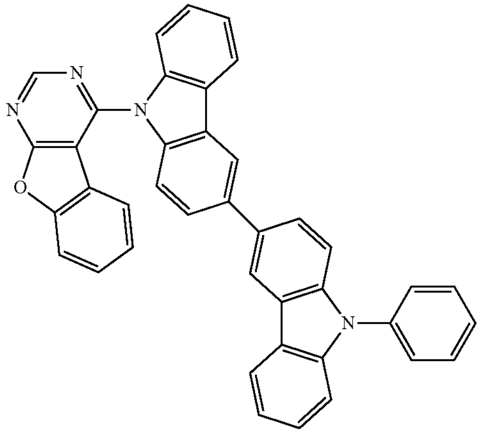
(141)
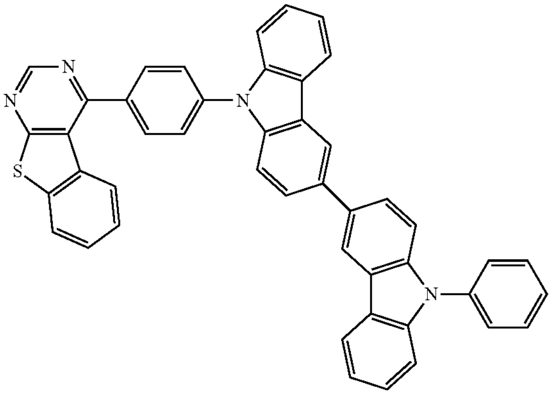

-continued

[Chemical Formulae 24]

(142)

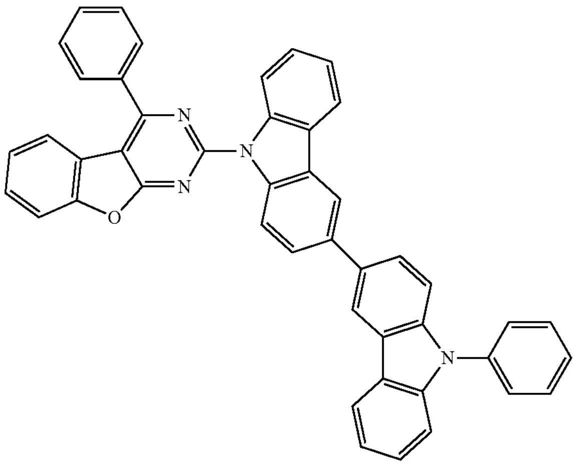

(143)

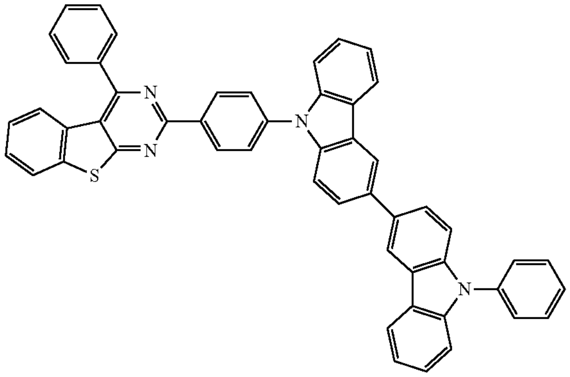

(144)

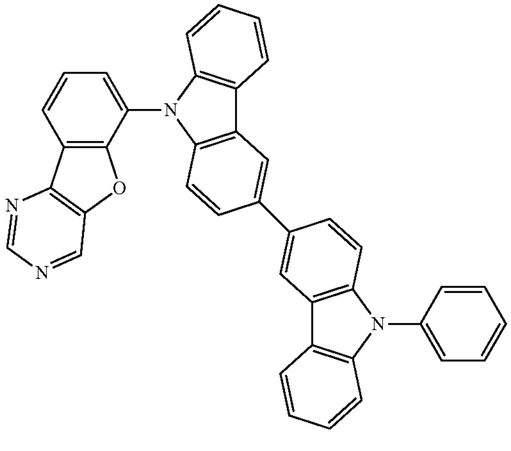

-continued (145)

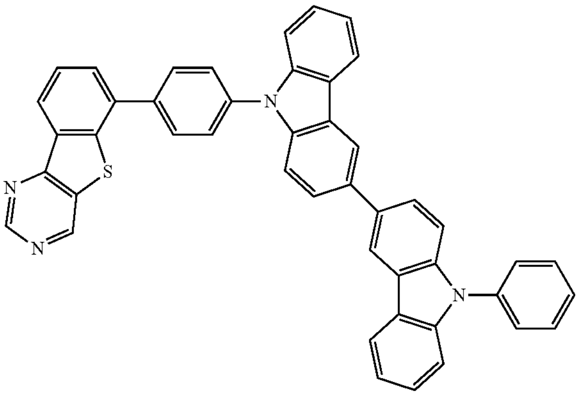

(146)

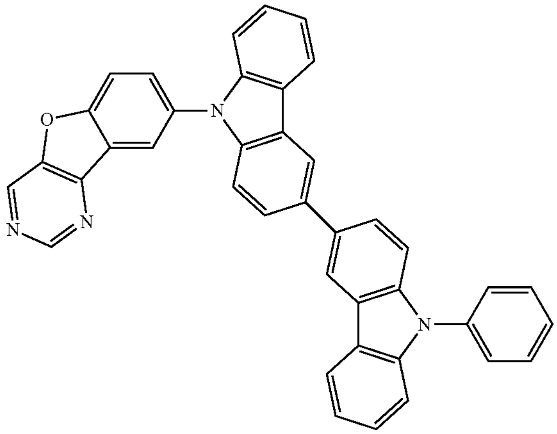

(147)

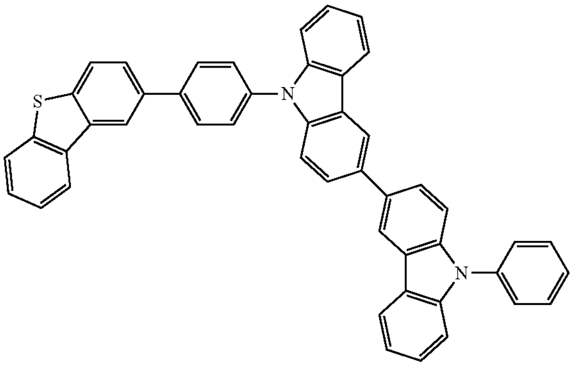

Compound Example 2

Note that although the host material 132 preferably has a small difference between the singlet excitation energy level and the triplet excitation energy level, the host material 132 need not necessarily have high reverse intersystem crossing efficiency, a high luminescence quantum yield, or a function of exhibiting thermally activated delayed fluorescence. In that case, the host material 132 preferably has a structure in which a skeleton having the π-electron deficient heteroaromatic ring and at least one of a skeleton having the π-electron rich heteroaromatic ring and an aromatic amine skeleton are bonded to each other through a structure including at least one of a m-phenylene group and an o-phenylene group. Alternatively, the skeletons are preferably bonded to each other through a biphenyldiyl group. Alternatively, the host material 132 preferably has a structure in which the skeletons are bonded to each other through an arylene group having at least one of a m-phenylene group and a o-phenylene group, and more preferably, the arylene group is a biphenyldiyl group. The host material 132 having the above-described structure can have a high T1 level. Note that also in this case, it is preferable that the skeleton having the π-electron deficient heteroaromatic ring have at least one of a diazine skeleton (a pyrimidine skeleton, a pyrazine skeleton, or a pyridazine skeleton) and a triazine skeleton. The skeleton having the π-electron rich heteroaromatic ring preferably includes at least one of an acridine skeleton, a phenoxazine skeleton, a phenothiazine skeleton, a furan skeleton, a thiophene skeleton, and a pyrrole skeleton. As the furan skeleton, a dibenzofuran skeleton is preferable. As the thiophene skeleton, a dibenzothiophene skeleton is preferable. As the pyrrole skeleton, an indole skeleton, a carbazole skeleton, or a 9-phenyl-3,3'-bi-9H-carbazole skeleton is particularly preferred. As the aromatic amine skeleton, a tertiary amine, which does not include an NH bond, is preferable, and a triarylamine skeleton is particularly preferable. As aryl groups of the triarylamine skeleton, substituted or unsubstituted aryl groups having 6 to 13 carbon atoms that form rings are preferable and examples thereof include phenyl groups, naphthyl groups, and fluorenyl groups.

As examples of the above-described aromatic amine skeleton and the skeleton having the π-electron rich heteroaromatic ring, skeletons represented by General Formulae (401) to (417) are given. Note that X in General Formulae (413) to (416) represents an oxygen atom or a sulfur atom.

[Chemical Formulae 25]

(401)

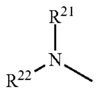

(402)

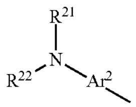

(403)

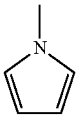

(404)

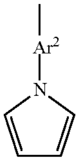

(405)

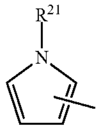

-continued (406)

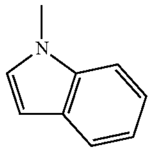

(407)

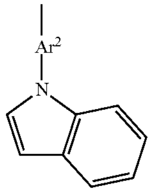

(408)

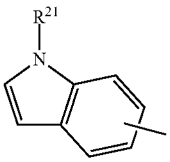

(409)

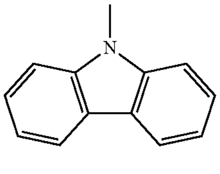

(410)

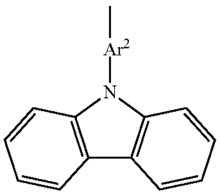

(411)

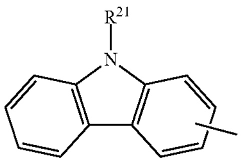

(412)

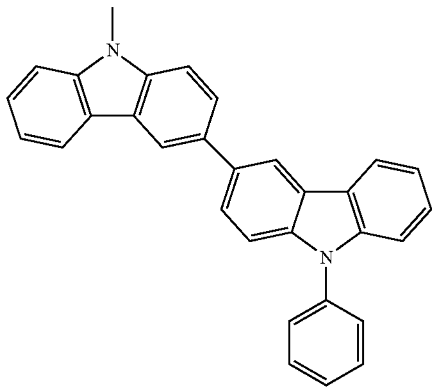

(413)

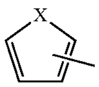

-continued
(414)
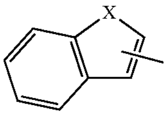
(415)
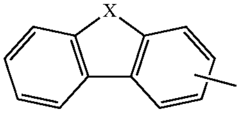
(416)
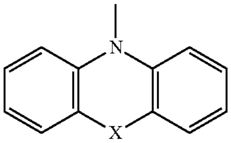
(417)
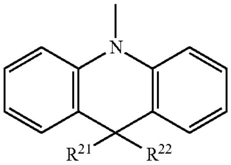
As examples of the above-described skeleton having the π-electron deficient heteroaromatic ring, skeletons represented by General Formulae (201) to (218) are given.
[Chemical Formulae 26]
(201)
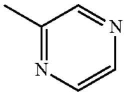
(202)
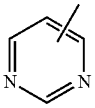
(203)
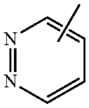
(204)
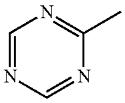
(205)
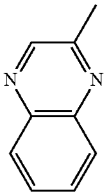
(206)
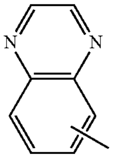
-continued
(207)
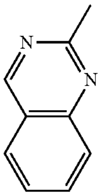
(208)
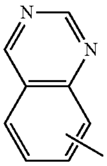
(209)
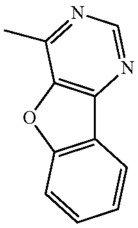
(210)
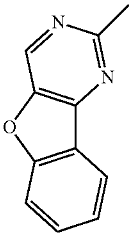
(211)
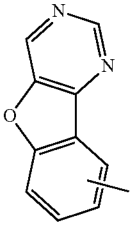
(212)
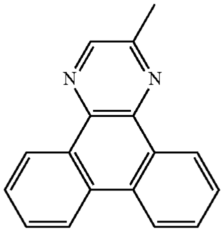
(213)
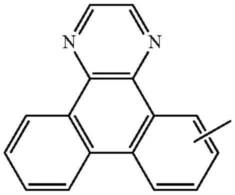

-continued (214)

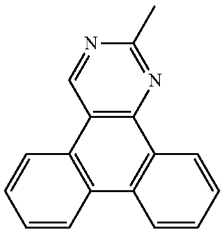

(215)

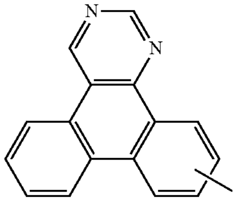

(216)

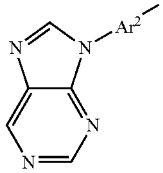

(217)

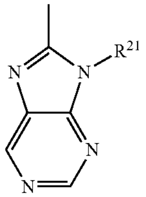

(218)

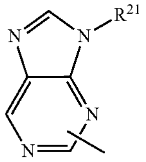

In the case where a skeleton having a hole-transport property (e.g., at least one of the skeleton having the π-electron rich heteroaromatic ring and the aromatic amine skeleton) and a skeleton having an electron-transport property (e.g., the skeleton having the π-electron deficient heteroaromatic ring) are bonded to each other through a bonding group including at least one of the m-phenylene group and the o-phenylene group, through a biphenyldiyl group as a bonding group, or through a bonding group including an arylene group including at least one of the m-phenylene group and the o-phenylene group, examples of the bonding group include skeletons represented by General Formulae (301) to (315). Examples of the above-described arylene group include a phenylene group, a biphenyldiyl group, a naphthalenediyl group, a fluorenediyl group, and a phenanthrenediyl group.

[Chemical Formulae 27]

(301)

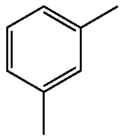

(302)

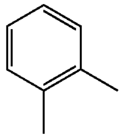

(303)

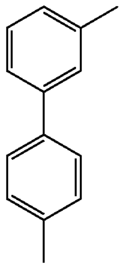

(304)

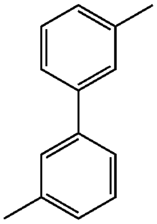

(305)

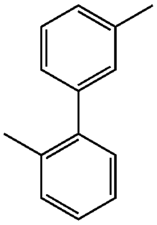

(306)

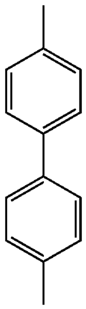

(307)

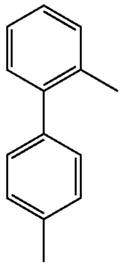

-continued (308)

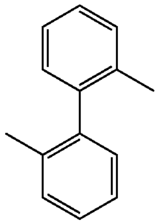

(309)

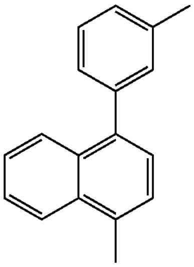

(310)

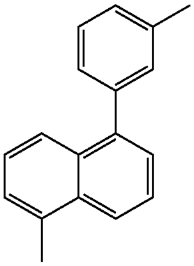

(311)

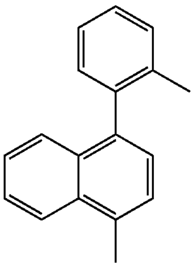

(312)

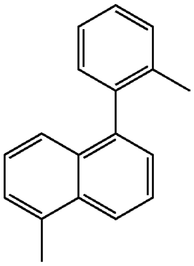

(313)

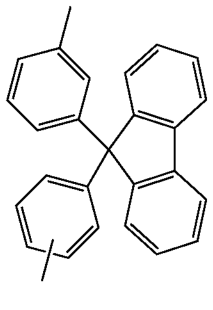

-continued (314)

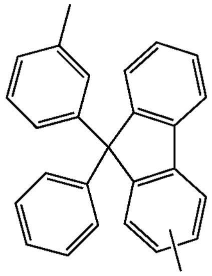

(315)

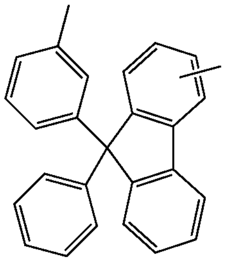

The above-described aromatic amine skeleton (e.g., the triarylamine skeleton), π-electron rich heteroaromatic ring skeleton (e.g., a ring including at least one of the acridine skeleton, the phenoxazine skeleton, the phenothiazine skeleton, the furan skeleton, the thiophene skeleton, and the pyrrole skeleton), and π-electron deficient heteroaromatic ring skeleton (e.g., a ring including at least one of the diazine skeleton and the triazine skeleton) or General Formulae (401) to (417), General Formulae (201) to (218), and General Formulae (301) to (315) may each have a substituent. As the substituent, an alkyl group having 1 to 6 carbon atoms, a cycloalkyl group having 3 to 6 carbon atoms, or a substituted or unsubstituted aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms are a phenyl group, a naphthyl group, a biphenyl group, and the like. The above substituents may be bonded to each other to form a ring. For example, in the case where a carbon atom at the 9-position in a fluorene skeleton has two phenyl groups as substituents, the phenyl groups are bonded to form a spirofluorene skeleton. Note that an unsubstituted group has an advantage in easy synthesis and an inexpensive raw material.

Furthermore, $Ar^2$ represents an arylene group having 6 to 13 carbon atoms. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 13 carbon atoms are a phenylene group, a naphthylene group, a biphenylene group, a fluorenediyl group, and the like. In the case where the arylene group has a substituent, as the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms are a phenyl group, a naphthyl group, a biphenyl group, and the like.

As the arylene group represented by $Ar^2$, for example, groups represented by Structural Formulae (Ar-1) to (Ar-18) can be used. Note that groups that can be used for $Ar^2$ are not limited to these.

Furthermore, $R^{21}$ and $R^{22}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above aryl group or phenyl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms include a phenyl group, a naphthyl group, a biphenyl group, and the like.

For example, groups represented by Structural Formulae (R-1) to (R-29) can be used as the alkyl group or aryl group represented by $R^{21}$ and $R^{22}$. Note that the group which can be used as an alkyl group or an aryl group is not limited thereto.

As a substituent that can be included in General formulae (401) to (417), General formulae (201) to (218), General Formulae (301) to (315), $Ar^2$, $R^{21}$, and $R^{22}$, the alkyl group or aryl group represented by Structural Formulae (R-1) to (R-24) can be used, for example. Note that the group which can be used as an alkyl group or an aryl group is not limited thereto.

Specific examples of structures of the above-described compounds include compounds represented by Structural Formulae (500) to (503) below.

[Chemical Formulae 28]

(500)

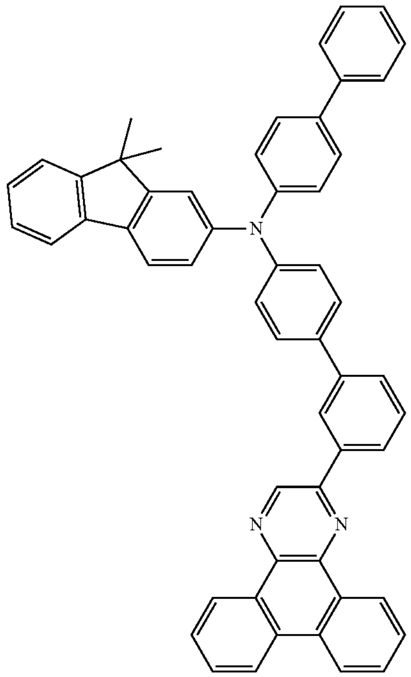

(501)

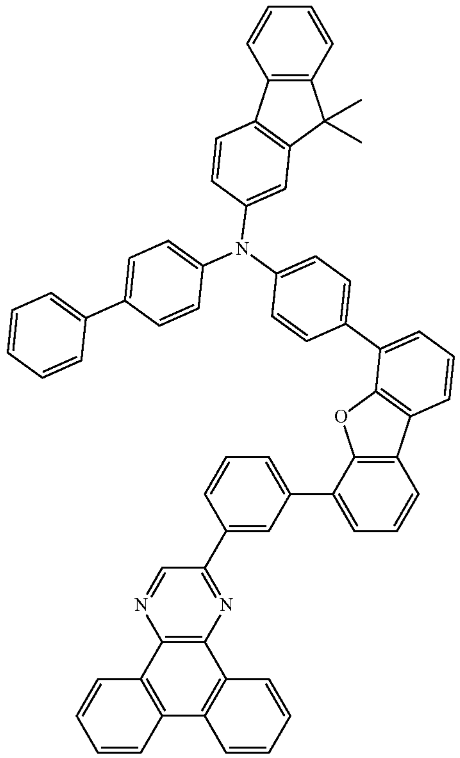

-continued (502)

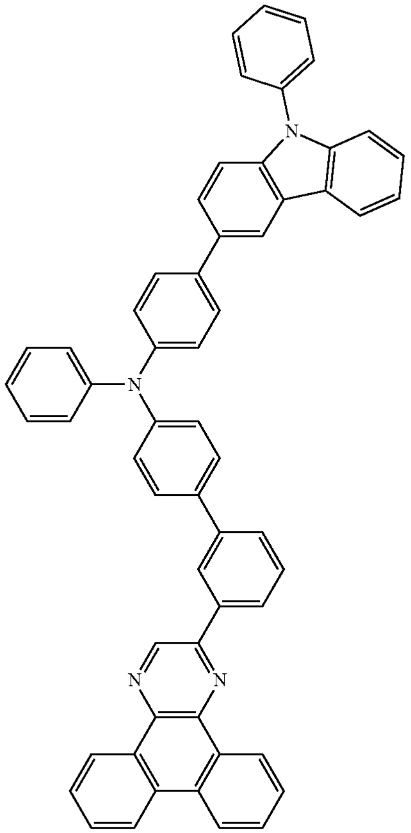

(503)

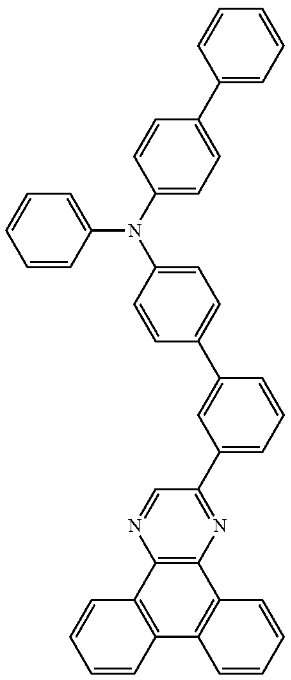

It is preferable that the host material 132 and the guest material 131 (the phosphorescent material) be selected such that the emission peak of the host material 132 overlaps with an absorption band, specifically an absorption band on the longest wavelength side, of a triplet metal to ligand charge transfer (MLCT) transition of the guest material 131 (the phosphorescent material). This makes it possible to provide a light-emitting element with drastically improved emission efficiency. Note that in the case where a thermally activated delayed fluorescent material is used instead of the phosphorescent material, it is preferable that the absorption band on the longest wavelength side be a singlet absorption band.

<<Guest Material 131>>

As the guest material 131 (the phosphorescent material), an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, or the like can be given. As the metal complex, a platinum complex having a porphyrin ligand or the like can be given.

It is preferable that the host material 132 and the guest material 131 (the phosphorescent material) be selected such that the LUMO level of the guest material 131 (the phosphorescent material) is lower than the LUMO level of the host material 132 and the energy difference between the LUMO level and the HOMO level of the guest material 131 (the phosphorescent material) is greater than the energy difference between the LUMO level and the HOMO level of the host material 132. With this structure, a light-emitting element with high emission efficiency and low driving voltage can be obtained.

Examples of the substance that has an emission peak in the blue or green wavelength range include organometallic iridium complexes having a 4H-triazole skeleton, such as tris{2-[5-(2-methylphenyl)-4-(2,6-dimethylphenyl)-4H-1,2,4-triazol-3-yl-K/2]phenyl-κC'}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), tris[4-(3-biphenyl)-5-isopropyl-3-phenyl-4H-1,2,4-triazolato]iridium (III) (abbreviation: Ir(iPrptz-3b)$_3$), and tris[3-(5-biphenyl)-5-isopropyl-4-phenyl-4H-1,2,4-triazolato]iridium(III) (abbreviation: Ir(iPr5btz)$_3$); organometallic iridium complexes having a 4H-triazole skeleton with an electron-withdrawing such as group, (OC-6-22)-tris{5-cyano-2-[4-(2,6-diisopropylphenyl)-5-(2-methylphenyl)-4H-1,2,4-triazol-3-yl-κN$^2$]phenyl-κC}iridium(III) (abbreviation: fac-Ir(mpCNptz-diPrp)$_3$), (OC-6-21)-tris{5-cyano-2-[4-(2,6-diisopropylphenyl)-5-(2-methylphenyl)-4H-1,2,4-triazol-3-yl-κN$^2$]phenyl-KC}iridium(III) (abbreviation: mer-Ir (mpCNptz-diPrp)$_3$), and tris{2-[4-(4-cyano-2,6-diisobutylphenyl)-5-(2-methylphenyl)-4H-1,2,4-triazol-3-yl-κN$^2$]phenyl-κC}iridium(III) (abbreviation: Ir(mpptz-diBuCNp)$_3$); organometallic iridium complexes having a 1H-triazole skeleton, such as tris[3-methyl-1-(2-methylphenyl)-5-phenyl-1H-1,2,4-triazolato]iridium(III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having an imidazole skeleton, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl) borate (abbreviation: FIr6), bis[2-(4',6'-difluorophenyl) pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III)picolinate (abbreviation: Ir($CF_3$ppy)$_2$ (pic)), and bis[2-(4',6'-difluorophenyl)pyridinato-N,$C^{2'}$] iridium(III) acetylacetonate (abbreviation: FIr(acac)). Among the substances given above, the organometallic iridium complexes including a nitrogen-containing five-membered heterocyclic skeleton, such as a 4H-triazole skeleton, a 1H-triazole skeleton, or an imidazole skeleton have high triplet excitation energy, reliability, and emission efficiency and are thus especially preferable.

Examples of the substance that has an emission peak in the green or yellow wavelength range include organometallic iridium complexes having a pyrimidine skeleton, such as tris(4-methyl-6-phenylpyrimidinato)iridium(III) (abbreviation: $Ir(mppm)_3$), tris(4-t-butyl-6-phenylpyrimidinato) iridium(III) (abbreviation: $Ir(tBuppm)_3$), (acetylacetonato) bis(6-methyl-4-phenylpyrimidinato)iridium(III) (abbreviation: $Ir(mppm)_2(acac)$), (acetylacetonato)bis(6-tert-butyl-4-phenylpyrimidinato)iridium(III) (abbreviation: $Ir(tBuppm)_2(acac)$), (abbreviation: (acetylacetonato)bis[4-(2-norbornyl)-6-phenylpyrimidinato]iridium(III) $Ir(nbppm)_2(acac)$), (acetylacetonato)bis[5-methyl-6-(2-methylphenyl)-4-phenylpyrimidinato]iridium(III) (abbreviation: $Ir(mpmppm)_2(acac)$), (acetylacetonato)bis{4,6-dimethyl-2-[6-(2,6-dimethylphenyl)-4-pyrimidinyl-κN3]phenyl-κC}iridium(III) (abbreviation: $Ir(dmppm-dmp)_2(acac)$), (acetylacetonato)bis(4,6-diphenylpyrimidinato)iridium(III) (abbreviation: $Ir(dppm)_2(acac)$); organometallic iridium complexes having a pyrazine skeleton, such as (acetylacetonato)bis(3,5-dimethyl-2-phenylpyrazinato)iridium(III) (abbreviation: $Ir(mppr-Me)_2(acac)$) and (acetylacetonato)bis (5-isopropyl-3-methyl-2-phenylpyrazinato)iridium(III) (abbreviation: $Ir(mppr-iPr)_2(acac)$); organometallic iridium complexes having a pyridine skeleton, such as tris(2-phenylpyridinato-N,$C^{2'}$)iridium(III) (abbreviation: $Ir(ppy)_3$), bis(2-phenylpyridinato-N,$C^{2'}$)iridium(III) acetylacetonate (abbreviation: $Ir(ppy)_2(acac)$), bis(benzo[h]quinolinato) iridium(III) acetylacetonate (abbreviation: $Ir(bzq)_2(acac)$), tris(benzo[h]quinolinato)iridium(III) (abbreviation: $Ir(bzq)_3$), tris(2-phenylquinolinato-N,$C^{2'}$)iridium(III) (abbreviation: $Ir(pq)_3$), and bis(2-phenylquinolinato-N,$C^{2'}$)iridium (III) acetylacetonate (abbreviation: $Ir(pq)_2(acac)$); organometallic iridium complexes such as (abbreviation: bis(2,4-diphenyl-1,3-oxazolato-N,$C^{2'}$)iridium(III)acetylacetonate $Ir(dpo)_2(acac)$), bis{2-[4'-(perfluorophenyl)phenyl] pyridinato-N,$C^{2'}$}iridium(III)acetylacetonate (abbreviation: $Ir(p-PF-ph)_2(acac)$), and bis(2-phenylbenzothiazolato-N, $C^{2'}$)iridium(III)acetylacetonate (abbreviation: $Ir(bt)_2(acac)$); and a rare earth metal complex such as tris(acetylacetonato) (monophenanthroline)terbium(III) (abbreviation: $Tb(acac)_3(Phen)$). Among the materials given above, the organometallic iridium complex having a pyrimidine skeleton has distinctively high reliability and emission efficiency and is thus especially preferable.

Examples of the substance that has an emission peak in the yellow or red wavelength range include organometallic iridium complexes having a pyrimidine skeleton, such as (diisobutyrylmethanato)bis[4,6-bis(3-methylphenyl)pyrimidinato]iridium(III) (abbreviation: $Ir(5mdppm)_2(dibm)$), bis [4,6-bis(3-methylphenyl)pyrimidinato] (dipivaloylmethanato)iridium(III) (abbreviation: $Ir(5mdppm)_2(dpm)$), and bis [4,6-di(naphthalen-1-yl)pyrimidinato] (dipivaloylmethanato)iridium(III) (abbreviation: $Ir(d1npm)_2(dpm)$); organometallic iridium complexes having a pyrazine skeleton, such as (acetylacetonato)bis(2,3,5-triphenylpyrazinato)iridium(III) (abbreviation: $Ir(tppr)_2(acac)$), bis(2,3,5-triphenylpyrazinato) (dipivaloylmethanato) iridium(III) (abbreviation: $Ir(tppr)_2(dpm)$), and (acetylacetonato)bis[2,3-bis(4-fluorophenyl)quinoxalinato]iridium(III) (abbreviation: $Ir(Fdpq)_2(acac)$); organometallic iridium complexes having a pyridine skeleton, such as tris(1-phenylisoquinolinato-N,$C^{2'}$)iridium(III) (abbreviation: $Ir(piq)_3$) and bis(1-phenylisoquinolinato-N,$C^{2'}$)iridium(III)acetylacetonate (abbreviation: $Ir(piq)_2(acac)$); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato) (monophenanthroline)europium(III) (abbreviation: $Eu(DBM)_3(Phen)$) and tris[1-(2-thenoyl)-3,3,3-trifluoroacetonato] (monophenanthroline)europium(III) (abbreviation: $Eu(TTA)_3(Phen)$). Among the materials given above, the organometallic iridium complex having a pyrimidine skeleton has distinctively high reliability and emission efficiency and is thus especially preferable. Further, the organometallic iridium complexes having pyrazine skeletons can provide red light emission with favorable chromaticity.

The above-described organometallic iridium complexes having a pyrimidine skeleton or a pyrazine skeleton have ligands with a high electron-accepting property and easily have a low LUMO level and thus are suitable for one embodiment of the present invention. Similarly, compounds (e.g., iridium complexes) with an electron-withdrawing group, such as a halogen group (e.g., a fluoro group) or a cyano group, easily have a low LUMO level and thus are suitable.

As the light-emitting material included in the light-emitting layer 130 and the light-emitting layer 135, any material can be used as long as the material can convert the triplet excitation energy into light emission. As an example of the material that can convert the triplet excitation energy into light emission, a thermally activated delayed fluorescent material can be given in addition to the phosphorescent material. Therefore, the term "phosphorescent material" in the description can be replaced with the term "thermally activated delayed fluorescent material".

<<Host Material 133>>

It is preferable that the host material 133, the host material 132, and the guest material 131 be selected such that the HOMO level of the host material 133 is lower than the HOMO level of the host material 132 and the LUMO level of the host material 133 is higher than the LUMO level of the guest material 131. With this structure, a light-emitting element with high emission efficiency and low driving voltage can be obtained. Note that the material described as an example of the host material 132 may be used as the host material 133.

A material having a property of transporting more electrons than holes can be used as the host material 133, and a material having an electron mobility of $1\times10^{-6}$ $cm^2/Vs$ or higher is preferable. A compound including a π-electron deficient heteroaromatic ring skeleton such as a nitrogen-containing heteroaromatic compound, or a zinc- or aluminum-based metal complex can be used, for example, as the material which easily accepts electrons (the material having an electron-transport property). Specific examples include a metal complex having a quinoline ligand, a benzoquinoline ligand, an oxazole ligand, or a thiazole ligand, an oxadiazole derivative, a triazole derivative, a benzimidazole derivative, a quinoxaline derivative, a dibenzoquinoxaline derivative, a phenanthroline derivative, a pyridine derivative, a bipyridine derivative, a pyrimidine derivative, and a triazine derivative.

Specific examples include metal complexes having a quinoline or benzoquinoline skeleton, such as tris(8-quinolinolato)aluminum(III) (abbreviation: Alq), tris(4-methyl-8-quinolinolato)aluminum(III) (abbreviation: $Almq_3$), bis(10- hydroxybenzo[h]quinolinato)beryllium(II) (abbreviation: $BeBq_2$), bis(2-methyl-8-quinolinolato) (4-phenylphenolato) aluminum(III) (abbreviation: BAlq) and bis(8-quinolinolato)zinc(II) (abbreviation: Znq), and the like. Alternatively, a metal complex having an oxazole-based or thiazole-based ligand, such as bis[2-(2-benzoxazolyl)phenolate]zinc(II) (abbreviation: ZnPBO) or bis[2-(2-benzothiazolyl)phenolato]zinc(II) (abbreviation: ZnBTZ) can be used. Other than such metal complexes, any of the following can be used: heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-ter-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: BPhen), and bathocuproine (abbreviation: BCP); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3-(3,9'-bi-9H-carbazol-9-yl)phenyl]dibenzo[f,h]quinoxaline (abbreviation: 2mCzCzPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-triazin e (abbreviation: PCCzPTzn); heterocyclic compounds having a pyridine skeleton such as 3,5-bis[3-(9H-carbazol-9-yl)phenyl]pyridine (abbreviation: 35DCzPPy); and heteroaromatic compounds such as 4,4'-bis(5-methylbenzoxazol-2-yl)stilbene (abbreviation: BzOs). Among the heterocyclic compounds, the heterocyclic compounds having at least one of a triazine skeleton, a diazine skeleton (pyrimidine, pyrazine, pyridazine), and a pyridine skeleton are highly reliable and stable and is thus preferably used. In addition, the heterocyclic compounds having the skeletons have a high electron-transport property to contribute to a reduction in driving voltage. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1\times10^{-6}$ $cm^2/Vs$ or higher. Note that other substances may also be used as long as their electron-transport properties are higher than their hole-transport properties.

As the host material 133, materials having a hole-transport property given below can be used.

A material having a property of transporting more holes than electrons can be used as the hole-transport material, and a material having a hole mobility of $1\times10^{-6}$ $cm^2/Vs$ or higher is preferable. Specifically, an aromatic amine, a carbazole derivative, an aromatic hydrocarbon, a stilbene derivative, or the like can be used. Furthermore, the hole-transport material may be a high molecular compound.

Examples of the material having a high hole-transport property are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivative are 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCZTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole derivative are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbons include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon having a hole mobility of $1\times10^{-6}$ $cm^2/Vs$ or more and having 14 to 42 carbon atoms is particularly preferable.

The aromatic hydrocarbon may have a vinyl skeleton. As aromatic hydrocarbon having a vinyl group, the following is given, for example: 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N-bis(4-butylphenyl)-N,N'-bis(phenyl)benzidine (abbreviation: Poly-TPD) can also be used.

Examples of the material having a high hole-transport property include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-

[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N'-diphenylamino) triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino] spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl) triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl] fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl) phenyl]-N,N'-diphenyl-9,9-dimethylfluorene-2,7-diamine (abbreviation: YGA2F). Other examples are amine compounds, carbazole compounds, thiophene compounds, furan compounds, fluorene compounds; triphenylene compounds; phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), 2,8-di (9H-carbazol-9-yl)-dibenzothiophene (abbreviation: Cz2DBT), 4-{3-[3-(9-phenyl-9H-fluoren-9-yl)phenyl] phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylene-2-yl)phenyl]dibenzothiophene (abbreviation: mDBTPTp-II). Among the above compounds, compounds including at least one of a pyrrole skeleton, a furan skeleton, a thiophene skeleton, and an aromatic amine skeleton are preferred because of their high stability and reliability. In addition, the compounds having such skeletons have a high hole-transport property to contribute to a reduction in driving voltage.

The light-emitting layer 130 and the light-emitting layer 135 can have a structure in which two or more layers are stacked. For example, in the case where the light-emitting layer 130 or the light-emitting layer 135 is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. A light-emitting material included in the first light-emitting layer may be the same as or different from a light-emitting material included in the second light-emitting layer. In addition, the materials may have functions of emitting light of the same color or light of different colors. Two kinds of light-emitting materials having functions of emitting light of different colors are used for the two light-emitting layers, so that light of a plurality of emission colors can be obtained at the same time. It is particularly preferable to select light-emitting materials of the light-emitting layers so that white light can be obtained by combining light emission from the two light-emitting layers.

The light-emitting layer 130 may include another material in addition to the host material 132 and the guest material 131. The light-emitting layer 135 may include another material in addition to the host material 133, the host material 132, and the guest material 131.

Note that the light-emitting layers 130 and 135 can be formed by an evaporation method (including a vacuum evaporation method), an ink-jet method, a coating method, gravure printing, or the like. Besides the above-mentioned materials, an inorganic compound such as a quantum dot or a high molecular compound (e.g., an oligomer, a dendrimer, and a polymer) may be used.

<<Quantum Dot>>

A quantum dot is a semiconductor nanocrystal with a size of several nanometers to several tens of nanometers and contains approximately $1\times10^3$ to $1\times10^6$ atoms. Since energy shift of quantum dots depend on their size, quantum dots made of the same substance emit light with different wavelengths depending on their size; thus, emission wavelengths can be easily adjusted by changing the size of quantum dots.

Since a quantum dot has an emission spectrum with a narrow peak, emission with high color purity can be obtained. In addition, a quantum dot is said to have a theoretical internal quantum efficiency of 100%, which far exceeds that of a fluorescent organic compound, i.e., 25%, and is comparable to that of a phosphorescent organic compound. Therefore, a quantum dot can be used as a light-emitting material to obtain a light-emitting element having high light-emitting efficiency. Furthermore, since a quantum dot which is an inorganic material has high inherent stability, a light-emitting element which is favorable also in terms of lifetime can be obtained.

Examples of a material of a quantum dot include a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide; cadmium sulfide; cadmium telluride; zinc selenide; zinc oxide; zinc sulfide; zinc telluride; mercury sulfide; mercury selenide; mercury telluride; indium arsenide; indium phosphide; gallium arsenide; gallium phosphide; indium nitride; gallium nitride; indium antimonide; gallium antimonide; aluminum phosphide; aluminum arsenide; aluminum antimonide; lead selenide; lead telluride; lead sulfide; indium selenide; indium telluride; indium sulfide; gallium selenide; arsenic sulfide; arsenic selenide; arsenic telluride; antimony sulfide; antimony selenide; antimony telluride; bismuth sulfide; bismuth selenide; bismuth telluride; silicon; silicon carbide; germanium; tin; selenium; tellurium; boron; carbon; phosphorus; boron nitride; boron phosphide; boron arsenide; aluminum nitride; aluminum sulfide; barium sulfide; barium selenide; barium telluride; calcium sulfide; calcium selenide; calcium telluride; beryllium sulfide; beryllium selenide; beryllium telluride; magnesium sulfide; magnesium selenide; germanium sulfide; germanium selenide; germanium telluride; tin sulfide; tin selenide; tin telluride; lead oxide; copper fluoride; copper chloride; copper bromide; copper iodide; copper oxide; copper selenide; nickel oxide; cobalt oxide; cobalt sulfide; iron oxide; iron sulfide; manganese oxide; molybdenum sulfide; vanadium oxide; tungsten oxide; tantalum oxide; titanium oxide; zirconium oxide; silicon nitride; germanium nitride; aluminum oxide; barium titanate; a compound of selenium, zinc, and cadmium; a compound of indium, arsenic, and phosphorus; a compound of cadmium, selenium, and sulfur; a compound of cadmium, selenium, and tellurium; a compound of indium, gallium, and arsenic; a compound of indium, gallium, and selenium; a compound of indium, selenium, and sulfur; a compound of copper, indium, and sulfur; and combinations thereof. What is called an alloyed quantum dot, whose composition is represented by a given ratio, may be used. For example, an alloyed quantum dot of cadmium, selenium, and sulfur is a means effective in obtaining blue light because the emission wavelength can be changed by changing the content ratio of elements.

As the quantum dot, any of a core-type quantum dot, a core-shell quantum dot, a core-multishell quantum dot, and the like can be used. Note that when a core is covered with a shell formed of another inorganic material having a wider band gap, the influence of defects and dangling bonds existing at the surface of a nanocrystal can be reduced. Since such a structure can significantly improve the quantum efficiency of light emission, it is preferable to use a core-shell or core-multishell quantum dot. Examples of the material of a shell include zinc sulfide and zinc oxide.

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxylethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolones; animoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds as such sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

Since band gaps of quantum dots are increased as their size is decreased, the size is adjusted as appropriate so that light with a desired wavelength can be obtained. Light emission from the quantum dots is shifted to a blue color side, i.e., a high energy side, as the crystal size is decreased; thus, emission wavelengths of the quantum dots can be adjusted over a wavelength region of a spectrum of an ultraviolet region, a visible light region, and an infrared region by changing the size of quantum dots. The range of size (diameter) of quantum dots which is usually used is 0.5 nm to 20 nm, preferably 1 nm to nm. The emission spectra are narrowed as the size distribution of the quantum dots gets smaller, and thus light can be obtained with high color purity. The shape of the quantum dots is not particularly limited and may be spherical shape, a rod shape, a circular shape, or the like. Quantum rods which are rod-like shape quantum dots have a function of emitting directional light; thus, quantum rods can be used as a light-emitting material to obtain a light-emitting element with higher external quantum efficiency.

In most organic EL elements, to improve emission efficiency, concentration quenching of the light-emitting materials is suppressed by dispersing light-emitting materials in host materials. The host materials need to be materials having singlet excitation energy levels or triplet excitation energy levels higher than or equal to those of the light-emitting materials. In the case of using blue phosphorescent materials as light-emitting materials, it is particularly difficult to develop host materials which have triplet excitation energy levels higher than or equal to those of the blue phosphorescent materials and which are excellent in terms of a lifetime. Even when a light-emitting layer is composed of quantum dots and made without a host material, the quantum dots enable emission efficiency to be ensured; thus, a light-emitting element which is favorable in terms of a lifetime can be obtained. In the case where the light-emitting layer is composed of quantum dots, the quantum dots preferably have core-shell structures (including core-multishell structures).

In the case of using quantum dots as the light-emitting material in the light-emitting layer, the thickness of the light-emitting layer is set to 3 nm to 100 nm, preferably 10 nm to 100 nm, and the light-emitting layer is made to contain 1 volume % to 100 volume % of the quantum dots. Note that it is preferable that the light-emitting layer be composed of the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, blade coating method, a roll coating method, an ink-jet method, a printing method, a spray coating method, a curtain coating method, or a Langmuir-Blodgett method) may be employed. For a light-emitting layer containing a phosphorescent material, a vacuum evaporation method, as well as the wet process, can be suitably employed.

An example of the liquid medium used for the wet process is an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like.

<<Hole-Injection Layer>>

The hole-injection layer 111 has a function of reducing a barrier for hole injection from one of the pair of electrodes (the electrode 101 or the electrode 102) to promote hole injection and is formed using a transition metal oxide, a phthalocyanine derivative, or an aromatic amine, for example. As the transition metal oxide, molybdenum oxide, vanadium oxide, ruthenium oxide, tungsten oxide, manganese oxide, or the like can be given. As the phthalocyanine derivative, phthalocyanine, metal phthalocyanine, or the like can be given. As the aromatic amine, a benzidine derivative, a phenylenediamine derivative, or the like can be given. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron accepting property and a layer containing a hole-transport material may also be used. In a steady state or in the presence of an electric field, electric charge can be transferred between these materials. As examples of the material having an electron accepting property, organic acceptors such as a quinodimethane derivative, a chloranil derivative, and a hexaazatriphenylene derivative can be given. A specific example is a compound having an electron-withdrawing group (a halogen group or a cyano group), such as 7,7,8,8-tetracyano-2,3,5,6-tetrafluoroquinodimethane (abbreviation: $F_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can also be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1\times10^{-6}$ $cm^2/Vs$ or higher is preferable. Specifically, any of the aromatic amine, carbazole derivative, aromatic hydrocarbon, stilbene derivative, and the like described as examples of the hole-transport material that can be used in the light-emitting layer can be used. Furthermore, the hole-transport material may be a high molecular compound.

<<Hole-Transport Layer>>

The hole-transport layer 112 is a layer containing a hole-transport material and can be formed using any of the hole-transport materials given as examples of the material of the hole-injection layer 111. In order that the hole-transport layer 112 has a function of transporting holes injected to the hole-injection layer 111 to the light-emitting layer, the highest occupied molecular orbital (HOMO) level of the hole-transport layer 112 is preferably equal or close to the HOMO level of the hole-injection layer 111.

As the hole-transport material, a substance having a hole mobility of $1\times10^{-6}$ $cm^2/Vs$ or higher is preferably used. Note that other than these substances, any substance that has a property of transporting more holes than electrons may be used. The layer containing a substance having a high hole-transport property is not limited to a single layer, and may include stacked two or more layers containing the aforementioned substances.

<<Electron-Transport Layer>>

The electron-transport layer 118 has a function of transporting, to the light-emitting layer, electrons injected from the other of the pair of electrodes (the electrode 101 or the electrode 102) through the electron-injection layer 119. A material having a property of transporting more electrons than holes can be used as an electron-transport material, and a material having an electron mobility of $1\times10^{-6}$ $cm^2/Vs$ or higher is preferable. As the compound which easily accepts electrons (the material having an electron-transport property), a π-electron deficient heteroaromatic compound such as a nitrogen-containing heteroaromatic compound, a metal complex, or the like can be used. Specifically, a metal complex having a quinoline ligand, a benzoquinoline ligand, an oxazole ligand, or a thiazole ligand, which are described as the electron-transport materials that can be used in the light-emitting layer, can be given. In addition, an oxadiazole derivative, a triazole derivative, a benzimidazole derivative, a quinoxaline derivative, a dibenzoquinoxaline derivative, a phenanthroline derivative, a pyridine derivative, a bipyridine derivative, a pyrimidine derivative, and a triazine derivative can be given. A substance having an electron mobility of higher than or equal to $1\times10^{-6}$ $cm^2/Vs$ is preferable. It is to be noted that any substance other than the above substances may also be used as long it is a substance in which the electron-transport property is higher than the hole-transport property. The electron-transport layer 118 is not limited to a single layer, and may include stacked two or more layers containing the aforementioned substances.

Between the electron-transport layer 118 and the light-emitting layer, a layer that controls transport of electron carriers may be provided. The layer is formed by addition of a small amount of a substance having a high electron-trapping property to a material having a high electron-transport property described above, and the layer is capable of adjusting carrier balance by suppressing transfer of electron carriers. Such a structure is very effective in preventing a problem (such as a reduction in element lifetime) caused when electrons pass through the light-emitting layer.

An n-type compound semiconductor may also be used, and an oxide such as titanium oxide, zinc oxide, silicon oxide, tin oxide, tungsten oxide, tantalum oxide, barium titanate, barium zirconate, zirconium oxide, hafnium oxide, aluminum oxide, yttrium oxide, or zirconium silicate; a nitride such as silicon nitride; cadmium sulfide; zinc selenide; or zinc sulfide can be used, for example.

<<Electron-Injection Layer>>

The electron-injection layer 119 has a function of reducing a barrier for electron injection from the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. As the material having an electron-donating property, a Group 1 metal, a Group 2 metal, an oxide of any of the metals, or the like can be given. Specifically, an alkali metal, an alkaline earth metal, or a compound thereof, such as lithium fluoride, sodium fluoride, cesium fluoride, calcium fluoride, or lithium oxide, can be used. Alternatively, a rare earth metal compound like erbium fluoride can be used. Electride may also be used for the electron-injection layer 119. Examples of the electride include a substance in which electrons are added at high concentration to calcium oxide-aluminum oxide. The electron-injection layer 119 can be formed using the substance that can be used for the electron-transport layer 118.

A composite material in which an organic compound and an electron donor (donor) are mixed may also be used for the electron-injection layer 119. Such a composite material is excellent in an electron-injection property and an electron-transport property because electrons are generated in the organic compound by the electron donor. In this case, the organic compound is preferably a material that is excellent in transporting the generated electrons. Specifically, the above-listed substances for forming the electron-transport layer 118 (e.g., the metal complexes and heteroaromatic compounds) can be used, for example. As the electron donor, a substance showing an electron-donating property with respect to the organic compound may be used. Specifically, an alkali metal, an alkaline earth metal, and a rare earth metal are preferable, and lithium, sodium, cesium, magnesium, calcium, erbium, and ytterbium are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, and a polymer) may be used in the light-emitting layer, the hole-injection layer, the hole-transport layer, the electron-transport layer, and the electron-injection layer.

<<Pair of Electrodes>>

The electrodes 101 and 102 function as an anode and a cathode of each light-emitting element. The electrodes 101 and 102 can be formed using a metal, an alloy, or a conductive compound, a mixture or a stack thereof, or the like.

One of the electrode 101 and the electrode 102 is preferably formed using a conductive material having a function of reflecting light. Examples of the conductive material include aluminum (Al), an alloy containing Al, and the like. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for manufacturing a light-emitting element with aluminum. Alternatively, silver (Ag), an alloy of Ag and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), and gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, an alloy containing silver and ytterbium, and the like. Besides, a transition metal such as tungsten, chromium (Cr), molybdenum (Mo), copper, or titanium can be used.

Light emitted from the light-emitting layer is extracted through the electrode 101 and/or the electrode 102. Thus, at least one of the electrode 101 and the electrode 102 is preferably formed using a conductive material having a function of transmitting light. As the conductive material, a conductive material having a visible light transmittance higher than or equal to 40% and lower than or equal to 100%, preferably higher than or equal to 60% and lower than or equal to 100%, and a resistivity lower than or equal to $1\times10^{-2}$ Ω·cm can be used.

The electrodes 101 and 102 may each be formed using a conductive material having functions of transmitting light and reflecting light. As the conductive material, a conductive material having a visible light reflectivity higher than or equal to 20% and lower than or equal to 80%, preferably higher than or equal to 40% and lower than or equal to 70%, and a resistivity lower than or equal to $1\times10^{-2}$ Ω·cm can be used. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (ITSO), indium oxide-zinc oxide (indium zinc oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and Yb, or the like can be used.

In this specification and the like, as the material transmitting light, a material that transmits visible light and has conductivity is used. Examples of the material include, in addition to the above-described oxide conductor typified by an ITO, an oxide semiconductor and an organic conductor containing an organic substance. Examples of the organic conductor containing an organic substance include a composite material in which an organic compound and an electron donor (donor material) are mixed and a composite material in which an organic compound and an electron acceptor (acceptor material) are mixed. Alternatively, an inorganic carbon-based material such as graphene may be used. The resistivity of the material is preferably lower than or equal to $1\times10^{5}$ Ω·cm, further preferably lower than or equal to $1\times10^{4}$ Ω·cm.

Alternatively, the electrode 101 and/or the electrode 102 may be formed by stacking two or more of these materials.

In order to improve the light extraction efficiency, a material whose refractive index is higher than that of an electrode having a function of transmitting light may be formed in contact with the electrode. The material may be electrically conductive or non-conductive as long as it has a function of transmitting visible light. In addition to the oxide conductors described above, an oxide semiconductor and an organic substance are given as the examples of the material. Examples of the organic substance include the materials for the light-emitting layer, the hole-injection layer, the hole-transport layer, the electron-transport layer, and the electron-injection layer. Alternatively, an inorganic carbon-based material or a metal film thin enough to transmit light can be used. Further alternatively, a plurality of layers each of which is formed using the material having a high refractive index and has a thickness of several nanometers to several tens of nanometers may be stacked.

In the case where the electrode 101 or the electrode 102 functions as the cathode, the electrode preferably contains a material having a low work function (lower than or equal to 3.8 eV). The examples include an element belonging to Group 1 or 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, an alloy containing aluminum and silver, and the like.

When the electrode 101 or the electrode 102 is used as an anode, a material with a high work function (4.0 eV or higher) is preferably used.

The electrode 101 and the electrode 102 may be a stacked layer of a conductive material having a function of reflecting light and a conductive material having a function of transmitting light. In that case, the electrode 101 and the electrode 102 can have a function of adjusting the optical path length so that light of a desired wavelength emitted from each light-emitting layer resonates and is intensified, which is preferable.

As the method for forming the electrode 101 and the electrode 102, a sputtering method, an evaporation method, a printing method, a coating method, a molecular beam epitaxy (MBE) method, a CVD method, a pulsed laser deposition method, an atomic layer deposition (ALD) method, or the like can be used as appropriate.

<<Substrate>>

A light-emitting element of one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used, for example. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting element or an optical element or as long as it has a function of protecting the light-emitting element or an optical element.

In this specification and the like, a light-emitting element can be formed using any of a variety of substrates, for example. The type of a substrate is not limited particularly. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, and paper which include a fibrous material, a base material film, and the like. As an example of a glass substrate, a barium borosilicate glass substrate, an aluminoborosilicate glass substrate, a soda lime glass substrate, and the like can be given. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a resin such as acrylic. Furthermore, polypropylene, polyester, polyvinyl fluoride, and polyvinyl chloride can be given as examples. Other examples are polyamide, polyimide, aramid, epoxy, an inorganic vapor deposition film, paper, and the like.

Alternatively, a flexible substrate may be used as the substrate such that the light-emitting element is provided directly on the flexible substrate. Further alternatively, a separation layer may be provided between the substrate and the light-emitting element. The separation layer can be used when part or the whole of a light-emitting element formed over the separation layer is separated from the substrate and transferred onto another substrate. In such a case, the light-emitting element can be transferred to a substrate having low heat resistance or a flexible substrate as well. For the above separation layer, a stack including inorganic films, which are a tungsten film and a silicon oxide film, or a structure in which a resin film of polyimide or the like is formed over a substrate can be used, for example.

In other words, after the light-emitting element is formed using a substrate, the light-emitting element may be transferred to another substrate. Example of the substrate to which the light-emitting element is transferred are, in addition to the above substrates, a cellophane substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), and the like), a leather substrate, a rubber substrate, and the like. When such a substrate is used, a light-emitting element with high durability, high heat resistance, reduced weight, or reduced thickness can be formed.

The light-emitting element 150 may be formed over an electrode electrically connected to a field-effect transistor (FET), for example, which is formed over any of the above-described substrates. Accordingly, an active matrix display device in which the FET controls the driving of the light-emitting element 150 can be manufactured.

In Embodiment 1, one embodiment of the present invention has been described. Other embodiments of the present invention are described in Embodiments 2 to 9. Note that one embodiment of the present invention is not limited thereto. That is, since various embodiments of the present invention are disclosed in Embodiment 1 and Embodiments 2 to 9, one embodiment of the present invention is not limited to a specific embodiment. The example in which one embodiment of the present invention is used in a light-emitting element is described; however, one embodiment of the present invention is not limited thereto. For example, depending on circumstances or conditions, one embodiment of the present invention is not necessarily used in a light-emitting element. One embodiment of the present shows, but is not limited to, the example in which a guest material capable of converting triplet excitation energy into light emission and at least one host material are included and in which the LUMO level of the guest material is lower than the LUMO level of the host material and the energy difference between the LUMO level and the HOMO level of the guest material is larger than the energy difference between the LUMO level and the HOMO level of the host material. Depending on circumstances or conditions, for example, the guest material in one embodiment of the present invention does not necessarily have a function of converting the triplet excitation energy into light emission. Alternatively, the LUMO level of the guest material is not necessarily lower than the LUMO level of the host material. Alternatively, the energy difference between the LUMO level and the HOMO level of the guest material is not necessarily larger than the energy difference between the LUMO level and the HOMO level of the host material. One embodiment of the present invention shows, but is not limited to, the example in which the host material has a difference of greater than 0 eV and less than or equal to 0.2 eV between the singlet excitation energy level and the triplet excitation energy level. Depending on circumstances or conditions, the host material in one embodiment of the present invention does not necessarily have a difference of greater than 0.2 eV between the singlet excitation energy level and the triplet excitation energy level, for example.

The structure described above in this embodiment can be combined with any of the structures described in the other embodiments as appropriate.

Embodiment 2

Figure 5A:
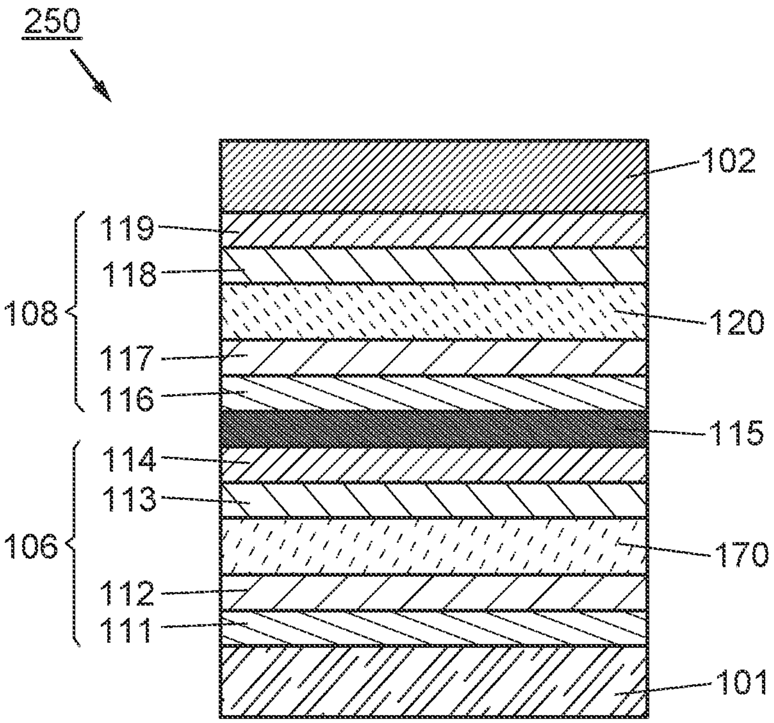
FIGS. 5A and 5B are schematic cross-sectional views of a light-emitting element of one embodiment of the present invention and FIG. 5C is a schematic view showing a correlation between energy levels in a light-emitting layer.

In this embodiment, a light-emitting element having a structure different from that described in Embodiment 1 and light emission mechanisms of the light-emitting element are described below with reference to FIGS. 5A to 5C and FIGS. 6A to 6C. In FIG. 5A and FIG. 6A, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

<Structure Example 1 of Light-Emitting Element>

FIG. 5A is a schematic cross-sectional view of a light-emitting element 250.

The light-emitting element 250 illustrated in FIG. 5A includes a plurality of light-emitting units (a light-emitting unit 106 and a light-emitting unit 108 in FIG. 5A) between a pair of electrodes (the electrode 101 and the electrode 102). One of light-emitting units preferably has the same structure as the EL layer 100. That is, it is preferable that each of the light-emitting element 150 in FIGS. 1A and 1B and the light-emitting element 152 in FIGS. 3A and 3B include one light-emitting unit, while the light-emitting element 250 include a plurality of light-emitting units. Note that the electrode 101 functions as an anode and the electrode 102 functions as a cathode in the following description of the light-emitting element 250; however, the functions may be interchanged in the light-emitting element 250.

In the light-emitting element 250 illustrated in FIG. 5A, the light-emitting unit 106 and the light-emitting unit 108 are stacked, and a charge-generation layer 115 is provided between the light-emitting unit 106 and the light-emitting unit 108. Note that the light-emitting unit 106 and the light-emitting unit 108 may have the same structure or different structures. For example, it is preferable that the EL layer 100 be used in the light-emitting unit 106.

The light-emitting element 250 includes a light-emitting layer 120 and a light-emitting layer 170. The light-emitting unit 106 includes the hole-injection layer 111, the hole-transport layer 112, an electron-transport layer 113, and an electron-injection layer 114 in addition to the light-emitting layer 170. The light-emitting unit 108 includes a hole-injection layer 116, a hole-transport layer 117, an electron-transport layer 118, and an electron-injection layer 119 in addition to the light-emitting layer 120.

The charge-generation layer 115 may have either a structure in which an acceptor substance that is an electron acceptor is added to a hole-transport material or a structure in which a donor substance that is an electron donor is added to an electron-transport material. Alternatively, both of these structures may be stacked.

In the case where the charge-generation layer 115 contains a composite material of an organic compound and an acceptor substance, the composite material that can be used for the hole-injection layer 111 described in Embodiment 1 may be used for the composite material. As the organic compound, a variety of compounds such as an aromatic amine compound, a carbazole compound, an aromatic hydrocarbon, and a high molecular compound (such as an oligomer, a dendrimer, or a polymer) can be used. A material having a hole mobility of $1\times10^{-6}$ $cm^2/Vs$ or higher is preferably used as the organic compound. Note that any other material may be used as long as it has a property of transporting more holes than electrons. Since the composite material of an organic compound and an acceptor substance has excellent carrier-injection and carrier-transport properties, low-voltage driving or low-current driving can be realized. Note that when a surface of a light-emitting unit on the anode side is in contact with the charge-generation layer 115, the charge-generation layer 115 can also serve as a hole-injection layer or a hole-transport layer of the light-emitting unit; thus, a hole-injection layer or a hole-transport layer need not be included in the light-emitting unit. When a surface of a light-emitting unit on the cathode side is in contact with the charge-generation layer 115, the charge-generation layer 115 can also serve as an electron-injection layer or an electron-transport layer of the light-emitting unit; thus, an electron-injection layer or an electron-transport layer need not be included in the light-emitting unit.

The charge-generation layer 115 may have a stacked structure of a layer containing the composite material of an organic compound and an acceptor substance and a layer containing another material. For example, the charge-generation layer 115 may be formed using a combination of a layer containing the composite material of an organic compound and an acceptor substance with a layer containing one compound selected from among electron-donating materials and a compound having a high electron-transport property. Furthermore, the charge-generation layer 115 may be formed using a combination of a layer containing the composite material of an organic compound and an acceptor substance with a layer containing a transparent conductive film.

The charge-generation layer 115 provided between the light-emitting unit 106 and the light-emitting unit 108 may have any structure as long as electrons can be injected to the light-emitting unit on one side and holes can be injected into the light-emitting unit on the other side in the case where a voltage is applied between the electrode 101 and the electrode 102. For example, in FIG. 5A, the charge-generation layer 115 injects electrons into the light-emitting unit 106 and holes into the light-emitting unit 108 when a voltage is applied such that the potential of the electrode 101 is higher than that of the electrode 102.

Note that in terms of light extraction efficiency, the charge-generation layer 115 preferably has a visible light transmittance (specifically, a visible light transmittance of higher than or equal to 40%). The charge-generation layer 115 functions even if it has lower conductivity than the pair of electrodes (the electrodes 101 and 102). Note that forming the charge-generation layer 115 by using any of the above materials can suppress an increase in drive voltage caused by the stack of the light-emitting layers.

The light-emitting element having two light-emitting units has been described with reference to FIG. 5A; however, a similar structure can be applied to a light-emitting element in which three or more light-emitting units are stacked. With a plurality of light-emitting units partitioned by the charge-generation layer between a pair of electrodes as in the light-emitting element 250, it is possible to provide a light-emitting element which can emit light having high luminance with the current density kept low and has a long lifetime. A light-emitting element with low power consumption can be provided.

When the structures described in Embodiment 1 is used for at least one of the plurality of units, a light-emitting element with high emission efficiency can be provided.

It is preferable that the light-emitting layer 170 of the light-emitting unit 106 have the structure of the light-emitting layer 130 or the light-emitting layer 135 described in Embodiment 1, in which case the light-emitting element 250 suitably has high emission efficiency.

Figure 5B:
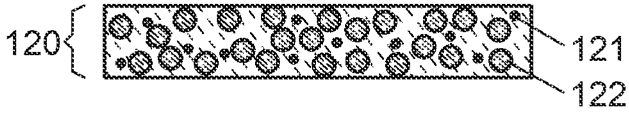
Figure 6A:
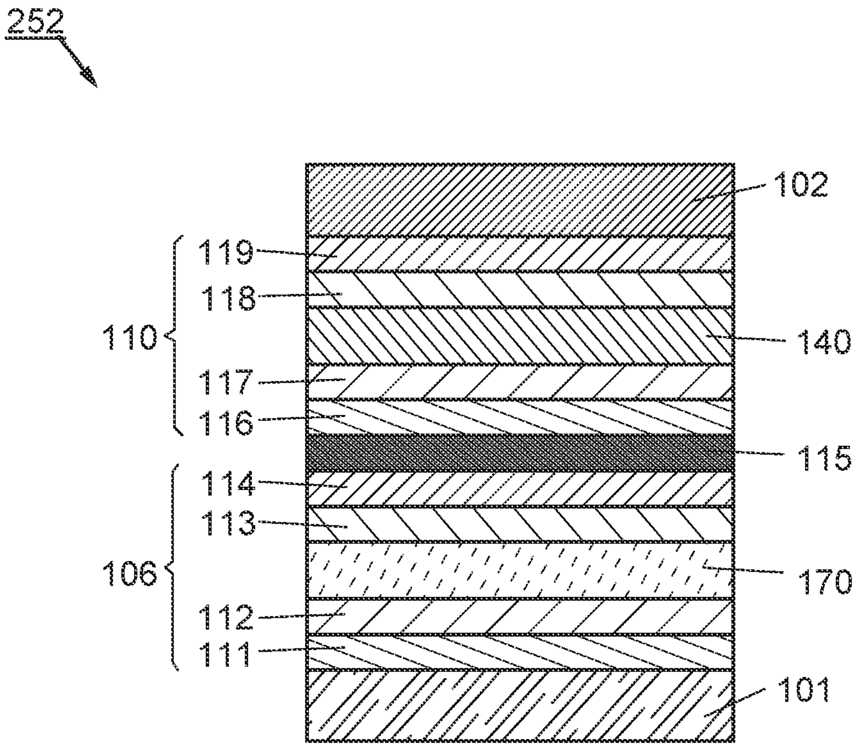
FIGS. 6A and 6B are schematic cross-sectional views of a light-emitting element of one embodiment of the present invention and FIG. 6C is a schematic view showing a correlation between energy levels in a light-emitting layer.

The light-emitting layer 120 included in the light-emitting unit 108 contains a guest material 121 and a host material 122 as illustrated in FIG. 5B. Note that the guest material 121 is described below as a fluorescent material.

<<Light Emission Mechanism of Light-Emitting Layer 120>>

The light emission mechanism of the light-emitting layer 120 is described below.

By recombination of the electrons and holes injected from the pair of electrodes (the electrode 101 and the electrode 102) or the charge-generation layer in the light-emitting layer 120, excitons are formed. Because the amount of the host material 122 is larger than that of the guest material 121, the host material 122 is brought into an excited state by the exciton generation.

Note that the term "exciton" refers to a carrier (electron and hole) pair. Since excitons have energy, a material where excitons are generated is brought into an excited state.

In the case where the formed excited state of the host material 122 is a singlet excited state, singlet excitation energy transfers from the S1 level of the host material 122 to the S1 level of the guest material 121, thereby forming the singlet excited state of the guest material 121.

Since the guest material 121 is a fluorescent material, when a singlet excited state is formed in the guest material 121, the guest material 121 immediately emits light. To obtain high light emission efficiency in this case, the fluorescence quantum yield of the guest material 121 is preferably high. The same can apply to a case where a singlet excited state is formed by recombination of carriers in the guest material 121.

Figure 5C:
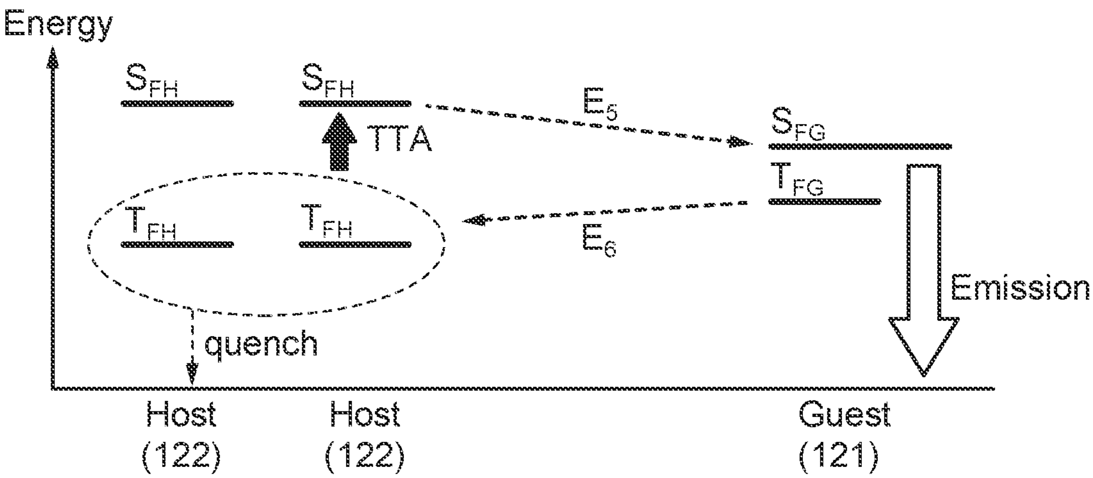

Next, a case where recombination of carriers forms a triplet excited state of the host material 122 is described. The correlation of energy levels of the host material 122 and the guest material 121 in this case is shown in FIG. 5C. The following explains what terms and signs in FIG. 5C represent. Note that because it is preferable that the T1 level of the host material 122 be lower than the T1 level of the guest material 121, FIG. 5C shows this preferable case. However, the T1 level of the host material 122 may be higher than the T1 level of the guest material 121.

Guest (121): the guest material 121 (the fluorescent material);

Host (122): the host material 122;

$S_{FG}$: the S1 level of the guest material 121 (the fluorescent material);

$T_{FG}$: the T1 level of the guest material 121 (the fluorescent material);

$S_{FH}$: the S1 level the host material 122; and $T_{FH}$: the T1 level of the host material 122.

As illustrated in FIG. 5C, triplet-triplet annihilation (TTA) occurs, that is, triplet excitons formed by carrier recombination interact with each other, and excitation energy is transferred and spin angular momenta are exchanged; as a result, a reaction in which the triplet excitons are converted into singlet exciton having energy of the S1 level of the host material 122 ($S_{FH}$) (see TTA in FIG. 5C). The singlet excitation energy of the host material 122 is transferred from $S_{FH}$ to the S1 level of the guest material 121 ($S_{FG}$) having a lower energy than $S_{FH}$ (see Route Es in FIG. 5C), and a singlet excited state of the guest material 121 is formed, whereby the guest material 121 emits light.

Note that in the case where the density of triplet excitons in the light-emitting layer 120 is sufficiently high (e.g., $1\times10^{-12}$ $cm^{-3}$ or higher), only the reaction of two triplet excitons close to each other can be considered whereas deactivation of a single triplet exciton can be ignored.

In the case where a triplet excited state of the guest material 121 is formed by carrier recombination, the triplet excited state of the guest material 121 is thermally deactivated and is difficult to use for light emission. However, in the case where the T1 level of the host material 122 ($T_{FH}$) is lower than the T1 level of the guest material 121 ($T_{FG}$), the triplet excitation energy of the guest material 121 can be transferred from the T1 level of the guest material 121 ($T_{FG}$) to the T1 level of the host material 122 ($T_{FH}$) (see Route $E_6$ in FIG. 5C) and then is utilized for TTA.

In other words, the host material 122 preferably has a function of converting triplet excitation energy into singlet excitation energy by causing TTA, so that the triplet excitation energy generated in the light-emitting layer 120 can be partly converted into singlet excitation energy by TTA in the host material 122. The singlet excitation energy can be transferred to the guest material 121 and extracted as fluorescence. In order to achieve this, the S1 level of the host material 122 ($S_{FH}$) is preferably higher than the S1 level of the guest material 121 ($S_{FG}$). In addition, the T1 level of the host material 122 ($T_{FH}$) is preferably lower than the T1 level of the guest material 121 ($T_{FG}$).

Note that particularly in the case where the T1 level of the guest material 121 ($T_{FG}$) is lower than the T1 level of the host material 122 ($T_{FH}$), the weight ratio of the guest material 121 to the host material 122 is preferably low. Specifically, the weight ratio of the guest material 121 to the host material 122 is preferably greater than 0 and less than or equal to 0.05, in which case the probability of carrier recombination in the guest material 121 can be reduced. In addition, the probability of energy transfer from the T1 level of the host material 122 ($T_{FH}$) to the T1 level of the guest material 121 ($T_{FG}$) can be reduced.

Note that the host material 122 may be composed of a single compound or a plurality of compounds.

In the case where the light-emitting units 106 and 108 contain guest materials with different emission colors, light emitted from the light-emitting layer 120 preferably has a peak on the shorter wavelength side than light emitted from the light-emitting layer 170. The luminance of a light-emitting element using a material having a high triplet excited energy level tends to degrade quickly. TTA is utilized in the light-emitting layer emitting light with a short wavelength so that a light-emitting element with less degradation of luminance can be provided.

<Structure Example 2 of Light-Emitting Element>

FIG. 6A is a schematic cross-sectional view of a light-emitting element 252.

The light-emitting element 252 illustrated in FIG. 6A includes, like the light-emitting element 250 described above, a plurality of light-emitting units (the light-emitting unit 106 and a light-emitting unit 110 in FIG. 6A) between a pair of electrodes (the electrode 101 and the electrode 102). At least one of the light-emitting units has a structure similar to that of the EL layer 100. Note that the light-emitting unit 106 and the light-emitting unit 110 may have the same structure or different structures.

In the light-emitting element 252 illustrated in FIG. 6A, the light-emitting unit 106 and the light-emitting unit 110 are stacked, and a charge-generation layer 115 is provided between the light-emitting unit 106 and the light-emitting unit 110. For example, it is preferable that the EL layer 100 be used in the light-emitting unit 106.

The light-emitting element 252 includes a light-emitting layer 140 and the light-emitting layer 170. The light-emitting unit 106 includes the hole-injection layer 111, the hole-transport layer 112, an electron-transport layer 113, and an electron-injection layer 114 in addition to the light-emitting layer 170. The light-emitting unit 110 includes a hole-injection layer 116, a hole-transport layer 117, an electron-transport layer 118, and an electron-injection layer 119 in addition to the light-emitting layer 140.

When the structure described in Embodiment 1 is used for at least one of the plurality of units, a light-emitting element with high emission efficiency can be provided.

The light-emitting layer of the light-emitting unit 110 preferably includes a phosphorescent material. In other words, it is preferable that the light-emitting layer 140 included in the light-emitting unit 110 include a phosphorescent material, and the light-emitting layer 170 included in the light-emitting unit 106 have the structure of the light-emitting layer 130 or the light-emitting layer 135 described in Embodiment 1. A structure example of the light-emitting element 252 in this case is described below.

Figure 6B:
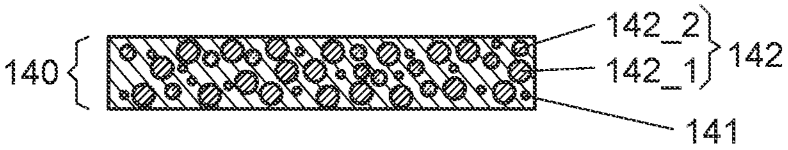

The light-emitting layer 140 included in the light-emitting unit 110 includes a guest material 141 and a host material 142 as illustrated in FIG. 6B. The host material 142 includes an organic compound 142_1 and an organic compound 142_2. In the following description, the guest material 141 included in the light-emitting layer 140 is a phosphorescent material.

<<Light Emission Mechanism of Light-Emitting Layer 140>>

Next, the light emission mechanism of the light-emitting layer 140 is described below.

The organic compound 142_1 and the organic compound 142_2 which are included in the light-emitting layer 140 form an exciplex.

Although it is acceptable as long as the combination of the organic compound 142_1 and the organic compound 142_2 can form an exciplex, it is preferable that one of them be a compound having a hole-transport property and the other be a compound having an electron-transport property.

Figure 6C:
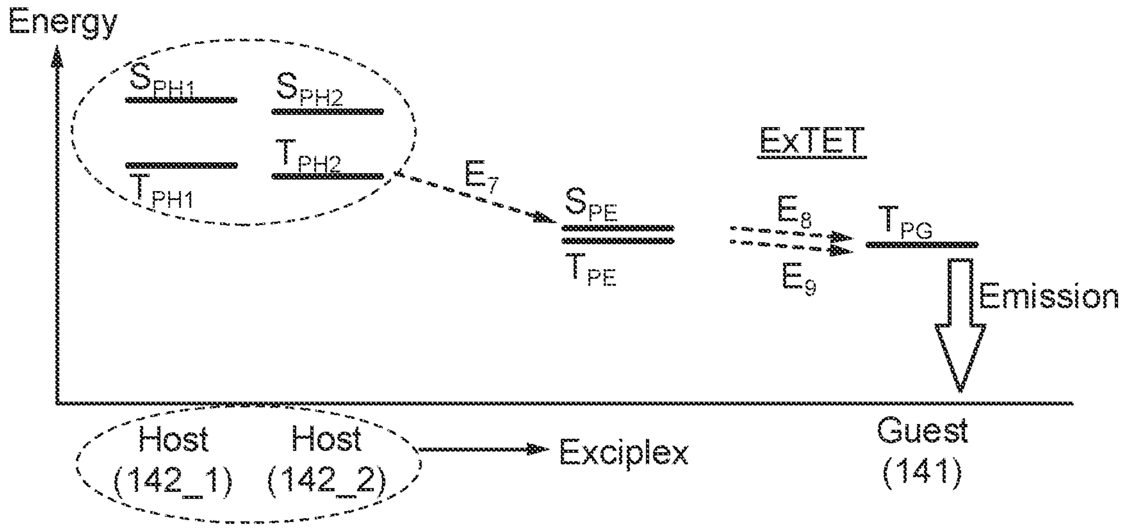

FIG. 6C shows a correlation between the energy levels of the organic compound 142_1, the organic compound 142_2, and the guest material 141 in the light-emitting layer 140. The following explains what terms and numerals in FIG. 6C represent:

Guest (141): the guest material 141 (phosphorescent material);

Host (142_1): the organic compound 142_1 (host material);

Host (142_2): the organic compound 142_2 (host material);

$T_{PG}$: a T1 level of the guest material 141 (phosphorescent material);

$S_{PH1}$: an S1 level of the organic compound 142_1 (host material);

$T_{PH1}$: a T1 level of the organic compound 142_1 (host material);

$S_{PH2}$: an S1 level of the organic compound 142_2 (host material);

$T_{PH2}$: a T1 level of the organic compound 142_2 (host material);

$S_{PE}$: an S1 level of the exciplex; and $T_{PE}$: a T1 level of the exciplex.

The organic compound 142_1 and the organic compound 142_2 form an exciplex, and the S1 level ($S_{PE}$) and the T1 level ($T_{PE}$) of the exciplex are energy levels adjacent to each other (see Route $E_7$ in FIG. 6C).

One of the organic compound 142_1 and the organic compound 142_2 receives a hole and the other receives an electron to readily form an exciplex. Alternatively, when one of the organic compounds is brought into an excited state, the other immediately interacts with the one to form an exciplex. Consequently, most excitons in the light-emitting layer 140 exist as exciplexes. Because the excitation energy levels ($S_{PE}$ and $T_{PE}$) of the exciplex are lower than the S1 levels ($S_{PH1}$ and $S_{PH2}$) of the host materials (the organic compounds 142_1 and 142_2) that form the exciplex, the excited state of the host material 142 can be formed with lower excitation energy. This can reduce the drive voltage of the light emitting element.

Both energies of $S_{PE}$ and $T_{PE}$ of the exciplex are then transferred to the T1 level of the guest material 141 (the phosphorescent material); thus, light emission is obtained (see Routes $E_8$ and $E_9$ in FIG. 6C).

Furthermore, the T1 level ($T_{PE}$) of the exciplex is preferably higher than the T1 level ($T_{PG}$) of the guest material 141. Thus, the singlet excitation energy and the triplet excitation energy of the formed exciplex can be transferred from the S1 level ($S_{PE}$) and the T1 level ($T_{PE}$) of the exciplex to the T1 level ($T_{PG}$) of the guest material 141.

Note that in order to efficiently transfer excitation energy from the exciplex to the guest material 141, the T1 level ($T_{PE}$) of the exciplex is preferably lower than or equal to the T1 levels ($T_{PH1}$ and $T_{PH2}$) of the organic compounds (the organic compound 142_1 and the organic compound 142_2) which form the exciplex. Thus, quenching of the triplet excitation energy of the exciplex due to the organic compounds (the organic compounds 142_1 and 142_2) is less likely to occur, resulting in efficient energy transfer from the exciplex to the guest material 141.

In order to efficiently form an exciplex by the organic compound 142_1 and the organic compound 142_2, it is preferable to satisfy the following: the HOMO level of one of the organic compound 142_1 and the organic compound 142_2 is higher than that of the other and the LUMO level of the one of the organic compound 142_1 and the organic compound 142_2 is higher than that of the other. For example, when the organic compound 142_1 has a hole-transport property and the organic compound 142_2 has an electron-transport property, it is preferable that the HOMO level of the organic compound 142_1 be higher than the HOMO level of the organic compound 142_2 and the LUMO level of the organic compound 142_1 be higher than the LUMO level of the organic compound 142_2. Alternatively, when the organic compound 142_2 has a hole-transport property and the organic compound 142_1 has an electron-transport property, it is preferable that the HOMO level of the organic compound 142_2 be higher than the HOMO level of the organic compound 142_1 and the LUMO level of the organic compound 142_2 be higher than the LUMO level of the organic compound 142_1. Specifically, the energy difference between the HOMO level of the organic compound 142_1 and the HOMO level of the organic compound 142_2 is preferably greater than or equal to 0.05 eV, further preferably greater than or equal to 0.1 eV, and still further preferably greater than or equal to 0.2 eV. Alternatively, the energy difference between the LUMO level of the organic compound 142_1 and the LUMO level of the organic compound 142_2 is preferably greater than or equal to 0.05 eV, more preferably greater than or equal to 0.1 eV, and still more preferably greater than or equal to 0.2 eV.

In the case where the combination of the organic compounds 142_1 and 142_2 is a combination of a compound having a hole-transport property and a compound having an electron-transport property, the carrier balance can be easily controlled by adjusting the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

Furthermore, the mechanism of the energy transfer process between the molecules of the host material 142 (exciplex) and the guest material 141 can be described using two mechanisms, i.e., Förster mechanism (dipole-dipole interaction) and Dexter mechanism (electron exchange interaction), as in Embodiment 1. For Förster mechanism and Dexter mechanism, Embodiment 1 can be referred to.

In order to facilitate energy transfer from the singlet excited state of the host material (exciplex) to the triplet excited state of the guest material 141 serving as an energy acceptor, it is preferable that the emission spectrum of the exciplex overlap with the absorption band of the guest material 141 which is on the longest wavelength side (lowest energy side). Thus, the efficiency of generating the triplet excited state of the guest material 141 can be increased.

When the light-emitting layer 140 has the above-described structure, light emission from the guest material 141 (the phosphorescent material) of the light-emitting layer 140 can be obtained efficiently.

Note that the above-described processes through Routes $E_7$, $E_8$, and $E_9$ may be referred to as exciplex-triplet energy transfer (ExTET) in this specification and the like. In other words, in the light-emitting layer 140, excitation energy is transferred from the exciplex to the guest material 141. In this case, the efficiency of reverse intersystem crossing from $T_{PE}$ to $S_{PE}$ and the emission quantum yield from $S_{PE}$ are not necessarily high; thus, materials can be selected from a wide range of options.

Note that light emitted from the light-emitting layer 170 preferably has a peak on the shorter wavelength side than light emitted from the light-emitting layer 140. Since the luminance of a light-emitting element using a phosphorescent material emitting light with a short wavelength tends to be degraded quickly, fluorescence with a short wavelength is employed so that a light-emitting element with less degradation of luminance can be provided.

Note that in each of the above-described structures, the emission colors of the guest materials used in the light-emitting unit 106 and the light-emitting unit 108 or in the light-emitting unit 106 and the light-emitting unit 110 may be the same or different. In the case where the same guest materials emitting light of the same color are used for the light-emitting unit 106 and the light-emitting unit 108 or for the light-emitting unit 106 and the light-emitting unit 110, the light-emitting element 250 and the light-emitting element 252 can exhibit high emission luminance at a small current value, which is preferable. In the case where guest materials emitting light of different colors are used for the light-emitting unit 106 and the light-emitting unit 108 or for the light-emitting unit 106 and the light-emitting unit 110, the light-emitting element 250 and the light-emitting element 252 can exhibit multi-color light emission, which is preferable. In that case, when a plurality of light-emitting materials with different emission wavelengths are used in one or both of the light-emitting layers 120 and 170 or in one or both of the light-emitting layers 140 and 170, lights with different emission peaks synthesize light emission from the light-emitting element 250 and the light-emitting element 252. That is, the emission spectrum of the light-emitting element 250 has at least two maximum values.

The above structure is also suitable for obtaining white light emission. When the light-emitting layer 120 and the light-emitting layer 170 or the light-emitting layer 140 and the light-emitting layer 170 emit light of complementary colors, white light emission can be obtained. It is particularly favorable to select the guest materials so that white light emission with high color rendering properties or light emission of at least red, green, and blue can be obtained.

At least one of the light-emitting layers 120, 140, and 170 may be divided into layers and each of the divided layers may contain a different light-emitting material. That is, at least one of the light-emitting layers 120, 140, and 170 may consist of two or more layers. For example, in the case where the light-emitting layer is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. In that case, a light-emitting material included in the first light-emitting layer may be the same as or different from a light-emitting material included in the second light-emitting layer. In addition, the materials may have functions of emitting light of the same color or light of different colors. White light emission with a high color rendering property that is formed of three primary colors or four or more colors can be obtained by using a plurality of light-emitting materials emitting light of different colors.

<Material that can be Used in Light-Emitting Layers>

Next, materials that can be used in the light-emitting layers 120, 140, and 170 are described.

<<Material that can be Used in Light-Emitting Layer 120>>

In the light-emitting layer 120, the host material 122 is present in the largest proportion by weight, and the guest material 121 (the fluorescent material) is dispersed in the host material 122. The S1 level of the host material 122 is preferably higher than the S1 level of the guest material 121 (the fluorescent material) while the T1 level of the host material 122 is preferably lower than the T1 level of the guest material 121 (the fluorescent material).

In the light-emitting layer 120, the guest material 121 is preferably, but not particularly limited to, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like, and for example, any of the following materials can be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9-phenyl-9H-fluoren-9-yl)phenyl]-N,N'-bis(4-tert-butylphenyl)pyrene-1,6-diamine (abbreviation: 1,6tBu-FLPAPrn), N,N'-diphenyl-N,N'-bis[4-(9-phenyl-9H-fluoren-9-yl)phenyl]-3,8-dicyclohexylpyrene-1,6-diamine (abbreviation: ch-1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and 5,10,15,20-tetraphenylbisbenzo[5,6]indeno[1,2,3-cd:1',2',3'-lm]perylene.

Although there is no particular limitation on a material that can be used as the host material 122 in the light-emitting layer 120, any of the following materials can be used, for example: metal complexes such as tris(8-quinolinolato)aluminum(III) (abbreviation: Alq), tris(4-methyl-8-quinolinolato)aluminum(III) (abbreviation: $Almq_3$), bis(10-hydroxybenzo[h]quinolinato)beryllium(II) (abbreviation: $BeBq_2$), bis(2-methyl-8-quinolinolato) (4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)-tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives can be given, and specific examples are 9,10-diphenylanthracene (abbreviation: DPAnth), N,N'-diphenyl-9-[4-(10-phenyl-9-anthryl)phenyl]9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), and the like. One or more substances having a wider energy gap than the guest material 121 is preferably selected from these substances and known substances.

The light-emitting layer 120 can have a structure in which two or more layers are stacked. For example, in the case where the light-emitting layer 120 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material.

In the light-emitting layer 120, the host material 122 may be composed of one kind of compound or a plurality of compounds. Alternatively, the light-emitting layer 120 may contain another material in addition to the host material 122 and the guest material 121.

<<Material that can be Used in Light-Emitting Layer 140>>

In the light-emitting layer 140, the host material 142 is present in the largest proportion by weight, and the guest material 141 (phosphorescent material) is dispersed in the host material 142. The T1 levels of the host materials 142 (organic compounds 142_1 and 142_2) of the light-emitting layer 140 are preferably higher than the T1 level of the guest material 141 of the light-emitting layer 140.

Examples of the organic compound 142_1 include a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, and a phenanthroline derivative. Other examples are an aromatic amine and a carbazole derivative. Specifically, the electron-transport material and the hole-transport material described in Embodiment 1 can be used.

As the organic compound 142_2, a substance which can form an exciplex together with the organic compound 142_1 is preferably used. Specifically, the electron-transport material and the hole-transport material described in Embodiment 1 can be used. In that case, it is preferable that the organic compound 142_1, the organic compound 142_2, and the guest material 141 (phosphorescent material) be selected such that the emission peak of the exciplex formed by the organic compound 142_1 and the organic compound 142_2 overlaps with an absorption band, specifically an absorption band on the longest wavelength side, of a triplet metal to ligand charge transfer (MLCT) transition of the guest material 141 (phosphorescent material). This makes it possible to provide a light-emitting element with drastically improved emission efficiency. Note that in the case where a thermally activated delayed fluorescence material is used instead of the phosphorescent material, it is preferable that the absorption band on the longest wavelength side be a singlet absorption band.

As the guest material 141 (phosphorescent material), an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given. Specifically, the material described in Embodiment 1 as an example of the guest material 131 can be used.

As the light-emitting material included in the light-emitting layer 140, any material can be used as long as the material can convert the triplet excitation energy into light emission. As an example of the material that can convert the triplet excitation energy into light emission, a thermally activated delayed fluorescent material can be given in addition to a phosphorescent material. Therefore, it is acceptable that the "phosphorescent material" in the description is replaced with the "thermally activated delayed fluorescence material".

The material that exhibits thermally activated delayed fluorescence may be a material that can form a singlet excited state from a triplet excited state by reverse intersystem crossing or may be a combination of a plurality of materials which form an exciplex.

In the case where the material exhibiting thermally activated delayed fluorescence is formed of one kind of material, any of the thermally activated delayed fluorescent materials described in Embodiment 1 can be specifically used.

In the case where the thermally activated delayed fluorescent material is used as the host material, it is preferable to use a combination of two kinds of compounds which form an exciplex. In this case, it is particularly preferable to use the above-described combination of a compound which easily accepts electrons and a compound which easily accepts holes, which forms an exciplex.

<<Material that can be Used in Light-Emitting Layer 170>>

As a material that can be used for the light-emitting layer 170, a material that can be used for the light-emitting layer in Embodiment 1 can be used, so that a light-emitting element with high emission efficiency can be formed.

There is no limitation on the emission colors of the light-emitting materials contained in the light-emitting layers 120, 140, and 170, and they may be the same or different. Light emitted from the light-emitting materials is mixed and extracted out of the element; therefore, for example, in the case where their emission colors are complementary colors, the light-emitting element can emit white light. In consideration of the reliability of the light-emitting element, the wavelength of the emission peak of the light-emitting material contained in the light-emitting layer 120 is preferably shorter than that of the light-emitting material contained in the light-emitting layer 170.

Note that the light-emitting units 106, 108, and 110, and the charge-generation layer 115 can be formed by an evaporation method (including a vacuum evaporation method), an ink-jet method, a coating method, gravure printing, or the like.

The structure described in this embodiment can be used in combination with any of the structures described in the other embodiments as appropriate.

Embodiment 3

In this embodiment, examples of light-emitting elements having structures different from those described in Embodiments 1 and 2 are described below with reference to FIGS. 7A and 7B, FIGS. 8A and 8B, FIGS. 9A to 9C, and FIGS. 10A to 10C.

<Structure Example 1 of Light-Emitting Element>

Figure 7A:
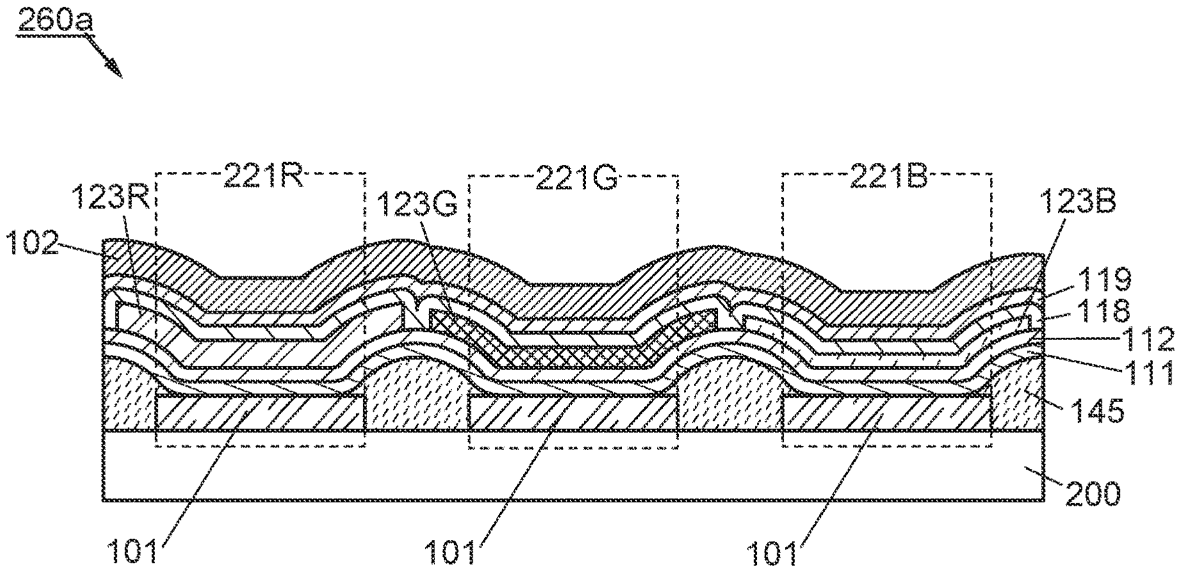
FIGS. 7A and 7B are each a schematic cross-sectional view of a light-emitting element of one embodiment of the present invention.
Figure 7B:
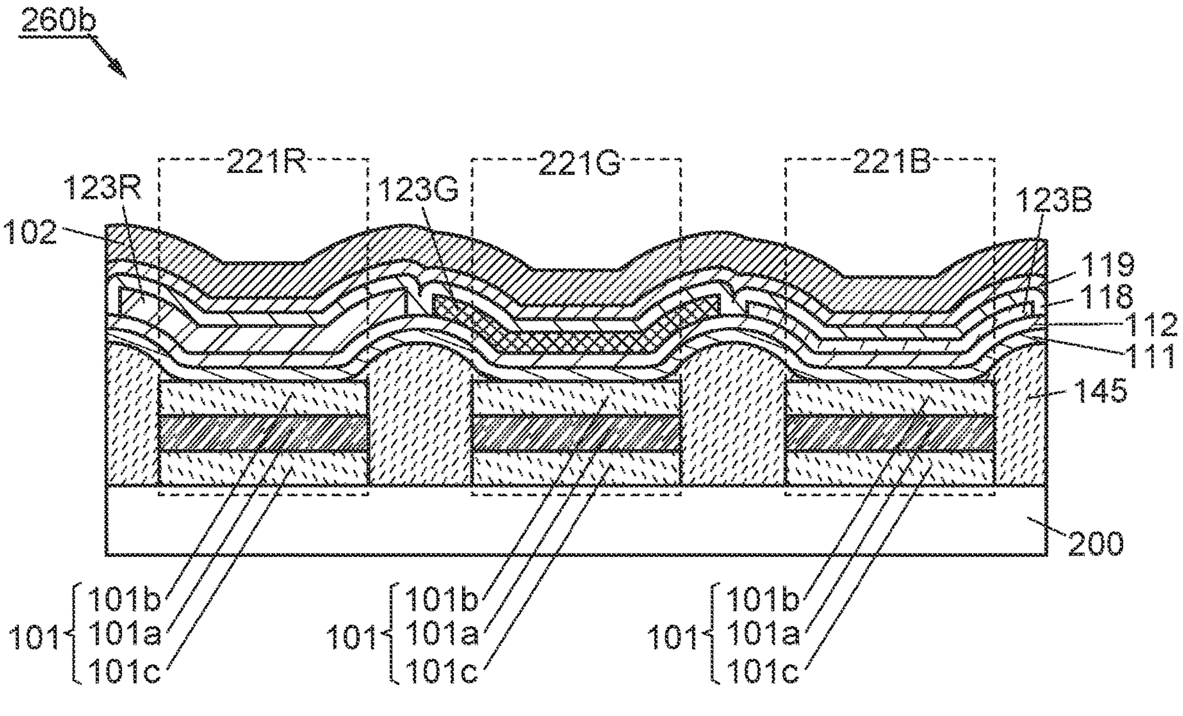

FIGS. 7A and 7B are cross-sectional views each illustrating a light-emitting element of one embodiment of the present invention. In FIGS. 7A and 7B, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

Light-emitting elements 260*a* and 260*b* in FIGS. 7A and 7B may have a bottom-emission structure in which light is extracted through the substrate 200 or may have a top-emission structure in which light emitted from the light-emitting element is extracted in the direction opposite to the substrate 200. However, one embodiment of the present invention is not limited to this structure, and a light-emitting element having a dual-emission structure in which light emitted from the light-emitting element is extracted in both top and bottom directions of the substrate 200 may be used.

In the case where the light-emitting elements 260*a* and 260*b* each have a bottom emission structure, the electrode 101 preferably has a function of transmitting light and the electrode 102 preferably has a function of reflecting light. Alternatively, in the case where the light-emitting elements 260*a* and 260*b* each have a top emission structure, the electrode 101 preferably has a function of reflecting light and the electrode 102 preferably has a function of transmitting light.

The light-emitting elements 260*a* and 260*b* each include the electrode 101 and the electrode 102 over the substrate 200. Between the electrodes 101 and 102, a light-emitting layer 123B, a light-emitting layer 123G, and a light-emitting layer 123R are provided. The hole-injection layer 111, the hole-transport layer 112, the electron-transport layer 118, and the electron-injection layer 119 are also provided.

The light-emitting element 260*b* includes, as part of the electrode 101, a conductive layer 101*a*, a conductive layer 101*b* over the conductive layer 101*a*, and a conductive layer 101*c* under the conductive layer 101*a*. In other words, the light-emitting element 260*b* includes the electrode 101 having a structure in which the conductive layer 101*a* is sandwiched between the conductive layer 101*b* and the conductive layer 101*c*.

In the light-emitting element 260*b*, the conductive layer 101*b* and the conductive layer 101*c* may be formed of different materials or the same material. The electrode 101 preferably has a structure in which the conductive layer 101*a* is sandwiched by the layers formed of the same conductive material, in which case patterning by etching in the process for forming the electrode 101 can be performed easily.

In the light-emitting element 260*b*, the electrode 101 may include one of the conductive layer 101*b* and the conductive layer 101*c*.

For each of the conductive layers 101*a*, 101*b*, and 101*c*, which are included in the electrode 101, the structure and materials of the electrode 101 or 102 described in Embodiment 1 can be used.

In FIGS. 7A and 7B, a partition wall 145 is provided between a region 221B, a region 221G, and a region 221R, which are sandwiched between the electrode 101 and the electrode 102. The partition wall 145 has an insulating property. The partition wall 145 covers end portions of the electrode 101 and has openings overlapping with the electrode. With the partition wall 145, the electrode 101 provided over the substrate 200 in the regions can be divided into island shapes.

Note that the light-emitting layer 123B and the light-emitting layer 123G may overlap with each other in a region where they overlap with the partition wall 145. The light-emitting layer 123G and the light-emitting layer 123R may overlap with each other in a region where they overlap with the partition wall 145. The light-emitting layer 123R and the light-emitting layer 123B may overlap with each other in a region where they overlap with the partition wall 145.

The partition wall 145 has an insulating property and is formed using an inorganic or organic material. Examples of the inorganic material include silicon oxide, silicon oxynitride, silicon nitride oxide, silicon nitride, aluminum oxide, and aluminum nitride. Examples of the organic material include photosensitive resin materials such as an acrylic resin and a polyimide resin.

Note that a silicon oxynitride film refers to a film in which the proportion of oxygen is higher than that of nitrogen. The silicon oxynitride film preferably contains oxygen, nitrogen, silicon, and hydrogen in the ranges of 55 atomic % to 65 atomic %, 1 atomic % to 20 atomic %, 25 atomic % to 35 atomic %, and 0.1 atomic % to 10 atomic %, respectively. A silicon nitride oxide film refers to a film in which the proportion of nitrogen is higher than that of oxygen. The silicon nitride oxide film preferably contains nitrogen, oxygen, silicon, and hydrogen in the ranges of 55 atomic % to 65 atomic %, 1 atomic % to 20 atomic %, 25 atomic % to 35 atomic %, and 0.1 atomic % to 10 atomic %, respectively.

The light-emitting layers 123R, 123G, and 123B preferably contain light-emitting materials having functions of emitting light of different colors. For example, when the light-emitting layer 123R contains a light-emitting material having a function of emitting red, the region 221R emits red light. When the light-emitting layer 123G contains a light-emitting material having a function of emitting green, the region 221G emits green light. When the light-emitting layer 123B contains a light-emitting material having a function of emitting blue, the region 221B emits blue light. The light-emitting element 260*a* or 260*b* having such a structure is used in a pixel of a display device, whereby a full-color display device can be fabricated. The thicknesses of the light-emitting layers may be the same or different.

One or more of the light-emitting layer 123B, the light-emitting layer 123G, and the light-emitting layer 123R preferably have at least one of the structures of the light-emitting layers 130 and 135 described in Embodiment 1. In that case, a light-emitting element with high emission efficiency can be fabricated.

One or more of the light-emitting layers 123B, 123G, and 123R may include two or more stacked layers.

When at least one light-emitting layer includes the light-emitting layer described in Embodiments 1 and 2 and the light-emitting element 260*a* or 260*b* including the light-emitting layer is used in pixels in a display device, a display device with high emission efficiency can be fabricated. The display device including the light-emitting element 260*a* or 260*b* can thus have reduced power consumption.

By providing an optical element (e.g., a color filter, a polarizing plate, and an anti-reflection film) on the light extraction side of the electrode through which light is extracted, the color purity of each of the light-emitting elements 260*a* and 260*b* can be improved. Therefore, the color purity of a display device including the light-emitting element 260*a* or 260*b* can be improved. Alternatively, the reflection of external light by each of the light-emitting elements 260*a* and 260*b* can be reduced. Therefore, the contrast ratio of a display device including the light-emitting element 260*a* or 260*b* can be improved.

For the other components of the light-emitting elements 260*a* and 260*b*, the components of the light-emitting element in Embodiments 1 and 2 may be referred to.

<Structure Example 2 of Light-Emitting Element>

Next, structure examples different from the light-emitting elements illustrated in FIGS. 7A and 7B will be described below with reference to FIGS. 8A and 8B.

Figure 8A:
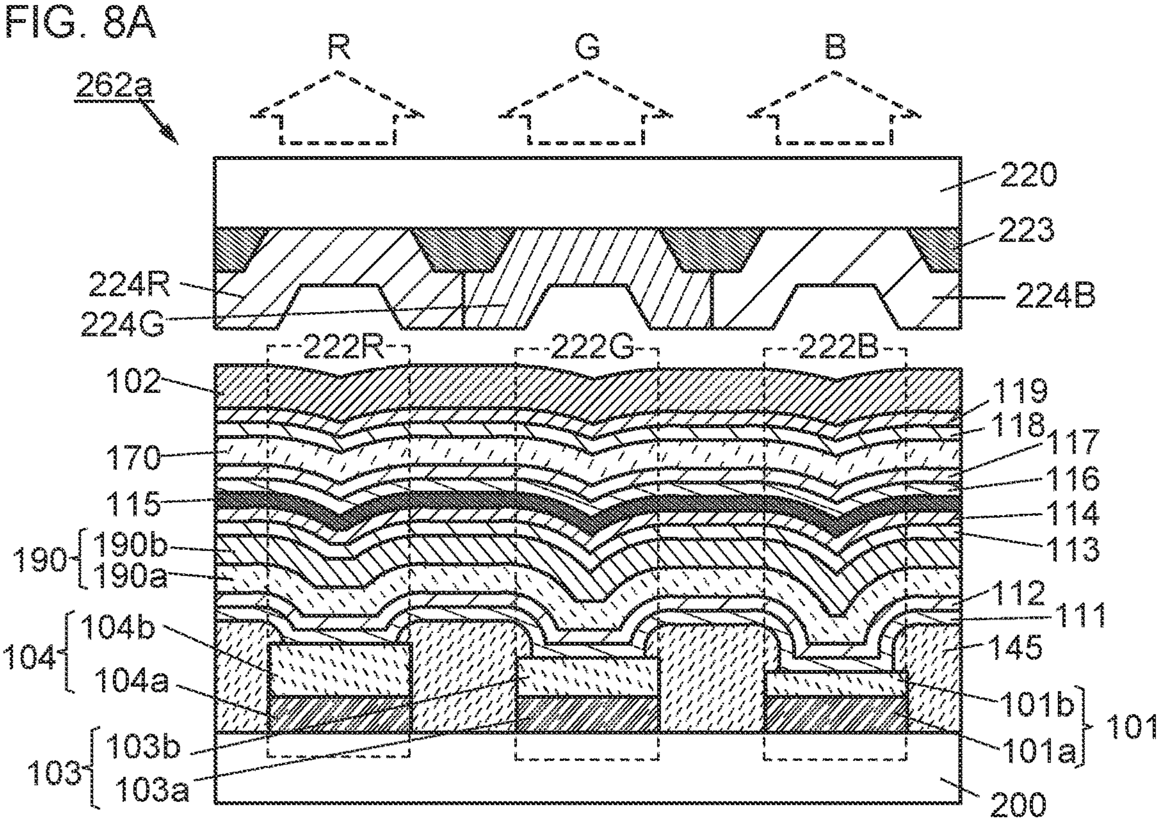
FIGS. 8A and 8B are each a schematic cross-sectional view of a light-emitting element of one embodiment of the present invention.
Figure 8B:
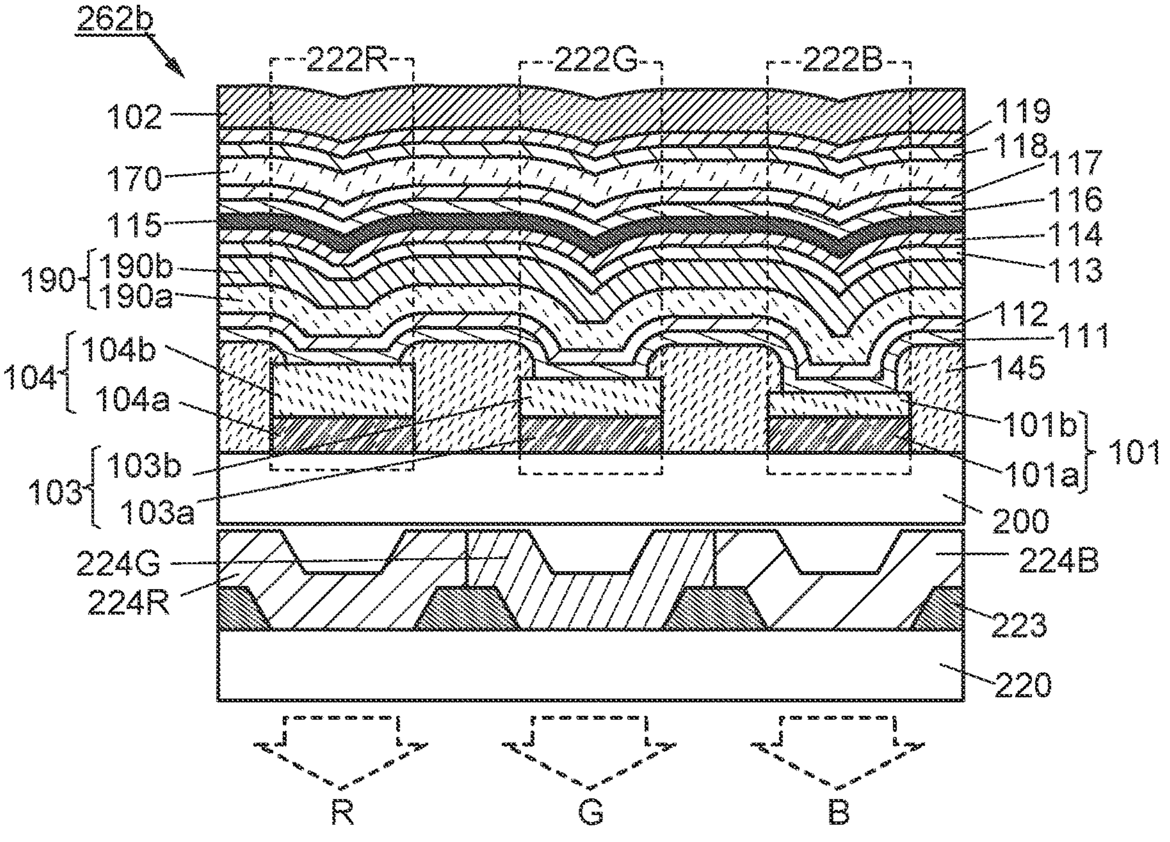

FIGS. 8A and 8B are cross-sectional views of a light-emitting element of one embodiment of the present invention. In FIGS. 8A and 8B, a portion having a function similar to that in FIGS. 7A and 7B is represented by the same hatch pattern as in FIGS. 7A and 7B and not especially denoted by a reference numeral in some cases. In addition, common reference numerals are used for portions having similar functions, and a detailed description of such portions is not repeated in some cases.

FIGS. 8A and 8B illustrate structure examples of a light-emitting element including the light-emitting layer between a pair of electrodes. A light-emitting element 262*a* illustrated in FIG. 8A has a top-emission structure in which light is extracted in a direction opposite to the substrate 200, and a light-emitting element 262*b* illustrated in FIG. 8B has a bottom-emission structure in which light is extracted to the substrate 200 side. However, one embodiment of the present invention is not limited to these structures and may have a dual-emission structure in which light emitted from the light-emitting element is extracted in both top and bottom directions with respect to the substrate 200 over which the light-emitting element is formed.

The light-emitting elements 262*a* and 262*b* each include the electrode 101, the electrode 102, an electrode 103, and an electrode 104 over the substrate 200. At least a light-emitting layer 170, a light-emitting layer 190, and the charge-generation layer 115 are provided between the electrode 101 and the electrode 102, between the electrode 102 and the electrode 103, and between the electrode 102 and the electrode 104. The hole-injection layer 111, the hole-transport layer 112, the electron-transport layer 113, the electron-injection layer 114, the hole-injection layer 116, the hole-transport layer 117, the electron-transport layer 118, and the electron-injection layer 119 are further provided.

The electrode 101 includes a conductive layer 101*a* and a conductive layer 101*b* over and in contact with the conductive layer 101*a*. The electrode 103 includes a conductive layer 103*a* and a conductive layer 103*b* over and in contact with the conductive layer 103*a*. The electrode 104 includes a conductive layer 104*a* and a conductive layer 104*b* over and in contact with the conductive layer 104*a*.

The light-emitting element 262*a* illustrated in FIG. 8A and the light-emitting element 262*b* illustrated in FIG. 8B each include a partition wall 145 between a region 222B sandwiched between the electrode 101 and the electrode 102, a region 222G sandwiched between the electrode 102 and the electrode 103, and a region 222R sandwiched between the electrode 102 and the electrode 104. The partition wall 145 has an insulating property. The partition wall 145 covers end portions of the electrodes 101, 103, and 104 and has openings overlapping with the electrodes. With the partition wall 145, the electrodes provided over the substrate 200 in the regions can be separated into island shapes.

The charge-generation layer 115 can be formed with a material obtained by adding an electron acceptor (acceptor) to a hole-transport material or a material obtained by adding an electron donor (donor) to an electron-transport material. Note that when the conductivity of the charge-generation layer 115 is as high as that of the pair of electrodes, carriers generated in the charge-generation layer 115 might transfer to an adjacent pixel and light emission might occur in the pixel. In order to prevent such false light emission from an adjacent pixel, the charge-generation layer 115 is preferably formed with a material whose conductivity is lower than that of the pair of electrodes.

The light-emitting elements 262*a* and 262*b* each include a substrate 220 provided with an optical element 224B, an optical element 224G, and an optical element 224R in the direction in which light emitted from the region 222B, light emitted from the region 222G, and light emitted from the region 222R are extracted. The light emitted from each region is emitted outside the light-emitting element through each optical element. In other words, the light from the region 222B, the light from the region 222G, and the light from the region 222R are emitted through the optical element 224B, the optical element 224G, and the optical element 224R, respectively.

The optical elements 224B, 224G, and 224R each have a function of selectively transmitting light of a particular color out of incident light. For example, the light emitted from the region 222B through the optical element 224B is blue light, the light emitted from the region 222G through the optical element 224G is green light, and the light emitted from the region 222R through the optical element 224R is red light.

For example, a coloring layer (also referred to as color filter), a band pass filter, a multilayer filter, or the like can be used for the optical elements 224R, 224G, and 224B. Alternatively, color conversion elements can be used as the optical elements. A color conversion element is an optical element that converts incident light into light having a longer wavelength than the incident light. As the color conversion elements, quantum-dot elements can be favorably used. The usage of the quantum dot can increase color reproducibility of the display device.

One or more optical elements may be stacked over each of the optical elements 224R, 224G, and 224B. As another optical element, a circularly polarizing plate, an anti-reflective film, or the like can be provided, for example. A circularly polarizing plate provided on the side where light emitted from the light-emitting element of the display device is extracted can prevent a phenomenon in which light entering from the outside of the display device is reflected inside the display device and returned to the outside. An anti-reflective film can weaken external light reflected by a surface of the display device. This leads to clear observation of light emitted from the display device.

Note that in FIGS. 8A and 8B, blue light (B), green light (G), and red light (R) emitted from the regions through the optical elements are schematically illustrated by arrows of dashed lines.

A light-blocking layer 223 is provided between the optical elements. The light-blocking layer 223 has a function of blocking light emitted from the adjacent regions. Note that a structure without the light-blocking layer 223 may also be employed.

The light-blocking layer 223 has a function of reducing the reflection of external light. The light-blocking layer 223 has a function of preventing mixture of light emitted from an adjacent light-emitting element. As the light-blocking layer 223, a metal, a resin containing black pigment, carbon black, a metal oxide, a composite oxide containing a solid solution of a plurality of metal oxides, or the like can be used.

Note that the optical element 224B and the optical element 224G may overlap with each other in a region where they overlap with the light-blocking layer 223. In addition, the optical element 224G and the optical element 224R may overlap with each other in a region where they overlap with the light-blocking layer 223. In addition, the optical element 224R and the optical element 224B may overlap with each other in a region where they overlap with the light-blocking layer 223.

As for the structures of the substrate 200 and the substrate 220 provided with the optical elements, Embodiment 1 can be referred to.

Furthermore, the light-emitting elements 262*a* and 262*b* have a microcavity structure.

<<Microcavity Structure>>

Light emitted from the light-emitting layer 170 and the light-emitting layer 190 resonates between a pair of electrodes (e.g., the electrode 101 and the electrode 102). The light-emitting layer 170 and the light-emitting layer 190 are formed at such a position as to intensify the light of a desired wavelength among light to be emitted. For example, by adjusting the optical length from a reflective region of the electrode 101 to the light-emitting region of the light-emitting layer 170 and the optical length from a reflective region of the electrode 102 to the light-emitting region of the light-emitting layer 170, the light of a desired wavelength among light emitted from the light-emitting layer 170 can be intensified. By adjusting the optical length from the reflective region of the electrode 101 to the light-emitting region of the light-emitting layer 190 and the optical length from the reflective region of the electrode 102 to the light-emitting region of the light-emitting layer 190, the light of a desired wavelength among light emitted from the light-emitting layer 190 can be intensified. In the case of a light-emitting element in which a plurality of light-emitting layers (here, the light-emitting layers 170 and 190) are stacked, the optical lengths of the light-emitting layers 170 and 190 are preferably optimized.

In each of the light-emitting elements 262*a* and 262*b*, by adjusting the thicknesses of the conductive layers (the conductive layer 101*b*, the conductive layer 103*b*, and the conductive layer 104*b*) in each region, the light of a desired wavelength among light emitted from the light-emitting layers 170 and 190 can be increased. Note that the thickness of at least one of the hole-injection layer 111 and the hole-transport layer 112 or at least one of the electron-injection layer 119 and the electron-transport layer 118 may differ between the regions to increase the light emitted from the light-emitting layers 170 and 190.

For example, in the case where the refractive index of the conductive material having a function of reflecting light in the electrodes 101 to 104 is lower than the refractive index of the light-emitting layer 170 or 190, the thickness of the conductive layer 101*b* of the electrode 101 is adjusted so that the optical length between the electrode 101 and the electrode 102 is $m_B\lambda_B/2$ ($m_B$ is a natural number and AB is the wavelength of light intensified in the region 222B). Similarly, the thickness of the conductive layer 103*b* of the electrode 103 is adjusted so that the optical length between the electrode 103 and the electrode 102 is $m_G\lambda_G/2$ ($m_G$ is a natural number and AG is the wavelength of light intensified in the region 222G). Furthermore, the thickness of the conductive layer 104*b* of the electrode 104 is adjusted so that the optical length between the electrode 104 and the electrode 102 is $m_R\lambda_R/2$ ($m_R$ is a natural number and $\lambda_R$ is the wavelength of light intensified in the region 222R).

In the case where it is difficult to precisely determine the reflective regions of the electrodes 101 to 104, the optical length for increasing the intensity of light emitted from the light-emitting layer 170 or the light-emitting layer 190 may be derived on the assumption that certain regions of the electrodes 101 to 104 are the reflective regions. In the case where it is difficult to precisely determine the light-emitting regions of the light-emitting layer 170 and the light-emitting layer 190, the optical length for increasing the intensity of light emitted from the light-emitting layer 170 and the light-emitting layer 190 may be derived on the assumption that certain regions of the light-emitting layer 170 and the light-emitting layer 190 are the light-emitting regions.

In the above manner, with the microcavity structure, in which the optical length between the pair of electrodes in the respective regions is adjusted, scattering and absorption of light in the vicinity of the electrodes can be suppressed, resulting in high light extraction efficiency.

In the above structure, the conductive layers 101*b*, 103*b*, and 104*b* preferably have a function of transmitting light. The materials of the conductive layers 101*b*, 103*b*, and 104*b* may be the same or different. It is preferable to use the same material for the conductive layer 101*b*, the conductive layer 103*b*, and the conductive layer 104*b* because patterning by etching in the formation process of the electrode 101, the electrode 103, and the electrode 104 can be performed easily. Each of the conductive layers 101*b*, 103*b*, and 104*b* may have a stacked structure of two or more layers.

Since the light-emitting element 262*a* illustrated in FIG. 8A has a top-emission structure, it is preferable that the conductive layer 101*a*, the conductive layer 103*a*, and the conductive layer 104*a* have a function of reflecting light. In addition, it is preferable that the electrode 102 have functions of transmitting light and reflecting light.

Since the light-emitting element 262*b* illustrated in FIG. 8B has a bottom-emission structure, it is preferable that the conductive layer 101*a*, the conductive layer 103*a*, and the conductive layer 104*a* have functions of transmitting light and reflecting light. In addition, it is preferable that the electrode 102 have a function of reflecting light.

In each of the light-emitting elements 262*a* and 262*b*, the conductive layers 101*a*, 103*a*, and 104*a* may be formed of different materials or the same material. When the conductive layers 101*a*, 103*a*, and 104*a* are formed of the same material, manufacturing cost of the light-emitting elements 262*a* and 262*b* can be reduced. Note that each of the conductive layers 101*a*, 103*a*, and 104*a* may have a stacked structure including two or more layers.

At least one of the structures described in Embodiments 1 and 2 is preferably used for at least one of the light-emitting layers 170 and 190 included in the light-emitting elements 262*a* and 262*b*. In this way, the light-emitting elements can have high emission efficiency.

Either or both of the light-emitting layers 170 and 190 may have a stacked structure of two layers like the light-emitting layers 190*a* and 190*b*, for example. Two kinds of light-emitting materials (a first compound and a second compound) for emitting light of different colors are used in the two light-emitting layers, so that light of a plurality of colors can be obtained at the same time. It is particularly preferable to select the light-emitting materials of the light-emitting layers so that white light can be obtained by combining light emissions from the light-emitting layers 170 and 190.

Either or both of the light-emitting layers 170 and 190 may have a stacked structure of three or more layers, in which a layer not including a light-emitting material may be included.

In the above-described manner, by using the light-emitting element 262*a* or 262*b* including the light-emitting layer having at least one of the structures described in Embodiments 1 and 2 in pixels in a display device, a display device with high emission efficiency can be fabricated. Accordingly, the display device including the light-emitting element 262*a* or 262*b* can have low power consumption.

For the other components of the light-emitting elements 262*a* and 262*b*, the components of the light-emitting element 260*a* or 260*b* or the light-emitting element in Embodiments 1 and 2 may be referred to.

<Fabrication Method of Light-Emitting Element>

Next, a method for fabricating a light-emitting element of one embodiment of the present invention is described below with reference to FIGS. 9A to 9C and FIGS. 10A to 10C. Here, a method for fabricating the light-emitting element 262*a* illustrated in FIG. 8A is described.

FIGS. 9A to 9C and FIGS. 10A to 10C are cross-sectional views illustrating a method for fabricating the light-emitting element of one embodiment of the present invention.

The method for fabricating the light-emitting element 262*a* described below includes first to seventh steps.

<<First Step>>

Figure 9A:
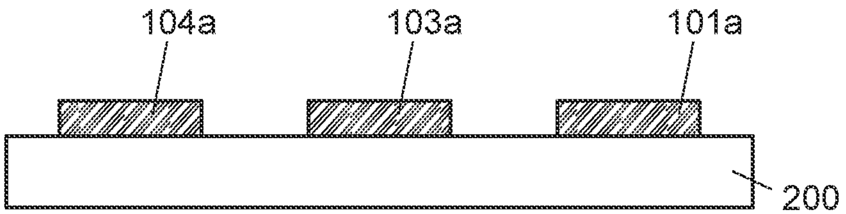
FIGS. 9A to 9C are schematic cross-sectional views illustrating a method for manufacturing a light-emitting element of one embodiment of the present invention.

In the first step, the electrodes (specifically the conductive layer 101*a* of the electrode 101, the conductive layer 103*a* of the electrode 103, and the conductive layer 104*a* of the electrode 104) of the light-emitting elements are formed over the substrate 200 (see FIG. 9A).

In this embodiment, a conductive layer having a function of reflecting light is formed over the substrate 200 and processed into a desired shape; whereby the conductive layers 101*a*, 103*a*, and 104*a* are formed. As the conductive layer having a function of reflecting light, an alloy film of silver, palladium, and copper (also referred to as an Ag—Pd—Cu film or APC) is used. The conductive layers 101*a*, 103*a*, and 104*a* are preferably formed through a step of processing the same conductive layer, because the manufacturing cost can be reduced.

Note that a plurality of transistors may be formed over the substrate 200 before the first step. The plurality of transistors may be electrically connected to the conductive layers 101*a*, 103*a*, and 104*a*.

<<Second Step>>

Figure 9B:
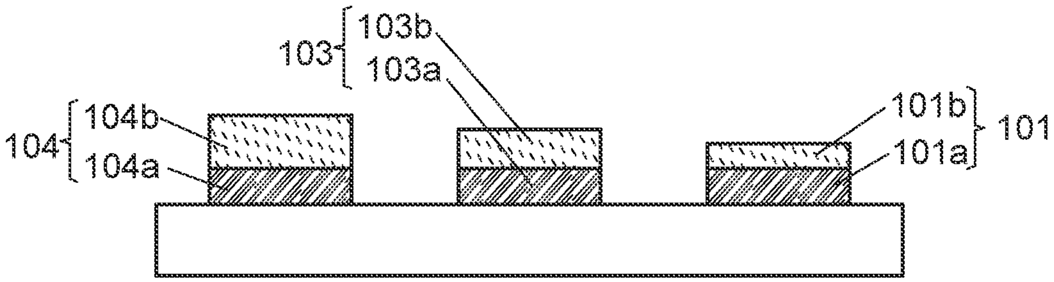

In the second step, the transparent conductive layer 101*b* having a function of transmitting light is formed over the conductive layer 101*a* of the electrode 101, the transparent conductive layer 103*b* having a function of transmitting light is formed over the conductive layer 103*a* of the electrode 103, and the transparent conductive layer 104*b* having a function of transmitting light is formed over the conductive layer 104*a* of the electrode 104 (see FIG. 9B).

In this embodiment, the conductive layers 101*b*, 103*b*, and 104*b* each having a function of transmitting light are formed over the conductive layers 101*a*, 103*a*, and 104*a* each having a function of reflecting light, respectively, whereby the electrode 101, the electrode 103, and the electrode 104 are formed. As the conductive layers 101*b*, 103*b*, and 104*b*, ITSO films are used.

The conductive layers 101*b*, 103*b*, and 104*b* having a function of transmitting light may be formed in a plurality of steps. When the conductive layers 101*b*, 103*b*, and 104*b* having a function of transmitting light are formed in a plurality of steps, they can be formed to have thicknesses which enable microcavity structures appropriate in the respective regions.

<<Third Step>>

Figure 9C:
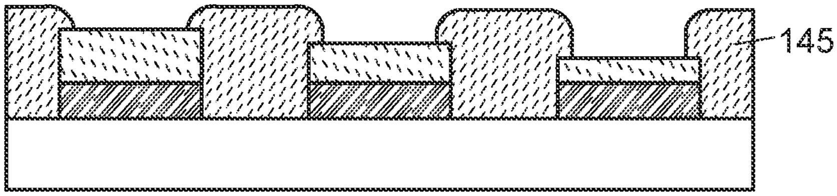

In the third step, the partition wall 145 that covers end portions of the electrodes of the light-emitting element is formed (see FIG. 9C).

The partition wall 145 includes an opening overlapping with the electrode. The conductive film exposed by the opening functions as the anode of the light-emitting element. As the partition wall 145, a polyimide-based resin is used in this embodiment.

In the first to third steps, since there is no possibility of damaging the EL layer (a layer containing an organic compound), a variety of film formation methods and micromachining technologies can be employed. In this embodiment, a reflective conductive layer is formed by a sputtering method, a pattern is formed over the conductive layer by a lithography method, and then the conductive layer is processed into an island shape by a dry etching method or a wet etching method to form the conductive layer 101*a* of the electrode 101, the conductive layer 103*a* of the electrode 103, and the conductive layer 104*a* of the electrode 104. Then, a transparent conductive film is formed by a sputtering method, a pattern is formed over the transparent conductive film by a lithography method, and then the transparent conductive film is processed into island shapes by a wet etching method to form the electrodes 101, 103, and 104.

<<Fourth Step>>

Figure 10A:
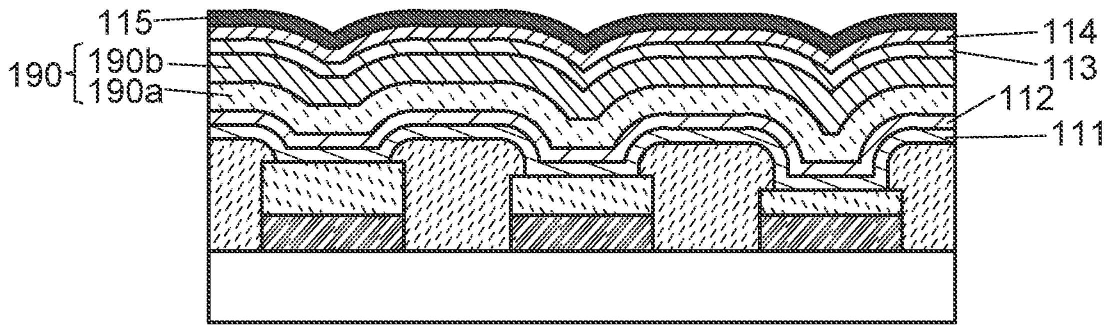
FIGS. 10A to 10C are schematic cross-sectional views illustrating the method for manufacturing a light-emitting element of one embodiment of the present invention.

In the fourth step, the hole-injection layer 111, the hole-transport layer 112, the light-emitting layer 190, the electron-transport layer 113, the electron-injection layer 114, and the charge-generation layer 115 are formed (see FIG. 10A).

The hole-injection layer 111 can be formed by co-evaporating a hole-transport material and a material containing an acceptor substance. Note that a co-evaporation method is an evaporation method in which a plurality of different substances are concurrently vaporized from respective different evaporation sources. The hole-transport layer 112 can be formed by evaporating a hole-transport material.

The light-emitting layer 190 can be formed by evaporating a guest material that emits light of at least one color selected from violet, blue, blue green, green, yellow green, yellow, orange, and red. As the guest material, a fluorescent or phosphorescent organic material can be used. The structure of the light-emitting layer described in Embodiments 1 and 2 is preferably employed. The light-emitting layer 190 may have a two-layer structure. In such a case, the two light-emitting layers each preferably contain a light-emitting material that emits light of a different color.

The electron-transport layer 113 can be formed by evaporating a substance having a high electron-transport property. The electron-injection layer 114 can be formed by evaporating a substance having a high electron-injection property.

The charge-generation layer 115 can be formed by evaporating a material obtained by adding an electron acceptor (acceptor) to a hole-transport material or a material obtained by adding an electron donor (donor) to an electron-transport material.

<<Fifth Step>>

Figure 10B:
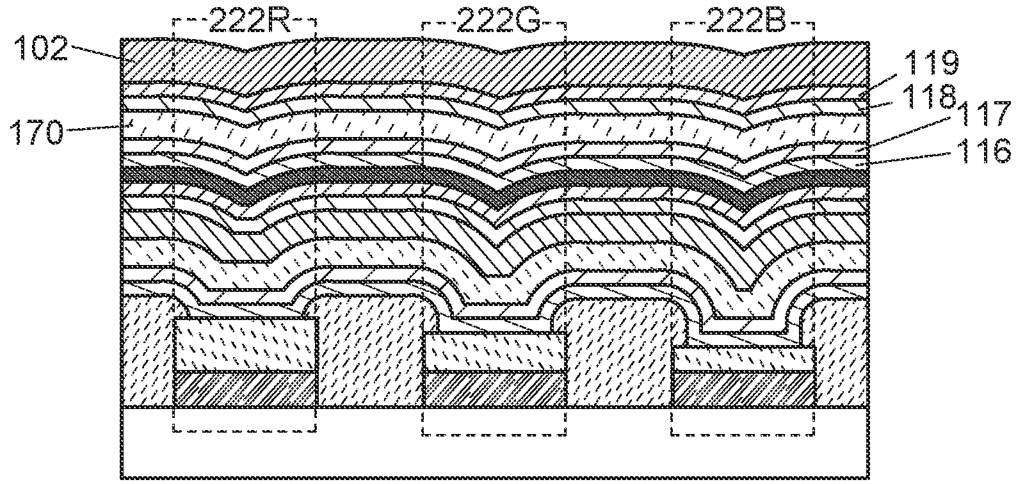

In the fifth step, the hole-injection layer 116, the hole-transport layer 117, the light-emitting layer 170, the electron-transport layer 118, the electron-injection layer 119, and the electrode 102 are formed (see FIG. 10B).

The hole-injection layer 116 can be formed by using a material and a method which are similar to those of the hole-injection layer 111. The hole-transport layer 117 can be formed by using a material and a method which are similar to those of the hole-transport layer 112.

The light-emitting layer 170 can be formed by evaporating a guest material that emits light of at least one color selected from violet, blue, blue green, green, yellow green, yellow, orange, and red. As the guest material, a fluorescent or phosphorescent organic compound can be used. The structure of the light-emitting layer described in Embodiments 1 and 2 is preferably employed. Note that at least one of the light-emitting layer 170 and the light-emitting layer 190 preferably has the structure of a light-emitting layer described in Embodiment 1. The light-emitting layer 170 and the light-emitting layer 190 preferably include light-emitting organic compounds exhibiting light of different colors.

The electron-transport layer 118 can be formed by using a material and a method which are similar to those of the electron-transport layer 113. The electron-injection layer 119 can be formed by using a material and a method which are similar to those of the electron-injection layer 114.

The electrode 102 can be formed by stacking a reflective conductive film and a light-transmitting conductive film. The electrode 102 may have a single-layer structure or a stacked-layer structure.

Through the above-described steps, the light-emitting element including the region 222B, the region 222G, and the region 222R over the electrode 101, the electrode 103, and the electrode 104, respectively, are formed over the substrate 200.

<<Sixth Step>>

Figure 10C:
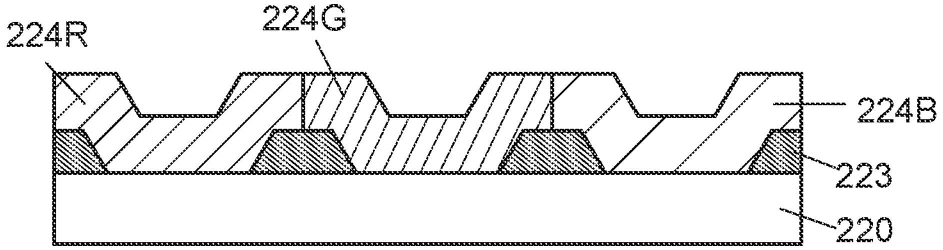

In the sixth step, the light-blocking layer 223, the optical element 224B, the optical element 224G, and the optical element 224R are formed over the substrate 220 (see FIG. 10C).

As the light-blocking layer 223, a resin film containing black pigment is formed in a desired region. Then, the optical element 224B, the optical element 224G, and the optical element 224R are formed over the substrate 220 and the light-blocking layer 223.

As the optical element 224B, a resin film containing blue pigment is formed in a desired region. As the optical element 224G, a resin film containing green pigment is formed in a desired region. As the optical element 224R, a resin film containing red pigment is formed in a desired region.

<<Seventh Step>>

In the seventh step, the light-emitting element formed over the substrate 200 is attached to the light-blocking layer 223, the optical element 224B, the optical element 224G, and the optical element 224R formed over the substrate 220, and sealed with a sealant (not illustrated).

Through the above-described steps, the light-emitting element 262*a* illustrated in FIG. 8A can be formed.

The structure described in this embodiment can be used in combination with any of the structures described in the other embodiments as appropriate.

Embodiment 4

In this embodiment, a display device of one embodiment of the present invention will be described below with reference to FIGS. 11A and 11B, FIGS. 12A and 12B, FIG. 13, FIGS. 14A and 14B, FIGS. 15A and 15B, FIG. 16, FIGS. 17A and 17B, FIG. 18, and FIGS. 19A and 19B.

<Structure Example 1 of Display Device>

Figure 11A:
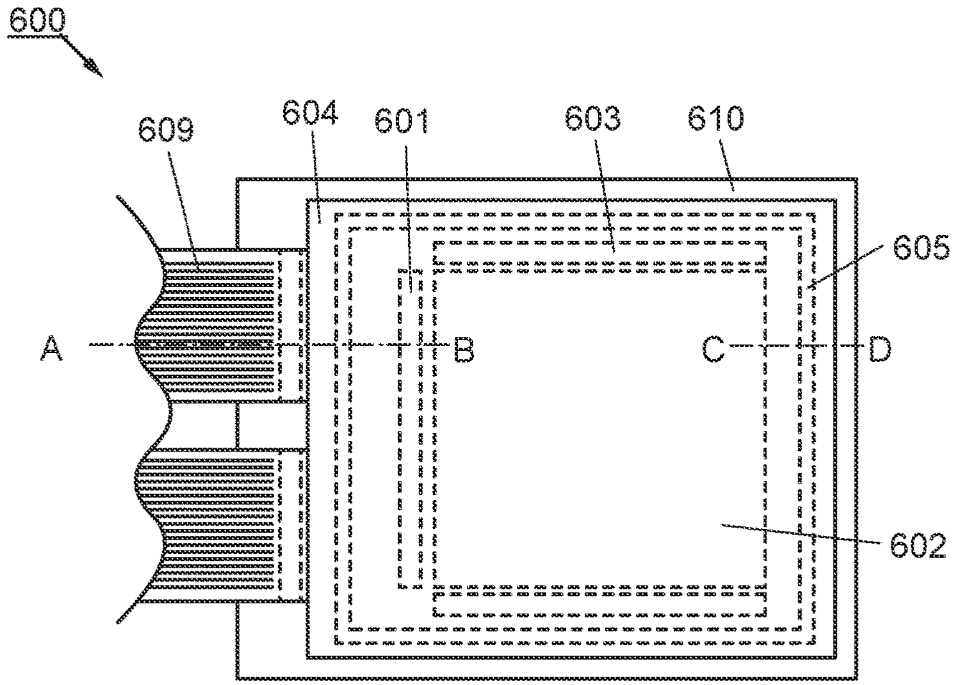
FIGS. 11A and 11B are a top view and a schematic cross-sectional view illustrating a display device of one embodiment of the present invention.
Figure 11B:
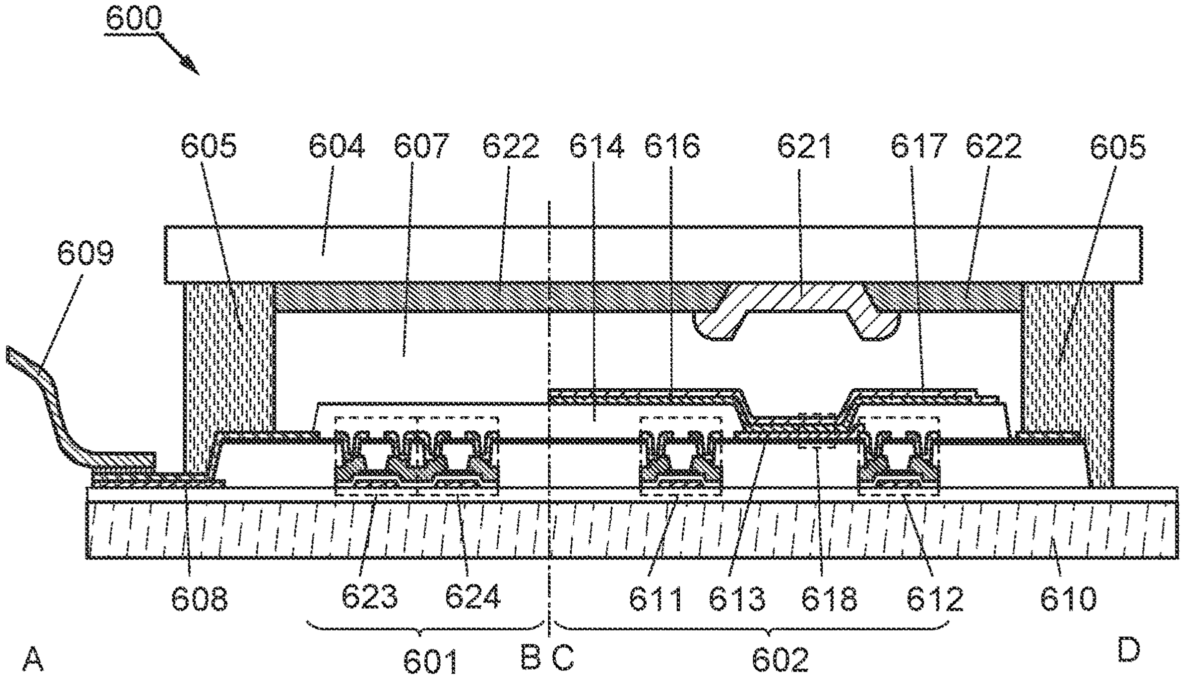

FIG. 11A is a top view illustrating a display device 600 and FIG. 11B is a cross-sectional view taken along the dashed-dotted line A-B and the dashed-dotted line C-D in FIG. 11A. The display device 600 includes driver circuit portions (a signal line driver circuit portion 601 and a scan line driver circuit portion 603) and a pixel portion 602. Note that the signal line driver circuit portion 601, the scan line driver circuit portion 603, and the pixel portion 602 have a function of controlling light emission from a light-emitting element.

The display device 600 also includes an element substrate 610, a sealing substrate 604, a sealant 605, a region 607 surrounded by the sealant 605, a lead wiring 608, and an FPC 609.

Note that the lead wiring 608 is a wiring for transmitting signals to be input to the signal line driver circuit portion 601 and the scan line driver circuit portion 603 and for receiving a video signal, a clock signal, a start signal, a reset signal, and the like from the FPC 609 serving as an external input terminal. Although only the FPC 609 is illustrated here, the FPC 609 may be provided with a printed wiring board (PWB).

As the signal line driver circuit portion 601, a CMOS circuit in which an n-channel transistor 623 and a p-channel transistor 624 are combined is formed. As the signal line driver circuit portion 601 or the scan line driver circuit portion 603, various types of circuits such as a CMOS circuit, a PMOS circuit, or an NMOS circuit can be used. Although a driver in which a driver circuit portion is formed and a pixel are formed over the same surface of a substrate in the display device of this embodiment, the driver circuit portion is not necessarily formed over the substrate and can be formed outside the substrate.

The pixel portion 602 includes a switching transistor 611, a current control transistor 612, and a lower electrode 613 electrically connected to a drain of the current control transistor 612. Note that a partition wall 614 is formed to cover end portions of the lower electrode 613. As the partition wall 614, for example, a positive type photosensitive acrylic resin film can be used.

In order to obtain favorable coverage, the partition wall 614 is formed to have a curved surface with curvature at its upper or lower end portion. For example, in the case of using a positive photosensitive acrylic as a material of the partition wall 614, it is preferable that only the upper end portion of the partition wall 614 have a curved surface with curvature (the radius of the curvature being 0.2 μm to 3 μm). As the partition wall 614, either a negative photosensitive resin or a positive photosensitive resin can be used.

Note that there is no particular limitation on a structure of each of the transistors (the transistors 611, 612, 623, and 624). For example, a staggered transistor can be used. In addition, there is no particular limitation on the polarity of these transistors. For these transistors, n-channel and p-channel transistors may be used, or either n-channel transistors or p-channel transistors may be used, for example. Furthermore, there is no particular limitation on the crystallinity of a semiconductor film used for these transistors. For example, an amorphous semiconductor film or a crystalline semiconductor film may be used. Examples of a semiconductor material include Group 14 semiconductors (e.g., a semiconductor including silicon), compound semiconductors (including oxide semiconductors), organic semiconductors, and the like. For example, it is preferable to use an oxide semiconductor that has an energy gap of 2 eV or more, preferably 2.5 eV or more and further preferably 3 eV or more, for the transistors, so that the off-state current of the transistors can be reduced. Examples of the oxide semiconductor include an In—Ga oxide and an In-M-Zn oxide (M is aluminum (Al), gallium (Ga), yttrium (Y), zirconium (Zr), lanthanum (La), cerium (Ce), tin (Sn), hafnium (Hf), or neodymium (Nd)). An EL layer 616 and an upper electrode 617 are formed over the lower electrode 613. Here, the lower electrode 613 functions as an anode and the upper electrode 617 functions as a cathode.

In addition, the EL layer 616 is formed by various methods such as an evaporation method with an evaporation mask, an ink-jet method, or a spin coating method. As another material included in the EL layer 616, a low molecular compound or a high molecular compound (including an oligomer or a dendrimer) may be used.

Note that a light-emitting element 618 is formed with the lower electrode 613, the EL layer 616, and the upper electrode 617. The light-emitting element 618 preferably has any of the structures described in Embodiments 1 to 3. In the case where the pixel portion includes a plurality of light-emitting elements, the pixel portion may include both any of the light-emitting elements described in Embodiments 1 to 3 and a light-emitting element having a different structure.

When the sealing substrate 604 and the element substrate 610 are attached to each other with the sealant 605, the light-emitting element 618 is provided in the region 607 surrounded by the element substrate 610, the sealing substrate 604, and the sealant 605. The region 607 is filled with a filler. In some cases, the region 607 is filled with an inert gas (nitrogen, argon, or the like) or filled with an ultraviolet curable resin or a thermosetting resin which can be used for the sealant 605. For example, a polyvinyl chloride (PVC)-based resin, an acrylic-based resin, a polyimide-based resin, an epoxy-based resin, a silicone-based resin, a polyvinyl butyral (PVB)-based resin, or an ethylene vinyl acetate (EVA)-based resin can be used. It is preferable that the sealing substrate be provided with a recessed portion and a desiccant be provided in the recessed portion, in which case deterioration due to influence of moisture can be inhibited. An optical element 621 is provided below the sealing substrate 604 to overlap with the light-emitting element 618. A light-blocking layer 622 is provided below the sealing substrate 604. The structures of the optical element 621 and the light-blocking layer 622 can be the same as those of the optical element and the light-blocking layer in Embodiment 3, respectively.

An epoxy-based resin or glass frit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), poly(vinyl fluoride) (PVF), polyester, acrylic, or the like can be used.

In the above-described manner, the display device including any of the light-emitting elements and the optical elements which are described in Embodiments 1 to 3 can be obtained.

<Structure Example 2 of Display Device>

Next, another example of the display device is described with reference to FIGS. 12A and 12B and FIG. 13. Note that FIGS. 12A and 12B and FIG. 13 are each a cross-sectional view of a display device of one embodiment of the present invention.

Figure 12A:
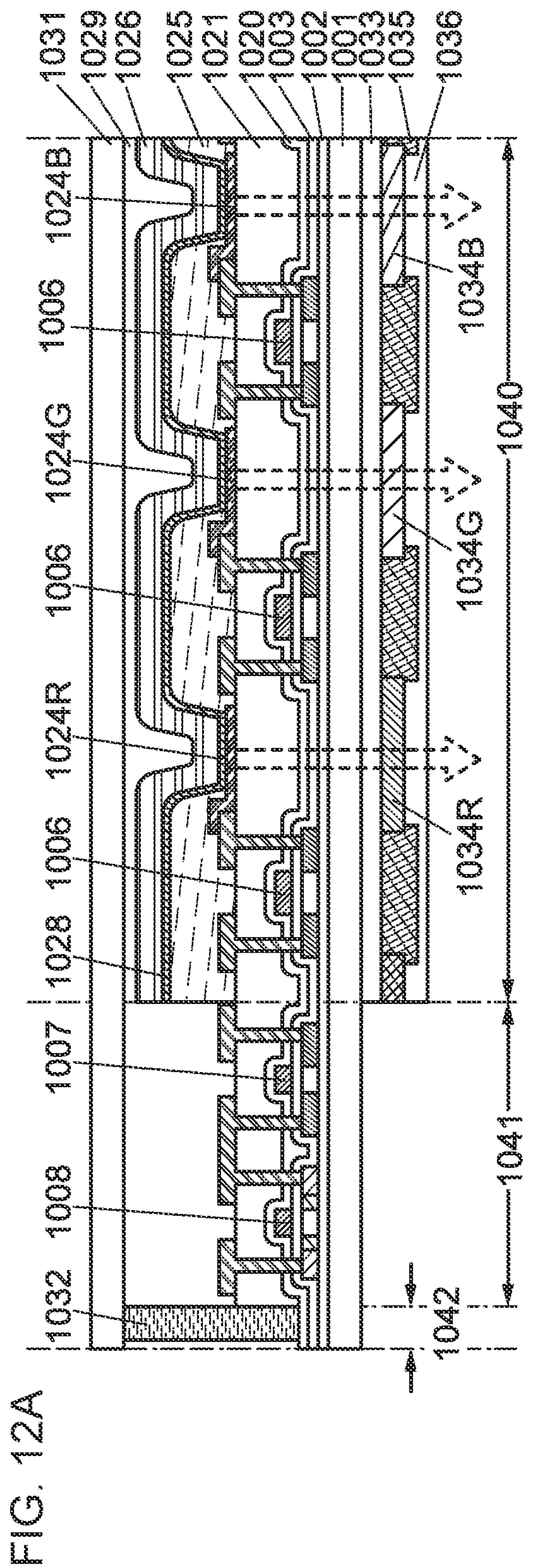
FIGS. 12A and 12B are each a schematic cross-sectional view illustrating a display device of one embodiment of the present invention.
Figure 13:
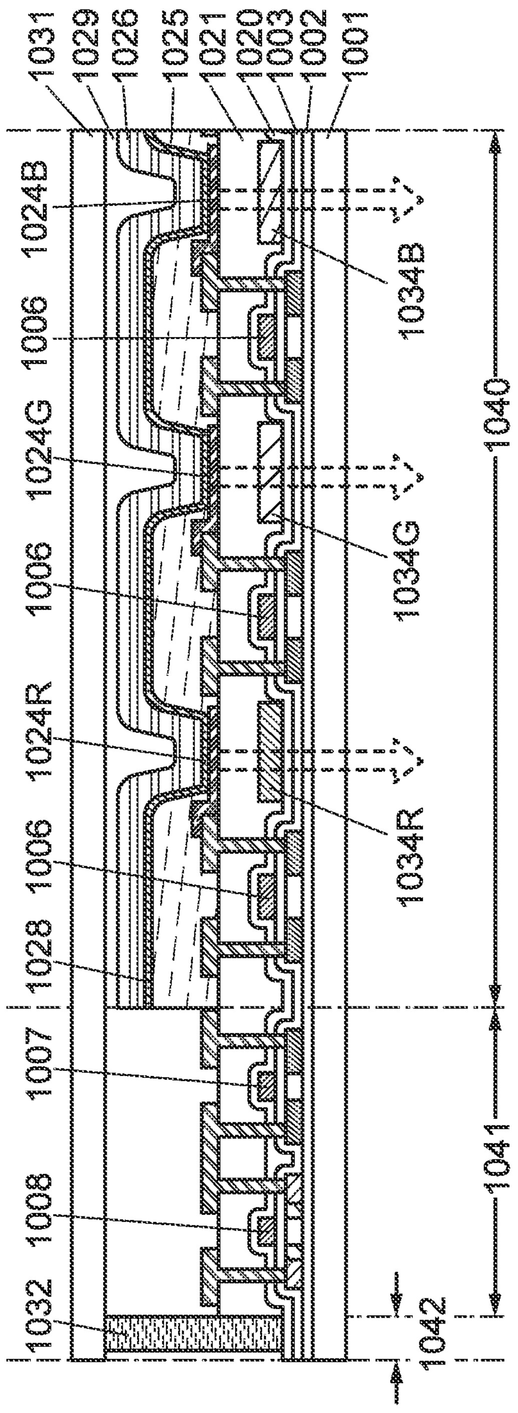
FIG. 13 is a schematic cross-sectional view illustrating a display device of one embodiment of the present invention.

In FIG. 12A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, lower electrodes 1024R, 1024G, and 1024B of light-emitting elements, a partition wall 1025, an EL layer 1028, an upper electrode 1026 of the light-emitting elements, a sealing layer 1029, a sealing substrate 1031, a sealant 1032, and the like are illustrated.

In FIG. 12A, examples of the optical elements, coloring layers (a red coloring layer 1034R, a green coloring layer 1034G, and a blue coloring layer 1034B) are provided on a transparent base material 1033. Further, a light-blocking layer 1035 may be provided. The transparent base material 1033 provided with the coloring layers and the light-blocking layer is positioned and fixed to the substrate 1001. Note that the coloring layers and the light-blocking layer are covered with an overcoat layer 1036. In the structure in FIG. 12A, red light, green light, and blue light transmit the coloring layers, and thus an image can be displayed with the use of pixels of three colors.

Figure 12B:
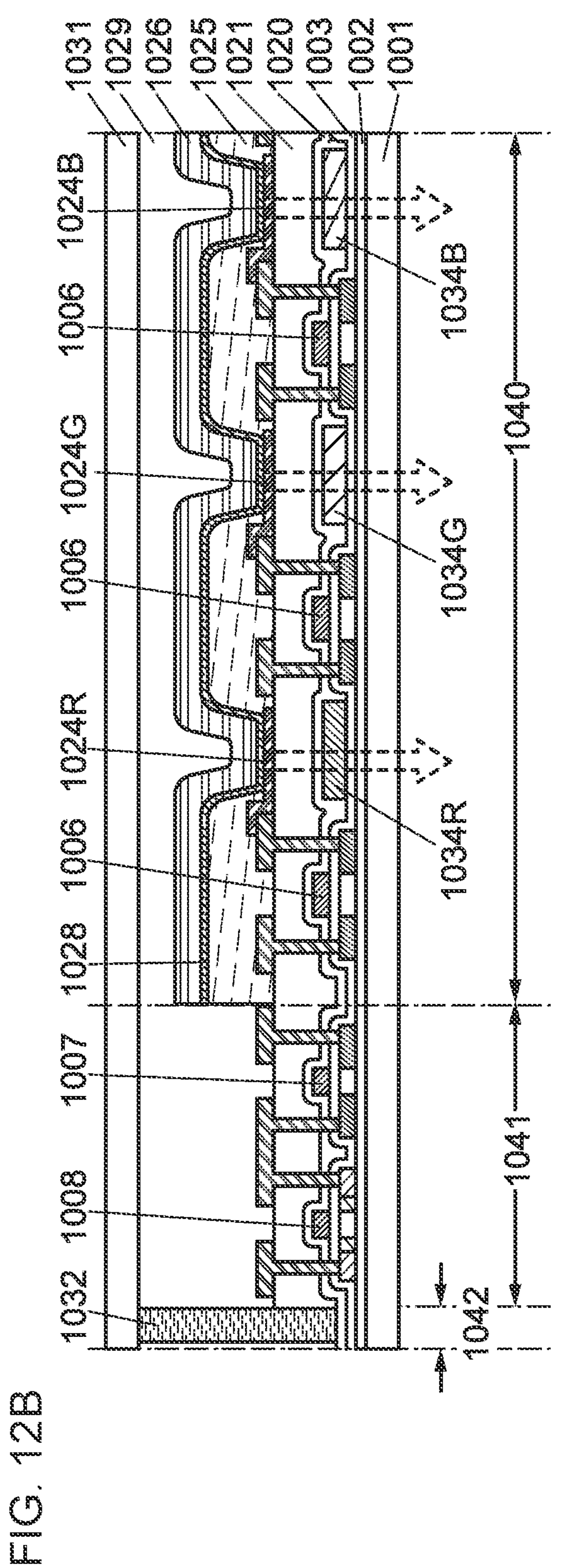

FIG. 12B illustrates an example in which, as examples of the optical elements, the coloring layers (the red coloring layer 1034R, the green coloring layer 1034G, and the blue coloring layer 1034B) are provided between the gate insulating film 1003 and the first interlayer insulating film 1020. As in this structure, the coloring layers may be provided between the substrate 1001 and the sealing substrate 1031.

FIG. 13 illustrates an example in which, as examples of the optical elements, the coloring layers (the red coloring layer 1034R, the green coloring layer 1034G, and the blue coloring layer 1034B) are provided between the first interlayer insulating film 1020 and the second interlayer insulating film 1021. As in this structure, the coloring layers may be provided between the substrate 1001 and the sealing substrate 1031.

The above-described display device has a structure in which light is extracted from the substrate 1001 side where the transistors are formed (a bottom-emission structure), but may have a structure in which light is extracted from the sealing substrate 1031 side (a top-emission structure).

<Structure Example 3 of Display Device>

Figure 14A:
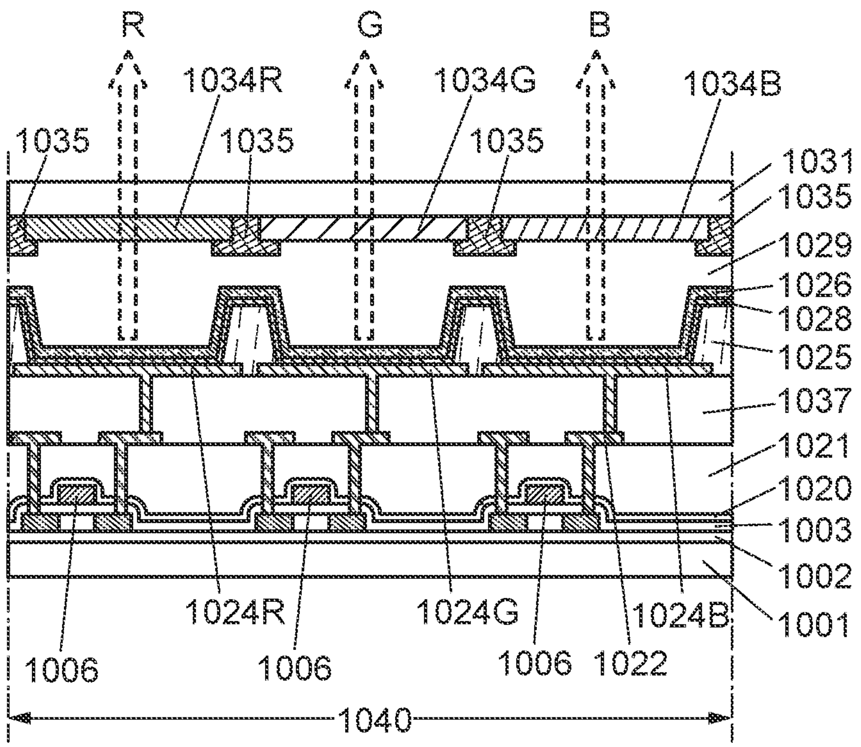
FIGS. 14A and 14B are schematic cross-sectional views each illustrating a display device of one embodiment of the present invention.
Figure 14B:
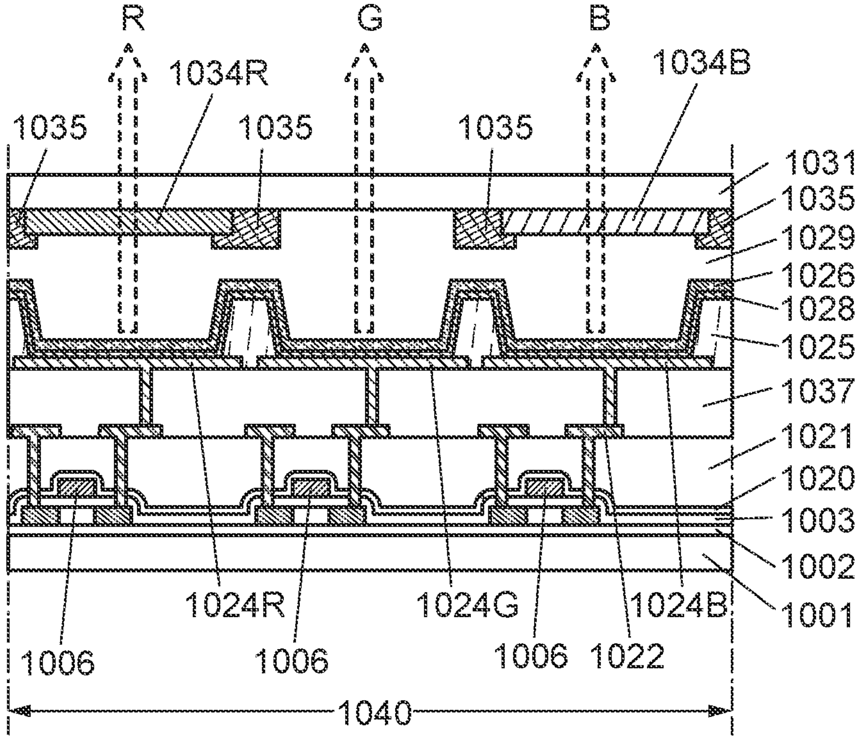

FIGS. 14A and 14B are each an example of a cross-sectional view of a display device having a top emission structure. Note that FIGS. 14A and 14B are each a cross-sectional view illustrating the display device of one embodiment of the present invention, and the driver circuit portion 1041, the peripheral portion 1042, and the like, which are illustrated in FIGS. 12A and 12B and FIG. 13, are not illustrated therein.

In this case, as the substrate 1001, a substrate that does not transmit light can be used. The process up to the step of forming a connection electrode which connects the transistor and the anode of the light-emitting element is performed in a manner similar to that of the display device having a bottom-emission structure. Then, a third interlayer insulating film 1037 is formed to cover an electrode 1022. This insulating film may have a planarization function. The third interlayer insulating film 1037 can be formed using a material similar to that of the second interlayer insulating film, or can be formed using any other various materials.

The lower electrodes 1024R, 1024G, and 1024B of the light-emitting elements each function as an anode here, but may function as a cathode. Further, in the case of a display device having a top-emission structure as illustrated in FIGS. 14A and 14B, the lower electrodes 1024R, 1024G, and 1024B preferably have a function of reflecting light. The upper electrode 1026 is provided over the EL layer 1028. It is preferable that the upper electrode 1026 have a function of reflecting light and a function of transmitting light and that a microcavity structure be used between the upper electrode 1026 and the lower electrodes 1024R, 1024G, and 1024B, in which case the intensity of light having a specific wavelength is increased.

In the case of a top-emission structure as illustrated in FIG. 14A, sealing can be performed with the sealing substrate 1031 on which the coloring layers (the red coloring layer 1034R, the green coloring layer 1034G, and the blue coloring layer 1034B) are provided. The sealing substrate 1031 may be provided with the light-blocking layer 1035 which is positioned between pixels. Note that a light-transmitting substrate is favorably used as the sealing substrate 1031.

FIG. 14A illustrates the structure provided with the light-emitting elements and the coloring layers for the light-emitting elements as an example; however, the structure is not limited thereto. For example, as shown in FIG. 14B, a structure including the red coloring layer 1034R and the blue coloring layer 1034B but not including a green coloring layer may be employed to achieve full color display with the three colors of red, green, and blue. The structure as illustrated in FIG. 14A where the light-emitting elements are provided with the coloring layers is effective to suppress reflection of external light. In contrast, the structure as illustrated in FIG. 14B where the light-emitting elements are provided with the red coloring layer and the blue coloring layer and without the green coloring layer is effective to reduce power consumption because of small energy loss of light emitted from the green light-emitting element.

<Structure Example 4 of Display Device>

Figure 15A:
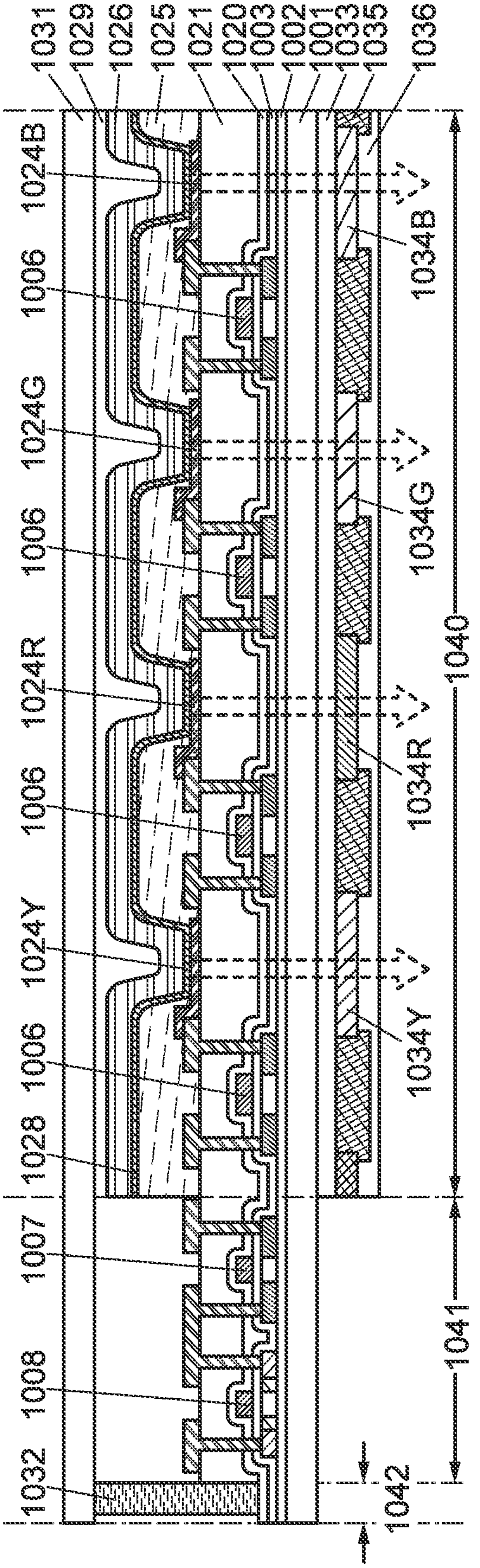
FIGS. 15A and 15B are schematic cross-sectional views illustrating a display device of one embodiment of the present invention.
Figure 15B:
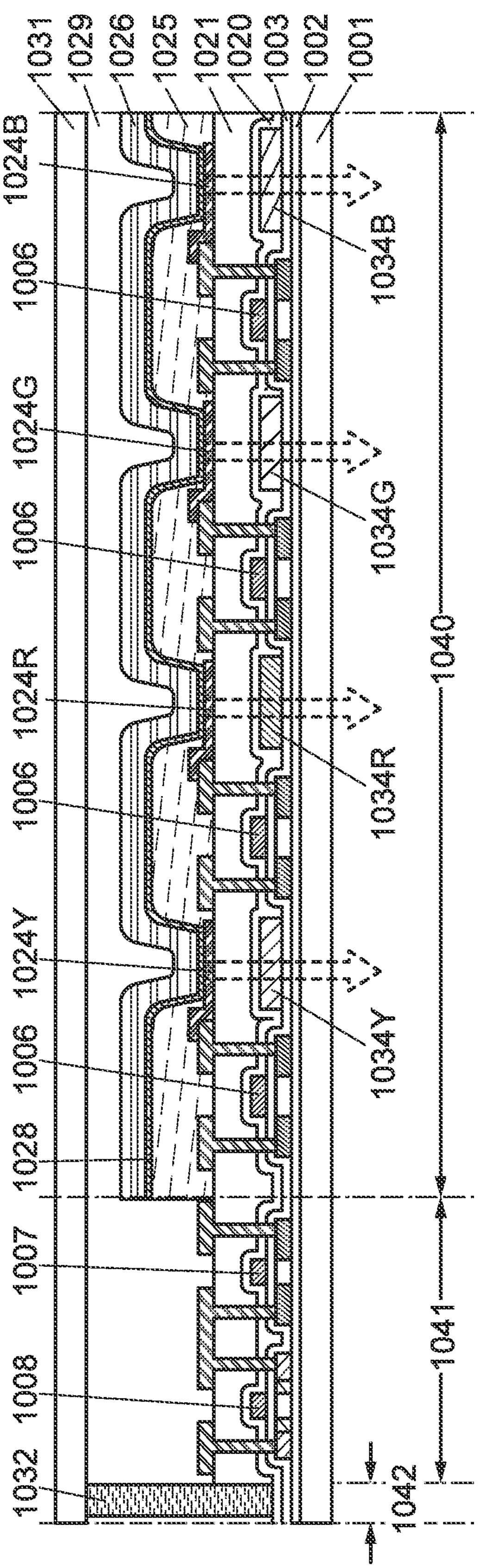
Figure 16:
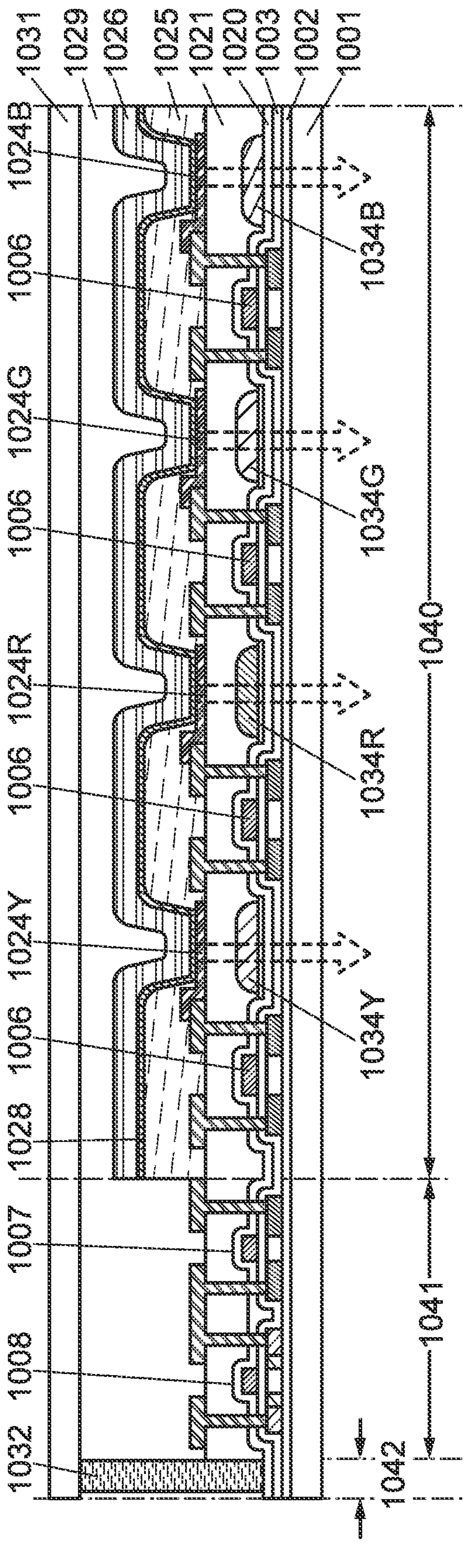
FIG. 16 is a schematic cross-sectional view illustrating a display device of one embodiment of the present invention.

Although a display device including sub-pixels of three colors (red, green, and blue) is described above, the number of colors of sub-pixels may be four (red, green, blue, and yellow, or red, green, blue, and white). FIGS. 15A and 15B, FIG. 16, and FIGS. 17A and 17B illustrate structures of display devices each including the lower electrodes 1024R, 1024G, 1024B, and 1024Y. FIGS. 15A and 15B and FIG. 16 each illustrate a display device having a structure in which light is extracted from the substrate 1001 side on which transistors are formed (bottom-emission structure), and FIGS. 17A and 17B each illustrate a display device having a structure in which light is extracted from the sealing substrate 1031 side (top-emission structure).

FIG. 15A illustrates an example of a display device in which optical elements (the coloring layer 1034R, the coloring layer 1034G, the coloring layer 1034B, and a coloring layer 1034Y) are provided on the transparent base material 1033. FIG. 15B illustrates an example of a display device in which optical elements (the coloring layer 1034R, the coloring layer 1034G, the coloring layer 1034B, and the coloring layer 1034Y) are provided between the gate insulating film 1003 and the first interlayer insulating film 1020. FIG. 16 illustrates an example of a display device in which optical elements (the coloring layer 1034R, the coloring layer 1034G, the coloring layer 1034B, and the coloring layer 1034Y) are provided between the first interlayer insulating film 1020 and the second interlayer insulating film 1021.

The coloring layer 1034R transmits red light, the coloring layer 1034G transmits green light, and the coloring layer 1034B transmits blue light. The coloring layer 1034Y transmits yellow light or transmits light of a plurality of colors selected from blue, green, yellow, and red. When the coloring layer 1034Y can transmit light of a plurality of colors selected from blue, green, yellow, and red, light released from the coloring layer 1034Y may be white light. Since the light-emitting element which transmits yellow or white light has high emission efficiency, the display device including the coloring layer 1034Y can have lower power consumption.

Figure 17A:
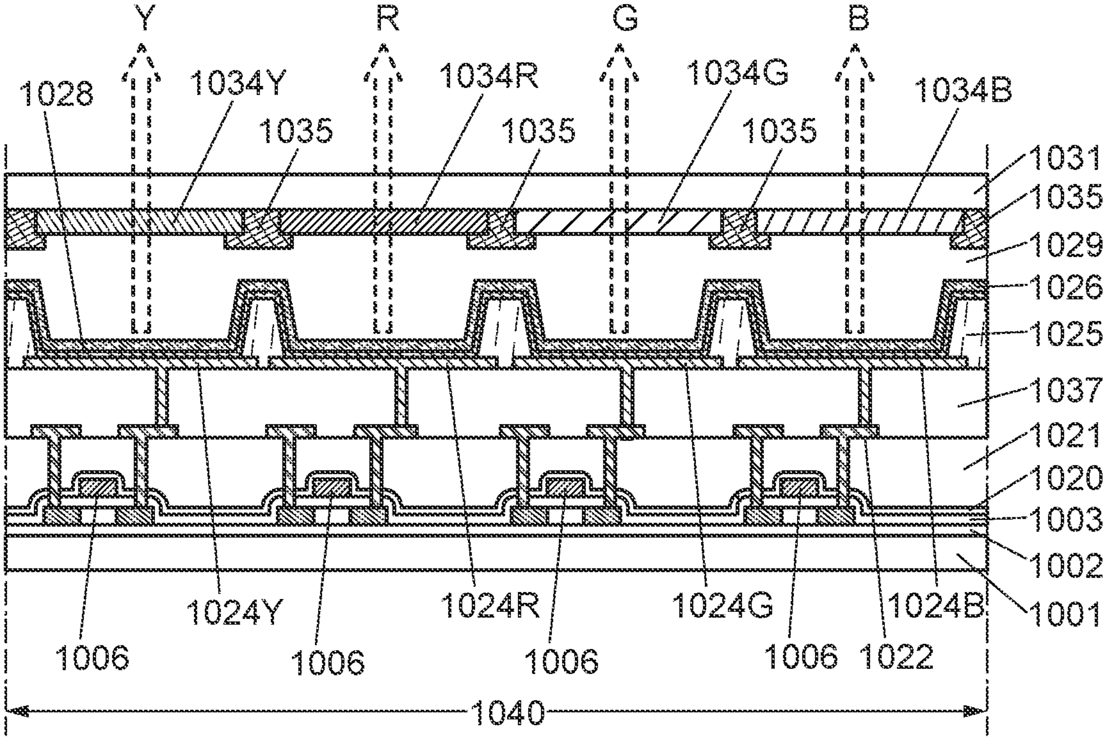
FIGS. 17A and 17B are each a schematic cross-sectional view illustrating a display device of one embodiment of the present invention.
Figure 17B:
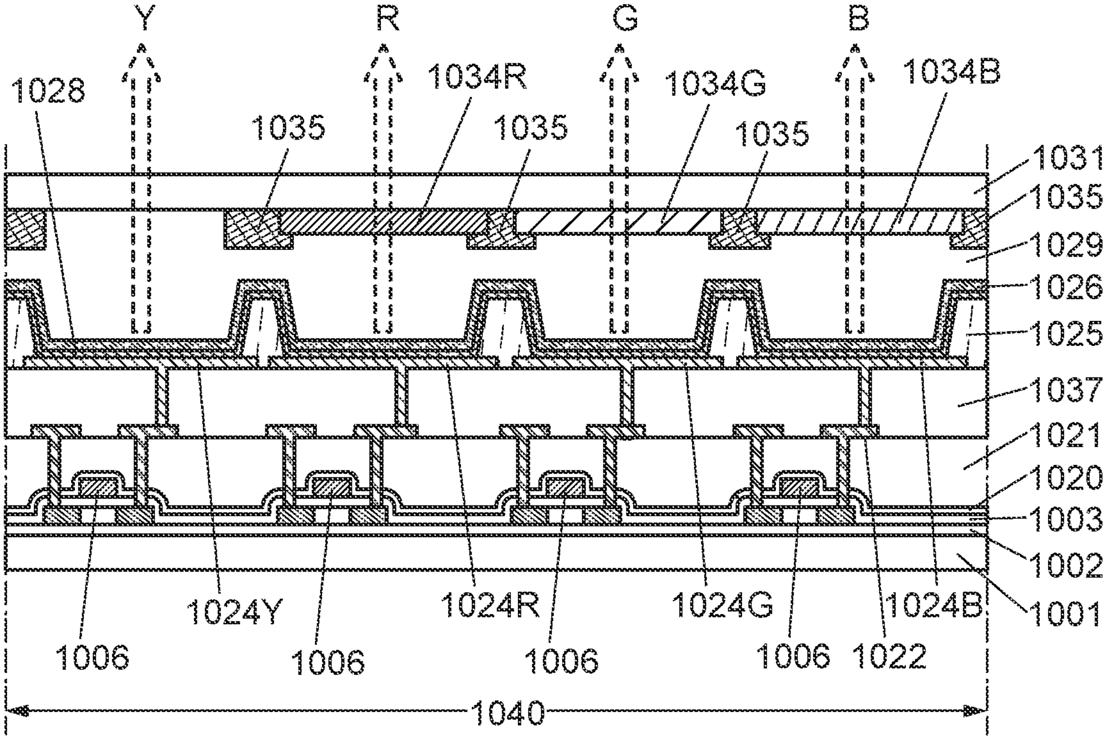

In the top-emission display devices illustrated in FIGS. 17A and 17B, a light-emitting element including the lower electrode 1024Y preferably has a microcavity structure between the lower electrode 1024Y and the upper electrode 1026 as in the display device illustrated in FIG. 14A. In the display device illustrated in FIG. 17A, sealing can be performed with the sealing substrate 1031 on which the coloring layers (the red coloring layer 1034R, the green coloring layer 1034G, the blue coloring layer 1034B, and the yellow coloring layer 1034Y) are provided.

Light emitted through the microcavity and the yellow coloring layer 1034Y has an emission spectrum in a yellow region. Since yellow is a color with a high luminosity factor, a light-emitting element emitting yellow light has high emission efficiency. Therefore, the display device of FIG. 17A can reduce power consumption.

FIG. 17A illustrates the structure provided with the light-emitting elements and the coloring layers for the light-emitting elements as an example; however, the structure is not limited thereto. For example, as shown in FIG. 17B, a structure including the red coloring layer 1034R, the green coloring layer 1034G, and the blue coloring layer 1034B but not including a yellow coloring layer may be employed to achieve full color display with the four colors of red, green, blue, and yellow or of red, green, blue, and white. The structure as illustrated in FIG. 17A where the light-emitting elements are provided with the coloring layers is effective to suppress reflection of external light. In contrast, the structure as illustrated in FIG. 17B where the light-emitting elements are provided with the red coloring layer, the green coloring layer, and the blue coloring layer and without the yellow coloring layer is effective to reduce power consumption because of small energy loss of light emitted from the yellow or white light-emitting element.

<Structure Example 5 of Display Device>

Figure 18:
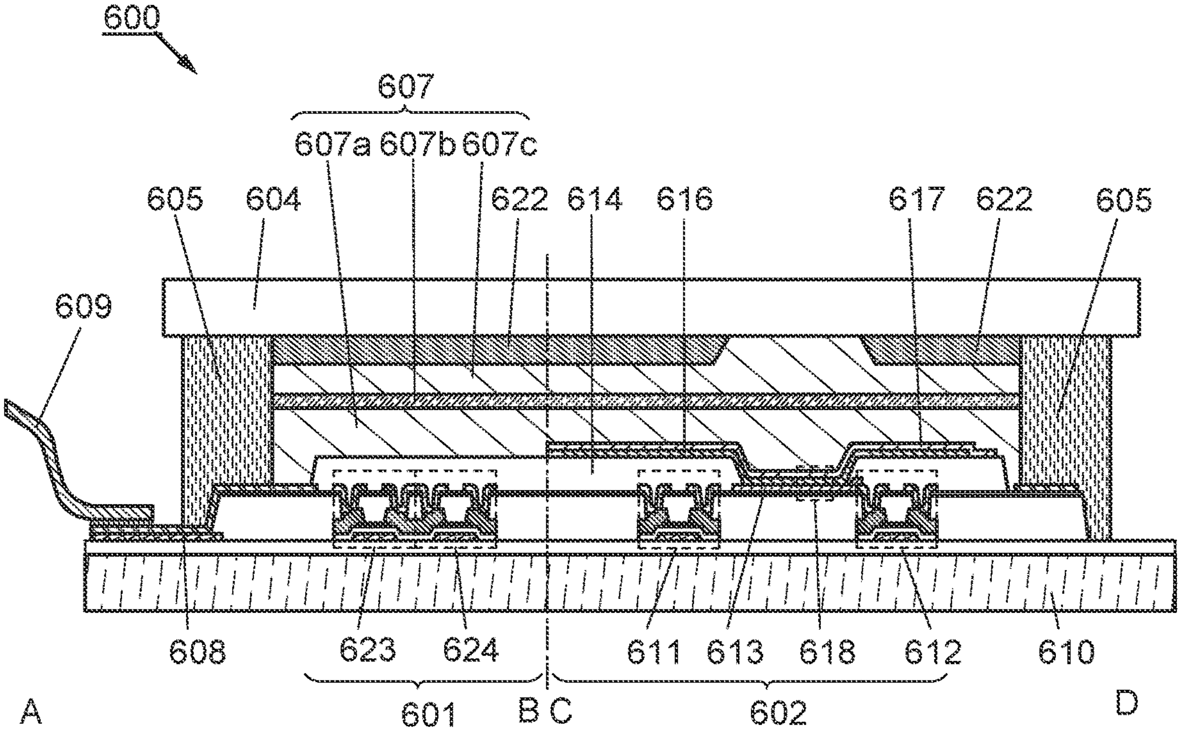
FIG. 18 is a schematic cross-sectional view illustrating a display device of one embodiment of the present invention.

Next, a display device of another embodiment of the present invention is described with reference to FIG. 18. FIG. 18 is a cross-sectional view taken along the dashed-dotted line A-B and the dashed-dotted line C-D in FIG. 11A. Note that in FIG. 18, portions having functions similar to those of portions in FIG. 11B are given the same reference numerals as in FIG. 11B, and a detailed description of the portions is omitted.

The display device 600 in FIG. 18 includes a sealing layer 607*a*, a sealing layer 607*b*, and a sealing layer 607*c* in a region 607 surrounded by the element substrate 610, the sealing substrate 604, and the sealant 605. For one or more of the sealing layer 607*a*, the sealing layer 607*b*, and the sealing layer 607*c*, a resin such as a polyvinyl chloride (PVC) based resin, an acrylic-based resin, a polyimide-based resin, an epoxy-based resin, a silicone-based resin, a polyvinyl butyral (PVB) based resin, or an ethylene vinyl acetate (EVA) based resin can be used. Alternatively, an inorganic material such as silicon oxide, silicon oxynitride, silicon nitride oxide, silicon nitride, aluminum oxide, or aluminum nitride can be used. The formation of the sealing layers 607*a*, 607*b*, and 607*c* can prevent deterioration of the light-emitting element 618 due to impurities such as water, which is preferable. In the case where the sealing layers 607*a*, 607*b*, and 607*c* are formed, the sealant 605 is not necessarily provided.

Alternatively, any one or two of the sealing layers 607*a*, 607*b*, and 607*c* may be provided or four or more sealing layers may be formed. When the sealing layer has a multilayer structure, the impurities such as water can be effectively prevented from entering the light-emitting element 618 which is inside the display device from the outside of the display device 600. In the case where the sealing layer has a multilayer structure, a resin and an inorganic material are preferably stacked.

<Structure Example 6 of Display Device>

Although the display devices in the structure examples 1 to 4 in this embodiment each have a structure including optical elements, one embodiment of the present invention does not necessarily include an optical element.

Figure 19A:
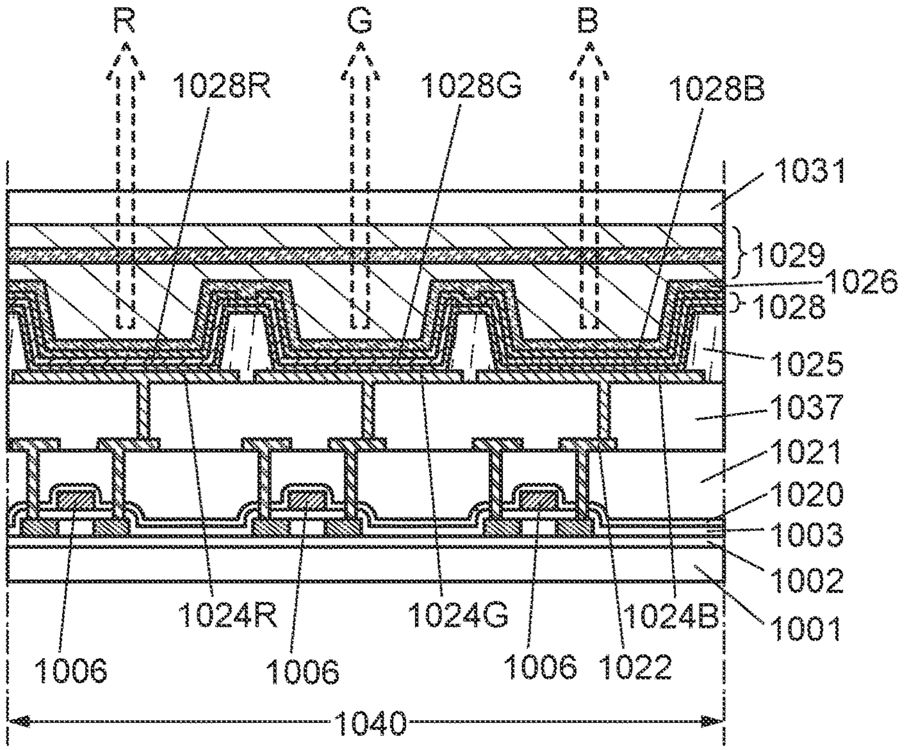
FIGS. 19A and 19B are each a schematic cross-sectional view illustrating a display device of one embodiment of the present invention.
Figure 19B:
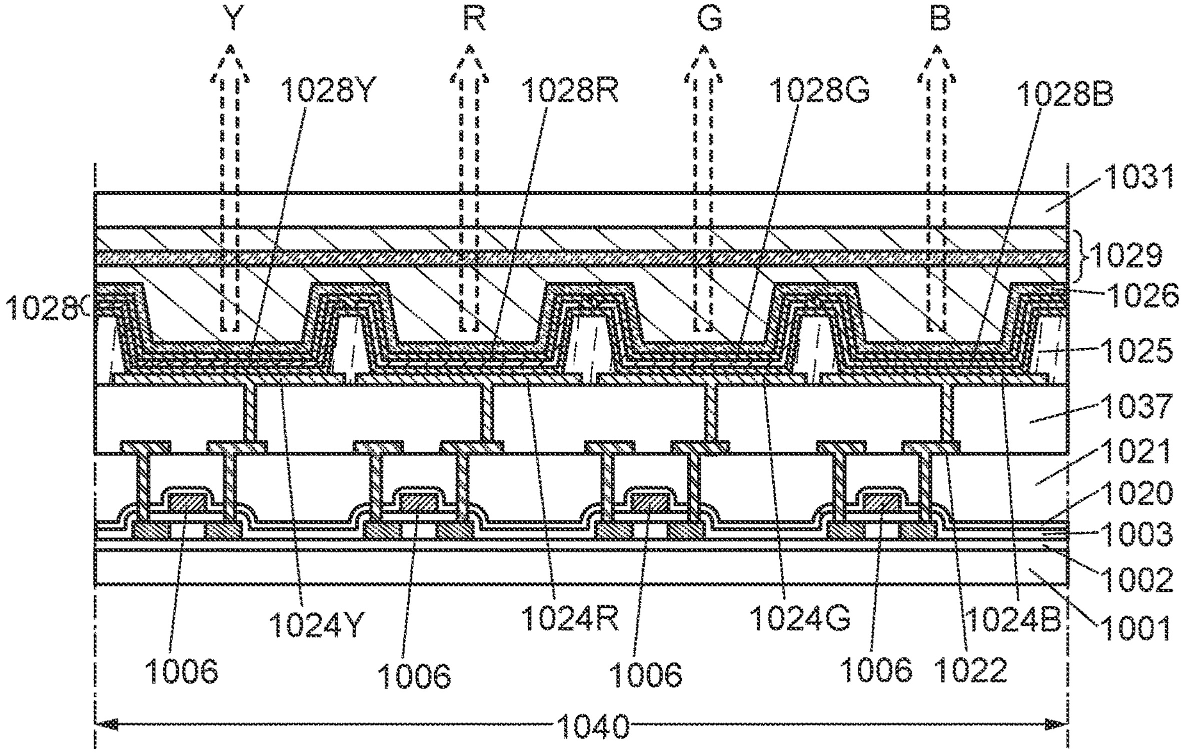

FIGS. 19A and 19B each illustrate a display device having a structure in which light is extracted from the sealing substrate 1031 side (a top-emission display device). FIG. 19A illustrates an example of a display device including a light-emitting layer 1028R, a light-emitting layer 1028G, and a light-emitting layer 1028B. FIG. 19B illustrates an example of a display device including a light-emitting layer 1028R, a light-emitting layer 1028G, a light-emitting layer 1028B, and a light-emitting layer 1028Y.

The light-emitting layer 1028R has a function of exhibiting red light, the light-emitting layer 1028G has a function of exhibiting green light, and the light-emitting layer 1028B has a function of exhibiting blue light. The light-emitting layer 1028Y has a function of exhibiting yellow light or a function of exhibiting light of a plurality of colors selected from blue, green, and red. The light-emitting layer 1028Y may exhibit white light. Since the light-emitting element which exhibits yellow or white light has high light emission efficiency, the display device including the light-emitting layer 1028Y can have lower power consumption.

Each of the display devices in FIGS. 19A and 19B does not necessarily include coloring layers serving as optical elements because EL layers exhibiting light of different colors are included in sub-pixels.

For the sealing layer 1029, a resin such as a polyvinyl chloride (PVC) based resin, an acrylic-based resin, a polyimide-based resin, an epoxy-based resin, a silicone-based resin, a polyvinyl butyral (PVB) based resin, or an ethylene vinyl acetate (EVA) based resin can be used. Alternatively, an inorganic material such as silicon oxide, silicon oxynitride, silicon nitride oxide, silicon nitride, aluminum oxide, or aluminum nitride can be used. The formation of the sealing layer 1029 can prevent deterioration of the light-emitting element due to impurities such as water, which is preferable.

Alternatively, the sealing layer 1029 may have a single-layer or two-layer structure, or four or more sealing layers may be formed as the sealing layer 1029. When the sealing layer has a multilayer structure, the impurities such as water can be effectively prevented from entering the inside of the display device from the outside of the display device. In the case where the sealing layer has a multilayer structure, a resin and an inorganic material are preferably stacked.

Note that the sealing substrate 1031 has a function of protecting the light-emitting element. Thus, for the sealing substrate 1031, a flexible substrate or a film can be used.

The structures described in this embodiment can be combined as appropriate with any of the other structures in this embodiment and the other embodiments.

Embodiment 5

In this embodiment, a display device including a light-emitting element of one embodiment of the present invention will be described with reference to FIGS. 20A and 20B, FIGS. 21A and 21B, and FIGS. 22A and 22B.

Figure 20A:
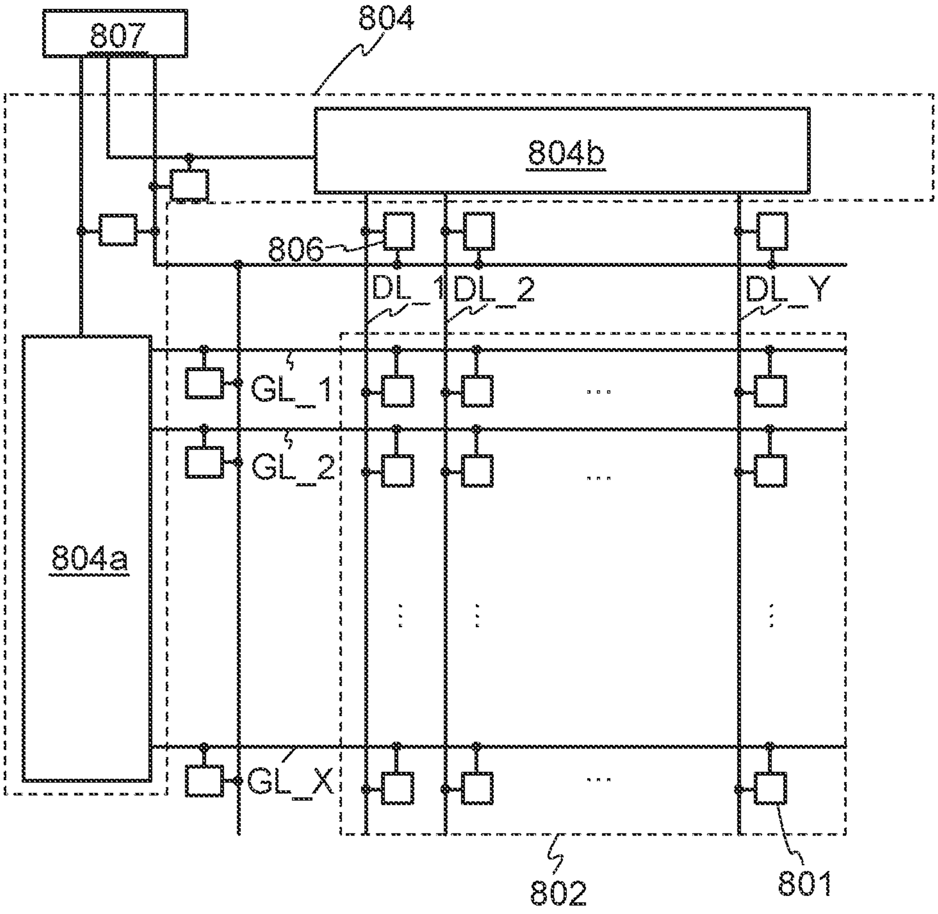
FIGS. 20A and 20B are a block diagram and a circuit diagram illustrating a display device of one embodiment of the present invention.
Figure 20B:
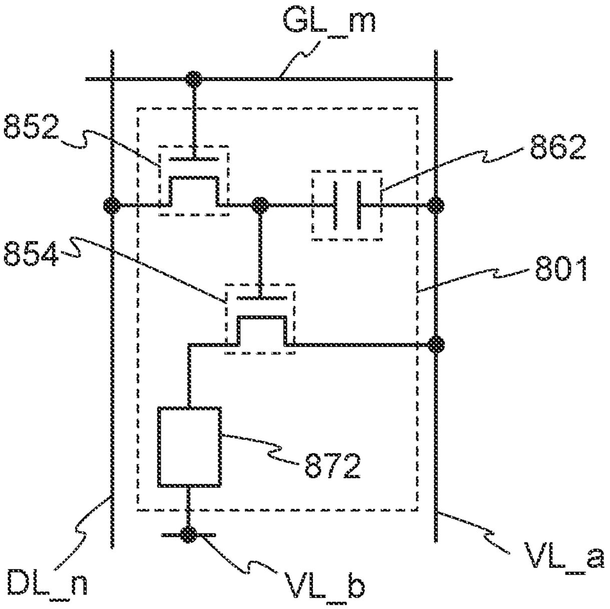

FIG. 20A is a block diagram illustrating the display device of one embodiment of the present invention, and FIG. 20B is a circuit diagram illustrating a pixel circuit of the display device of one embodiment of the present invention.

<Description of Display Device>

The display device illustrated in FIG. 20A includes a region including pixels of display elements (the region is hereinafter referred to as a pixel portion 802), a circuit portion provided outside the pixel portion 802 and including circuits for driving the pixels (the portion is hereinafter referred to as a driver circuit portion 804), circuits having a function of protecting elements (the circuits are hereinafter referred to as protection circuits 806), and a terminal portion 807. Note that the protection circuits 806 are not necessarily provided.

A part or the whole of the driver circuit portion 804 is preferably formed over a substrate over which the pixel portion 802 is formed, in which case the number of components and the number of terminals can be reduced. When a part or the whole of the driver circuit portion 804 is not formed over the substrate over which the pixel portion 802 is formed, the part or the whole of the driver circuit portion 804 can be mounted by COG or tape automated bonding (TAB).

The pixel portion 802 includes a plurality of circuits for driving display elements arranged in X rows (X is a natural number of 2 or more) and Y columns (Y is a natural number of 2 or more) (such circuits are hereinafter referred to as pixel circuits 801). The driver circuit portion 804 includes driver circuits such as a circuit for supplying a signal (scan signal) to select a pixel (the circuit is hereinafter referred to as a scan line driver circuit 804*a*) and a circuit for supplying a signal (data signal) to drive a display element in a pixel (the circuit is hereinafter referred to as a signal line driver circuit 804*b*).

The scan line driver circuit 804*a* includes a shift register or the like. Through the terminal portion 807, the scan line driver circuit 804*a* receives a signal for driving the shift register and outputs a signal. For example, the scan line driver circuit 804*a* receives a start pulse signal, a clock signal, or the like and outputs a pulse signal. The scan line driver circuit 804*a* has a function of controlling the potentials of wirings supplied with scan signals (such wirings are hereinafter referred to as scan lines GL_1 to GL_X). Note that a plurality of scan line driver circuits 804*a* may be provided to control the scan lines GL_1 to GL_X separately. Alternatively, the scan line driver circuit 804*a* has a function of supplying an initialization signal. Without being limited thereto, the scan line driver circuit 804*a* can supply another signal.

The signal line driver circuit 804*b* includes a shift register or the like. The signal line driver circuit 804*b* receives a signal (image signal) from which a data signal is derived, as well as a signal for driving the shift register, through the terminal portion 807. The signal line driver circuit 804*b* has a function of generating a data signal to be written to the pixel circuit 801 which is based on the image signal. In addition, the signal line driver circuit 804*b* has a function of controlling output of a data signal in response to a pulse signal produced by input of a start pulse signal, a clock signal, or the like. Furthermore, the signal line driver circuit 804*b* has a function of controlling the potentials of wirings supplied with data signals (such wirings are hereinafter referred to as data lines DL_1 to DL_Y). Alternatively, the signal line driver circuit 804*b* has a function of supplying an initialization signal. Without being limited thereto, the signal line driver circuit 804*b* can supply another signal.

The signal line driver circuit 804*b* includes a plurality of analog switches or the like, for example. The signal line driver circuit 804*b* can output, as the data signals, signals obtained by time-dividing the image signal by sequentially turning on the plurality of analog switches. The signal line driver circuit 804*b* may include a shift register or the like.

A pulse signal and a data signal are input to each of the plurality of pixel circuits 801 through one of the plurality of scan lines GL supplied with scan signals and one of the plurality of data lines DL supplied with data signals, respectively. Writing and holding of the data signal to and in each of the plurality of pixel circuits 801 are controlled by the scan line driver circuit 804*a*. For example, to the pixel circuit 801 in the m-th row and the n-th column (m is a natural number of less than or equal to X, and n is a natural number of less than or equal to Y), a pulse signal is input from the scan line driver circuit 804*a* through the scan line GL_m, and a data signal is input from the signal line driver circuit 804*b* through the data line DL_n in accordance with the potential of the scan line GL_m.

The protection circuit 806 shown in FIG. 20A is connected to, for example, the scan line GL between the scan line driver circuit 804*a* and the pixel circuit 801. Alternatively, the protection circuit 806 is connected to the data line DL between the signal line driver circuit 804*b* and the pixel circuit 801. Alternatively, the protection circuit 806 can be connected to a wiring between the scan line driver circuit 804*a* and the terminal portion 807. Alternatively, the protection circuit 806 can be connected to a wiring between the signal line driver circuit 804*b* and the terminal portion 807. Note that the terminal portion 807 means a portion having terminals for inputting power, control signals, and image signals to the display device from external circuits.

The protection circuit 806 is a circuit that electrically connects a wiring connected to the protection circuit to another wiring when a potential out of a certain range is applied to the wiring connected to the protection circuit.

As illustrated in FIG. 20A, the protection circuits 806 are connected to the pixel portion 802 and the driver circuit portion 804, so that the resistance of the display device to overcurrent generated by electrostatic discharge (ESD) or the like can be improved. Note that the configuration of the protection circuits 806 is not limited to that, and for example, a configuration in which the protection circuits 806 are connected to the scan line driver circuit 804*a* or a configuration in which the protection circuits 806 are connected to the signal line driver circuit 804*b* may be employed. Alternatively, the protection circuits 806 may be configured to be connected to the terminal portion 807.

In FIG. 20A, an example in which the driver circuit portion 804 includes the scan line driver circuit 804*a* and the signal line driver circuit 804*b* is shown; however, the structure is not limited thereto. For example, only the scan line driver circuit 804*a* may be formed and a separately prepared substrate where a signal line driver circuit is formed (e.g., a driver circuit substrate formed with a single crystal semiconductor film or a polycrystalline semiconductor film) may be mounted.

<Structure Example of Pixel Circuit>

Each of the plurality of pixel circuits 801 in FIG. 20A can have a structure illustrated in FIG. 20B, for example.

The pixel circuit 801 illustrated in FIG. 20B includes transistors 852 and 854, a capacitor 862, and a light-emitting element 872.

One of a source electrode and a drain electrode of the transistor 852 is electrically connected to a wiring to which a data signal is supplied (a data line DL_n). A gate electrode of the transistor 852 is electrically connected to a wiring to which a gate signal is supplied (a scan line GL_m).

The transistor 852 has a function of controlling whether to write a data signal.

One of a pair of electrodes of the capacitor 862 is electrically connected to a wiring to which a potential is supplied (hereinafter referred to as a potential supply line VL_a), and the other is electrically connected to the other of the source electrode and the drain electrode of the transistor 852.

The capacitor 862 functions as a storage capacitor for storing written data.

One of a source electrode and a drain electrode of the transistor 854 is electrically connected to the potential supply line VL_a. Furthermore, a gate electrode of the transistor 854 is electrically connected to the other of the source electrode and the drain electrode of the transistor 852.

One of an anode and a cathode of the light-emitting element 872 is electrically connected to a potential supply line VL_b, and the other is electrically connected to the other of the source electrode and the drain electrode of the transistor 854.

As the light-emitting element 872, any of the light-emitting elements described in Embodiments 1 to 3 can be used.

Note that a high power supply potential VDD is supplied to one of the potential supply line VL_a and the potential supply line VL_b, and a low power supply potential VSS is supplied to the other.

In the display device including the pixel circuits 801 in FIG. 20B, the pixel circuits 801 are sequentially selected row by row by the scan line driver circuit 804*a* in FIG. 20A, for example, whereby the transistors 852 are turned on and a data signal is written.

When the transistors 852 are turned off, the pixel circuits 801 in which the data has been written are brought into a holding state. Furthermore, the amount of current flowing between the source electrode and the drain electrode of the transistor 854 is controlled in accordance with the potential of the written data signal. The light-emitting element 872 emits light with a luminance corresponding to the amount of flowing current. This operation is sequentially performed row by row; thus, an image is displayed.

Alternatively, the pixel circuit can have a function of compensating variation in threshold voltages or the like of a transistor. FIGS. 21A and 21B and FIGS. 22A and 22B illustrate examples of the pixel circuit.

Figure 21A:
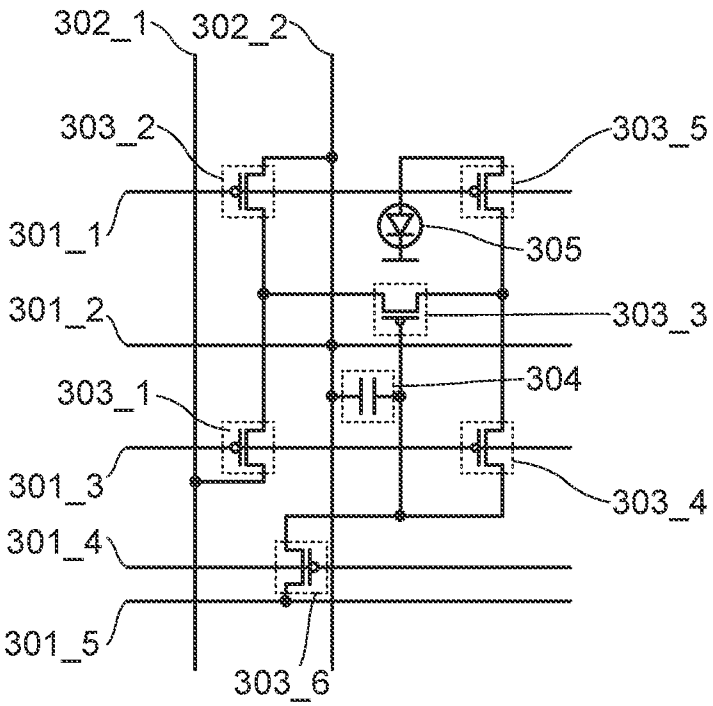
FIGS. 21A and 21B are circuit diagrams each illustrating a pixel circuit of a display device of one embodiment of the present invention.

The pixel circuit illustrated in FIG. 21A includes six transistors (transistors 303_1 to 303_6), a capacitor 304, and a light-emitting element 305. The pixel circuit illustrated in FIG. 21A is electrically connected to wirings 301_1 to 301_5 and wirings 302_1 and 302_2. Note that as the transistors 303_1 to 303_6, for example, p-channel transistors can be used.

Figure 21B:
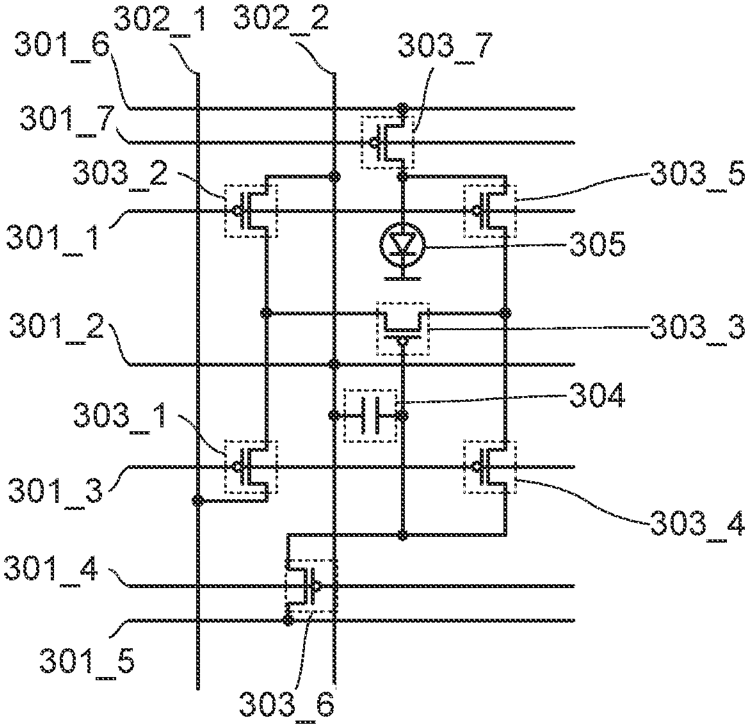

The pixel circuit shown in FIG. 21B has a configuration in which a transistor 303_7 is added to the pixel circuit shown in FIG. 21A. The pixel circuit illustrated in FIG. 21B is electrically connected to wirings 301_6 and 301_7. The wirings 301_5 and 301_6 may be electrically connected to each other. Note that as the transistor 303_7, for example, a p-channel transistor can be used.

Figure 22A:
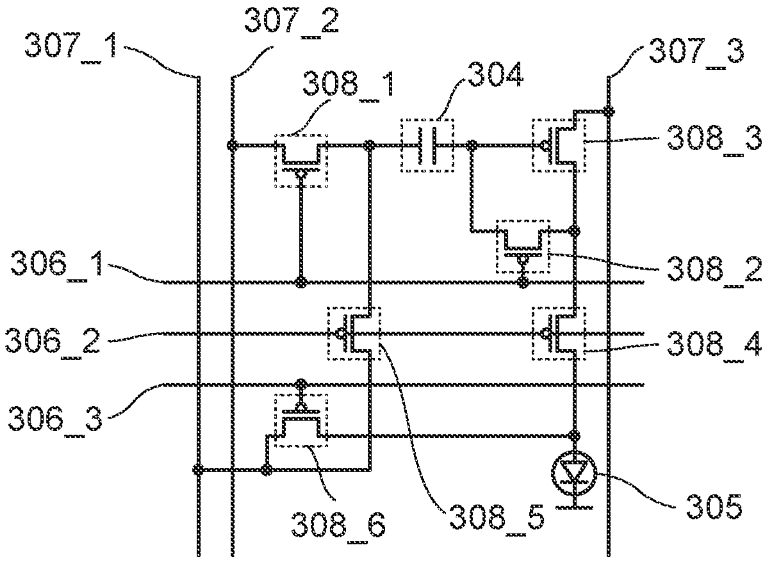
FIGS. 22A and 22B are circuit diagrams each illustrating a pixel circuit of a display device of one embodiment of the present invention.

The pixel circuit shown in FIG. 22A includes six transistors (transistors 308_1 to 308_6), the capacitor 304, and the light-emitting element 305. The pixel circuit illustrated in FIG. 22A is electrically connected to wirings 306_1 to 306_3 and wirings 307_1 to 307_3. The wirings 306_1 and 306_3 may be electrically connected to each other. Note that as the transistors 308_1 to 308_6, for example, p-channel transistors can be used.

Figure 22B:
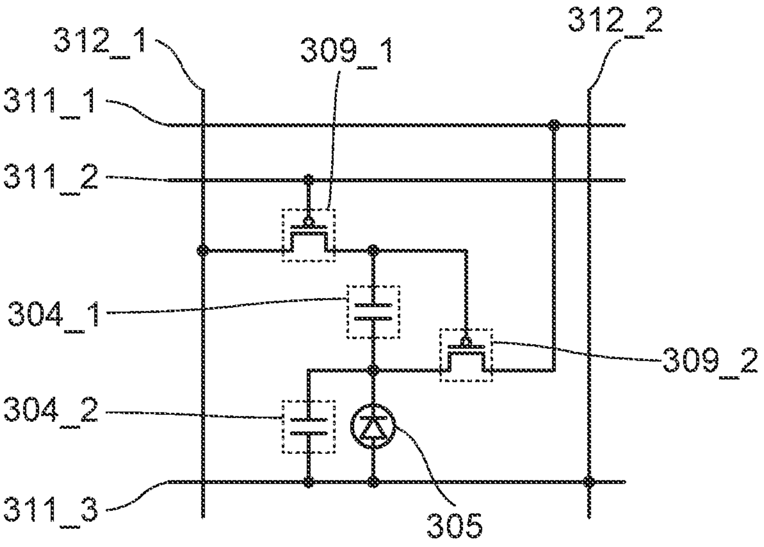

The pixel circuit illustrated in FIG. 22B includes two transistors (transistors 309_1 and 309_2), two capacitors (capacitors 304_1 and 304_2), and the light-emitting element 305. The pixel circuit illustrated in FIG. 22B is electrically connected to wirings 311_1 to 311_3 and wirings 312_1 and 312_2. With the configuration of the pixel circuit illustrated in FIG. 22B, the pixel circuit can be driven by a voltage inputting current driving method (also referred to as CVCC). Note that as the transistors 309_1 and 309_2, for example, p-channel transistors can be used.

A light-emitting element of one embodiment of the present invention can be used for an active matrix method in which an active element is included in a pixel of a display device or a passive matrix method in which an active element is not included in a pixel of a display device.

In the active matrix method, as an active element (a non-linear element), not only a transistor but also a variety of active elements (non-linear elements) can be used. For example, a metal insulator metal (MIM), a thin film diode (TFD), or the like can also be used. Since these elements can be formed with a smaller number of manufacturing steps, manufacturing cost can be reduced or yield can be improved. Alternatively, since the size of these elements is small, the aperture ratio can be improved, so that power consumption can be reduced and higher luminance can be achieved.

As a method other than the active matrix method, the passive matrix method in which an active element (a non-linear element) is not used can also be used. Since an active element (a non-linear element) is not used, the number of manufacturing steps is small, so that manufacturing cost can be reduced or yield can be improved. Alternatively, since an active element (a non-linear element) is not used, the aperture ratio can be improved, so that power consumption can be reduced or higher luminance can be achieved, for example.

The structure described in this embodiment can be used in combination with any of the structures described in the other embodiments as appropriate.

Embodiment 6

In this embodiment, a display device including a light-emitting element of one embodiment of the present invention and an electronic device in which the display device is provided with an input device will be described with reference to FIGS. 23A and 23B, FIGS. 24A to 24C, FIGS. 25A and 25B, FIGS. 26A and 26B, and FIG. 27.

<Description 1 of Touch Panel>

In this embodiment, a touch panel 2000 including a display device and an input device will be described as an example of an electronic device. In addition, an example in which a touch sensor is included as an input device will be described.

Figure 23A:
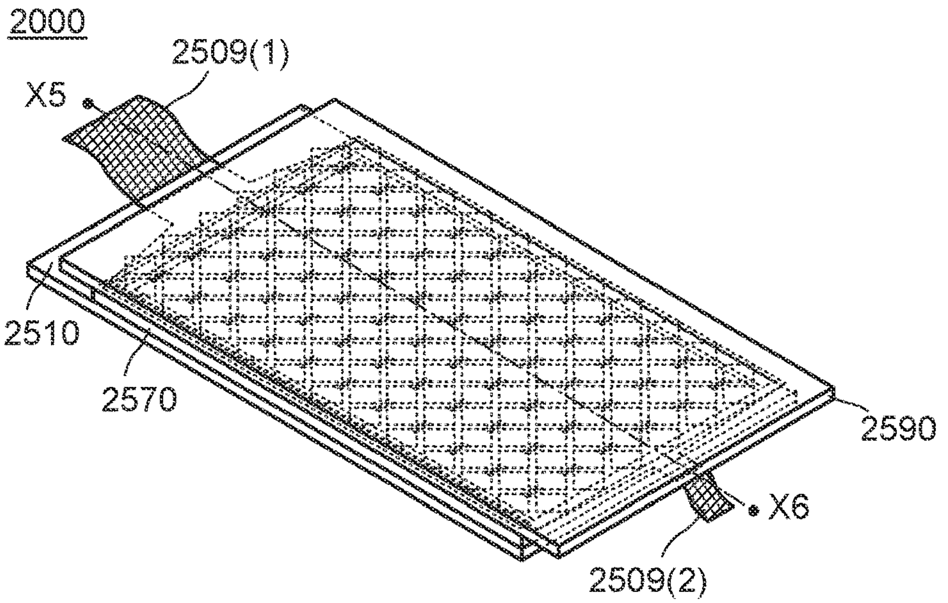
FIGS. 23A and 23B are perspective views of an example of a touch panel of one embodiment of the present invention.
Figure 23B:
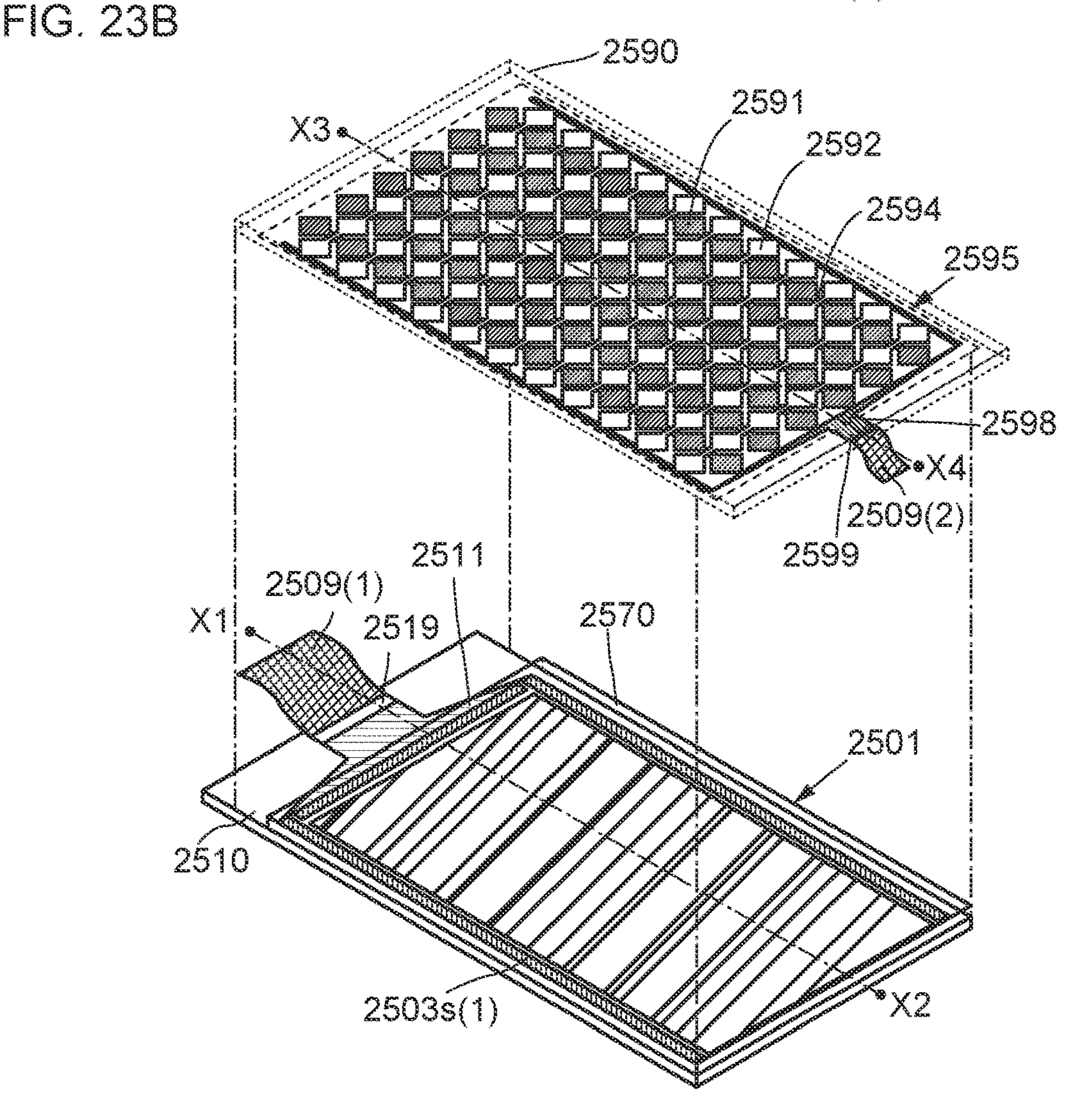

FIGS. 23A and 23B are perspective views of the touch panel 2000. Note that FIGS. 23A and 23B illustrate only main components of the touch panel 2000 for simplicity.

The touch panel 2000 includes a display device 2501 and a touch sensor 2595 (see FIG. 23B). The touch panel 2000 also includes a substrate 2510, a substrate 2570, and a substrate 2590. The substrate 2510, the substrate 2570, and the substrate 2590 each have flexibility. Note that one or all of the substrates 2510, 2570, and 2590 may be inflexible.

The display device 2501 includes a plurality of pixels over the substrate 2510 and a plurality of wirings 2511 through which signals are supplied to the pixels. The plurality of wirings 2511 are led to a peripheral portion of the substrate 2510, and parts of the plurality of wirings 2511 form a terminal 2519. The terminal 2519 is electrically connected to an FPC 2509(1). The plurality of wirings 2511 can supply signals from a signal line driver circuit 2503*s*(1) to the plurality of pixels.

The substrate 2590 includes the touch sensor 2595 and a plurality of wirings 2598 electrically connected to the touch sensor 2595. The plurality of wirings 2598 are led to a peripheral portion of the substrate 2590, and parts of the plurality of wirings 2598 form a terminal. The terminal is electrically connected to an FPC 2509(2). Note that in FIG. 23B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used. Examples of the capacitive touch sensor are a surface capacitive touch sensor and a projected capacitive touch sensor.

Examples of the projected capacitive touch sensor are a self capacitive touch sensor and a mutual capacitive touch sensor, which differ mainly in the driving method.

The use of a mutual capacitive type is preferable because multiple points can be sensed simultaneously.

Note that the touch sensor 2595 illustrated in FIG. 23B is an example of using a projected capacitive touch sensor.

Note that a variety of sensors that can sense proximity or touch of a sensing target such as a finger can be used as the touch sensor 2595.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598.

The electrodes 2592 each have a shape of a plurality of quadrangles arranged in one direction with one corner of a quadrangle connected to one corner of another quadrangle as illustrated in FIGS. 23A and 23B.

The electrodes 2591 each have a quadrangular shape and are arranged in a direction intersecting with the direction in which the electrodes 2592 extend.

A wiring 2594 electrically connects two electrodes 2591 between which the electrode 2592 is positioned. The intersecting area of the electrode 2592 and the wiring 2594 is preferably as small as possible. Such a structure allows a reduction in the area of a region where the electrodes are not provided, reducing variation in transmittance. As a result, variation in luminance of light passing through the touch sensor 2595 can be reduced.

Note that the shapes of the electrodes 2591 and the electrodes 2592 are not limited thereto and can be any of a variety of shapes. For example, a structure may be employed in which the plurality of electrodes 2591 are arranged so that gaps between the electrodes 2591 are reduced as much as possible, and the electrodes 2592 are spaced apart from the electrodes 2591 with an insulating layer interposed therebetween to have regions not overlapping with the electrodes 2591. In this case, it is preferable to provide, between two adjacent electrodes 2592, a dummy electrode electrically insulated from these electrodes because the area of regions having different transmittances can be reduced.

<Description of Display Device>

Figure 24A:
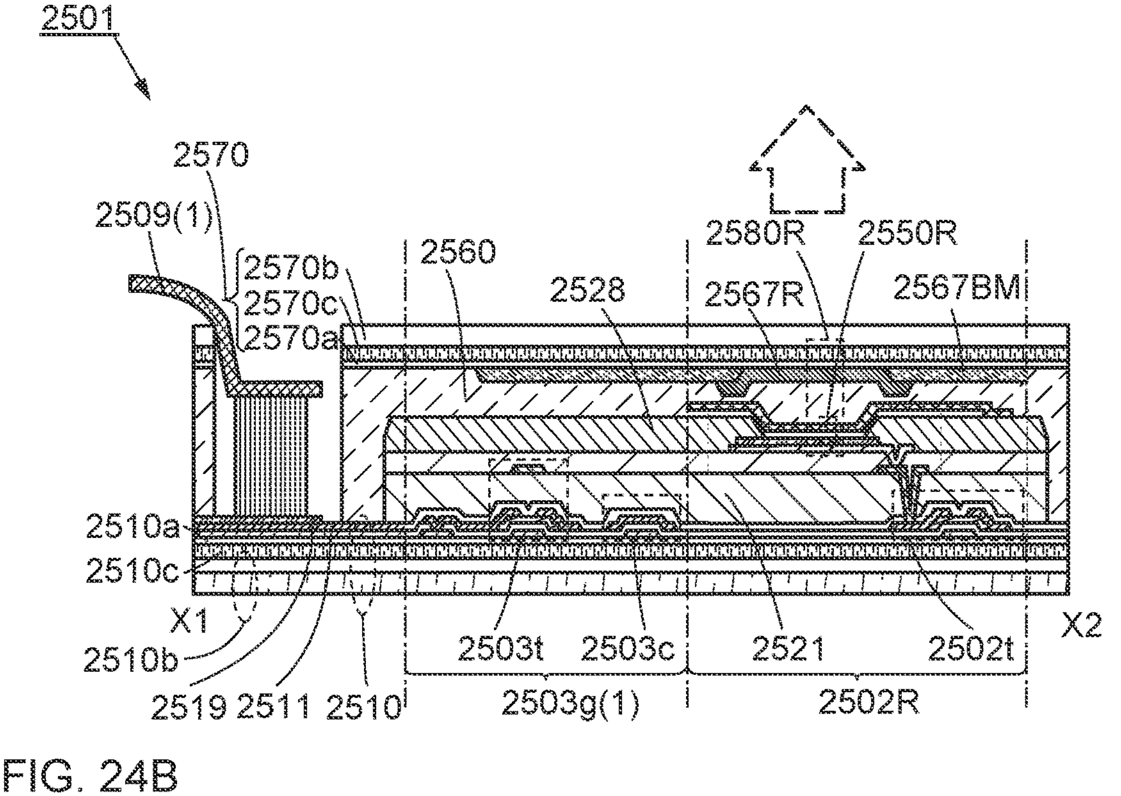
FIGS. 24A to 24C are cross-sectional views of examples of a display device and a touch sensor of one embodiment of the present invention.

Next, the display device 2501 will be described in detail with reference to FIG. 24A. FIG. 24A corresponds to a cross-sectional view taken along dashed-dotted line X1-X2 in FIG. 23B.

The display device 2501 includes a plurality of pixels arranged in a matrix. Each of the pixels includes a display element and a pixel circuit for driving the display element.

In the following description, an example of using a light-emitting element that emits white light as a display element will be described; however, the display element is not limited to such an element. For example, light-emitting elements that emit light of different colors may be included so that the light of different colors can be emitted from adjacent pixels.

For the substrate 2510 and the substrate 2570, for example, a flexible material with a vapor permeability of lower than or equal to $1\times10^{-5}$ $g\cdot m^{-2}\cdot day^{-1}$, preferably lower than or equal to $1\times10^{-6}$ $g\cdot m^{-2}\cdot day^{-1}$ can be favorably used. Alternatively, materials whose thermal expansion coefficients are substantially equal to each other are preferably used for the substrate 2510 and the substrate 2570. For example, the coefficients of linear expansion of the materials are preferably lower than or equal to $1\times10^{-3}$/K, further preferably lower than or equal to $5\times10^{-5}$/K, and still further preferably lower than or equal to $1\times10^{-5}$/K.

Note that the substrate 2510 is a stacked body including an insulating layer 2510*a* for preventing impurity diffusion into the light-emitting element, a flexible substrate 2510*b*, and an adhesive layer 2510*c* for attaching the insulating layer 2510*a* and the flexible substrate 2510*b* to each other. The substrate 2570 is a stacked body including an insulating layer 2570*a* for preventing impurity diffusion into the light-emitting element, a flexible substrate 2570*b*, and an adhesive layer 2570*c* for attaching the insulating layer 2570*a* and the flexible substrate 2570*b* to each other.

For the adhesive layer 2510*c* and the adhesive layer 2570*c*, for example, polyester, polyolefin, polyamide (e.g., nylon, aramid), polyimide, polycarbonate, or an acrylic resin, polyurethane, or an epoxy resin can be used. Alternatively, a material that includes a resin having a siloxane bond such as silicone can be used.

A sealing layer 2560 is provided between the substrate 2510 and the substrate 2570. The sealing layer 2560 preferably has a refractive index higher than that of air. In the case where light is extracted to the sealing layer 2560 side as illustrated in FIG. 24A, the sealing layer 2560 can also serve as an optical adhesive layer.

A sealant may be formed in the peripheral portion of the sealing layer 2560. With the use of the sealant, a light-emitting element 2550R can be provided in a region surrounded by the substrate 2510, the substrate 2570, the sealing layer 2560, and the sealant. Note that an inert gas (such as nitrogen and argon) may be used instead of the sealing layer 2560. A drying agent may be provided in the inert gas so as to adsorb moisture or the like. A resin such as an acrylic resin or an epoxy resin may be used. An epoxy-based resin or a glass frit is preferably used as the sealant. As a material used for the sealant, a material which is impermeable to moisture and oxygen is preferably used.

The display device 2501 includes a pixel 2502R. The pixel 2502R includes a light-emitting module 2580R.

The pixel 2502R includes the light-emitting element 2550R and a transistor 2502*t* that can supply electric power to the light-emitting element 2550R. Note that the transistor 2502*t* functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode. As the light-emitting element 2550R, any of the light-emitting elements described in Embodiments 1 to 3 can be used.

A microcavity structure may be employed between the lower electrode and the upper electrode so as to increase the intensity of light having a specific wavelength.

In the case where the sealing layer 2560 is provided on the light extraction side, the sealing layer 2560 is in contact with the light-emitting element 2550R and the coloring layer 2567R.

The coloring layer 2567R is positioned in a region overlapping with the light-emitting element 2550R. Accordingly, part of light emitted from the light-emitting element 2550R passes through the coloring layer 2567R and is emitted to the outside of the light-emitting module 2580R as indicated by an arrow in the drawing.

The display device 2501 includes a light-blocking layer 2567BM on the light extraction side. The light-blocking layer 2567BM is provided so as to surround the coloring layer 2567R.

The coloring layer 2567R is a coloring layer having a function of transmitting light in a particular wavelength region. For example, a color filter for transmitting light in a red wavelength region, a color filter for transmitting light in a green wavelength region, a color filter for transmitting light in a blue wavelength region, a color filter for transmitting light in a yellow wavelength region, or the like can be used. Each color filter can be formed with any of various materials by a printing method, an inkjet method, an etching method using a photolithography technique, or the like.

An insulating layer 2521 is provided in the display device 2501. The insulating layer 2521 covers the transistor 2502*t*. Note that the insulating layer 2521 has a function of covering unevenness caused by the pixel circuit. The insulating layer 2521 may have a function of suppressing impurity diffusion. This can prevent the reliability of the transistor 2502*t* or the like from being lowered by impurity diffusion.

The light-emitting element 2550R is formed over the insulating layer 2521. A partition 2528 is provided so as to overlap with an end portion of the lower electrode of the light-emitting element 2550R. Note that a spacer for controlling the distance between the substrate 2510 and the substrate 2570 may be formed over the partition 2528.

A scan line driver circuit 2503*g*(1) includes a transistor 2503*t* and a capacitor 2503*c*. Note that the driver circuit can be formed in the same process and over the same substrate as those of the pixel circuits.

The wirings 2511 through which signals can be supplied are provided over the substrate 2510. The terminal 2519 is provided over the wirings 2511. The FPC 2509(1) is electrically connected to the terminal 2519. The FPC 2509(1) has a function of supplying a video signal, a clock signal, a start signal, a reset signal, or the like. Note that the FPC 2509(1) may be provided with a PWB.

Figure 24B:
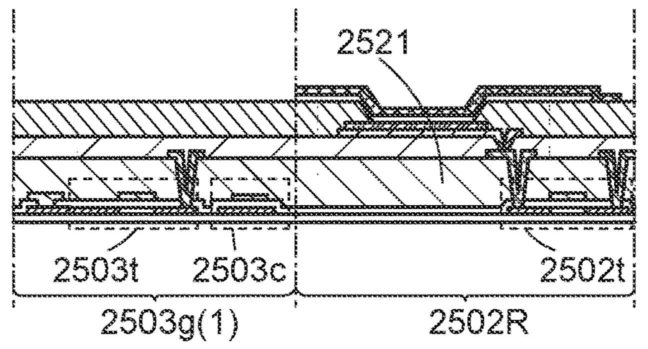

In the display device 2501, transistors with any of a variety of structures can be used. FIG. 24A illustrates an example of using bottom-gate transistors; however, the present invention is not limited to this example, and top-gate transistors may be used in the display device 2501 as illustrated in FIG. 24B.

In addition, there is no particular limitation on the polarity of the transistor 2502*t* and the transistor 2503*t*. For these transistors, n-channel and p-channel transistors may be used, or either n-channel transistors or p-channel transistors may be used, for example. Furthermore, there is no particular limitation on the crystallinity of a semiconductor film used for the transistors 2502*t* and 2503*t*. For example, an amorphous semiconductor film or a crystalline semiconductor film may be used. Examples of semiconductor materials include Group 14 semiconductors (e.g., a semiconductor including silicon), compound semiconductors (including oxide semiconductors), organic semiconductors, and the like. An oxide semiconductor that has an energy gap of 2 eV or more, preferably 2.5 eV or more, further preferably 3 eV or more is preferably used for one of the transistors 2502*t* and 2503*t* or both, so that the off-state current of the transistors can be reduced. Examples of the oxide semiconductors include an In—Ga oxide, an In-M-Zn oxide (M represents Al, Ga, Y, Zr, La, Ce, Sn, Hf, or Nd), and the like.

<Description of Touch Sensor>

Figure 24C:
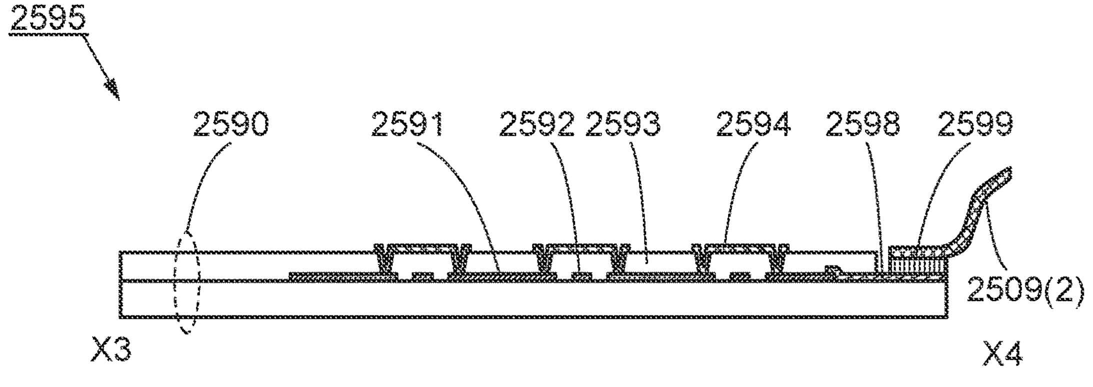

Next, the touch sensor 2595 will be described in detail with reference to FIG. 24C. FIG. 24C corresponds to a cross-sectional view taken along dashed-dotted line X3-X4 in FIG. 23B.

The touch sensor 2595 includes the electrodes 2591 and the electrodes 2592 provided in a staggered arrangement on the substrate 2590, an insulating layer 2593 covering the electrodes 2591 and the electrodes 2592, and the wiring 2594 that electrically connects the adjacent electrodes 2591 to each other.

The electrodes 2591 and the electrodes 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film including graphene may be used as well. The film including graphene can be formed, for example, by reducing a film containing graphene oxide. As a reducing method, a method with application of heat or the like can be employed.

The electrodes 2591 and the electrodes 2592 may be formed by, for example, depositing a light-transmitting conductive material on the substrate 2590 by a sputtering method and then removing an unnecessary portion by any of various pattern forming techniques such as photolithography.

Examples of a material for the insulating layer 2593 are a resin such as an acrylic resin or an epoxy resin, a resin having a siloxane bond such as silicone, and an inorganic insulating material such as silicon oxide, silicon oxynitride, or aluminum oxide.

Openings reaching the electrodes 2591 are formed in the insulating layer 2593, and the wiring 2594 electrically connects the adjacent electrodes 2591. A light-transmitting conductive material can be favorably used as the wiring 2594 because the aperture ratio of the touch panel can be increased. Moreover, a material with higher conductivity than the conductivities of the electrodes 2591 and 2592 can be favorably used for the wiring 2594 because electric resistance can be reduced.

One electrode 2592 extends in one direction, and a plurality of electrodes 2592 are provided in the form of stripes. The wiring 2594 intersects with the electrode 2592.

Adjacent electrodes 2591 are provided with one electrode 2592 provided therebetween. The wiring 2594 electrically connects the adjacent electrodes 2591.

Note that the plurality of electrodes 2591 are not necessarily arranged in the direction orthogonal to one electrode 2592 and may be arranged to intersect with one electrode 2592 at an angle of more than 0 degrees and less than 90 degrees.

The wiring 2598 is electrically connected to any of the electrodes 2591 and 2592. Part of the wiring 2598 functions as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Note that an insulating layer that covers the insulating layer 2593 and the wiring 2594 may be provided to protect the touch sensor 2595.

A connection layer 2599 electrically connects the wiring 2598 to the FPC 2509(2).

As the connection layer 2599, any of various anisotropic conductive films (ACF), anisotropic conductive pastes (ACP), or the like can be used.

<Description 2 of Touch Panel>

Figure 25A:
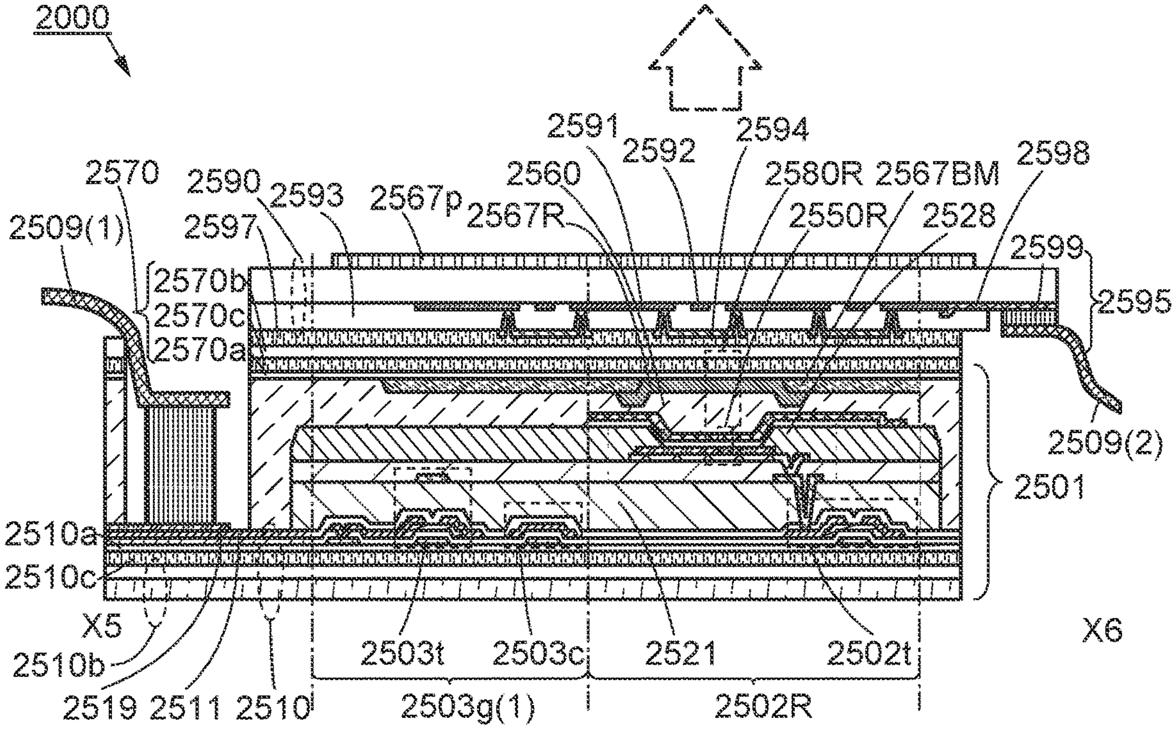
FIGS. 25A and 25B are cross-sectional views each illustrating an example of a touch panel of one embodiment of the present invention.

Next, the touch panel 2000 will be described in detail with reference to FIG. 25A. FIG. 25A corresponds to a cross-sectional view taken along dashed-dotted line X5-X6 in FIG. 23A.

In the touch panel 2000 illustrated in FIG. 25A, the display device 2501 described with reference to FIG. 24A and the touch sensor 2595 described with reference to FIG. 24C are attached to each other.

The touch panel 2000 illustrated in FIG. 25A includes an adhesive layer 2597 and an anti-reflective layer 2567*p* in addition to the components described with reference to FIGS. 24A and 24C.

The adhesive layer 2597 is provided in contact with the wiring 2594. Note that the adhesive layer 2597 attaches the substrate 2590 to the substrate 2570 so that the touch sensor 2595 overlaps with the display device 2501. The adhesive layer 2597 preferably has a light-transmitting property. A heat curable resin or an ultraviolet curable resin can be used for the adhesive layer 2597. For example, an acrylic resin, a urethane-based resin, an epoxy-based resin, or a siloxane-based resin can be used.

The anti-reflective layer 2567*p* is positioned in a region overlapping with pixels. As the anti-reflective layer 2567*p*, a circularly polarizing plate can be used, for example.

Next, a touch panel having a structure different from that illustrated in FIG. 25A will be described with reference to FIG. 25B.

Figure 25B:
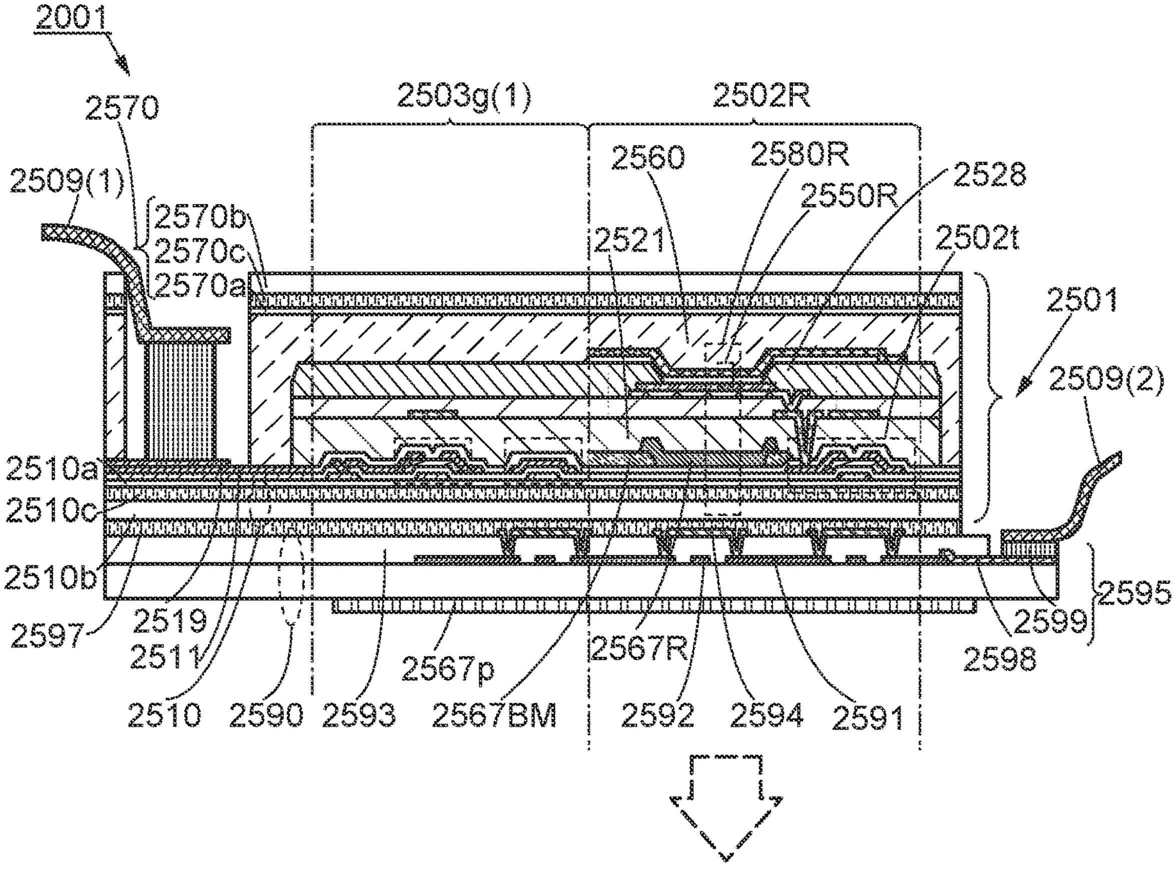

FIG. 25B is a cross-sectional view of a touch panel 2001. The touch panel 2001 illustrated in FIG. 25B differs from the touch panel 2000 illustrated in FIG. 25A in the position of the touch sensor 2595 relative to the display device 2501. Different parts are described in detail below, and the above description of the touch panel 2000 is referred to for the other similar parts.

The coloring layer 2567R is positioned in a region overlapping with the light-emitting element 2550R. The light-emitting element 2550R illustrated in FIG. 25B emits light to the side where the transistor 2502*t* is provided. Accordingly, part of light emitted from the light-emitting element 2550R passes through the coloring layer 2567R and is emitted to the outside of the light-emitting module 2580R as indicated by an arrow in FIG. 25B.

The touch sensor 2595 is provided on the substrate 2510 side of the display device 2501.

The adhesive layer 2597 is provided between the substrate 2510 and the substrate 2590 and attaches the touch sensor 2595 to the display device 2501.

As illustrated in FIG. 25A or 25B, light may be emitted from the light-emitting element through one or both of the substrate 2510 and the substrate 2570.

<Description of Method for Driving Touch Panel>

Next, an example of a method for driving a touch panel will be described with reference to FIGS. 26A and 26B.

Figure 26A:
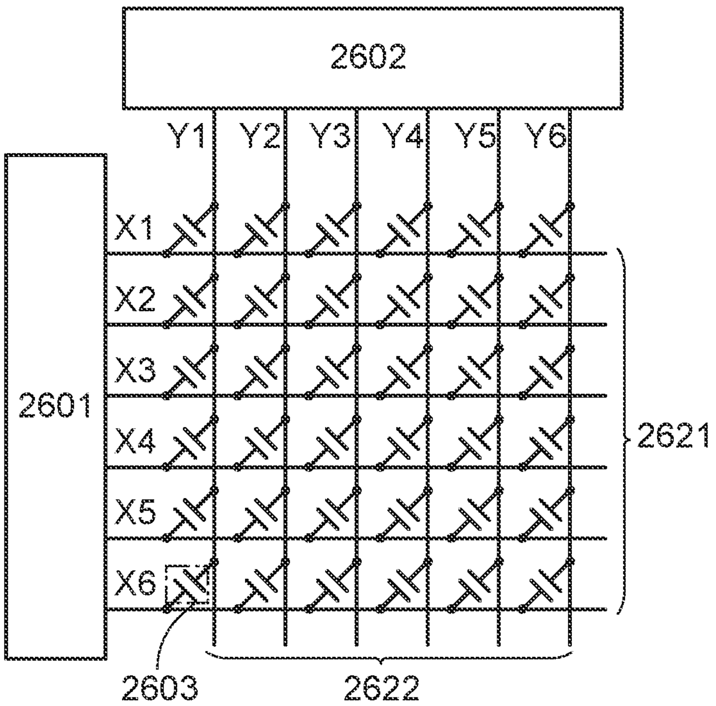
FIGS. 26A and 26B are a block diagram and a timing chart of a touch sensor of one embodiment of the present invention.

FIG. 26A is a block diagram illustrating the structure of a mutual capacitive touch sensor. FIG. 26A illustrates a pulse voltage output circuit 2601 and a current sensing circuit 2602. Note that in FIG. 26A, six wirings X1 to X6 represent the electrodes 2621 to which a pulse voltage is applied, and six wirings Y1 to Y6 represent the electrodes 2622 that detect changes in current. FIG. 26A also illustrates capacitors 2603 that are each formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for detecting changes in current flowing through the wirings Y1 to Y6 that are caused by the change in mutual capacitance in the capacitor 2603. No change in current value is detected in the wirings Y1 to Y6 when there is no approach or contact of a sensing target, whereas a decrease in current value is detected when mutual capacitance is decreased owing to the approach or contact of a sensing target. Note that an integrator circuit or the like is used for sensing of current values.

Figure 26B:
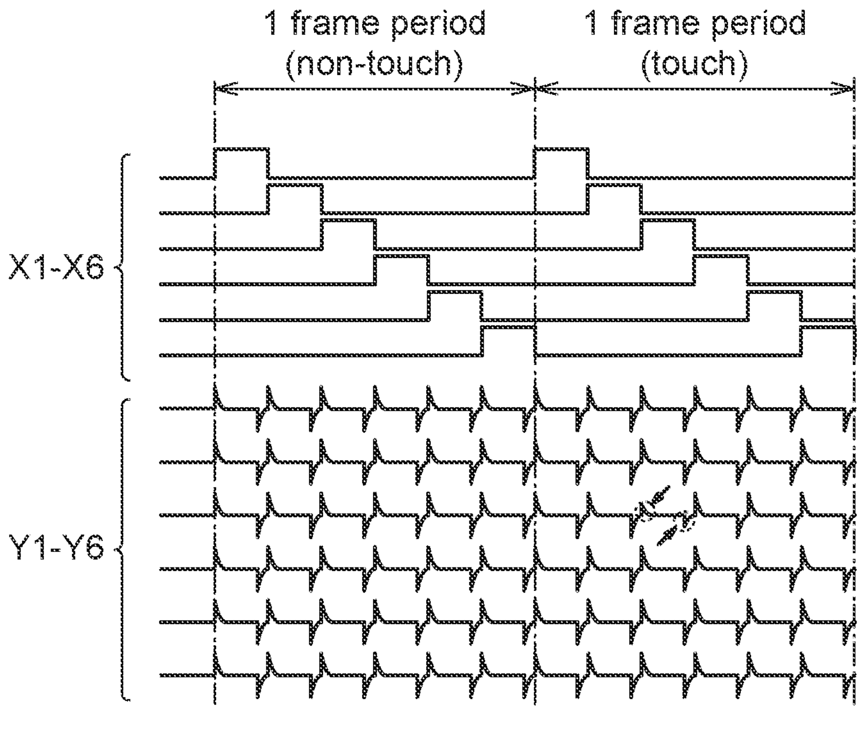

FIG. 26B is a timing chart showing input and output waveforms in the mutual capacitive touch sensor illustrated in FIG. 26A. In FIG. 26B, sensing of a sensing target is performed in all the rows and columns in one frame period. FIG. 26B shows a period when a sensing target is not sensed (not touched) and a period when a sensing target is sensed (touched). In FIG. 26B, sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change uniformly in accordance with changes in the voltages of the wirings X1 to X6.

The current value is decreased at the point of approach or contact of a sensing target and accordingly the waveform of the voltage value changes.

By detecting a change in mutual capacitance in this manner, the approach or contact of a sensing target can be sensed.

<Description of Sensor Circuit>

Figure 27:
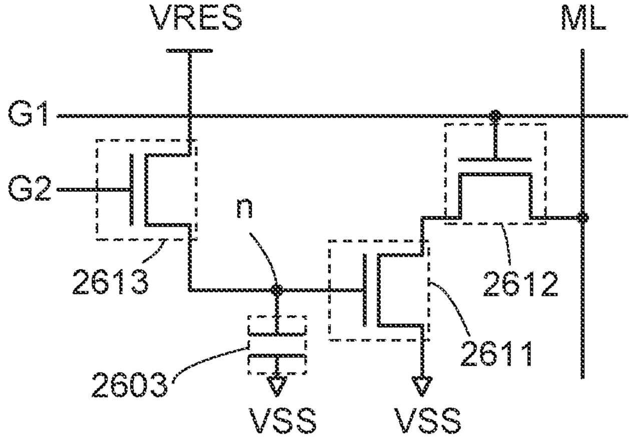
FIG. 27 is a circuit diagram of a touch sensor of one embodiment of the present invention.

Although FIG. 26A illustrates a passive matrix type touch sensor in which only the capacitor 2603 is provided at the intersection of wirings as a touch sensor, an active matrix type touch sensor including a transistor and a capacitor may be used. FIG. 27 illustrates an example of a sensor circuit included in an active matrix type touch sensor. The sensor circuit in FIG. 27 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit in FIG. 27 will be described. First, a potential for turning on the transistor 2613 is supplied as the signal G2, and a potential with respect to the voltage VRES is thus applied to the node n connected to the gate of the transistor 2611. Then, a potential for turning off the transistor 2613 is applied as the signal G2, whereby the potential of the node n is maintained.

Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613 so that the potential of the node n can be held for a long time and the frequency of operation of resupplying VRES to the node n (refresh operation) can be reduced.

The structure described in this embodiment can be used in combination with any of the structures described in the other embodiments as appropriate.

Embodiment 7

In this embodiment, a display module and electronic devices including a light-emitting element of one embodiment of the present invention will be described with reference to FIG. 28, FIGS. 29A to 29G, FIGS. 30A to 30F, FIGS. 31A to 31D, and FIGS. 32A and 32B.

<Display Module>

Figure 28:
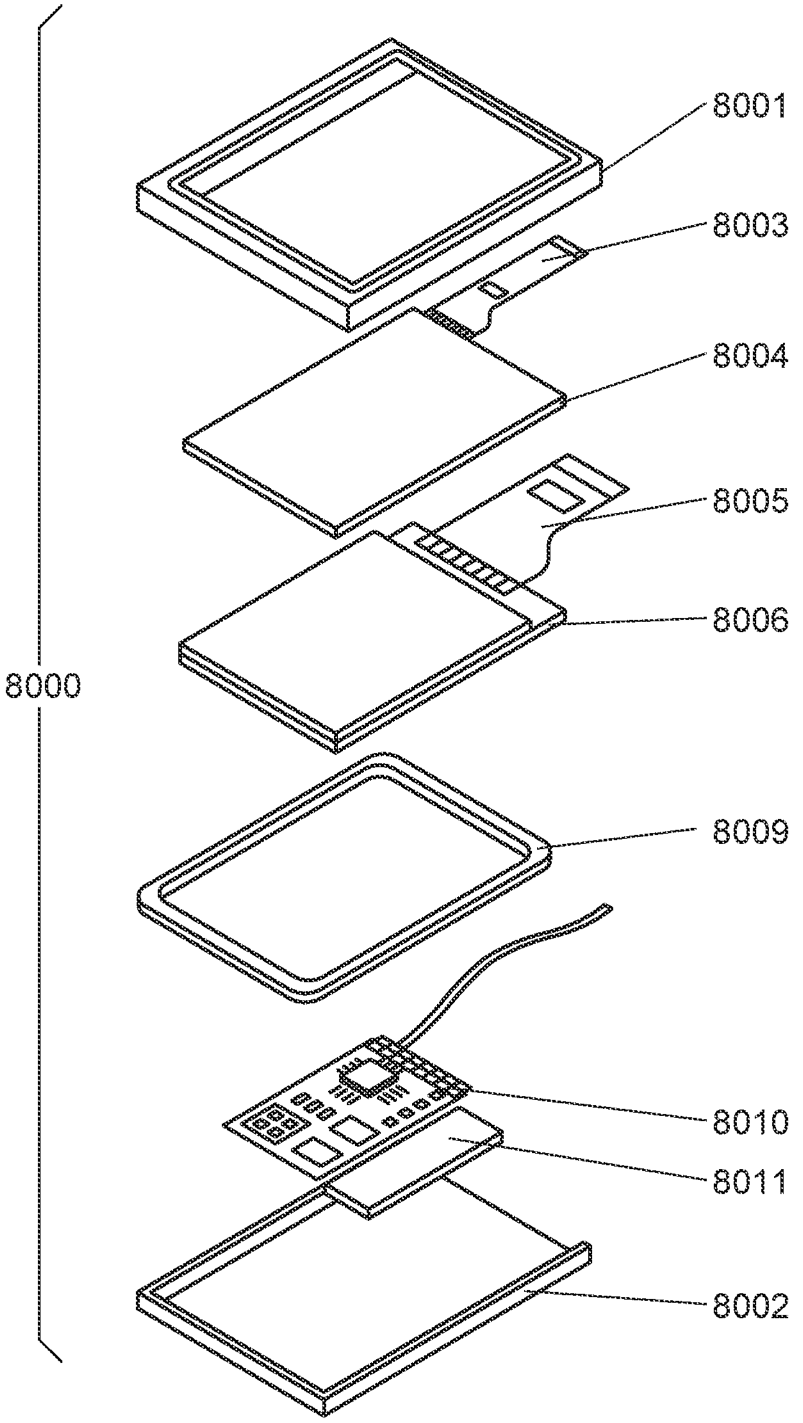
FIG. 28 is a perspective view illustrating a display module of one embodiment of the present invention.

In a display module 8000 in FIG. 28, a touch sensor 8004 connected to an FPC 8003, a display device 8006 connected to an FPC 8005, a frame 8009, a printed board 8010, and a battery 8011 are provided between an upper cover 8001 and a lower cover 8002.

The light-emitting element of one embodiment of the present invention can be used for the display device 8006, for example.

The shapes and sizes of the upper cover 8001 and the lower cover 8002 can be changed as appropriate in accordance with the sizes of the touch sensor 8004 and the display device 8006.

The touch sensor 8004 can be a resistive touch sensor or a capacitive touch sensor and may be formed to overlap with the display device 8006. A counter substrate (sealing substrate) of the display device 8006 can have a touch sensor function. A photosensor may be provided in each pixel of the display device 8006 so that an optical touch sensor is obtained.

The frame 8009 protects the display device 8006 and also serves as an electromagnetic shield for blocking electromagnetic waves generated by the operation of the printed board 8010. The frame 8009 may serve as a radiator plate.

The printed board 8010 has a power supply circuit and a signal processing circuit for outputting a video signal and a clock signal. As a power source for supplying power to the power supply circuit, an external commercial power source or the battery 8011 provided separately may be used. The battery 8011 can be omitted in the case of using a commercial power source.

The display module 8000 can be additionally provided with a member such as a polarizing plate, a retardation plate, or a prism sheet.

<Electronic Devices>

FIGS. 29A to 29G illustrate electronic devices. These electronic devices can include a housing 9000, a display portion 9001, a speaker 9003, operation keys 9005 (including a power switch or an operation switch), a connection terminal 9006, a sensor 9007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 9008, and the like. In addition, the sensor 9007 may have a function of measuring biological information like a pulse sensor and a finger print sensor.

The electronic devices illustrated in FIGS. 29A to 29G can have a variety of functions, for example, a function of displaying a variety of data (a still image, a moving image, a text image, and the like) on the display portion, a touch sensor function, a function of displaying a calendar, date, time, and the like, a function of controlling a process with a variety of software (programs), a wireless communication function, a function of being connected to a variety of computer networks with a wireless communication function, a function of transmitting and receiving a variety of data with a wireless communication function, a function of reading a program or data stored in a memory medium and displaying the program or data on the display portion, and the like. Note that functions that can be provided for the electronic devices illustrated in FIGS. 29A to 29G are not limited to those described above, and the electronic devices can have a variety of functions. Although not illustrated in FIGS. 29A to 29G, the electronic devices may include a plurality of display portions. The electronic devices may have a camera or the like and a function of taking a still image, a function of taking a moving image, a function of storing the taken image in a memory medium (an external memory medium or a memory medium incorporated in the camera), a function of displaying the taken image on the display portion, or the like.

The electronic devices illustrated in FIGS. 29A to 29G will be described in detail below.

Figure 29A:
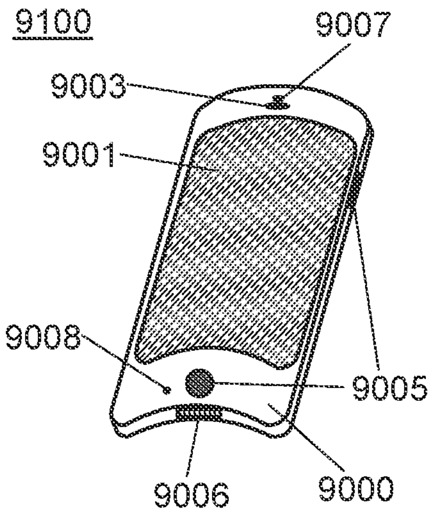
FIGS. 29A to 29G illustrate electronic devices of one embodiment of the present invention.

FIG. 29A is a perspective view of a portable information terminal 9100. The display portion 9001 of the portable information terminal 9100 is flexible. Therefore, the display portion 9001 can be incorporated along a bent surface of a bent housing 9000. In addition, the display portion 9001 includes a touch sensor, and operation can be performed by touching the screen with a finger, a stylus, or the like. For example, when an icon displayed on the display portion 9001 is touched, an application can be started.

Figure 29D:
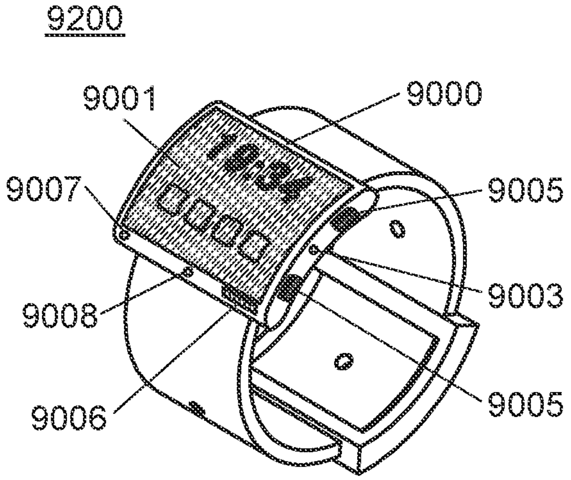
Figure 29B:
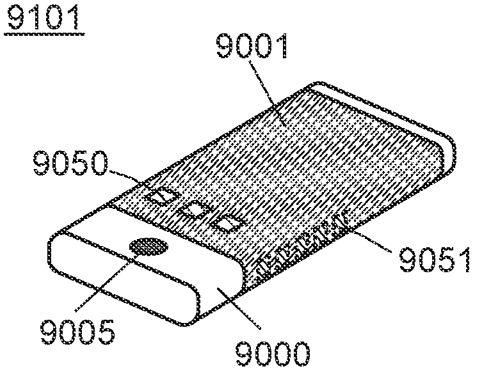

FIG. 29B is a perspective view of a portable information terminal 9101. The portable information terminal 9101 functions as, for example, one or more of a telephone set, a notebook, and an information browsing system. Specifically, the portable information terminal can be used as a smartphone. Note that the speaker 9003, the connection terminal 9006, the sensor 9007, and the like, which are not shown in FIG. 29B, can be positioned in the portable information terminal 9101 as in the portable information terminal 9100 shown in FIG. 29A. The portable information terminal 9101 can display characters and image information on its plurality of surfaces. For example, three operation buttons 9050 (also referred to as operation icons, or simply, icons) can be displayed on one surface of the display portion 9001. Furthermore, information 9051 indicated by dashed rectangles can be displayed on another surface of the display portion 9001. Examples of the information 9051 include display indicating reception of an incoming email, social networking service (SNS) message, call, and the like; the title and sender of an email and SNS message; the date; the time; remaining battery; and display indicating the strength of a received signal such as a radio wave. Instead of the information 9051, the operation buttons 9050 or the like may be displayed on the position where the information 9051 is displayed.

As a material of the housing 9000, an alloy, plastic, ceramic, or a material containing carbon fiber can be used. As the material containing carbon fiber, carbon fiber reinforced plastic (CFRP) has advantages of lightweight and corrosion-free; however, it is black and thus limits the exterior and design of the housing. The CFRP can be regarded as a kind of reinforced plastic, which may use glass fiber or aramid fiber. Since the fiber might be separated from a resin by high impact, the alloy is preferred. As the alloy, an aluminum alloy and a magnesium alloy can be given. An amorphous alloy (also referred to as metallic glass) containing zirconium, copper, nickel, and titanium especially has high elastic strength. This amorphous alloy has a glass transition region at room temperature, which is also referred to as a bulk-solidifying amorphous alloy and substantially has an amorphous atomic structure. An alloy material is molded in a mold of at least the part of the housing and coagulated by a solidification casting method, whereby part of the housing is formed with the bulk-solidifying amorphous alloy. The amorphous alloy may contain beryllium, silicon, niobium, boron, gallium, molybdenum, tungsten, manganese, iron, cobalt, yttrium, vanadium, phosphorus, carbon, or the like in addition to zirconium, copper, nickel, and titanium. The amorphous alloy may be formed by a vacuum evaporation method, a sputtering method, an electroplating method, an electroless plating method, or the like instead of the solidification casting method. The amorphous alloy may include a microcrystal or a nanocrystal as long as a state without a long-range order (a periodic structure) is maintained as a whole. Note that the term alloy includes both a complete solid solution alloy having a single solid-phase structure and a partial solution having two or more phases. The housing 9000 using the amorphous alloy can have high elastic strength. Even if the portable information terminal 9101 is dropped and the impact causes temporary deformation, the use of the amorphous alloy in the housing 9000 allows a return to the original shape; thus, the impact resistance of the portable information terminal 9101 can be improved.

Figure 29E:
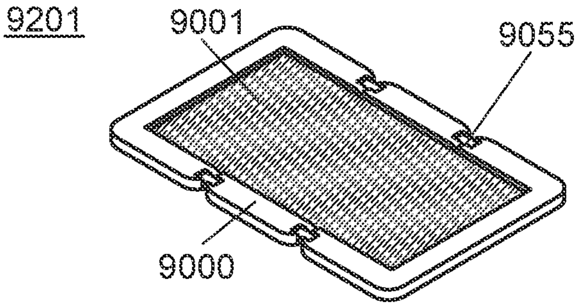
Figure 29F:
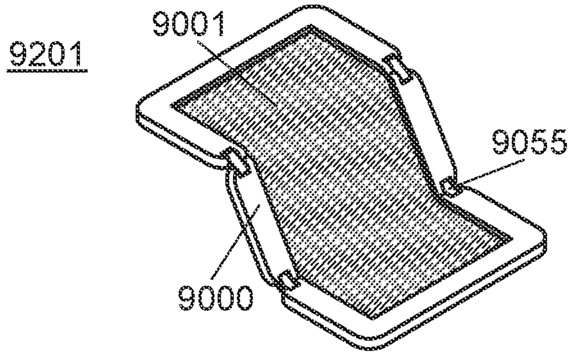
Figure 29C:
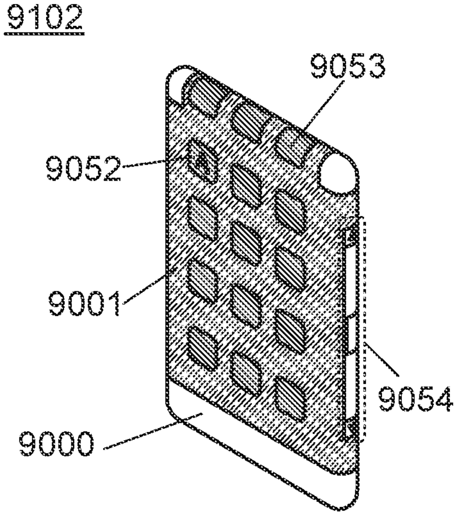

FIG. 29C is a perspective view of a portable information terminal 9102. The portable information terminal 9102 has a function of displaying information on three or more surfaces of the display portion 9001. Here, information 9052, information 9053, and information 9054 are displayed on different surfaces. For example, a user of the portable information terminal 9102 can see the display (here, the information 9053) with the portable information terminal 9102 put in a breast pocket of his/her clothes. Specifically, a caller's phone number, name, or the like of an incoming call is displayed in a position that can be seen from above the portable information terminal 9102. Thus, the user can see the display without taking out the portable information terminal 9102 from the pocket and decide whether to answer the call.

FIG. 29D is a perspective view of a watch-type portable information terminal 9200. The portable information terminal 9200 is capable of executing a variety of applications such as mobile phone calls, e-mailing, viewing and editing texts, music reproduction, Internet communication, and computer games. The display surface of the display portion 9001 is bent, and images can be displayed on the bent display surface. The portable information terminal 9200 can employ near field communication that is a communication method based on an existing communication standard. In that case, for example, mutual communication between the portable information terminal 9200 and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is possible. Note that the charging operation may be performed by wireless power feeding without using the connection terminal 9006.

Figure 29G:
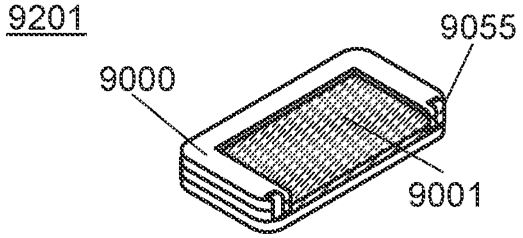

FIGS. 29E, 29F, and 29G are perspective views of a foldable portable information terminal 9201. FIG. 29E is a perspective view illustrating the portable information terminal 9201 that is opened. FIG. 29F is a perspective view illustrating the portable information terminal 9201 that is being opened or being folded. FIG. 29G is a perspective view illustrating the portable information terminal 9201 that is folded. The portable information terminal 9201 is highly portable when folded. When the portable information terminal 9201 is opened, a seamless large display region is highly browsable. The display portion 9001 of the portable information terminal 9201 is supported by three housings 9000 joined together by hinges 9055. By folding the portable information terminal 9201 at a connection portion between two housings 9000 with the hinges 9055, the portable information terminal 9201 can be reversibly changed in shape from an opened state to a folded state. For example, the portable information terminal 9201 can be bent with a radius of curvature of greater than or equal to 1 mm and less than or equal to 150 mm.

Examples of electronic devices are a television set (also referred to as a television or a television receiver), a monitor of a computer or the like, a camera such as a digital camera or a digital video camera, a digital photo frame, a mobile phone handset (also referred to as a mobile phone or a mobile phone device), a goggle-type display (head mounted display), a portable game machine, a portable information terminal, an audio reproducing device, and a large-sized game machine such as a pachinko machine.

Furthermore, the electronic device of one embodiment of the present invention may include a secondary battery. It is preferable that the secondary battery be capable of being charged by non-contact power transmission.

Examples of the secondary battery include a lithium ion secondary battery such as a lithium polymer battery using a gel electrolyte (lithium ion polymer battery), a lithium-ion battery, a nickel-hydride battery, a nickel-cadmium battery, an organic radical battery, a lead storage battery, an air secondary battery, a nickel-zinc battery, and a silver-zinc battery.

The electronic device of one embodiment of the present invention may include an antenna. When a signal is received by the antenna, the electronic device can display an image, data, or the like on a display portion. When the electronic device includes a secondary battery, the antenna may be used for non-contact power transmission.

Figure 30A:
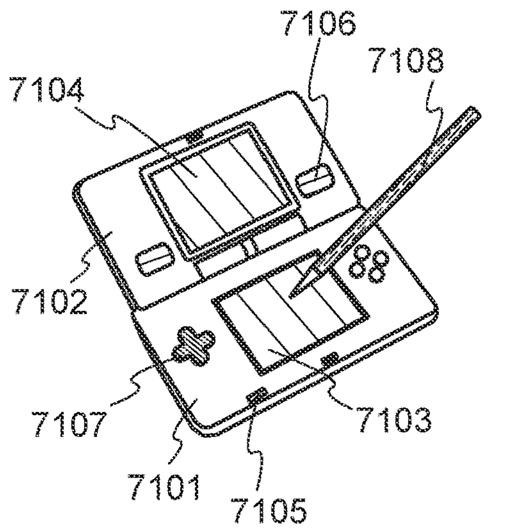
FIGS. 30A to 30F illustrate electronic devices of one embodiment of the present invention.

FIG. 30A illustrates a portable game machine including a housing 7101, a housing 7102, display portions 7103 and 7104, a microphone 7105, speakers 7106, an operation key 7107, a stylus 7108, and the like. When the light-emitting device of one embodiment of the present invention is used as the display portion 7103 or 7104, it is possible to provide a user-friendly portable game machine with quality that hardly deteriorates. Although the portable game machine illustrated in FIG. 30A includes two display portions, the display portions 7103 and 7104, the number of display portions included in the portable game machine is not limited to two.

Figure 30B:
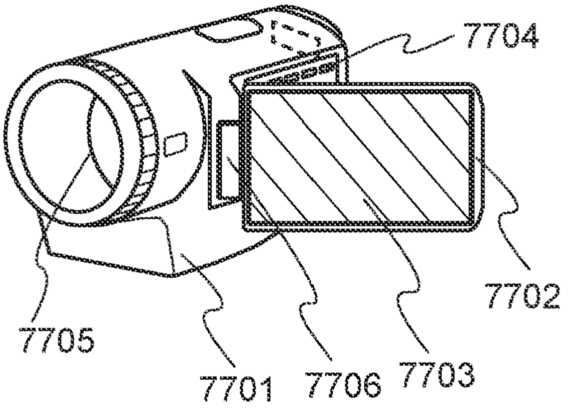

FIG. 30B illustrates a video camera including a housing 7701, a housing 7702, a display portion 7703, operation keys 7704, a lens 7705, a joint 7706, and the like. The operation keys 7704 and the lens 7705 are provided for the housing 7701, and the display portion 7703 is provided for the housing 7702. The housing 7701 and the housing 7702 are connected to each other with the joint 7706, and the angle between the housing 7701 and the housing 7702 can be changed with the joint 7706. Images displayed on the display portion 7703 may be switched in accordance with the angle at the joint 7706 between the housing 7701 and the housing 7702.

Figure 30C:
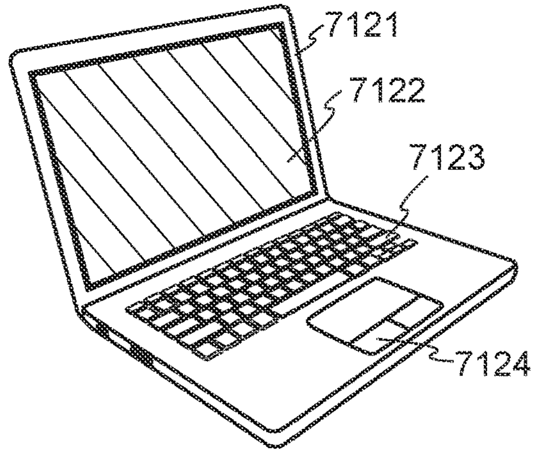

FIG. 30C illustrates a notebook personal computer including a housing 7121, a display portion 7122, a keyboard 7123, a pointing device 7124, and the like. Note that the display portion 7122 is small- or medium-sized but can perform 8*k* display because it has greatly high pixel density and high resolution; therefore, a significantly clear image can be obtained.

Figure 30D:
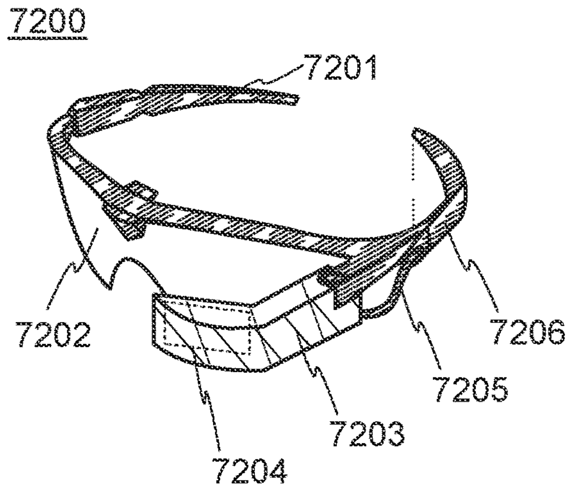

FIG. 30D is an external view of a head-mounted display 7200.

The head-mounted display 7200 includes a mounting portion 7201, a lens 7202, a main body 7203, a display portion 7204, a cable 7205, and the like. The mounting portion 7201 includes a battery 7206.

Power is supplied from the battery 7206 to the main body 7203 through the cable 7205. The main body 7203 includes a wireless receiver or the like to receive video data, such as image data, and display it on the display portion 7204. The movement of the eyeball and the eyelid of a user is captured by a camera in the main body 7203 and then coordinates of the points the user looks at are calculated using the captured data to utilize the eye point of the user as an input means.

The mounting portion 7201 may include a plurality of electrodes so as to be in contact with the user. The main body 7203 may be configured to sense current flowing through the electrodes with the movement of the user's eyeball to recognize the direction of his or her eyes. The main body 7203 may be configured to sense current flowing through the electrodes to monitor the user's pulse. The mounting portion 7201 may include sensors, such as a temperature sensor, a pressure sensor, or an acceleration sensor, so that the user's biological information can be displayed on the display portion 7204. The main body 7203 may be configured to sense the movement of the user's head or the like to move an image displayed on the display portion 7204 in synchronization with the movement of the user's head or the like.

Figure 30E:
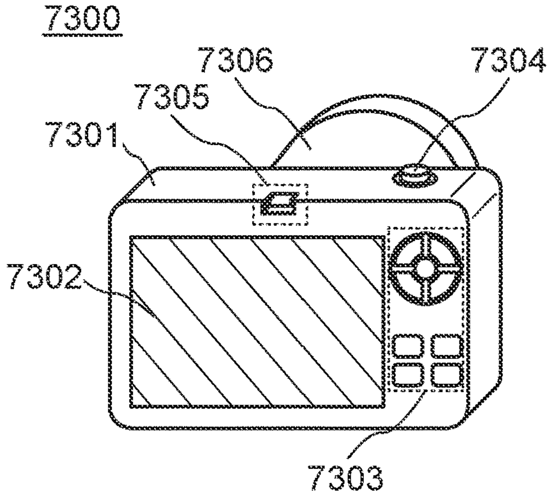

FIG. 30E is an external view of a camera 7300. The camera 7300 includes a housing 7301, a display portion 7302, an operation button 7303, a shutter button 7304, a connection portion 7305, and the like. A lens 7306 can be put on the camera 7300. The connection portion 7305 includes an electrode to connect with a finder 7400, which is described below, a stroboscope, or the like.

Although the lens 7306 of the camera 7300 here is detachable from the housing 7301 for replacement, the lens 7306 may be included in the housing 7301.

Images can be taken at the touch of the shutter button 7304. In addition, images can be taken by operation of the display portion 7302 including a touch sensor.

In the display portion 7302, the display device of one embodiment of the present invention or a touch sensor can be used.

Figure 30F:
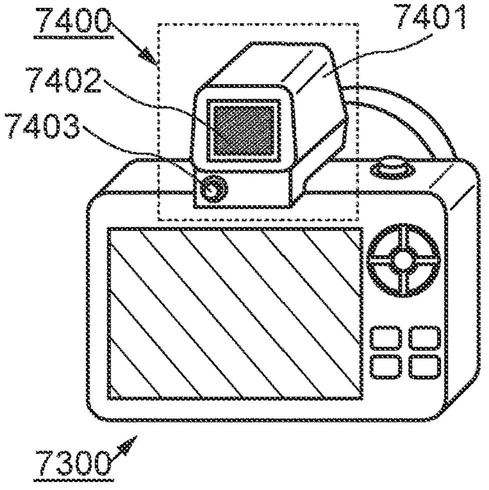

FIG. 30F shows the camera 7300 with the finder 7400 connected.

The finder 7400 includes a housing 7401, a display portion 7402, and a button 7403.

The housing 7401 includes a connection portion for engagement with the connection portion 7305 of the camera 7300 so that the finder 7400 can be connected to the camera 7300. The connection portion includes an electrode, and an image or the like received from the camera 7300 through the electrode can be displayed on the display portion 7402.

The button 7403 has a function of a power button, and the display portion 7402 can be turned on and off with the button 7403.

Although the camera 7300 and the finder 7400 are separate and detachable electronic devices in FIGS. 30E and 30F, the housing 7301 of the camera 7300 may include a finder having a display device of one embodiment of the present invention or a touch sensor.

Figure 31A:
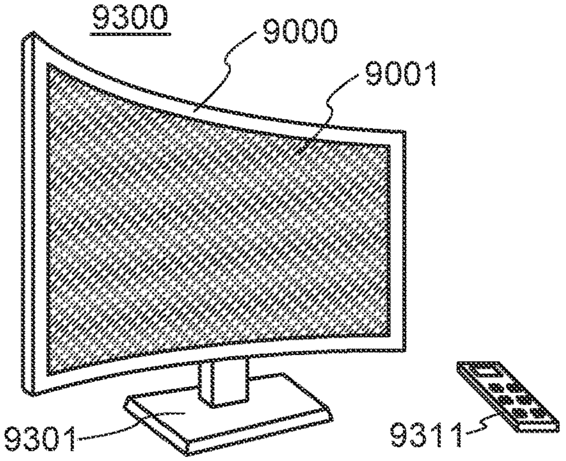
FIGS. 31A to 31D illustrate electronic devices of one embodiment of the present invention.

FIG. 31A illustrates an example of a television set. In the television set 9300, the display portion 9001 is incorporated into the housing 9000. Here, the housing 9000 is supported by a stand 9301.

The television set 9300 illustrated in FIG. 31A can be operated with an operation switch of the housing 9000 or a separate remote controller 9311. The display portion 9001 may include a touch sensor. The television set 9300 can be operated by touching the display portion 9001 with a finger or the like. The remote controller 9311 may be provided with a display portion for displaying data output from the remote controller 9311. With operation keys or a touch panel of the remote controller 9311, channels or volume can be controlled and images displayed on the display portion 9001 can be controlled.

The television set 9300 is provided with a receiver, a modem, or the like. A general television broadcast can be received with the receiver. When the television set is connected to a communication network with or without wires via the modem, one-way (from a transmitter to a receiver) or two-way (between a transmitter and a receiver or between receivers) data communication can be performed.

The electronic device or the lighting device of one embodiment of the present invention has flexibility and therefore can be incorporated along a curved inside/outside wall surface of a house or a building or a curved interior/exterior surface of a car.

Figure 31B:
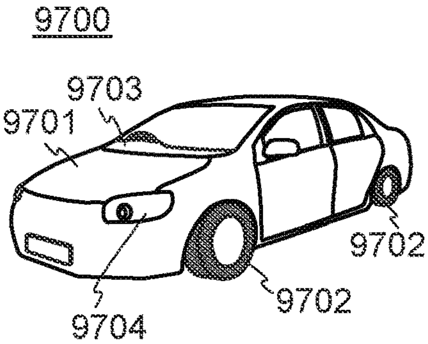
Figure 31C:
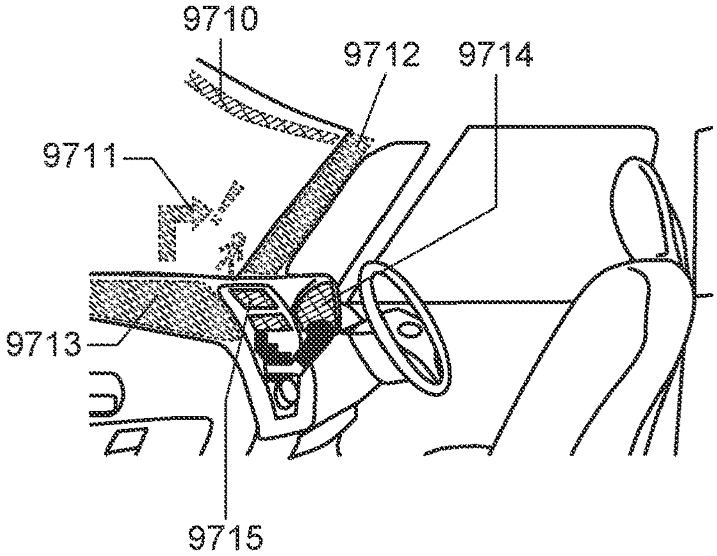

FIG. 31B is an external view of an automobile 9700. FIG. 31C illustrates a driver's seat of the automobile 9700. The automobile 9700 includes a car body 9701, wheels 9702, a dashboard 9703, lights 9704, and the like. The display device, the light-emitting device, or the like of one embodiment of the present invention can be used in a display portion or the like of the automobile 9700. For example, the display device, the light-emitting device, or the like of one embodiment of the present invention can be used in display portions 9710 to 9715 illustrated in FIG. 31C.

The display portion 9710 and the display portion 9711 are each a display device provided in an automobile windshield. The display device, the light-emitting device, or the like of one embodiment of the present invention can be a see-through display device, through which the opposite side can be seen, using a light-transmitting conductive material for its electrodes and wirings. Such a see-through display portion 9710 or 9711 does not hinder driver's vision during driving the automobile 9700. Thus, the display device, the light-emitting device, or the like of one embodiment of the present invention can be provided in the windshield of the automobile 9700. Note that in the case where a transistor or the like for driving the display device, the light-emitting device, or the like is provided, a transistor having a light-transmitting property, such as an organic transistor using an organic semiconductor material or a transistor using an oxide semiconductor, is preferably used.

The display portion 9712 is a display device provided on a pillar portion. For example, an image taken by an imaging unit provided in the car body is displayed on the display portion 9712, whereby the view hindered by the pillar portion can be compensated. The display portion 9713 is a display device provided on the dashboard. For example, an image taken by an imaging unit provided in the car body is displayed on the display portion 9713, whereby the view hindered by the dashboard can be compensated. That is, by displaying an image taken by an imaging unit provided on the outside of the automobile, blind areas can be eliminated and safety can be increased. Displaying an image to compensate for the area which a driver cannot see, makes it possible for the driver to confirm safety easily and comfortably.

Figure 31D:
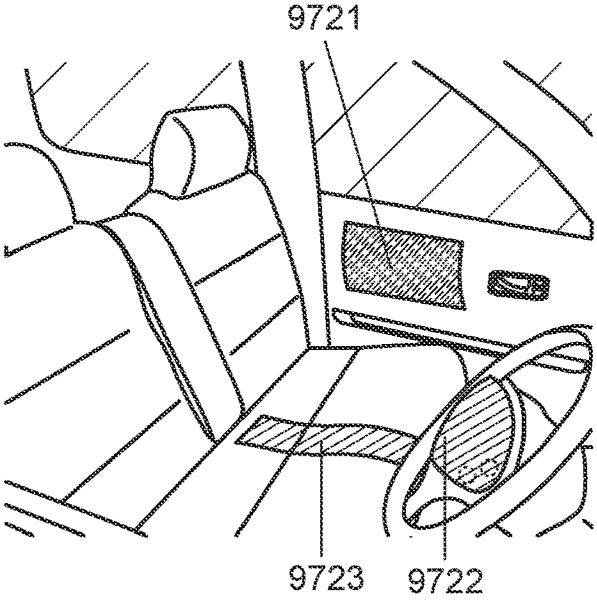

FIG. 31D illustrates the inside of a car in which bench seats are used for a driver seat and a front passenger seat. A display portion 9721 is a display device provided in a door portion. For example, an image taken by an imaging unit provided in the car body is displayed on the display portion 9721, whereby the view hindered by the door can be compensated. A display portion 9722 is a display device provided in a steering wheel. A display portion 9723 is a display device provided in the middle of a seating face of the bench seat. Note that the display device can be used as a seat heater by providing the display device on the seating face or backrest and by using heat generation of the display device as a heat source.

The display portion 9714, the display portion 9715, and the display portion 9722 can provide a variety of kinds of information such as navigation data, a speedometer, a tachometer, a mileage, a fuel meter, a gearshift indicator, and air-condition setting. The content, layout, or the like of the display on the display portions can be changed freely by a user as appropriate. The information listed above can also be displayed on the display portions 9710 to 9713, 9721, and 9723. The display portions 9710 to 9715 and 9721 to 9723 can also be used as lighting devices. The display portions 9710 to 9715 and 9721 to 9723 can also be used as heating devices.

Figure 32A:
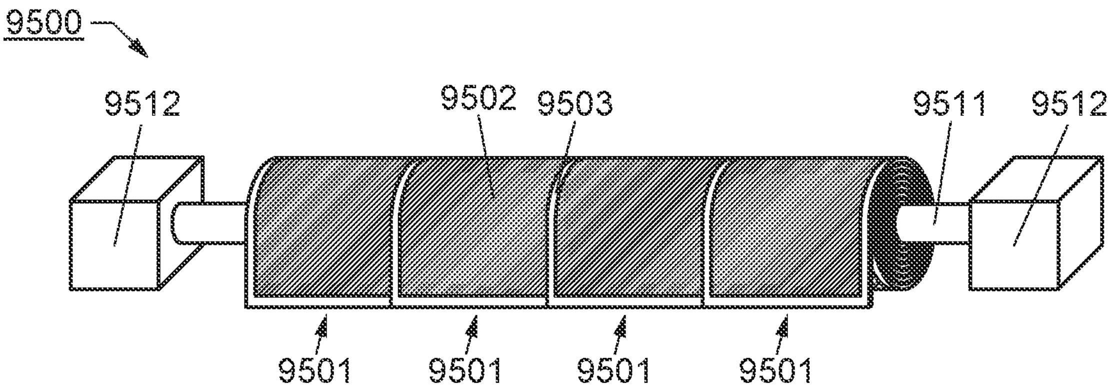
FIGS. 32A and 32B are perspective views illustrating a display device of one embodiment of the present invention.
Figure 32B:
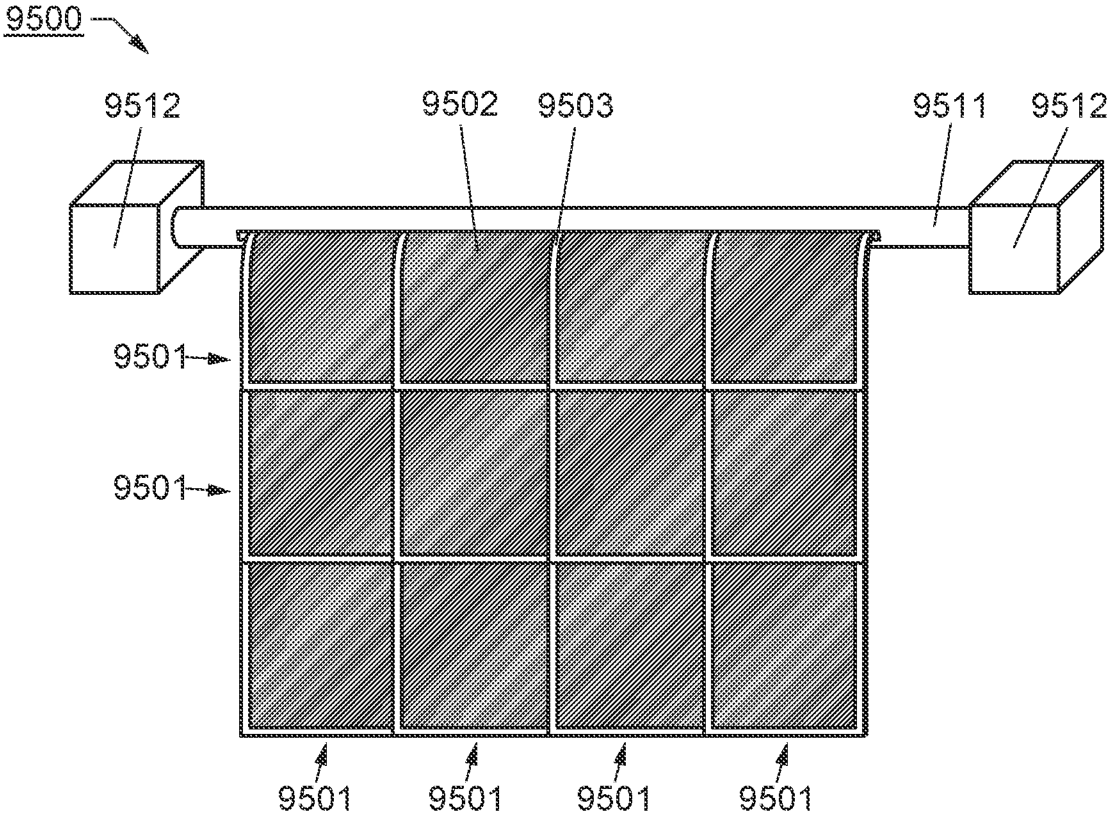

A display device 9500 illustrated in FIGS. 32A and 32B includes a plurality of display panels 9501, a hinge 9511, and a bearing 9512. The plurality of display panels 9501 each include a display region 9502 and a light-transmitting region 9503.

Each of the plurality of display panels 9501 is flexible. Two adjacent display panels 9501 are provided so as to partly overlap with each other. For example, the light-transmitting regions 9503 of the two adjacent display panels 9501 can be overlapped each other. A display device having a large screen can be obtained with the plurality of display panels 9501. The display device is highly versatile because the display panels 9501 can be wound depending on its use.

Moreover, although the display regions 9502 of the adjacent display panels 9501 are separated from each other in FIGS. 32A and 32B, without limitation to this structure, the display regions 9502 of the adjacent display panels 9501 may overlap with each other without any space so that a continuous display region 9502 is obtained, for example.

The electronic devices described in this embodiment each include the display portion for displaying some sort of data. Note that the light-emitting element of one embodiment of the present invention can also be used for an electronic device which does not have a display portion. The structure in which the display portion of the electronic device described in this embodiment is flexible and display can be performed on the bent display surface or the structure in which the display portion of the electronic device is foldable is described as an example; however, the structure is not limited thereto and a structure in which the display portion of the electronic device is not flexible and display is performed on a plane portion may be employed.

The structure described in this embodiment can be used in combination with any of the structures described in the other embodiments as appropriate.

Embodiment 8

In this embodiment, a light-emitting device including the light-emitting element of one embodiment of the present invention will be described with reference to FIGS. 33A to 33C and FIGS. 34A to 34D.

Figure 33A:
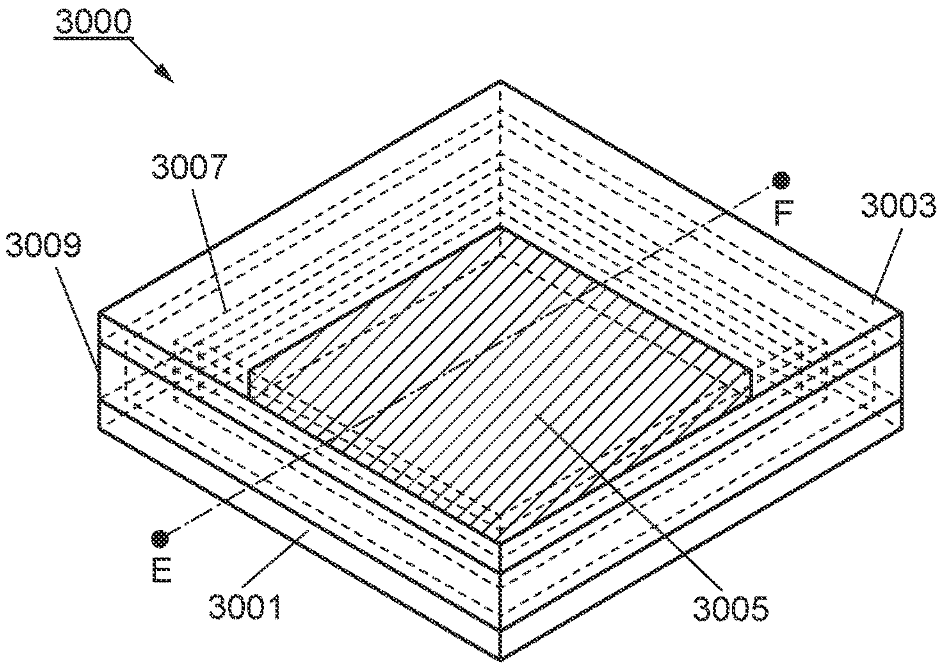
FIGS. 33A to 33C are a perspective view and cross-sectional views illustrating light-emitting devices of one embodiment of the present invention.
Figure 33B:
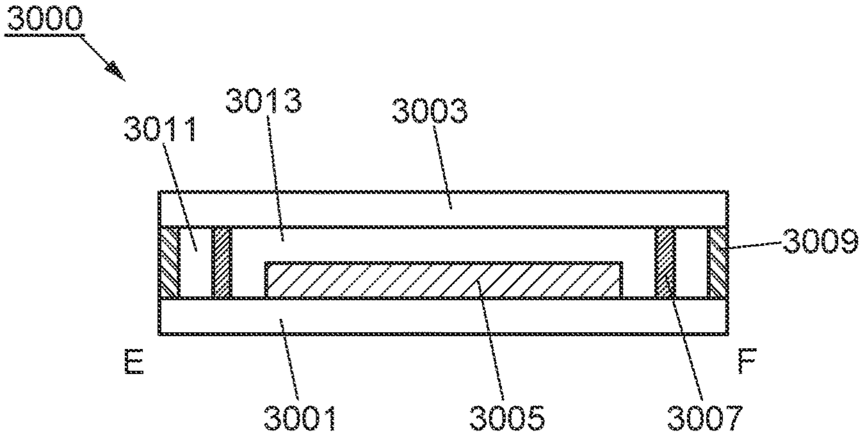

FIG. 33A is a perspective view of a light-emitting device 3000 shown in this embodiment, and FIG. 33B is a cross-sectional view along dashed-dotted line E-F in FIG. 33A. Note that in FIG. 33A, some components are illustrated by broken lines in order to avoid complexity of the drawing.

The light-emitting device 3000 illustrated in FIGS. 33A and 33B includes a substrate 3001, a light-emitting element 3005 over the substrate 3001, a first sealing region 3007 provided around the light-emitting element 3005, and a second sealing region 3009 provided around the first sealing region 3007.

Light is emitted from the light-emitting element 3005 through one or both of the substrate 3001 and a substrate 3003. In FIGS. 33A and 33B, a structure in which light is emitted from the light-emitting element 3005 to the lower side (the substrate 3001 side) is illustrated.

As illustrated in FIGS. 33A and 33B, the light-emitting device 3000 has a double sealing structure in which the light-emitting element 3005 is surrounded by the first sealing region 3007 and the second sealing region 3009. With the double sealing structure, entry of impurities (e.g., water, oxygen, and the like) from the outside into the light-emitting element 3005 can be favorably suppressed. Note that it is not necessary to provide both the first sealing region 3007 and the second sealing region 3009. For example, only the first sealing region 3007 may be provided.

Note that in FIG. 33B, the first sealing region 3007 and the second sealing region 3009 are each provided in contact with the substrate 3001 and the substrate 3003. However, without limitation to such a structure, for example, one or both of the first sealing region 3007 and the second sealing region 3009 may be provided in contact with an insulating film or a conductive film provided on the substrate 3001. Alternatively, one or both of the first sealing region 3007 and the second sealing region 3009 may be provided in contact with an insulating film or a conductive film provided on the substrate 3003.

The substrate 3001 and the substrate 3003 can have structures similar to those of the substrate 200 and the substrate 220 described in the above embodiment, respectively. The light-emitting element 3005 can have a structure similar to that of any of the light-emitting elements described in the above embodiments.

For the first sealing region 3007, a material containing glass (e.g., a glass frit, a glass ribbon, and the like) can be used. For the second sealing region 3009, a material containing a resin can be used. With the use of the material containing glass for the first sealing region 3007, productivity and a sealing property can be improved. Moreover, with the use of the material containing a resin for the second sealing region 3009, impact resistance and heat resistance can be improved. However, the materials used for the first sealing region 3007 and the second sealing region 3009 are not limited to such, and the first sealing region 3007 may be formed using the material containing a resin and the second sealing region 3009 may be formed using the material containing glass.

The glass frit may contain, for example, magnesium oxide, calcium oxide, strontium oxide, barium oxide, cesium oxide, sodium oxide, potassium oxide, boron oxide, vanadium oxide, zinc oxide, tellurium oxide, aluminum oxide, silicon dioxide, lead oxide, tin oxide, phosphorus oxide, ruthenium oxide, rhodium oxide, iron oxide, copper oxide, manganese dioxide, molybdenum oxide, niobium oxide, titanium oxide, tungsten oxide, bismuth oxide, zirconium oxide, lithium oxide, antimony oxide, lead borate glass, tin phosphate glass, vanadate glass, or borosilicate glass. The glass frit preferably contains at least one kind of transition metal to absorb infrared light.

As the above glass frits, for example, a frit paste is applied to a substrate and is subjected to heat treatment, laser light irradiation, or the like. The frit paste contains the glass frit and a resin (also referred to as a binder) diluted by an organic solvent. Note that an absorber which absorbs light having the wavelength of laser light may be added to the glass frit. For example, an Nd: YAG laser or a semiconductor laser is preferably used as the laser. The shape of laser light may be circular or quadrangular.

As the above material containing a resin, for example, polyester, polyolefin, polyamide (e.g., nylon, aramid), polyimide, polycarbonate, or an acrylic resin, polyurethane, or an epoxy resin can be used. Alternatively, a material that includes a resin having a siloxane bond such as silicone can be used.

Note that in the case where the material containing glass is used for one or both of the first sealing region 3007 and the second sealing region 3009, the material containing glass preferably has a thermal expansion coefficient close to that of the substrate 3001. With the above structure, generation of a crack in the material containing glass or the substrate 3001 due to thermal stress can be suppressed.

For example, the following advantageous effect can be obtained in the case where the material containing glass is used for the first sealing region 3007 and the material containing a resin is used for the second sealing region 3009.

The second sealing region 3009 is provided closer to an outer portion of the light-emitting device 3000 than the first sealing region 3007 is. In the light-emitting device 3000, distortion due to external force or the like increases toward the outer portion. Thus, the light-emitting device 3000 is sealed using the material containing a resin for the outer portion of the light-emitting device 3000 where a larger amount of distortion is generated, that is, the second sealing region 3009, and the light-emitting device 3000 is sealed using the material containing glass for the first sealing region 3007 provided on an inner side of the second sealing region 3009, whereby the light-emitting device 3000 is less likely to be damaged even when distortion due to external force or the like is generated.

Furthermore, as illustrated in FIG. 33B, a first region 3011 corresponds to the region surrounded by the substrate 3001, the substrate 3003, the first sealing region 3007, and the second sealing region 3009. A second region 3013 corresponds to the region surrounded by the substrate 3001, the substrate 3003, the light-emitting element 3005, and the first sealing region 3007.

The first region 3011 and the second region 3013 are preferably filled with, for example, an inert gas such as a rare gas or a nitrogen gas. Alternatively, the first region 3011 and the second region 3013 are preferably filled with a resin such as an acrylic resin or an epoxy resin. Note that for the first region 3011 and the second region 3013, a reduced pressure state is preferred to an atmospheric pressure state.

Figure 33C:
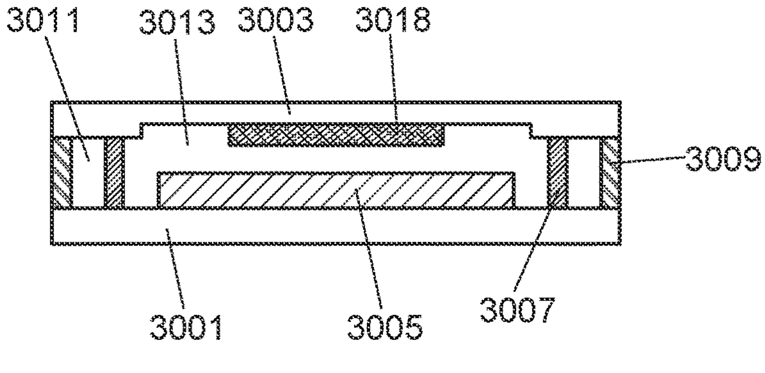

FIG. 33C illustrates a modification example of the structure in FIG. 33B. FIG. 33C is a cross-sectional view illustrating the modification example of the light-emitting device 3000.

FIG. 33C illustrates a structure in which a desiccant 3018 is provided in a recessed portion provided in part of the substrate 3003. The other components are the same as those of the structure illustrated in FIG. 33B.

As the desiccant 3018, a substance which adsorbs moisture and the like by chemical adsorption or a substance which adsorbs moisture and the like by physical adsorption can be used. Examples of the substance that can be used as the desiccant 3018 include alkali metal oxides, alkaline earth metal oxide (e.g., calcium oxide, barium oxide, and the like), sulfate, metal halides, perchlorate, zeolite, silica gel, and the like.

Next, modification examples of the light-emitting device 3000 which is illustrated in FIG. 33B are described with reference to FIGS. 34A to 34D. Note that FIGS. 34A to 34D are cross-sectional views illustrating the modification examples of the light-emitting device 3000 illustrated in FIG. 33B.

In each of the light-emitting devices illustrated in FIGS. 34A to 34D, the second sealing region 3009 is not provided but only the first sealing region 3007 is provided. Moreover, in each of the light-emitting devices illustrated in FIGS. 34A to 34D, a region 3014 is provided instead of the second region 3013 illustrated in FIG. 33B.

For the region 3014, for example, polyester, polyolefin, polyamide (e.g., nylon, aramid), polyimide, polycarbonate, or an acrylic resin, polyurethane, or an epoxy resin can be used. Alternatively, a material that includes a resin having a siloxane bond such as silicone can be used.

When the above-described material is used for the region 3014, what is called a solid-sealing light-emitting device can be obtained.

Figure 34A:
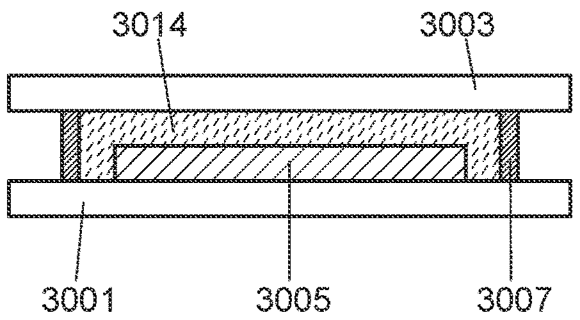
FIGS. 34A to 34D are each a cross-sectional view illustrating a light-emitting device of one embodiment of the present invention.
Figure 34B:
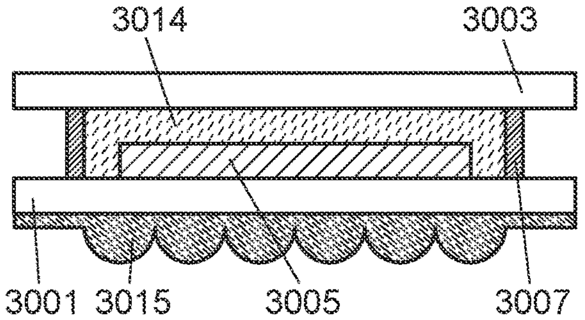

In the light-emitting device illustrated in FIG. 34B, a substrate 3015 is provided on the substrate 3001 side of the light-emitting device illustrated in FIG. 34A.

The substrate 3015 has unevenness as illustrated in FIG. 34B. With a structure in which the substrate 3015 having unevenness is provided on the side through which light emitted from the light-emitting element 3005 is extracted, the efficiency of extraction of light from the light-emitting element 3005 can be improved. Note that instead of the structure having unevenness and illustrated in FIG. 34B, a substrate having a function as a diffusion plate may be provided.

Figure 34C:
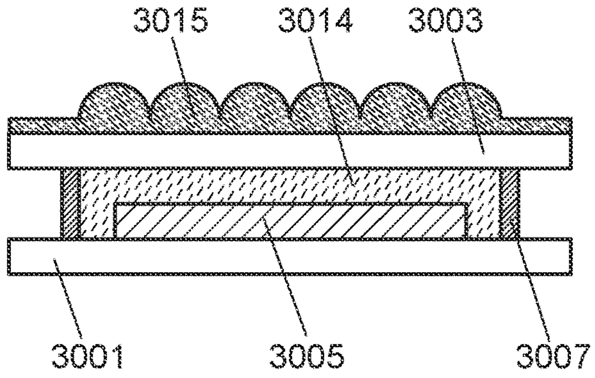

In the light-emitting device illustrated in FIG. 34C, light is extracted through the substrate 3003 side, unlike in the light-emitting device illustrated in FIG. 34A, in which light is extracted through the substrate 3001 side.

The light-emitting device illustrated in FIG. 34C includes the substrate 3015 on the substrate 3003 side. The other components are the same as those of the light-emitting device illustrated in FIG. 34B.

Figure 34D:
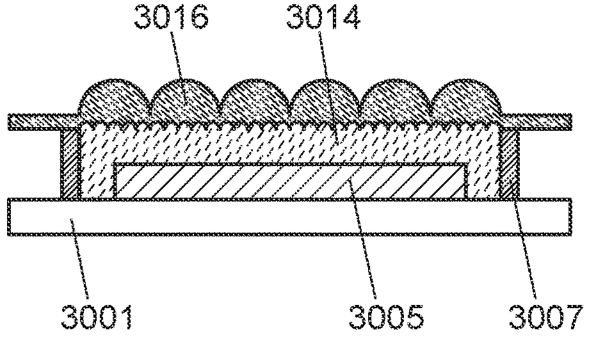

In the light-emitting device illustrated in FIG. 34D, the substrate 3003 and the substrate 3015 included in the light-emitting device illustrated in FIG. 34C are not provided but a substrate 3016 is provided.

The substrate 3016 includes first unevenness positioned closer to the light-emitting element 3005 and second unevenness positioned farther from the light-emitting element 3005. With the structure illustrated in FIG. 34D, the efficiency of extraction of light from the light-emitting element 3005 can be further improved.

Thus, the use of the structure described in this embodiment can provide a light-emitting device in which deterioration of a light-emitting element due to impurities such as moisture and oxygen is suppressed. Alternatively, with the structure described in this embodiment, a light-emitting device having high light extraction efficiency can be obtained.

Note that the structure described in this embodiment can be combined as appropriate with any of the structures described in the other embodiments.

Embodiment 9

In this embodiment, examples in which the light-emitting element of one embodiment of the present invention is used for various lighting devices and electronic devices will be described with reference to FIGS. 35A to 35C and FIG. 36.

An electronic device or a lighting device that has a light-emitting region with a curved surface can be obtained with the use of the light-emitting element of one embodiment of the present invention which is manufactured over a substrate having flexibility.

Furthermore, a light-emitting device to which one embodiment of the present invention is applied can also be used for lighting for motor vehicles, examples of which are lighting for a dashboard, a windshield, a ceiling, and the like.

Figure 35A:
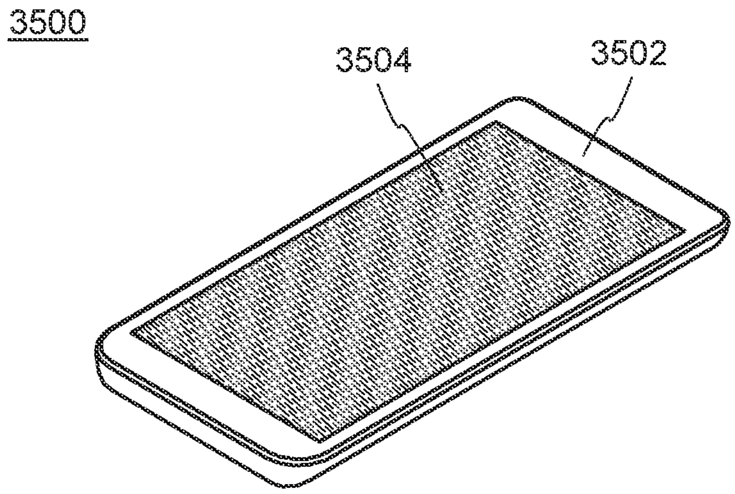
FIGS. 35A to 35C illustrate an electronic device and a lighting device of one embodiment of the present invention.
Figure 35B:
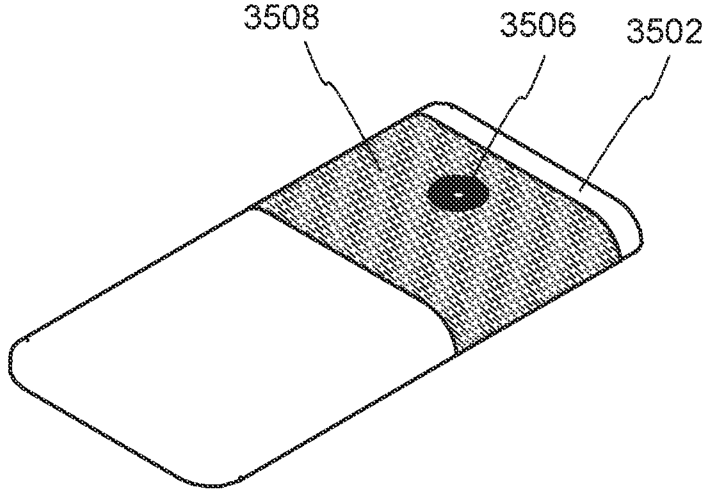

FIG. 35A is a perspective view illustrating one surface of a multifunction terminal 3500, and FIG. 35B is a perspective view illustrating the other surface of the multifunction terminal 3500. In a housing 3502 of the multifunction terminal 3500, a display portion 3504, a camera 3506, lighting 3508, and the like are incorporated. The light-emitting device of one embodiment of the present invention can be used for the lighting 3508.

The lighting 3508 that includes the light-emitting device of one embodiment of the present invention functions as a planar light source. Thus, unlike a point light source typified by an LED, the lighting 3508 can provide light emission with low directivity. When the lighting 3508 and the camera 3506 are used in combination, for example, imaging can be performed by the camera 3506 with the lighting 3508 lighting or flashing. Because the lighting 3508 functions as a planar light source, a photograph as if taken under natural light can be taken.

Note that the multifunction terminal 3500 illustrated in FIGS. 35A and 35B can have a variety of functions as in the electronic devices illustrated in FIGS. 29A to 29G.

The housing 3502 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. When a detection device including a sensor for detecting inclination, such as a gyroscope or an acceleration sensor, is provided inside the multifunction terminal 3500, display on the screen of the display portion 3504 can be automatically switched by determining the orientation of the multifunction terminal 3500 (whether the multifunction terminal is placed horizontally or vertically for a landscape mode or a portrait mode).

The display portion 3504 may function as an image sensor. For example, an image of a palm print, a fingerprint, or the like is taken when the display portion 3504 is touched with the palm or the finger, whereby personal authentication can be performed. Furthermore, by providing a backlight or a sensing light source which emits near-infrared light in the display portion 3504, an image of a finger vein, a palm vein, or the like can be taken. Note that the light-emitting device of one embodiment of the present invention may be used for the display portion 3504.

Figure 35C:
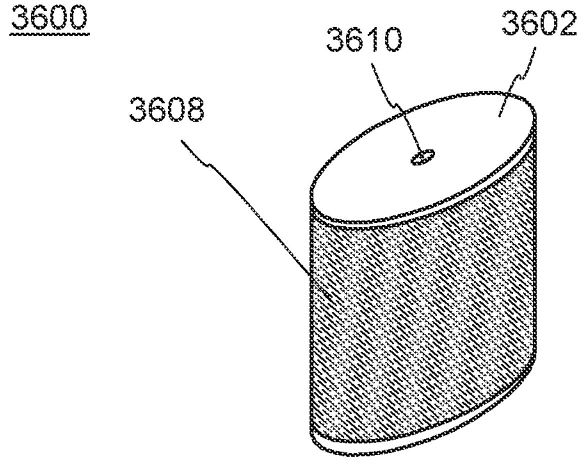

FIG. 35C is a perspective view of a security light 3600. The security light 3600 includes lighting 3608 on the outside of the housing 3602, and a speaker 3610 and the like are incorporated in the housing 3602. The light-emitting device of one embodiment of the present invention can be used for the lighting 3608.

The security light 3600 emits light when the lighting 3608 is gripped or held, for example. An electronic circuit that can control the manner of light emission from the security light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may be incorporated.

The security light 3600 can emit light in various directions; therefore, it is possible to intimidate a thug or the like with light, or light and sound. Moreover, the security light 3600 may include a camera such as a digital still camera to have a photography function.

Figure 36:
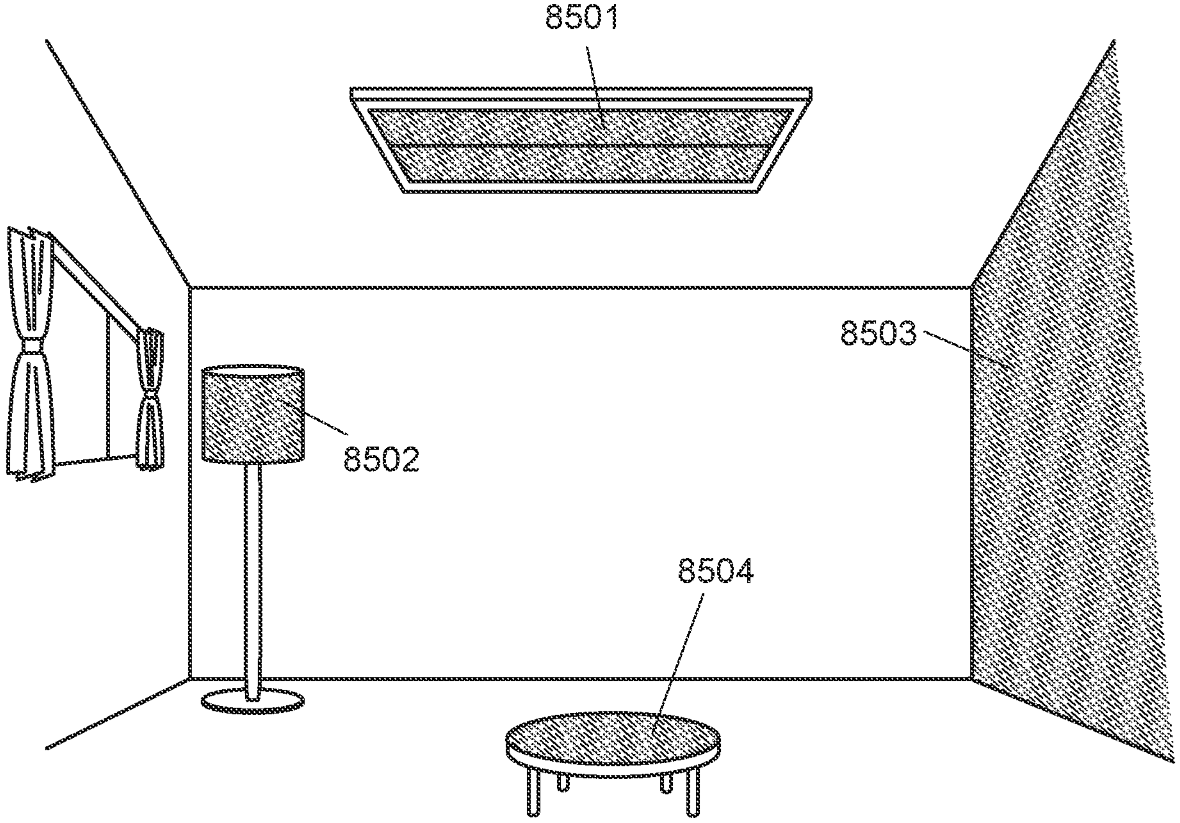
FIG. 36 illustrates lighting devices of one embodiment of the present invention.

FIG. 36 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with the use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function as a table can be obtained. When the light-emitting element is used as part of other furniture, a lighting device which has a function as the furniture can be obtained.

As described above, lighting devices and electronic devices can be obtained by application of the light-emitting device of one embodiment of the present invention. Note that the light-emitting device can be used for electronic devices in a variety of fields without being limited to the lighting devices and the electronic devices described in this embodiment.

The structure described in this embodiment can be used in combination with any of the structures described in the other embodiments as appropriate.

Example 1

Figure 37A:
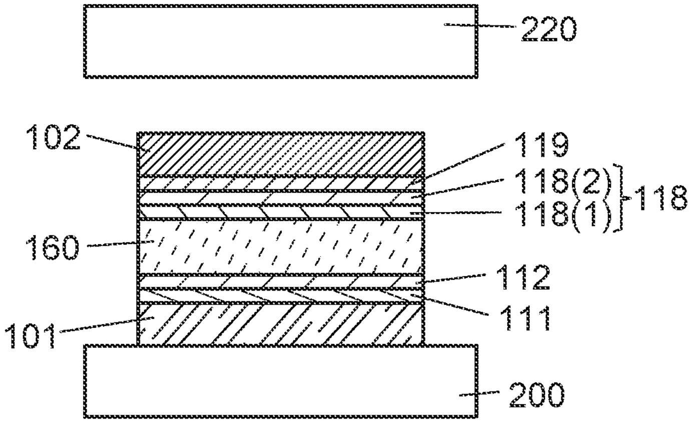
FIGS. 37A and 37B are each a schematic cross-sectional view illustrating a light-emitting element in Example.

In this example, examples of fabricating light-emitting elements of embodiments of the present invention are described. FIG. 37A is a schematic cross-sectional view of each of the light-emitting elements fabricated in this example, and Table 1 shows details of the element structures. In addition, structures and abbreviations of compounds used here are given below.

[Chemical Formulae 29]

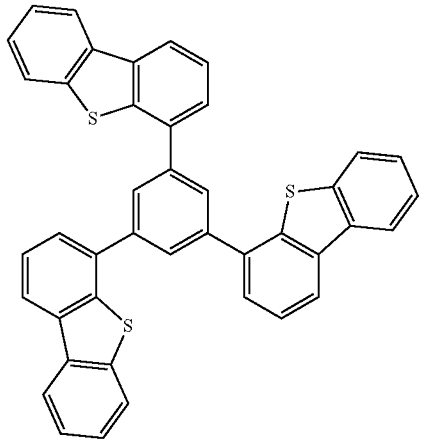

DBT3P-II

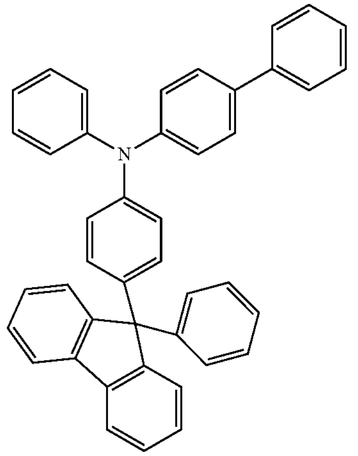

BPAFLP

-continued

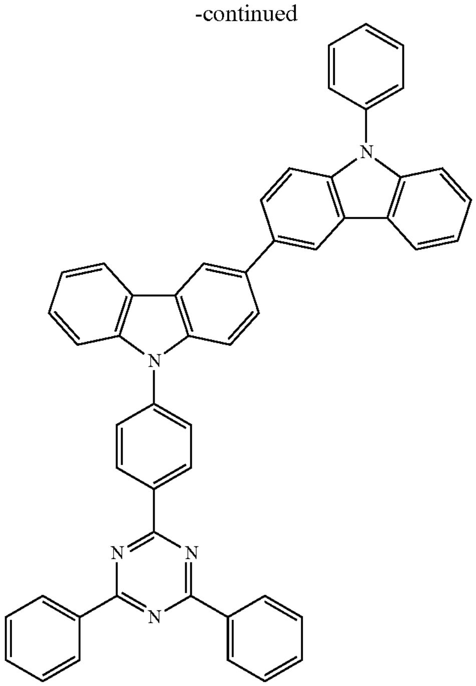

PCCzPTzn

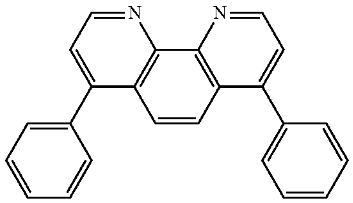

Bphen

-continued

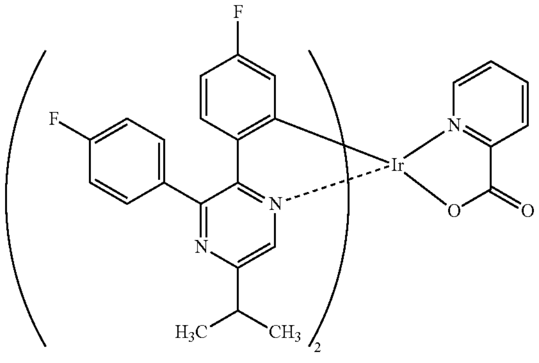

$Ir(Fdppr-iPr)_2(pic)$

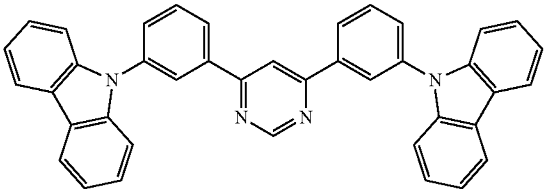

4,6mCzP2Pm

TABLE 1

| | Layer | Symbol | Thickness (nm) | Material | Weight ratio |
|---|---|---|---|---|---|
| Light-emitting element 1 | Electrode | 102 | 200 | Al | — |
| | Electron-injection layer | 119 | 1 | LiF | — |
| | Electron-transport layer | 118(2) | 10 | Bphen | — |
| | | 118(1) | 20 | 4,6mCzP2Pm | — |
| | Light-emitting layer | 160 | 40 | PCCzPTzn:$Ir(Fdppr-iPr)_2(pic)$ | 1:0.06 |
| | Hole-transport layer | 112 | 20 | BPAFLP | — |
| | Hole-injection layer | 111 | 60 | DBT3P-II:$MoO_3$ | 1:0.5 |
| | Electrode | 101 | 70 | ITSO | — |
| Light-emitting element 2 | Electrode | 102 | 200 | Al | — |
| | Electron-injection layer | 119 | 1 | LiF | — |
| | Electron-transport layer | 118(2) | 10 | Bphen | — |
| | | 118(1) | 20 | 4,6mCzP2Pm | — |
| | Light-emitting layer | 160 | 40 | PCCzPTzn | — |
| | Hole-transport layer | 112 | 20 | BPAFLP | — |
| | Hole-injection layer | 111 | 60 | DBT3P-II:$MoO_3$ | 1:0.5 |
| | Electrode | 101 | 70 | ITSO | — |

<Fabrication of Light-Emitting Elements>

<<Fabrication of Light-Emitting Element 1>>

As the electrode 101, an ITSO film was formed to a thickness of 70 nm over the substrate 200. The electrode area of the electrode 101 was set to 4 $mm^2$ (2 mm×2 mm).

As the hole-injection layer 111, 4,4',4"-(benzene-1,3,5-triyl)tri(dibenzothiophene) (abbreviation: DBT3P-II) and molybdenum oxide ($MoO_3$) were deposited over the electrode 101 by co-evaporation such that the deposited layer had a weight ratio of DBT3P-II:$MoO_3$=1:0.5 and a thickness of 60 nm.

As the hole-transport layer 112, 4-phenyl-4'-(9-phenylfluoren-9-yl)triphenylamine (abbreviation: BPAFLP) was deposited over the hole-injection layer 111 by evaporation to a thickness of 20 nm.

As the light-emitting layer 160, 2-{4-[3-(N-phenyl-9H-carbazol-3-yl)-9H-carbazol-9-yl]phenyl}-4,6-diphenyl-1,3,5-triazin e (abbreviation: PCCzPTzn) and bis[2,3-bis(4-fluorophenyl)-5-isopropylpyrazinato](picolinato)iridium (III) (abbreviation: Ir(Fdppr-iPr)$_2$(pic)) were deposited over the hole-transport layer 112 by co-evaporation such that the deposited layer had a weight ratio of PCCzPTzn:Ir(Fdppr-iPr)$_2$(pic)=1:0.06 and a thickness of 40 nm. Note that in the light-emitting layer 160, Ir(Fdppr-iPr)$_2$(pic) corresponds to a guest material and PCCzPTzn corresponds to a host material.

As the electron-transport layer 118, 4,6-bis[3-(9H-carbazol-9-yl)phenyl]pyrimidine (abbreviation: 4,6mCzP2Pm) and bathophenanthroline (abbreviation: BPhen) were successively deposited by evaporation to thicknesses of 20 nm and 10 nm, respectively, over the light-emitting layer 160. As the electron-injection layer 119, lithium fluoride (LiF) was deposited over the electron-transport layer 118 by evaporation to a thickness of 1 nm.

As the electrode 102, aluminum (Al) was formed over the electron-injection layer 119 to a thickness of 200 nm.

Next, in a glove box containing a nitrogen atmosphere, the light-emitting element 1 was sealed by fixing the substrate 220 to the substrate 200 over which the organic material was deposited using a sealant for an organic EL device. Specifically, after the sealant was applied to surround the organic material over the substrate 200 and the substrate 200 was bonded to the substrate 220, irradiation with ultraviolet light having a wavelength of 365 nm at 6 J/$cm^2$ and heat treatment at 80° C. for one hour were performed. Through the above steps, the light-emitting element 1 was obtained.

<<Fabrication of Light-Emitting Element 2>>

For comparison, a light-emitting element 2 in which a guest material was not included and PCCzPTzn was included as a light-emitting material was fabricated. The light-emitting element 2 was fabricated through the same steps as those for the light-emitting element 1 except for the step of forming the light-emitting layer 160.

As the light-emitting layer 160 of the light-emitting element 2, PCCzPTzn was deposited by evaporation to a thickness of 40 nm.

<Characteristics of Light-Emitting Elements>

Then, the characteristics of the fabricated light-emitting elements 1 and 2 were measured. Luminances and CIE chromaticities were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 38:
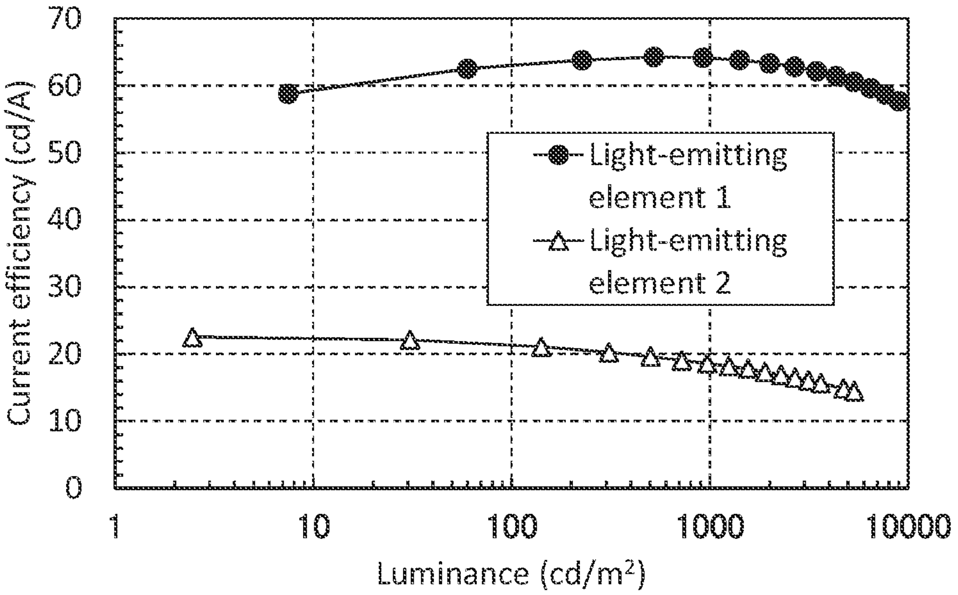
FIG. 38 shows the current efficiency vs. luminance characteristics of light-emitting elements in Example.
Figure 39:
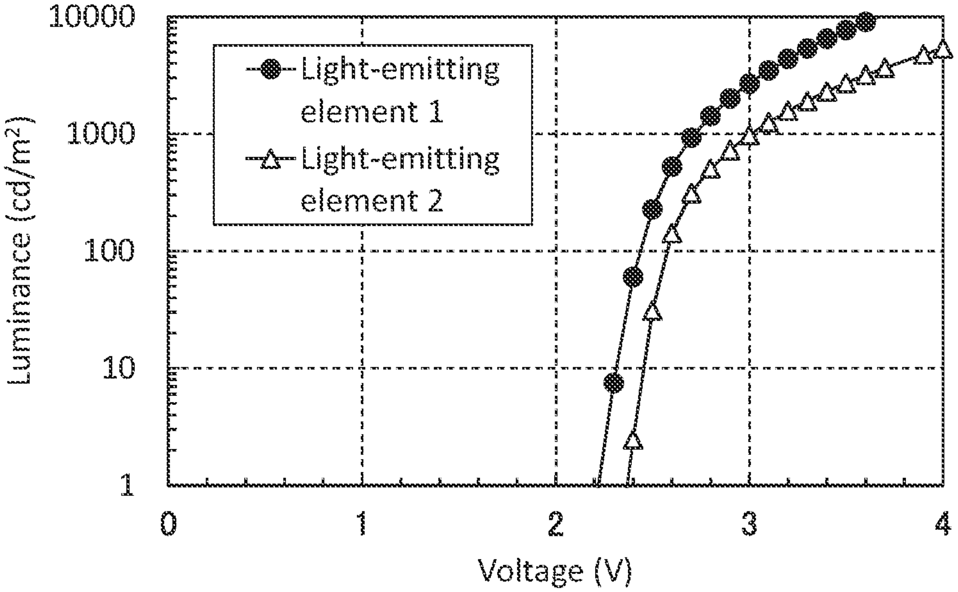
FIG. 39 shows luminance vs. voltage characteristics of light-emitting elements in Example.
Figure 40:
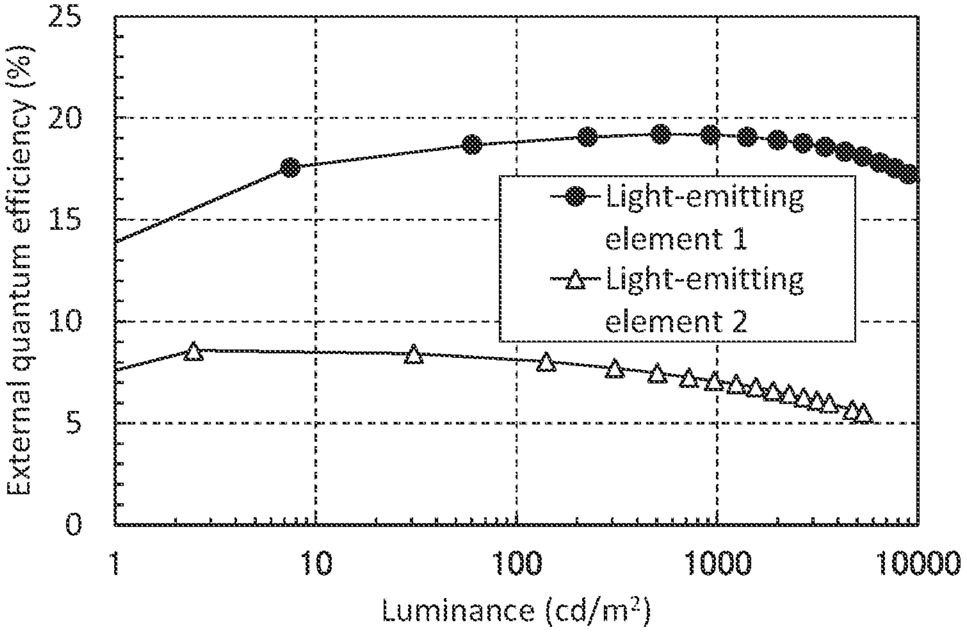
FIG. 40 shows the external quantum efficiency vs. luminance characteristics of light-emitting elements in Example.
Figure 41:
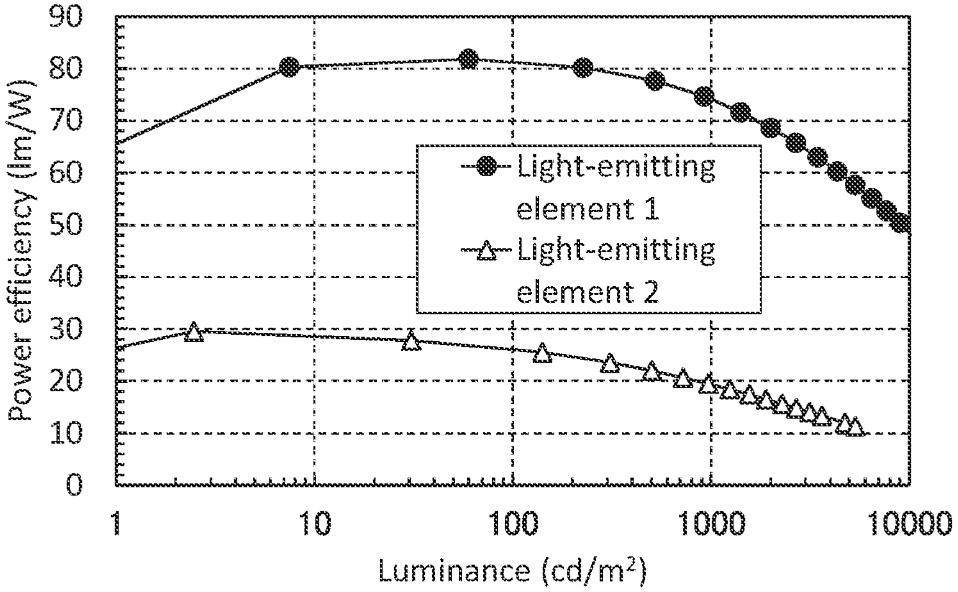
FIG. 41 shows power efficiency vs. luminance characteristics of light-emitting elements in Example.

FIG. 38 shows current efficiency vs. luminance characteristics of the light-emitting elements 1 and 2; FIG. 39 shows luminance vs. voltage characteristics thereof; FIG. 40 shows external quantum efficiency vs. luminance characteristics thereof; and FIG. 41 shows power efficiency vs. luminance characteristics thereof. The measurement for the light-emitting elements was performed at room temperature (in an atmosphere kept at 23° C.).

Table 2 shows element characteristics of the light-emitting elements 1 and 2 at around 1000 cd/$m^2$.

TABLE 2

| | Voltage (V) | Current density (mA/$cm^2$) | CIE Chromaticity (x, y) | Luminance (cd/$m^2$) | Current efficiency (cd/A) | Power efficiency (lm/W) | External quantum efficiency (%) |
|---|---|---|---|---|---|---|---|
| Light-emitting element 1 | 2.70 | 1.44 | (0.451, 0.543) | 926 | 64.2 | 74.6 | 19.2 |
| Light-emitting element 2 | 3.00 | 5.23 | (0.265, 0.458) | 972 | 18.6 | 19.5 | 7.08 |

Figure 42:
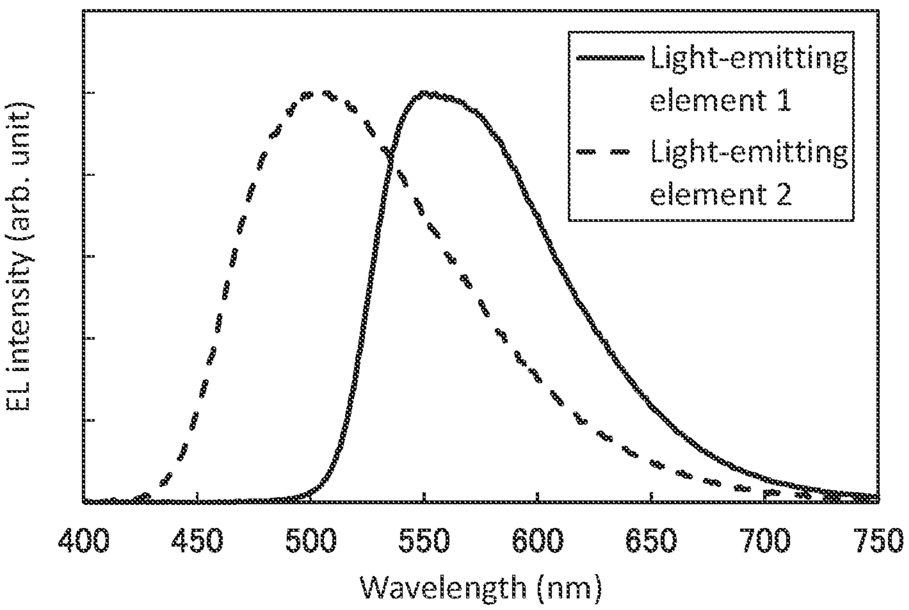
FIG. 42 shows electroluminescence spectra of light-emitting elements in Example.

FIG. 42 shows emission spectra when a current at a current density of 2.5 mA/$cm^2$ was supplied to the light-emitting elements 1 and 2.

As shown in FIG. 38 to FIG. 41 and Table 2, the light-emitting element 1 has high current efficiency and high external quantum efficiency, and the external quantum efficiency of the light-emitting element 1 is higher than 19%, which is an excellent value.

As shown in FIG. 42, the light-emitting element 1 emits green light. The electroluminescence spectrum of the light-emitting element 1 has a peak at a wavelength of 550 nm and a full width at half maximum of 91 nm. Note that the emission spectrum of the light-emitting element 2 has a full width at half maximum of 111 nm, which is wide. Thus, the light-emitting element 1 including a guest material exhibits higher color purity and better chromaticity than the light-emitting element 2.

The light-emitting element 1 was driven at an extremely low voltage of 2.7 V at around 1000 cd/$m^2$ and thus exhibited high power efficiency. Furthermore, the light emission start voltage (voltages at the time when the luminance exceeds 1 cd/$m^2$) of the light-emitting element 1 was 2.3 V. The voltage is lower than a voltage corresponding to the energy difference between the LUMO level and the HOMO level of the guest material Ir(Fdppr-iPr)$_2$(pic), which is described later. The results suggest that emission in the light-emitting element 1 is obtained not by direct recombination of carriers in the guest material but by recombination of carriers in the host material having a smaller energy gap.

<Emission Spectra of Host Material>

Figure 43:
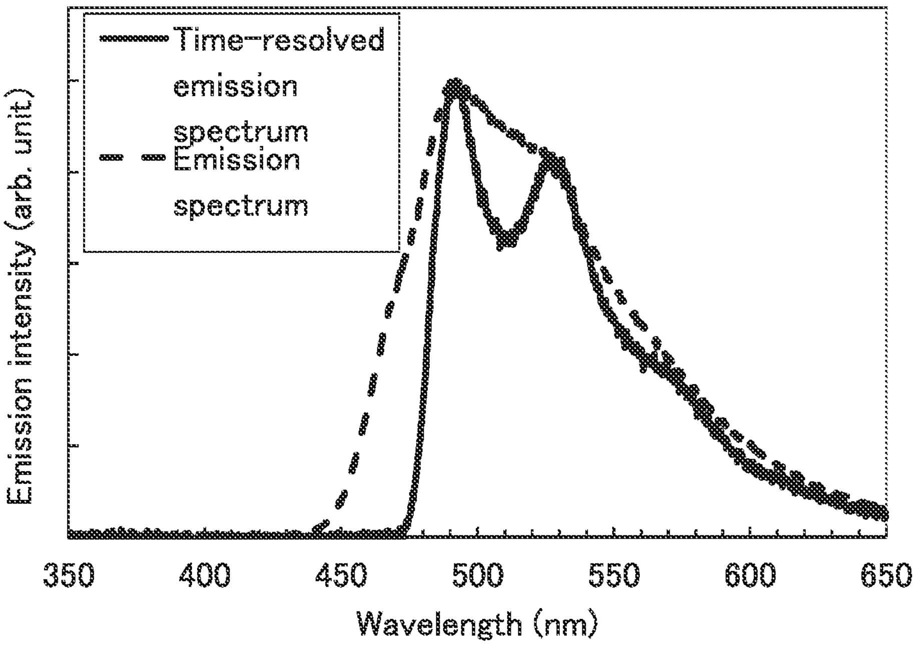
FIG. 43 shows emission spectra of a host material in Example.

In the fabricated light-emitting element 1, PCCzPTzn was used as the host material. FIG. 43 shows measurement results of emission spectra of a thin film of PCCzPTzn.

For the emission spectra measurement, a thin film sample was formed over a quartz substrate by a vacuum evaporation method. The emission spectra measurement was performed with a PL microscope, LabRAM HR-PL, produced by HORIBA, Ltd., a He—Cd laser (wavelength: 325 nm) as excitation light, and a CCD detector, at a measurement temperature of 10 K. The S1 level and the T1 level were calculated from peaks (including shoulders) on the shortest wavelength sides and the rising portions on the shorter wavelength sides of the emission spectra obtained by the measurement. The sample used for the measurement was fabricated as follows: a 50-nm thin film was formed over a quartz substrate, and, to the quartz substrate, a quartz substrate was attached from the film formation surface side in a nitrogen atmosphere.

Note that in the measurement of the emission spectra, in addition to the measurement of a normal emission spectrum, the measurement of a time-resolved emission spectrum in which light emission with a long lifetime is focused on was also performed. Since in this measurement method of emission spectra, the measurement temperature was set at a low temperature (10K), in the measurement of the normal emission spectrum, in addition to fluorescence, which is the main emission component, phosphorescence was observed. Furthermore, in the measurement of the time-resolved emission spectrum in which light emission with a long lifetime is focused on, phosphorescence was mainly observed. That is, in the measurement of the normal emission spectrum, fluorescent components of light were mainly observed, and, in the measurement of the time-resolved emission spectrum, phosphorescent components of light were mainly observed.

As shown in FIG. 43, the wavelengths of peaks (including shoulders) on the shortest wavelength sides of the emission spectra of PCCzPTzn that indicate fluorescent components and phosphorescent components are 472 nm and 491 nm, respectively. Thus, the S1 level and the T1 level calculated from the wavelengths of the peaks (including shoulders) are 2.63 eV and 2.53 eV, respectively. That is, the energy difference between the S1 level and the T1 level of PCCzPTzn calculated from the wavelengths of the peaks (including shoulders) was 0.1 eV, which is extremely small.

Furthermore, as shown in FIG. 43, the wavelengths of the rising portions on the shorter wavelength sides of the emission spectra of PCCzPTzn that indicate fluorescent components and phosphorescent components are 450 nm and 477 nm, respectively. Thus, the S1 level and the T1 level calculated from the wavelengths of the rising portions are 2.76 eV and 2.60 eV, respectively. That is, the energy difference between the S1 level and the T1 level calculated from the wavelengths of the rising portions of the emission spectra of PCCzPTzn is 0.16 eV, which is also extremely small. Note that the wavelength of the rising portion on the shorter wavelength side of the emission spectrum is a wavelength at the intersection of the horizontal axis and a tangent to the spectrum at a point where the slope of the tangent has a maximum value.

As described above, the energy difference between the S1 level and the T1 level of PCCzPTzn which is calculated from the wavelengths of the peaks (including shoulders) on the shortest wavelength sides of the emission spectra and the energy difference between the S1 level and the T1 level of PCCzPTzn which is calculated from the wavelengths of the rising portions on the shorter wavelength sides thereof are each greater than 0 eV and less than or equal to 0.2 eV, which is extremely small. Therefore, PCCzPTzn can have a function of converting triplet excitation energy into singlet excitation energy by reverse intersystem crossing.

The peak wavelength on the shortest wavelength side of the emission spectrum of light emission of PCCzPTzn that indicates phosphorescent components is shorter than that of the electroluminescence spectrum of the guest material ($Ir(Fdppr\text{-}iPr)_2(pic)$) of the light-emitting element 1. Since $Ir(Fdppr\text{-}iPr)_2(pic)$ serving as a guest material is a phosphorescent material, light is emitted from the triplet excited state. That is, the T1 level of PCCzPTzn is higher than the T1 level of the guest material.

In addition, as described later, an absorption band on the lowest energy side (the longest wavelength side) of an absorption spectrum of $Ir(Fdppr\text{-}iPr)_2(pic)$ is at around 500 nm and has a region overlapping with the emission spectrum of PCCzPTzn. Therefore, in the light-emitting element 1 using PCCzPTzn as a host material, excitation energy can be effectively transferred from the host material to the guest material.

<Transient Fluorescent Characteristics of Host Material>

Next, transient fluorescent characteristics of PCCzPTzn were measured using time-resolved emission measurement.

The time-resolved emission measurement was performed on a thin-film sample in which PCCzPTzn was deposited over a quartz substrate to a thickness of 50 nm.

A picosecond fluorescence lifetime measurement system (manufactured by Hamamatsu Photonics K.K.) was used for the measurement. In this measurement, the thin film was irradiated with pulsed laser, and emission of the thin film which was attenuated from the laser irradiation underwent time-resolved measurement using a streak camera to measure the lifetime of fluorescent emission of the thin film. A nitrogen gas laser with a wavelength of 337 nm was used as the pulsed laser. The thin film was irradiated with pulsed laser with a pulse width of 500 ps at a repetition rate of 10 Hz. By integrating data obtained by the repeated measurement, data with a high S/N ratio was obtained. The measurement was performed at room temperature (in an atmosphere kept at 23° C.).

Figure 44:
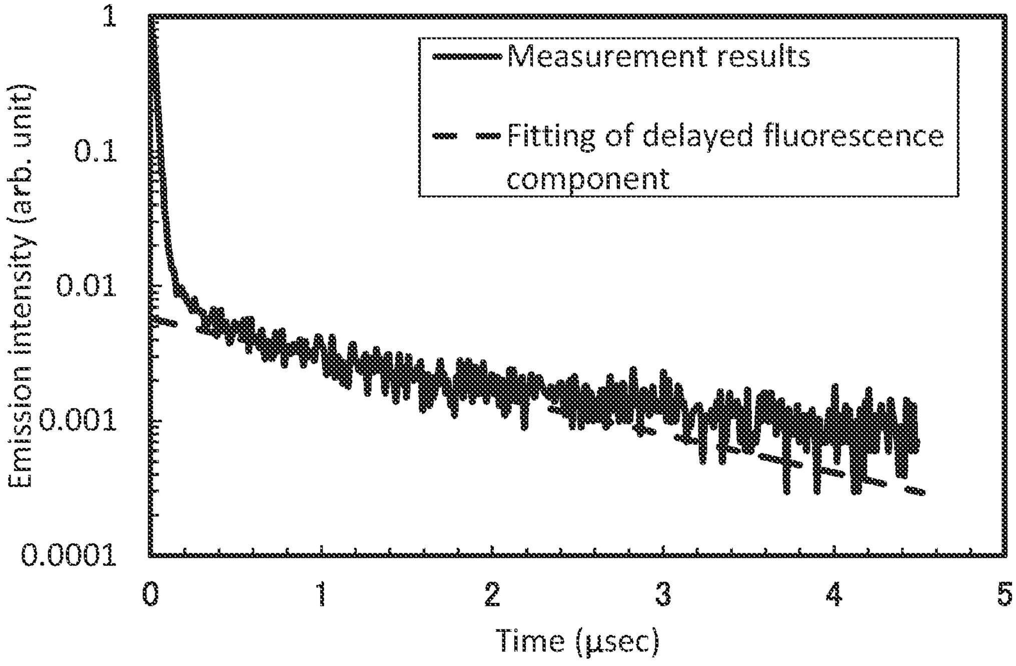
FIG. 44 shows transient fluorescence characteristics of a host material in Example.

FIG. 44 shows transient fluorescent characteristics of PCCzPTzn obtained by the measurement.

The attenuation curve shown in FIG. 44 was fitted with Formula 4.

$$L = \sum_{n=1} A_n \exp\left(-\frac{t}{a_n}\right) \quad \text{[Formula 4]}$$

In Formula 4, L and t represent normalized emission intensity and elapsed time, respectively. This fitting results show that the emission component of the PCCzPTzn thin-film sample contains at least a fluorescent component having an emission lifetime of 0.015 us and a delayed fluorescence component having an emission lifetime of 1.5 us. In other words, it is found that PCCzPTzn is a thermally activated delayed fluorescent material exhibiting delayed fluorescent at room temperature.

As shown in FIG. 38 to FIG. 41 and Table 2, it is found that the maximum external quantum efficiency of the light-emitting element 2 is 8.6%, which is a high value, though the light-emitting element 2 does not include a phosphorescent material as a guest material. Since the maximum probability of formation of singlet excitons by recombination of carriers (holes and electrons) injected from a pair of electrodes is 25%, the maximum external quantum efficiency in the case where the light extraction efficiency to the outside is 25% is 6.25%. The reason why the external quantum efficiency of the light-emitting element 2 is higher than 6.25% is that, as described above, PCCzPTzn is a material having a small energy difference between the S1 level and the T1 level and exhibiting thermally activated delayed fluorescence, and therefore has a function of emitting light originating from singlet excitons generated by reverse intersystem crossing from triplet excitons as well as light originating from singlet excitons generated by recombination of carriers (holes and electrons) injected from the pair of electrodes.

Meanwhile, as shown in FIG. 42, the wavelength of a peak of the electroluminescence spectrum of the light-emitting element 2 is 507 nm, which is shorter than the wavelength of the peak of the electroluminescence spectrum of the light-emitting element 1. The electroluminescence spectrum of the light-emitting element 1 indicates light originating from phosphorescence of the guest material (Ir(Fdppr-iPr)$_2$(pic)). The electroluminescence spectrum of the light-emitting element 2 indicates light originating from fluorescence and thermally activated delayed fluorescence of PCCzPTzn. Note that as described above, the energy difference between the S1 level and the T1 level of PCCzPTzn is as small as 0.1 eV. Therefore, the above-described measurement results of the electroluminescence spectra of the light-emitting elements 1 and 2 also show that the T1 level of PCCzPTzn is higher than the T1 level of the guest material (Ir(Fdppr-iPr)$_2$(pic)) and PCCzPTzn can be suitably used as the host material of the light-emitting element 1.

<Results of CV Measurement>

The electrochemical characteristics (oxidation reaction characteristics and reduction reaction characteristics) of the compounds used as the guest material and the host material of the light-emitting element 1 were examined by cyclic voltammetry (CV).

Note that for the measurement, an electrochemical analyzer (ALS model 600A or 600C, produced by BAS Inc.) was used, and measurement was performed on a solution obtained by dissolving each compound in N,N'-dimethylformamide (abbreviation: DMF). In the measurement, the potential of a working electrode with respect to the reference electrode was changed within an appropriate range, so that the oxidation peak potential and the reduction peak potential were obtained. In addition, the HOMO and LUMO levels of each compound were calculated from the estimated redox potential of the reference electrode of 4.94 eV and the obtained peak potentials.

Table 3 shows oxidation potentials and reduction potentials obtained by CV measurement and HOMO levels and LUMO levels of the compounds calculated from the CV measurement results.

TABLE 3

| Abbreviation | Oxidation potential (V) | Reduction potential (V) | HOMO level calculated from oxidation potential (eV) | LUMO level calculated from reduction potential (eV) |
|---|---|---|---|---|
| Ir(Fdppr-iPr)$_2$(pic) | 0.91 | −1.92 | −5.85 | −3.03 |
| PCCzPTzn | 0.70 | −1.97 | −5.64 | −2.97 |

As shown in Table 3, in the light-emitting element 1, the reduction potential of the guest material (Ir(Fdppr-iPr)$_2$(pic)) is higher than the reduction potential of the host material (PCCzPTzn), and the oxidation potential of the guest material (Ir(Fdppr-iPr)$_2$(pic)) is higher than the oxidation potential of the host material (PCCzPTzn). Therefore, the LUMO level of the guest material (Ir(Fdppr-iPr)$_2$(pic)) is lower than the LUMO level of the host material (PCCzPTzn), and the HOMO level of the guest material (Ir(Fdppr-iPr)$_2$(pic)) is lower than the HOMO level of the host material (PCCzPTzn). The energy difference between the LUMO level and the HOMO level of the guest material (Ir(Fdppr-iPr)$_2$(pic)) is larger than the energy difference between the LUMO level and the HOMO level of the host material (PCCzPTzn).

<Absorption Spectrum and Emission Spectrum of Guest Material>

Figure 45:
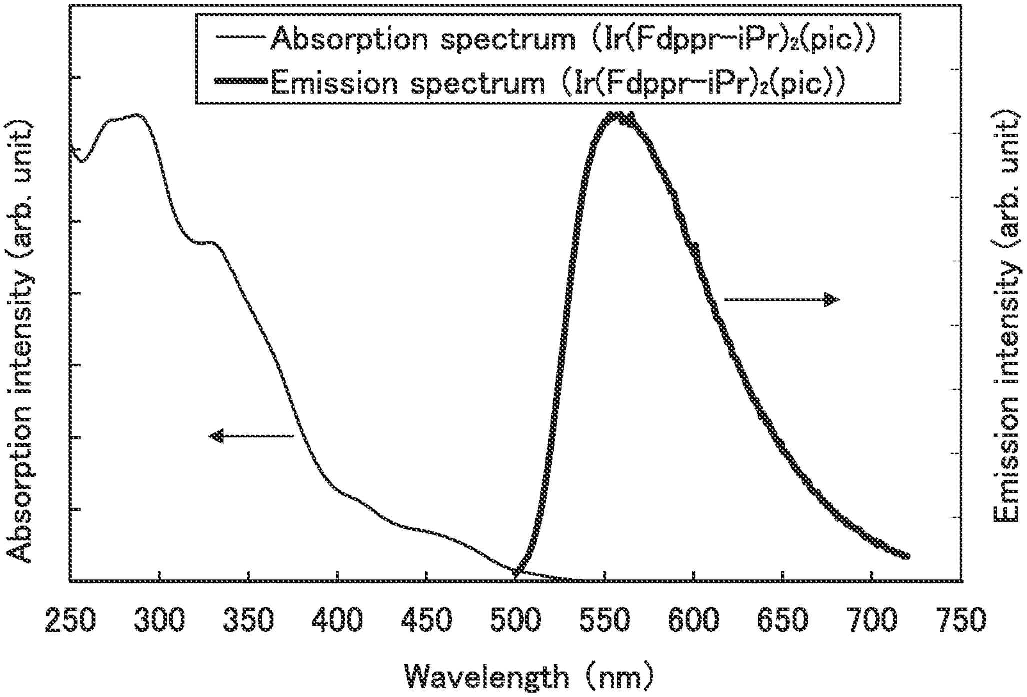
FIG. 45 shows an absorption spectrum and an emission spectrum of a guest material in Example.

FIG. 45 shows the measurement results of the absorption spectrum and emission spectrum of Ir(Fdppr-iPr)$_2$(pic) that is the guest material in the light-emitting element 1.

For the measurement of the absorption spectrum and emission spectrum, a dichloromethane solution in which Ir(Fdppr-iPr)$_2$(pic) was dissolved was prepared, and a quartz cell was used. The absorption spectrum was measured using an ultraviolet-visible spectrophotometer (V-550, produced by JASCO Corporation). Then, the absorption spectrum of a quartz cell was subtracted from the measured spectrum of the sample. Note that the emission spectrum of the solution was measured with a PL-EL measurement apparatus (manufactured by Hamamatsu Photonics K.K.). The measurement was performed at room temperature (in an atmosphere kept at 23° C.).

As shown in FIG. 45, the absorption band on the lowest energy side (the longest wavelength side) of the absorption spectrum of Ir(Fdppr-iPr)$_2$(pic) is at around 500 nm. The absorption edge was obtained from data of the absorption spectrum, and the transition energy was estimated from a Tauc plot assuming direct transition. As a result, the transition energy of Ir(Fdppr-iPr)$_2$(pic) was calculated to be 2.38 eV.

The energy difference between the LUMO level and the HOMO level of Ir(Fdppr-iPr)$_2$(pic) was 2.82 eV. This value was calculated from the CV measurement results shown in Table 3.

That is, the energy difference between the LUMO level and the HOMO level of Ir(Fdppr-iPr)$_2$(pic) is larger than the transition energy thereof calculated from the absorption edge of the absorption spectrum by 0.44 eV.

As shown in FIG. 42, the wavelength of the peak on the shortest wavelength side of the electroluminescence spectrum of the light-emitting element 1 is 550 nm. According to that, the light emission energy of Ir(Fdppr-iPr)$_2$(pic) was calculated to be 2.25 eV.

That is, the energy difference between the LUMO level and the HOMO level of Ir(Fdppr-iPr)$_2$(pic) was larger than the light emission energy by 0.57 eV.

Consequently, in the guest material of the light-emitting element 1, the energy difference between the LUMO level and the HOMO level is greater than the transition energy calculated from the absorption edge by 0.4 eV or more. In addition, the energy difference between the LUMO level and the HOMO level is greater than the light emission energy by 0.4 eV or more. Therefore, high energy corresponding to the energy difference between the LUMO level and the HOMO level is needed, that is, high voltage is needed when carriers injected from a pair of electrodes are directly recombined in the guest material.

Meanwhile, the energy difference between the LUMO level and the HOMO level of the host material (PCCzPTzn) in the light-emitting element 1 was calculated to be 2.67 eV from Table 3. That is, the energy difference between the LUMO level and the HOMO level of the host material (PCCzPTzn) of the light-emitting element 1 is smaller than the energy difference (2.82 eV) between the LUMO level and the HOMO level of the guest material (Ir(Fdppr-iPr)$_2$ (pic)), greater than the transition energy (2.38 eV) calculated from the absorption edge, and greater than the light emission energy (2.25 eV). Therefore, in the light-emitting element 1, the guest material can be excited by energy transfer through an excited state of the host material without the direct carrier recombination in the guest material, whereby the driving voltage can be lowered. Thus, the power consumption of the light-emitting element of one embodiment of the present invention can be reduced.

According to the CV measurement results in Table 3, among carriers (electrons and holes) injected from the pair of electrodes of the light-emitting element 1, electrons tend to be injected into the guest material ($Ir(Fdppr-iPr)_2(pic)$) with a low LUMO level, whereas holes tend to be injected into the host material (PCCzPTzn) with a high HOMO level. That is, there is a possibility that an exciplex is formed by the host material and the guest material.

The energy difference between the LUMO level of the guest material ($Ir(Fdppr-iPr)_2(pic)$) and the HOMO level of the host material (PCCzPTzn) was calculated from the CV measurement results shown in Table 3 and found to be 2.61 eV.

From these results, in the light-emitting element 1, the energy difference (2.61 eV) between the LUMO level of the guest material ($Ir(Fdppr-iPr)_2(pic)$) and the HOMO level of the host material (PCCzPTzn) is greater than or equal to the transition energy (2.38 eV) calculated from the absorption edge of the absorption spectrum of the guest material. Furthermore, the energy difference (2.61 eV) between the LUMO level of the guest material and the HOMO level of the host material is greater than or equal to the energy (2.25 eV) of light emitted by the guest material. Accordingly, rather than formation of an exciplex by the host material and the guest material, transfer of excitation energy to the guest material is more facilitated eventually, whereby efficient light emission from the guest material is achieved. This relationship is a feature of one embodiment of the present invention for efficient light emission.

In the case where the LUMO level of a guest material is lower than the LUMO level of a host material and the energy difference between the LUMO level and the HOMO level of the guest material is larger than the energy difference between the LUMO level and the HOMO level of the host material as in the above-described light-emitting element 1, a light-emitting element with high emission efficiency and low driving voltage can be obtained when the energy difference between the LUMO level of the guest material and the HOMO level of the host material is greater than or equal to the transition energy calculated from the absorption edge of the absorption spectrum of the guest material or greater than or equal to the light emission energy of the guest material. Furthermore, in the case where the energy difference between the LUMO level and the HOMO level of a guest material is greater than the transition energy calculated from the absorption edge of the absorption spectrum of the guest material or the light emission energy of the guest material by 0.4 eV or more, a light-emitting element with high emission efficiency and low driving voltage can be obtained.

As described above, by employing the structure of one embodiment of the present invention, a light-emitting element having high emission efficiency can be fabricated. Furthermore, a light-emitting element with reduced power consumption can be fabricated.

The structures described in this example can be used in an appropriate combination with any of the other embodiments.

Example 2

Figure 37B:
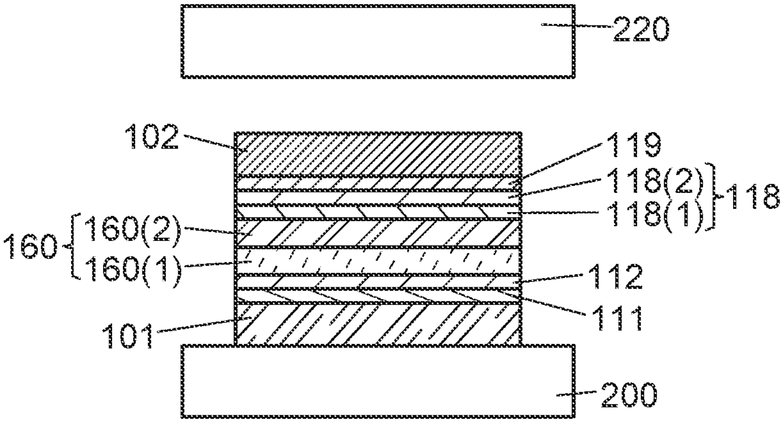

In this example, examples of fabricating light-emitting elements of embodiments of the present invention are described. FIG. 37B is a schematic cross-sectional view of each of the light-emitting elements fabricated in this example, and Table 4 shows details of the element structures. In addition, structures and abbreviations of compounds used here are given below. Note that Example 1 can be referred to for other compounds.

[Chemical Formulae 30]

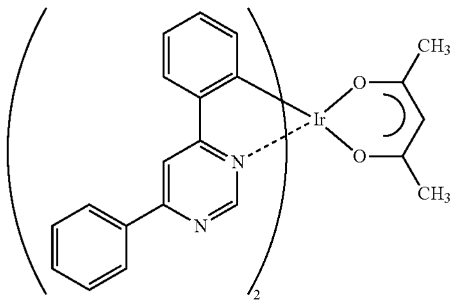

Ir(dppm)2(acac)

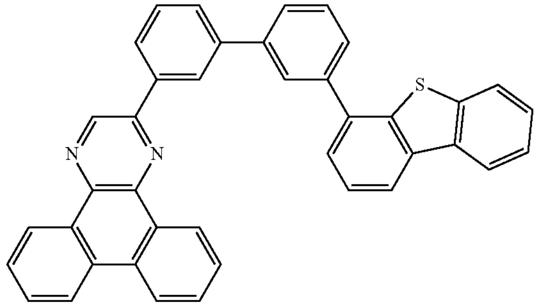

2mDBTBPDBq-II

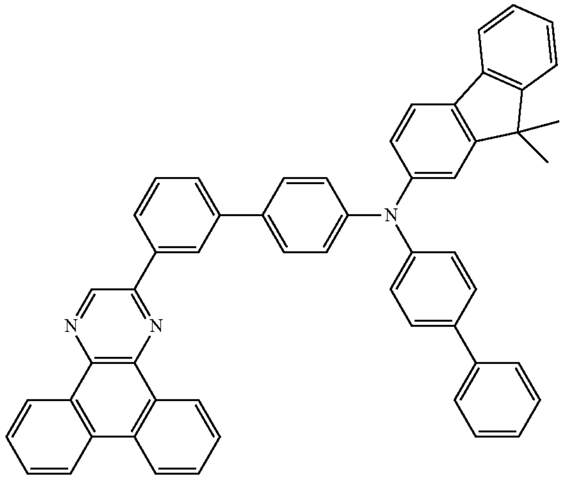

2mpFBiBPDBq

TABLE 4

| | Layer | Symbol | Thickness (nm) | Material | Weight ratio |
|---|---|---|---|---|---|
| Light-emitting element 3 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mDBTBPDBq-II | — |
| | Light-emitting layer | 160(2) | 20 | 2mDBTBPDBq-II:2mpFBiBPDBq:Ir(dppm)$_2$(acac) | 0.8:0.2:0.05 |
| | | 160(1) | 20 | 2mDBTBPDBq-II:2mpFBiBPDBq:Ir(dppm)$_2$(acac) | 0.6:0.4:0.05 |
| | Hot-transport layer | 112 | 20 | BPAFLP | — |
| | Hole-injection layer | 111 | 60 | DBT3P-II:MoO$_3$ | 1:0.5 |
| | Electrode | 101 | 70 | ITSO | — |

<Fabrication of Light-Emitting Element>

<<Fabrication of Light-Emitting Element 3>>

As the electrode 101, an ITSO film was formed to a thickness of 70 nm over the substrate 200. The electrode area of the electrode 101 was set to 4 mm$^2$ (2 mm×2 mm).

As the hole-injection layer 111, DBT3P-II and molybdenum oxide ($MoO_3$) were deposited over the electrode 101 by co-evaporation such that the deposited layer had a weight ratio of DBT3P-II:$MoO_3$=1:0.5 and a thickness of 60 nm.

As the hole-transport layer 112, BPAFLP was deposited over the hole-injection layer 111 by evaporation to a thickness of 20 nm.

As the light-emitting layer 160, 2mDBTBPDBq-II, N-(4-biphenyl)-N-(9,9-dimethyl-9H-fluoren-2-yl)-4-[3-(dibenzo[f,h]quinoxalin-2-yl)phenyl]phenylamine (abbreviation: 2mpFBiBPDBq), and bis[2-(6-phenyl-4-pyrimidinyl-κN3)phenyl-κC](2,4-pentanedionato-κ$^2$O,O')iridium(III) (abbreviation: Ir(dppm)$_2$(acac)) were deposited over the hole-transport layer 112 by co-evaporation such that the deposited layer had a weight ratio of 2mDBTBPDBq-II: 2mFBiBPDBq: Ir(dppm)$_2$(acac)=0.6:0.4:0.05 and a thickness of 20 nm. Then, 2mDBTBPDBq-II, 2mFBiBPDBq, and Ir(dppm)$_2$(acac) were deposited by co-evaporation such that the deposited layer had a weight ratio of 2mDBTBPDBq-II:2mFBiBPDBq:Ir(dppm)$_2$(acac)=0.8:0.2:0.05 and a thickness of 20 nm. Note that in the light-emitting layer 160, 2mpFBiBPDBq corresponds to a host material and Ir(dppm)$_2$(acac) corresponds to a guest material.

As the electron-transport layer 118, 2mDBTBPDBq-II and BPhen were successively deposited by evaporation to thicknesses of 20 nm and 10 nm, respectively, over the light-emitting layer 160. As the electron-injection layer 119, lithium fluoride LiF was deposited over the electron-transport layer 118 by evaporation to a thickness of 1 nm.

As the electrode 102, aluminum (Al) was formed over the electron-injection layer 119 to a thickness of 200 nm.

Next, in a glove box containing a nitrogen atmosphere, the light-emitting element 3 was sealed by fixing the substrate 220 to the substrate 200 over which the organic material was deposited using a sealant for an organic EL device. For the detailed method, description of the light-emitting element 1 can be referred to. Through the above steps, the light-emitting element 3 was obtained.

<Characteristics of Light-Emitting Elements>

Figure 46:
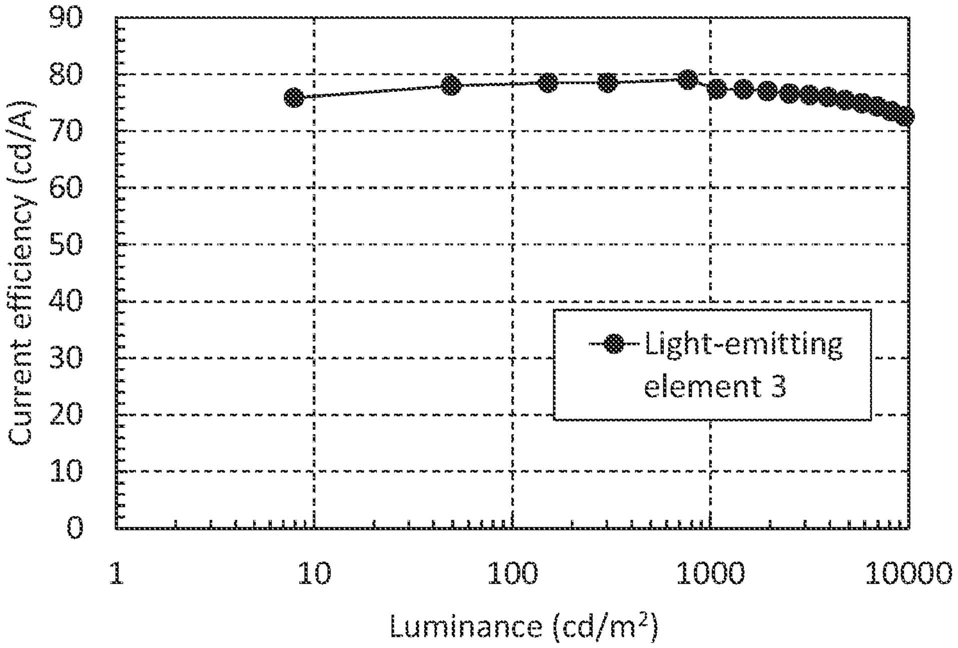
FIG. 46 shows current efficiency vs. luminance characteristics of a light-emitting element in Example.
Figure 47:
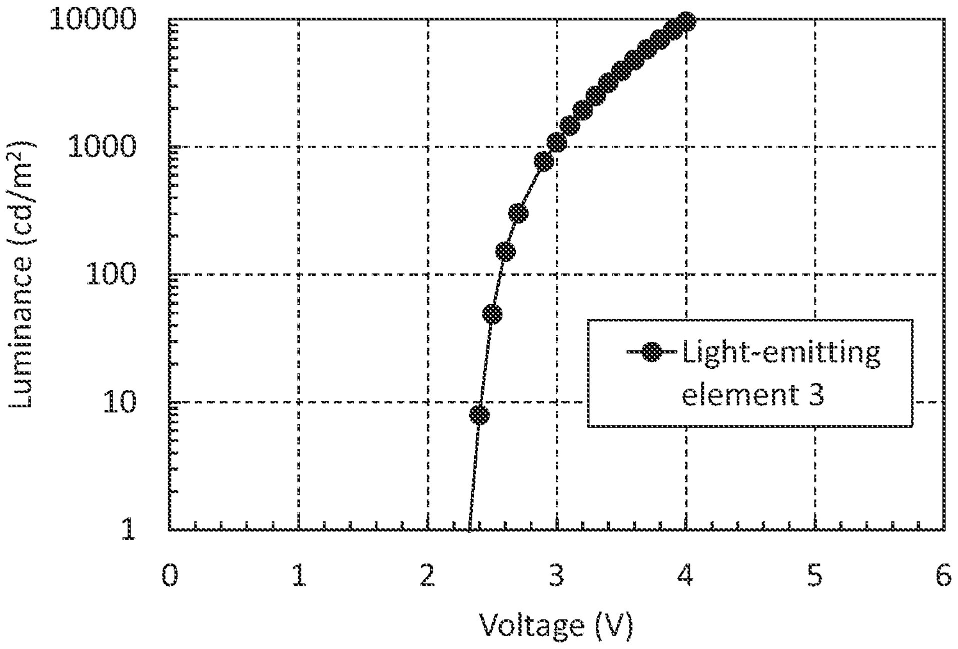
FIG. 47 shows luminance vs. voltage characteristics of a light-emitting element in Example.
Figure 48:
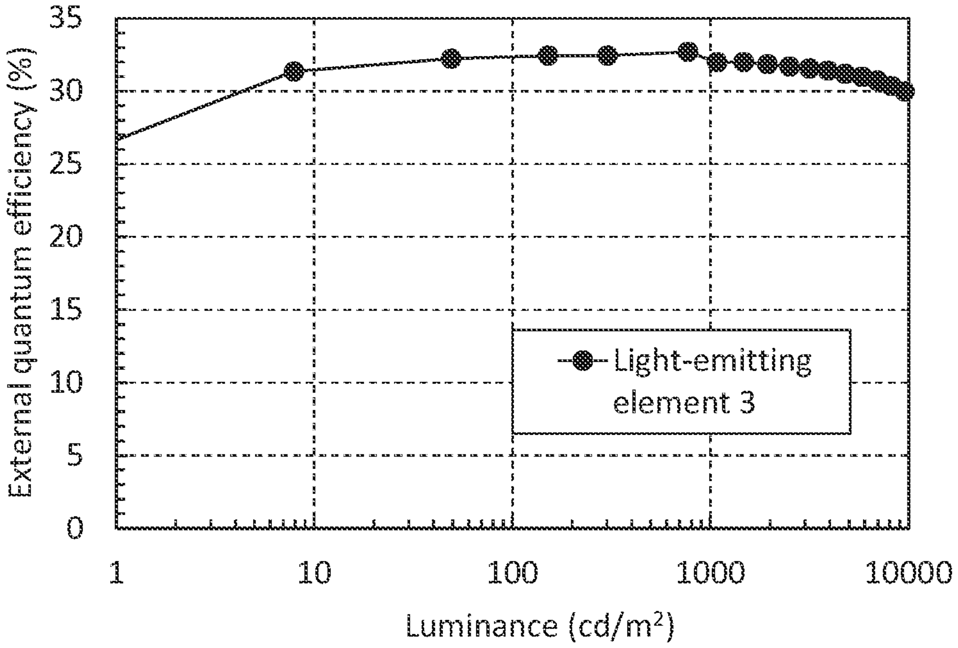
FIG. 48 shows external quantum efficiency vs. luminance characteristics of a light-emitting element in Example.
Figure 49:
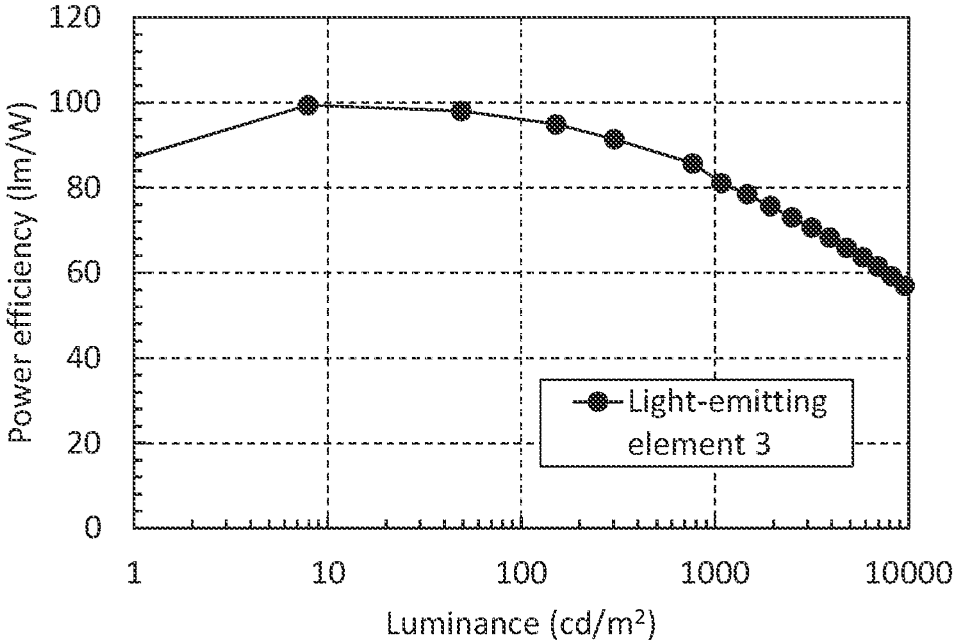
FIG. 49 shows power efficiency vs. luminance characteristics of a light-emitting element in Example.

FIG. 46 shows current efficiency vs. luminance characteristics of the light-emitting element 3; FIG. 47 shows luminance vs. voltage characteristics thereof; FIG. 48 shows external quantum efficiency vs. luminance characteristics thereof; and FIG. 49 shows power efficiency vs. luminance characteristics thereof. The measurement for the light-emitting element was performed at room temperature (in an atmosphere kept at 23° C.) by a measurement method similar to that used in Example 1.

Table 5 shows element characteristics of the light-emitting element 3 at around 1000 cd/m$^2$

TABLE 5

| | Voltage (V) | Current density (mA/cm$^2$) | CIE Chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 3 | 3.00 | 1.40 | (0.564, 0.435) | 1080 | 77.4 | 81.1 | 32.0 |

Figure 50:
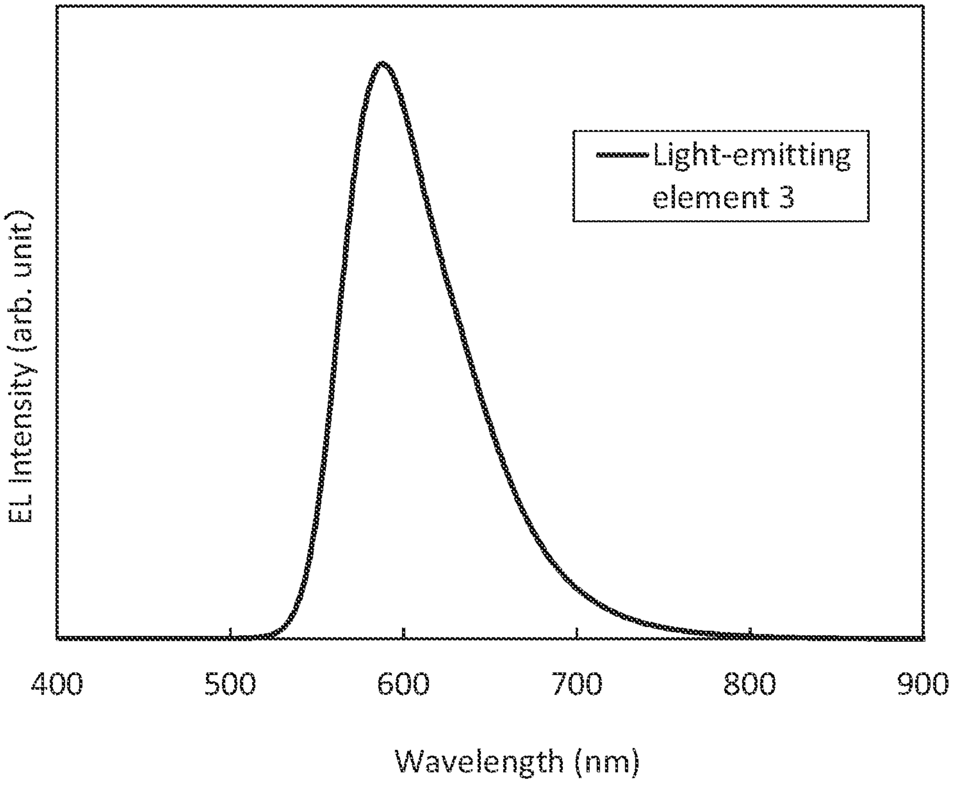
FIG. 50 shows an electroluminescence spectrum of a light-emitting element in Example.

FIG. 50 shows an emission spectrum when a current at a current density of 2.5 mA/cm$^2$ was supplied to the light-emitting element 3.

As shown in FIG. 46 to FIG. 48 and Table 5, the light-emitting element 3 has high current efficiency and high external quantum efficiency, and the maximum external quantum efficiency of the light-emitting element 3 is higher than 32%, which is an excellent value.

As shown in FIG. 50, the light-emitting element 3 emits orange light. The electroluminescence spectrum of the light-emitting element 3 has a peak at a wavelength of 588 nm and a full width at half maximum of 76 nm. The obtained emission spectrum reveals that the orange light is emitted from Ir(dppm)$_2$(acac) as a guest material.

The light-emitting element 3 was driven at a low voltage of 3.0 V at around 1000 cd/m$^2$ and thus exhibited high power efficiency. Furthermore, the light emission start voltage (voltages at the time when the luminance exceeds 1 cd/m$^2$) of the light-emitting element 1 was 2.3 V. The voltage is lower than a voltage corresponding to the energy difference between the LUMO level and the HOMO level of the guest material Ir(dppm)$_2$(acac), which is described later. The results suggest that emission in the light-emitting element 3 is obtained not by direct recombination of carriers in the guest material but by recombination of carriers in the host material having a smaller energy gap.

<Emission Spectra of Host Material>

Figure 51:
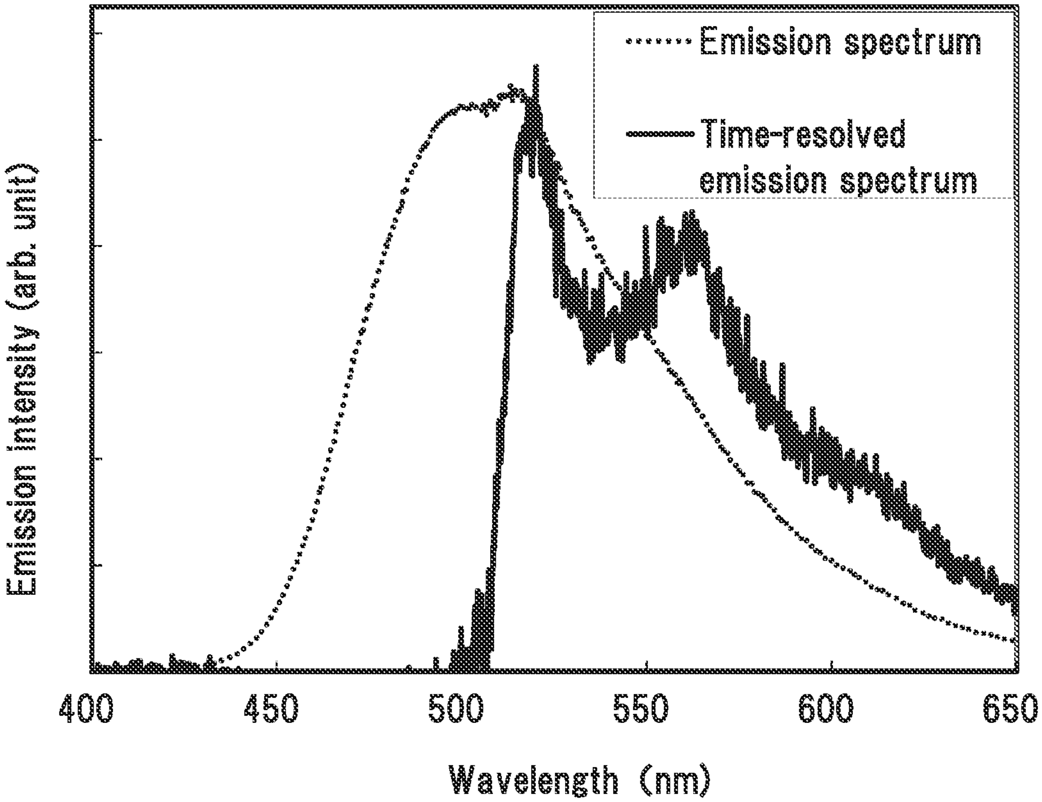
FIG. 51 shows emission spectra of a host material in Example.

In the fabricated light-emitting element 3, 2mpFBiBPDBq was used as the host material. FIG. 51 shows measurement results of emission spectra of a thin film of 2mpFBiBPDBq. Note that the measurement method is similar to that used in Example 1.

As shown in FIG. 51, the wavelengths of peaks (including shoulders) on the shortest wavelength sides of the emission spectra of 2mpFBiBPDBq that indicate fluorescent components and phosphorescent components are 495 nm and 518 nm, respectively. Thus, the S1 level and the T1 level calculated from the wavelengths of the peaks (including shoulders) are 2.51 eV and 2.39 eV, respectively. That is, the energy difference between the S1 level and the T1 level of 2mpFBiBPDBq calculated from the wavelengths of the peaks (including shoulders) was 0.12 eV, which is extremely small.

As described above, the energy difference between the S1 level and the T1 level of 2mpFBiBPDBq which is calculated from the wavelengths of the peaks (including shoulders) on the shortest wavelength sides of the emission spectra is greater than 0 eV and less than or equal to 0.2 eV, which is extremely small. Therefore, 2mpFBiBPDBq can have a function of converting triplet excitation energy into singlet excitation energy by reverse intersystem crossing.

The peak wavelength on the shortest wavelength side of the emission spectrum of light emission of 2mpFBiBPDBq that indicates phosphorescent components is shorter than that of the electroluminescence spectrum of the guest material ($Ir(dppm)_2(acac)$) of the light-emitting element 3. Since $Ir(dppm)_2(acac)$ serving as a guest material is a phosphorescent material, light is emitted from the triplet excited state. That is, the T1 level of 2mpFBiBPDBq is higher than the T1 level of the guest material.

In addition, as described later, an absorption band on the lowest energy side (the longest wavelength side) of an absorption spectrum of $Ir(dppm)_2(acac)$ is at around 560 nm and has a region overlapping with the emission spectrum of 2mpFBiBPDBq. Therefore, in the light-emitting element 3 using 2mpFBiBPDBq as a host material, excitation energy can be effectively transferred to the guest material. This suggests that 2mpFBiBPDBq is suitably used as the host material of the light-emitting element 3.

<Results of CV Measurement>

The electrochemical characteristics (oxidation reaction characteristics and reduction reaction characteristics) of the compounds used as the guest material and the host material of the light-emitting element were examined by cyclic voltammetry (CV). Note that the measurement method is similar to that used in Example 1.

Table 6 shows oxidation potentials and reduction potentials obtained by CV measurement and HOMO levels and LUMO levels of the compounds calculated from the CV measurement results.

TABLE 6

| Abbreviation | Oxidation potential (V) | Reduction potential (V) | HOMO level calculated from oxidation potential (eV) | LUMO level calculated from reduction potential (eV) |
|---|---|---|---|---|
| $Ir(dppm)_2(acac)$ | 0.52 | −1.96 | −5.56 | −2.98 |
| 2mpFBiBPDBq | 0.48 | −2.01 | −5.42 | −2.93 |

As shown in Table 6, in the light-emitting element 3, the reduction potential of the guest material ($Ir(dppm)_2(acac)$) is higher than the reduction potential of the host material (2mpFBiBPDBq), and the oxidation potential of the guest material ($Ir(dppm)_2(acac)$) is higher than the oxidation potential of the host material (2mpFBiBPDBq). Therefore, the LUMO level of the guest material ($Ir(dppm)_2(acac)$) is lower than the LUMO level of the host material (2mpFBiBPDBq), and the HOMO level of the guest material ($Ir(dppm)_2(acac)$) is lower than the HOMO level of the host material (2mpFBiBPDBq). The energy difference between the LUMO level and the HOMO level of the guest material ($Ir(dppm)_2(acac)$) is larger than the energy difference between the LUMO level and the HOMO level of the host material (2mpFBiBPDBq).

<Absorption Spectrum and Emission Spectrum of Guest Material>

Figure 52:
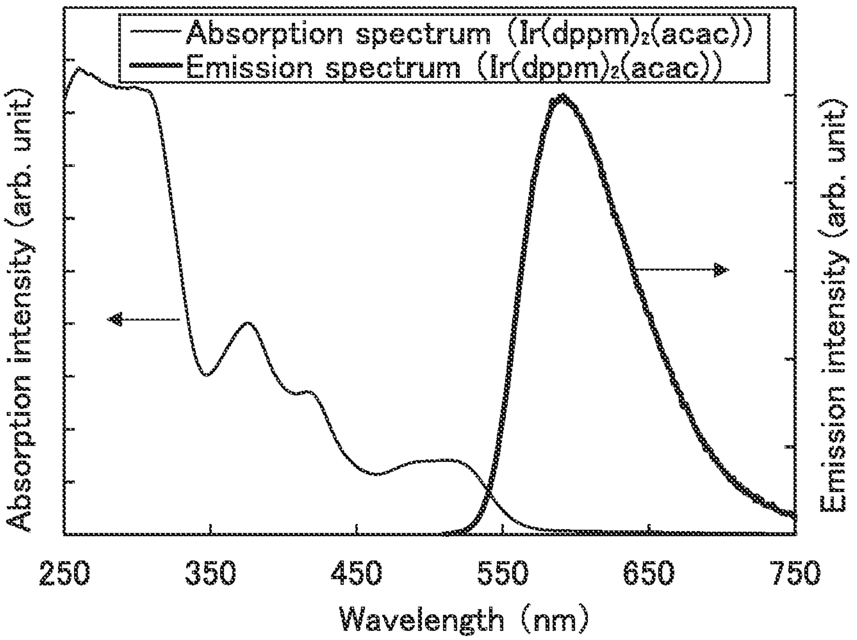
FIG. 52 shows an absorption spectrum and an emission spectrum of a guest material in Example.

FIG. 52 shows the measurement results of the absorption spectrum and emission spectrum of $Ir(dppm)_2(acac)$ that is the guest material in the light-emitting element. Note that the measurement method is similar to that used in Example 1.

As shown in FIG. 52, the absorption band on the lowest energy side (the longest wavelength side) of the absorption spectrum of $Ir(dppm)_2(acac)$ is at around 560 nm. The absorption edge was obtained from data of the absorption spectrum, and the transition energy was estimated from a Tauc plot assuming direct transition. As a result, the transition energy of $Ir(dppm)_2(acac)$ was calculated to be 2.22 eV.

The energy difference between the LUMO level and the HOMO level of $Ir(dppm)_2(acac)$ was 2.58 eV. This value was calculated from the CV measurement results shown in Table 6.

That is, the energy difference between the LUMO level and the HOMO level of $Ir(dppm)_2(acac)$ is larger than the transition energy thereof calculated from the absorption edge of the absorption spectrum by 0.36 eV.

As shown in FIG. 52, the wavelength of the peak on the shortest wavelength side of the emission spectrum of $Ir(dppm)_2(acac)$ is 592 nm. According to that, the light emission energy of $Ir(dppm)_2(acac)$ was calculated to be 2.09 eV.

That is, the energy difference between the LUMO level and the HOMO level of $Ir(dppm)_2(acac)$ was larger than the light emission energy by 0.49 eV.

Consequently, in the guest material of the light-emitting element 3, the energy difference between the LUMO level and the HOMO level is greater than the transition energy calculated from the absorption edge by 0.3 eV or more. In addition, the energy difference between the LUMO level and the HOMO level is greater than the light emission energy by 0.4 eV or more. Therefore, high energy corresponding to the energy difference between the LUMO level and the HOMO level is needed, that is, high voltage is needed when carriers injected from a pair of electrodes are directly recombined in the guest material.

Meanwhile, the energy difference between the LUMO level and the HOMO level of the host material (2mpFBiBPDBq) in the light-emitting element 3 was calculated to be 2.49 eV from Table 6. That is, the energy difference between the LUMO level and the HOMO level of the host material (2mpFBiBPDBq) of the light-emitting element 3 is smaller than the energy difference (2.58 eV) between the LUMO level and the HOMO level of the guest material ($Ir(dppm)_2(acac)$), greater than the transition energy (2.22 eV) calculated from the absorption edge, and greater than the light emission energy (2.09 eV). Therefore, in the light-emitting element 3, the guest material can be excited by energy transfer through an excited state of the host material without the direct carrier recombination in the guest material, whereby the driving voltage can be lowered. Thus, the power consumption of the light-emitting element of one embodiment of the present invention can be reduced.

According to the CV measurement results in Table 6, among carriers (electrons and holes) injected from the pair of electrodes of the light-emitting element 3, electrons tend to be injected into the guest material ($Ir(dppm)_2(acac)$) with a low LUMO level, whereas holes tend to be injected into the host material (2mpFBiBPDBq) with a high HOMO level. That is, there is a possibility that an exciplex is formed by the host material and the guest material.

The energy difference between the LUMO level of the guest material ($Ir(dppm)_2(acac)$) and the HOMO level of the host material (2mpFBiBPDBq) was calculated from the CV measurement results shown in Table 6 and found to be 2.44 eV.

From these results, in the light-emitting element 3, the energy difference (2.44 eV) between the LUMO level of the guest material ($Ir(dppm)_2(acac)$) and the HOMO level of the host material (2mpFBiBPDBq) is greater than or equal to the transition energy (2.22 eV) calculated from the absorption edge of the absorption spectrum of the guest material. Furthermore, the energy difference (2.44 eV) between the LUMO level of the guest material and the HOMO level of the host material is greater than or equal to the energy (2.09 eV) of light emitted by the guest material. Accordingly, rather than formation of an exciplex by the host material and the guest material, transfer of excitation energy to the guest material is more facilitated eventually, whereby efficient light emission from the guest material is achieved. This relationship is a feature of one embodiment of the present invention for efficient light emission.

In the case where the LUMO level of a guest material is lower than the LUMO level of a host material and the energy difference between the LUMO level and the HOMO level of the guest material is larger than the energy difference between the LUMO level and the HOMO level of the host material as in the above-described light-emitting element 3, a light-emitting element with high emission efficiency and low driving voltage can be obtained when the energy difference between the LUMO level of the guest material and the HOMO level of the host material is greater than or equal to the transition energy calculated from the absorption edge of the absorption spectrum of the guest material or greater than or equal to the light emission energy of the guest material. Furthermore, in the case where the energy difference between the LUMO level and the HOMO level of a guest material is greater than the transition energy calculated from the absorption edge of the absorption spectrum of the guest material or the light emission energy of the guest material by 0.3 eV or more, a light-emitting element with high emission efficiency and low driving voltage can be obtained.

As described above, by employing the structure of one embodiment of the present invention, a light-emitting element having high emission efficiency can be fabricated. Furthermore, a light-emitting element with reduced power consumption can be fabricated.

The structures described in this example can be used in an appropriate combination with any of the other embodiments.

Example 3

In this example, examples of fabricating light-emitting elements of embodiments of the present invention are described. FIG. 37B is a schematic cross-sectional view of each of the light-emitting elements fabricated in this example, and Table 7 shows details of the element structures. In addition, structures and abbreviations of compounds used here are given below. Note that Example 1 can be referred to for other compounds.

[Chemical Formulae 31]

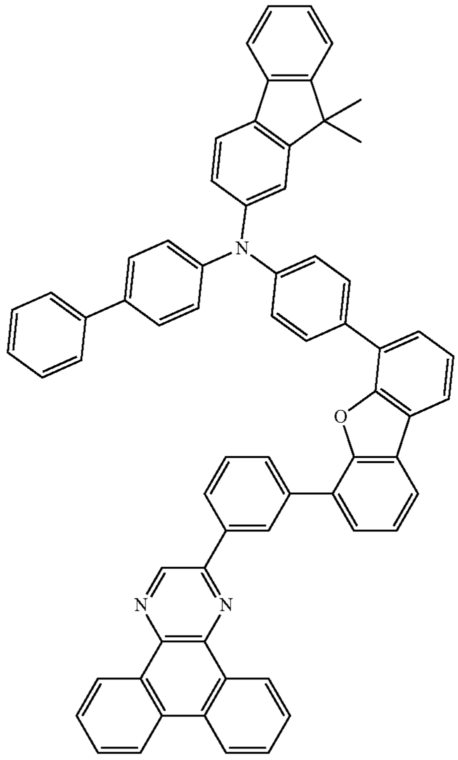

2mFBiPDBfPDBq

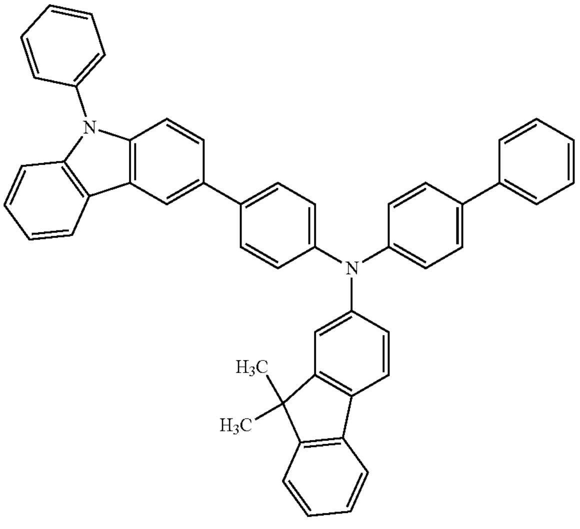

PCBBiF

-continued

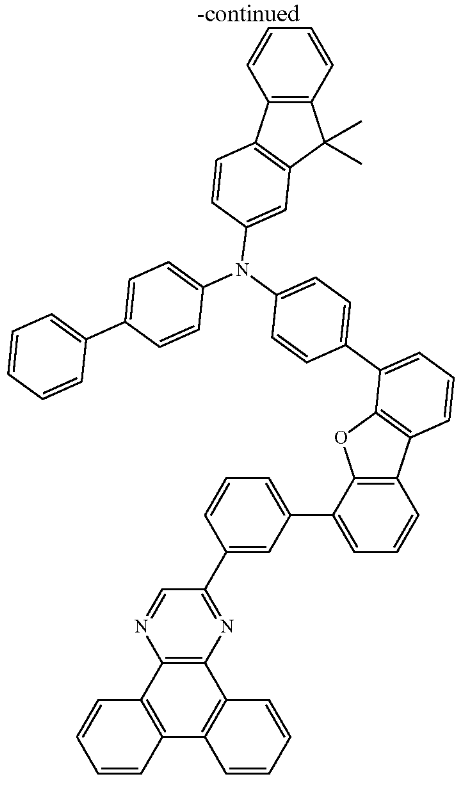

2mpPCBABPDBq

As the light-emitting layer 160, N-(4-biphenyl)-N-(4-{6-[3-(dibenzo[f,h]quinoxalin-2-yl)phenyl]dibenzofuran-4-yl}phenyl)-9,9-dimethyl-9H-fluoren-2-amine (abbreviation: 2mFBiPDBfPDBq), N-(1,1'-biphenyl-4-yl)-N-[4-(9-phenyl-9H-carbazol-3-yl)phenyl]-9,9-dimethyl-9H-fluoren-2-amine (abbreviation: PCBBiF), and $Ir(dppm)_2(acac)$ were deposited over the hole-transport layer 112 by co-evaporation such that the deposited layer had a weight ratio of 2mFBiPDBfPDBq:PCBBiF:$Ir(dppm)_2(acac)$=0.7:0.3:0.05 and a thickness of 20 nm. Then, 2mFBiPDBfPDBq, PCBBiF, and $Ir(dppm)_2(acac)$ were deposited by co-evaporation such that the deposited layer had a weight ratio of 2mFBiPDBfPDBq:PCBBiF:$Ir(dppm)_2(acac)$=0.8:0.2:0.05 and a thickness of 20 nm. Note that in the light-emitting layer 160, 2mFBiPDBfPDBq corresponds to a host material and $Ir(dppm)_2(acac)$ corresponds to a guest material.

As the electron-transport layer 118, 2mFBiPDBfPDBq and BPhen were successively deposited by evaporation to thicknesses of 20 nm and 10 nm, respectively, over the light-emitting layer 160. As the electron-injection layer 119, lithium fluoride lithium fluoride (LiF) was deposited over the electron-transport layer 118 by evaporation to a thickness of 1 nm.

As the electrode 102, aluminum (Al) was formed over the electron-injection layer 119 to a thickness of 200 nm.

Next, in a glove box containing a nitrogen atmosphere, the light-emitting element 4 was sealed by fixing the substrate 220 to the substrate 200 over which the organic material was deposited using a sealant for an organic EL device. For the detailed method, description of the light-emitting element 1 can be referred to. Through the above steps, the light-emitting element 4 was obtained.

TABLE 7

| | Layer | Symbol | Thickness (nm) | Material | Weight ratio |
|---|---|---|---|---|---|
| Light-emitting element 4 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mFBiPDBiPDBq | — |
| | Light-emitting layer | 160(2) | 20 | 2mFBiPDBiPDBq:PCBiBF:$Ir(dppm)_2(acac)$ | 0.8:0.2:0.05 |
| | | 160(1) | 20 | 2mFBiPDBiPDBq:PCBBiF:$Ir(dppm)_2(acac)$ | 0.7:0.3:0.05 |
| | Hole-transport layer | 112 | 20 | BPAFLP | — |
| | Hole-injection layer | 111 | 60 | DBT3P-II:$MoO_3$ | 1:0.5 |
| | Electrode | 101 | 70 | ITSO | — |
| Light-emitting element 5 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 2mpPCBABPDBq | — |
| | Light emitting layer | 160(2) | 20 | 2mpPCBABPDBq:PCBBiF:$Ir(dppm)_2(acac)$ | 0.8:0.2:0.05 |
| | | 160(1) | 20 | 2mpPCBABPDBq:PCBBiF:$Ir(dppm)_2(acac)$ | 0.7:0.3:0.05 |
| | Hole-transport layer | 112 | 20 | BPAFLP | — |
| | Hole-injection layer | 111 | 60 | DBT3P-II:$MoO_3$ | 1:0.5 |
| | Electrode | 101 | 70 | ITSO | — |

<Fabrication of Light-Emitting Elements>

<<Fabrication of Light-Emitting Element 4>>

As the electrode 101, an ITSO film was formed to a thickness of 70 nm over the substrate 200. The electrode area of the electrode 101 was set to 4 $mm^2$ (2 mm×2 mm).

As the hole-injection layer 111, DBT3P-II and $MoO_3$ were deposited over the electrode 101 by co-evaporation such that the deposited layer had a weight ratio of DBT3P-II:$MoO_3$=1:0.5 and a thickness of 60 nm.

As the hole-transport layer 112, BPAFLP was deposited over the hole-injection layer 111 by evaporation to a thickness of 20 nm.

<<Fabrication of Light-Emitting Element 5>>

Steps, materials, mixing ratios, and thicknesses for the light-emitting element 5 were the same as those for the above-described light-emitting element 4 except for the host material in the light-emitting layer 160 and the material in the electron-transport layer 118(1), as shown in Table 7.

As the host material in the light-emitting layer 160 and the material in the electron-transport layer of the light-emitting element 118(1) 5, N-phenyl-N-4-(9-phenyl-9H-carbazol-3-yl)phenyl-4-[3-(dibenzo[f,h]quinoxalin-2-yl)phenyl]phenylamine (abbreviation: 2mpPCBABPDBq) was used.

<Characteristics of Light-Emitting Elements>

Figure 53:
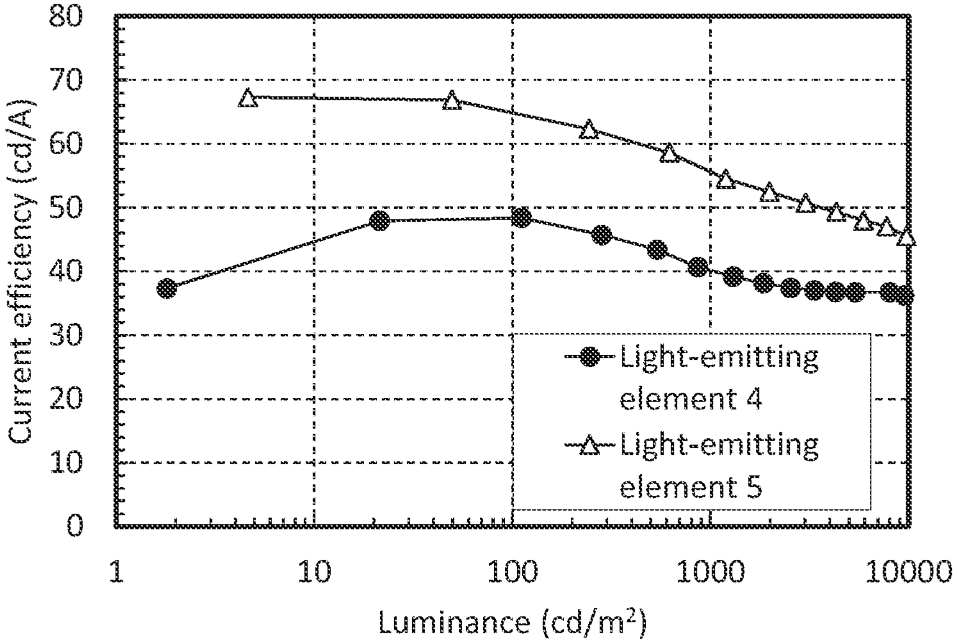
FIG. 53 shows current efficiency vs. luminance characteristics of light-emitting elements in Example.
Figure 54:
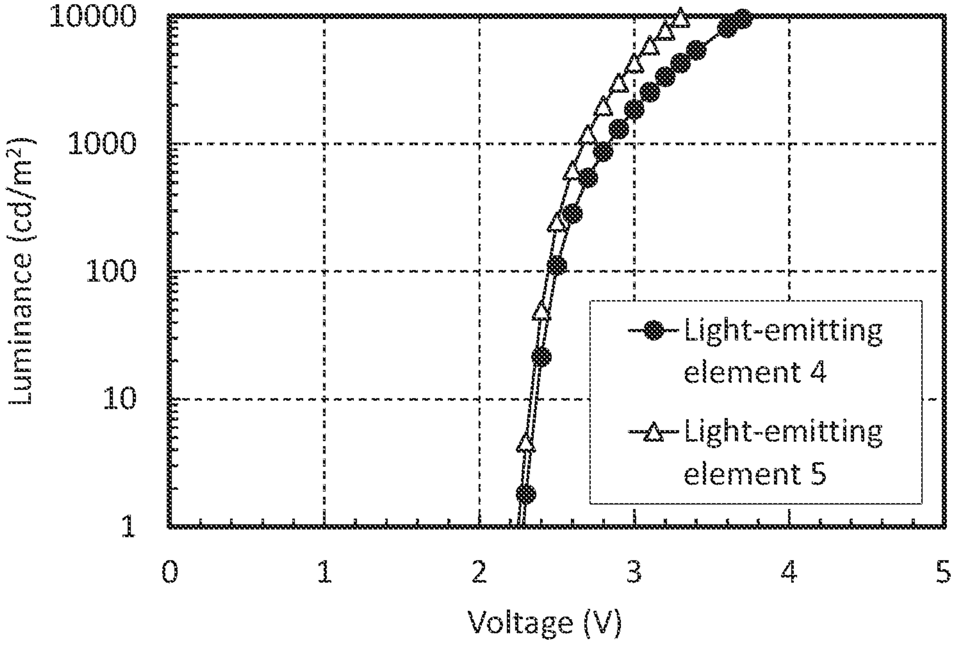
FIG. 54 shows luminance vs. voltage characteristics of light-emitting elements in Example.
Figure 55:
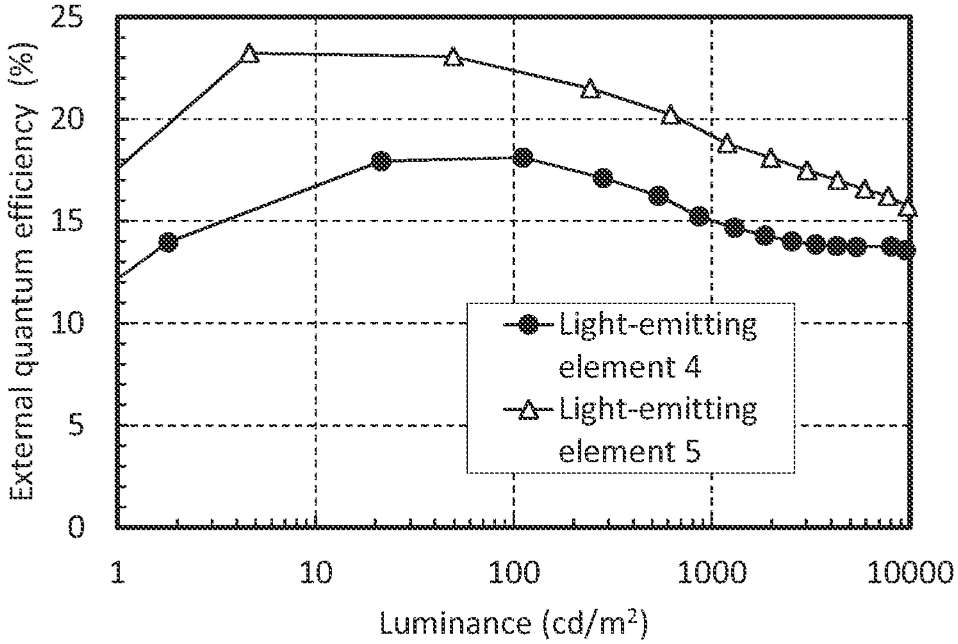
FIG. 55 shows external quantum efficiency vs. luminance characteristics of light-emitting elements in Example.
Figure 56:
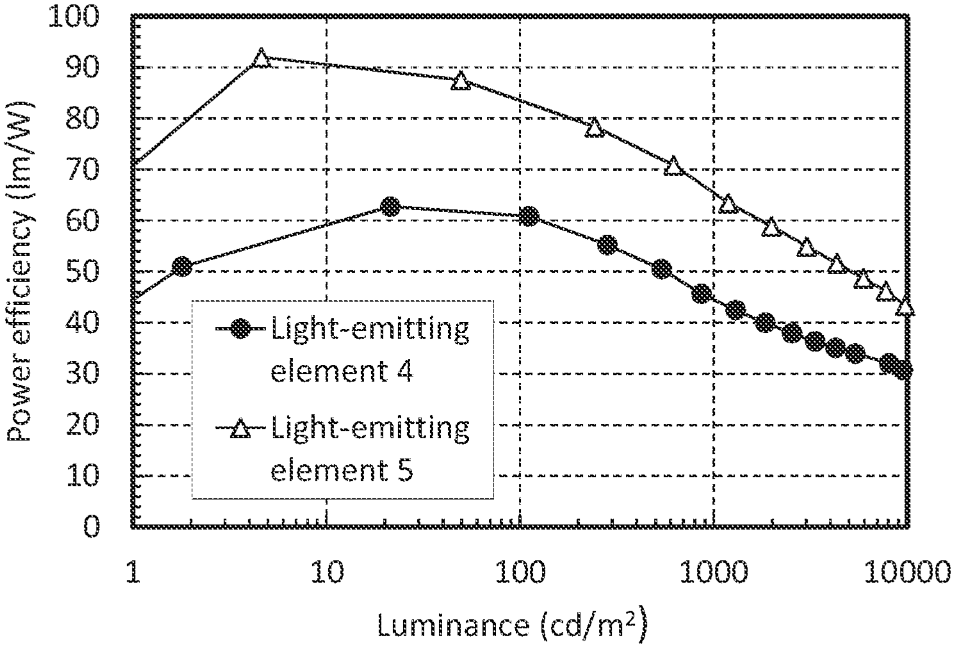
FIG. 56 shows power efficiency vs. luminance characteristics of light-emitting elements in Example.

FIG. 53 shows current efficiency vs. luminance characteristics of the light-emitting elements 4 and 5; FIG. 54 shows luminance vs. voltage characteristics thereof; FIG. 55 shows external quantum efficiency vs. luminance characteristics thereof; and FIG. 56 shows power efficiency vs. luminance characteristics thereof. The measurement for the light-emitting elements was performed at room temperature (in an atmosphere kept at 23° C.) by a measurement method similar to that used in Example 1.

Table 8 shows element characteristics of the light-emitting elements 4 and 5 at around 1000 cd/$m^2$.

TABLE 8

| | Voltage (V) | Current density (mA/$cm^2$) | CIE Chromaticity (x, y) | Luminance (cd/$m^2$) | Current efficiency (cd/A) | Power efficiency (lm/W) | External quantum efficiency (%) |
|---|---|---|---|---|---|---|---|
| Light-emitting element 4 | 2.80 | 2.13 | (0.550, 0.447) | 865 | 40.7 | 45.6 | 15.2 |
| Light-emitting element 5 | 2.70 | 2.19 | (0.532, 0.463) | 1200 | 54.5 | 63.4 | 18.8 |

Figure 57:
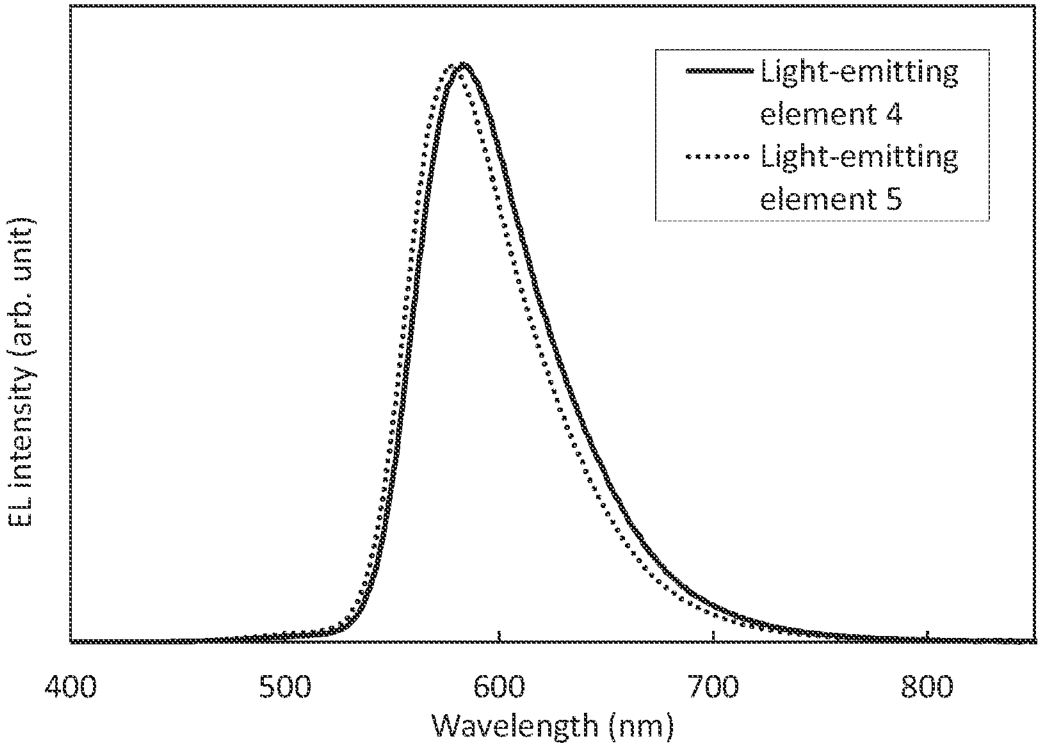
FIG. 57 shows electroluminescence spectra of light-emitting elements in Example.

FIG. 57 shows emission spectra when a current at a current density of 2.5 mA/$cm^2$ was supplied to the light-emitting elements 4 and 5.

As shown in FIG. 53 to FIG. 55 and Table 8, the light-emitting element 4 has high current efficiency and high external quantum efficiency, and the maximum external quantum efficiencies of the light-emitting elements 4 and 5 are higher than 18% and higher than 23%, respectively, which are excellent values.

As shown in FIG. 57, the light-emitting elements 4 and 5 emit orange light. The electroluminescence spectra of the light-emitting elements 4 and 5 have peaks at wavelengths of 583 nm and 578 nm, respectively, and full widths at half maximum of 70 nm and 65 nm, respectively. The obtained emission spectrum reveals that the orange light is emitted from $Ir(dppm)_2(acac)$ as a guest material.

The light-emitting elements 4 and 5 were driven at extremely low voltages of 2.8 V and 2.7 V, respectively, at around 1000 cd/$m^2$ and thus exhibited high power efficiency. Furthermore, the light emission start voltage (voltages at the time when the luminance exceeds 1 cd/$m^2$) of each of the light-emitting elements 4 and 5 was 2.3 V. The voltage is lower than a voltage corresponding to the energy difference between the LUMO level and the HOMO level of the guest material $Ir(dppm)_2(acac)$, which is described later. The results suggest that emission in the light-emitting elements 4 and 5 is obtained not by direct recombination of carriers in the guest material but by recombination of carriers in the host material having a smaller energy gap.

<Emission Spectra of Host Material>

Figure 58:
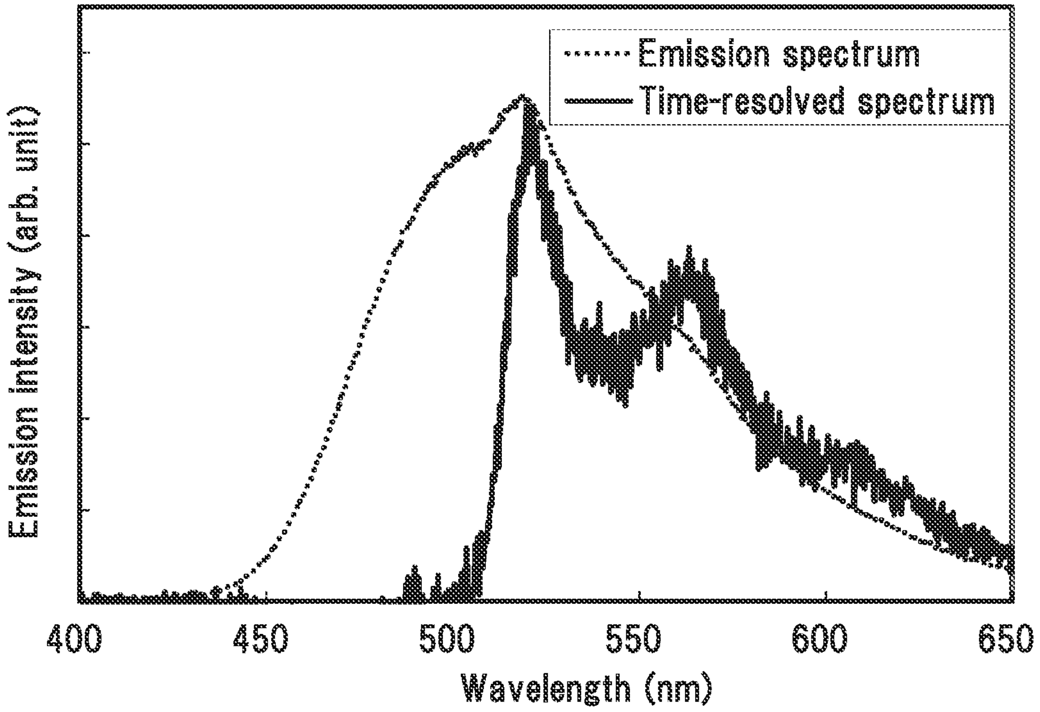
FIG. 58 shows emission spectra of a host material in Example.
Figure 59:
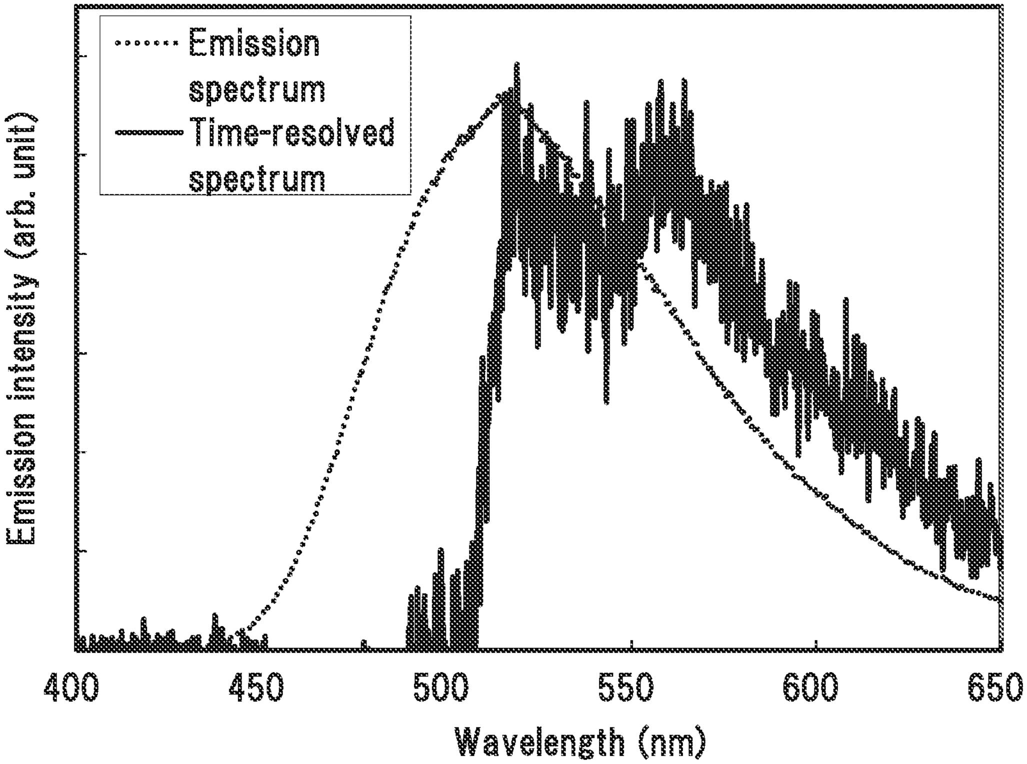
FIG. 59 shows emission spectra of a host material in Example.

In the fabricated light-emitting elements 4 and 5, 2mFBiPDBfPDBq and 2mpPCBABPDBq were used as the host materials. FIG. 58 and FIG. 59 show measurement results of emission spectra of thin films of 2mFBiBPDBq and 2mpPCBABPDBq, respectively. Note that the measurement method is similar to that used in Example 1.

As shown in FIG. 58, the wavelengths of peaks (including shoulders) on the shortest wavelength sides of the emission spectra of 2mFBiPDBfPDBq that indicate fluorescent components and phosphorescent components are 506 nm and 519 nm, respectively. Thus, the S1 level and the T1 level calculated from the wavelengths of the peaks (including shoulders) are 2.45 eV and 2.39 eV, respectively. That is, the energy difference between the S1 level and the T1 level of 2mFBiPDBfPDBq calculated from the wavelengths of the peaks (including shoulders) was 0.06 eV, which is extremely small.

As shown in FIG. 59, the wavelengths of peaks (including shoulders) on the shortest wavelength sides of the emission spectra of 2mpPCBABPDBq that indicate fluorescent components and phosphorescent components are 500 nm and 518 nm, respectively. Thus, the S1 level and the T1 level calculated from the wavelengths of the peaks (including shoulders) are 2.48 eV and 2.39 eV, respectively. That is, the energy difference between the S1 level and the T1 level of 2mpPCBABPDBq calculated from the wavelengths of the peaks (including shoulders) was 0.09 eV, which is extremely small.

As described above, the energy difference between the S1 level and the T1 level of each of 2mFBiPDBfPDBq and 2mpPCBABPDBq which is calculated from the wavelengths of the peaks (including shoulders) on the shortest wavelength sides of the emission spectra is greater than 0 eV and less than or equal to 0.2 eV, which is extremely small. Therefore, 2mFBiPDBfPDBq and 2mpPCBABPDBq can have a function of converting triplet excitation energy into singlet excitation energy by reverse intersystem crossing.

The peak wavelengths on the shortest wavelength sides of the emission spectra of light emission of 2mFBiPDBfPDBq and 2mpPCBABPDBq that indicate phosphorescent components are shorter than those of the electroluminescence spectra of the guest materials ($Ir(dppm)_2(acac)$) of the light-emitting elements 4 and 5. Since $Ir(dppm)_2(acac)$ serving as a guest material is a phosphorescent material, light is emitted from the triplet excited state. That is, the T1 level of each of 2mFBiPDBfPDBq and 2mpPCBABPDBq is higher than the T1 level of the guest material.

In addition, as described in Example 2, the absorption band on the lowest energy side (the longest wavelength side) of the absorption spectrum of $Ir(dppm)_2(acac)$ is at around 560 nm and has a region overlapping with the phosphorescence spectrum of 2mFBiPDBfPDBq and 2mpPCBABPDBq. Therefore, in the light-emitting elements 4 and 5 using 2mFBiPDBfPDBq and 2mpPCBABPDBq as host materials, excitation energy can be effectively transferred to the guest material. This suggests that 2mFBiPDBfPDBq and 2mpPCBABPDBq are suitably used as the host materials of the light-emitting elements 4 and 5.

<Results of CV Measurement>

The electrochemical characteristics (oxidation reaction characteristics and reduction reaction characteristics) of the compounds used as the guest material and the host material of the light-emitting element were examined by cyclic voltammetry (CV). Note that the measurement method is similar to that used in Example 1.

Table 9 shows oxidation potentials and reduction potentials obtained by CV measurement and HOMO levels and LUMO levels of the compounds calculated from the CV measurement results.

TABLE 9

| Abbreviation | Oxidation potential (V) | Reduction potential (V) | HOMO level calculated from oxidation potential (eV) | LUMO level calculated from reduction potential (eV) |
|---|---|---|---|---|
| $Ir(dppm)_2(acac)$ | 0.52 | −1.96 | −5.56 | −2.98 |
| 2mFBiPDBfPDBq | 0.48 | −2.01 | −5.42 | −2.93 |
| 2mpPCBABPDBq | 0.49 | −2.00 | −5.43 | −2.94 |

As shown in Table 9, in the light-emitting elements 4 and 5, the reduction potential of the guest material ($Ir(dppm)_2(acac)$) is higher than the reduction potentials of the host materials (2mFBiPDBfPDBq and 2mpPCBABPDBq), and the oxidation potential of the guest material ($Ir(dppm)_2(acac)$) is higher than the oxidation potentials of the host materials (2mFBiPDBfPDBq and 2mpPCBABPDBq). Therefore, the LUMO level of the guest material ($Ir(dppm)_2(acac)$) is lower than the LUMO levels of the host materials (2mFBiPDBfPDBq and 2mpPCBABPDBq), and the HOMO level of the guest material ($Ir(dppm)_2(acac)$) is lower than the HOMO levels of the host materials (2mFBiPDBfPDBq and 2mpPCBABPDBq). The energy difference between the LUMO level and the HOMO level of the guest material ($Ir(dppm)_2(acac)$) is larger than the energy difference between the LUMO level and the HOMO levels of the host materials (2mFBiPDBfPDBq and 2mpPCBABPDBq).

The energy difference between the LUMO level and the HOMO level of $Ir(dppm)_2(acac)$ was 2.58 eV. This value was calculated from the CV measurement results shown in Table 9.

As described in Example 2, the transition energy of $Ir(dppm)_2(acac)$ calculated from the absorption edge of the absorption spectrum of $Ir(dppm)_2(acac)$ is 2.22 eV and the energy difference between the LUMO level and the HOMO level of $Ir(dppm)_2(acac)$ is larger than the transition energy calculated from the absorption edge by 0.36 eV.

As shown in FIG. 52, the wavelength of the peak on the shortest wavelength side of the emission spectrum of $Ir(dppm)_2(acac)$ is 592 nm. According to that, the light emission energy of $Ir(dppm)_2(acac)$ was calculated to be 2.09 eV.

That is, the energy difference between the LUMO level and the HOMO level of $Ir(dppm)_2(acac)$ was larger than the light emission energy by 0.49 eV.

Consequently, in the guest materials of the light-emitting elements 4 and 5, the energy difference between the LUMO level and the HOMO level is greater than the transition energy calculated from the absorption edge by 0.3 eV or more. In addition, the energy difference between the LUMO level and the HOMO level is greater than the light emission energy by 0.4 eV or more. Therefore, high energy corresponding to the energy difference between the LUMO level and the HOMO level is needed, that is, high voltage is needed when carriers injected from a pair of electrodes are directly recombined in the guest material.

Meanwhile, the energy difference between the LUMO level and the HOMO level of each of the host materials (2mFBiPDBfPDBq and 2mpPCBABPDBq) in the light-emitting elements 4 and 5 was calculated to be 2.49 eV from Table 9. That is, the energy difference between the LUMO level and the HOMO level of each of the host material (2mFBiPDBfPDBq and 2mpPCBABPDBq) of the light-emitting elements 4 and 5 is smaller than the energy difference (2.58 eV) between the LUMO level and the HOMO level of the guest material ($Ir(dppm)_2(acac)$), greater than the transition energy (2.22 eV) calculated from the absorption edge, and greater than the light emission energy (2.09 eV). Therefore, in the light-emitting elements 4 and 5, the guest material can be excited by energy transfer through an excited state of the host material without the direct carrier recombination in the guest material, whereby the driving voltage can be lowered. Thus, the power consumption of the light-emitting element of one embodiment of the present invention can be reduced.

According to the CV measurement results in Table 9, among carriers (electrons and holes) injected from the pair of electrodes of the light-emitting elements 4 and 5, electrons tend to be injected into the guest material ($Ir(dppm)_2(acac)$) with a low LUMO level, whereas holes tend to be injected into the host materials (2mFBiPDBfPDBq and 2mpPCBABPDBq) with high HOMO levels. That is, there is a possibility that an exciplex is formed by the host material and the guest material.

The energy difference between the LUMO level of the guest material ($Ir(dppm)_2(acac)$) and the HOMO level of the host material (2mFBiPDBfPDBq) was calculated from the CV measurement results shown in Table 9 and found to be 2.44 eV. The energy difference between the LUMO level of the guest material ($Ir(dppm)_2(acac)$) and the HOMO level of the host material (2mpPCBABPDBq) was calculated from the CV measurement results shown in Table 9 and found to be 2.45 eV.

From these results, in the light-emitting elements 4 and 5, the energy difference (2.44 eV) between the LUMO level of the guest material ($Ir(dppm)_2(acac)$) and the HOMO level of the host material (2mFBiPDBfPDBq) and the energy difference (2.45 eV) between the LUMO level of the guest material ($Ir(dppm)_2(acac)$) and the HOMO level of the host material (2mpPCBABPDBq) are greater than or equal to the transition energy (2.22 eV) calculated from the absorption edge of the absorption spectrum of the guest material. Furthermore, the energy differences (2.44 eV and 2.45 eV) between the LUMO level of the guest material and the HOMO levels of the host materials are greater than or equal to the energy (2.09 eV) of light emitted by the guest material. Accordingly, rather than formation of an exciplex by the host material and the guest material, transfer of excitation energy to the guest material is more facilitated eventually, whereby efficient light emission from the guest material is achieved. This relationship is a feature of one embodiment of the present invention for efficient light emission.

In the case where the LUMO level of a guest material is lower than the LUMO level of a host material and the energy difference between the LUMO level and the HOMO level of the guest material is larger than the energy difference between the LUMO level and the HOMO level of the host material as in the above-described light-emitting elements 4 and 5, a light-emitting element with high emission efficiency and low driving voltage can be obtained when the energy difference between the LUMO level of the guest material and the HOMO level of the host material is greater than or equal to the transition energy calculated from the absorption edge of the absorption spectrum of the guest material or greater than or equal to the light emission energy of the guest material. Furthermore, in the case where the energy difference between the LUMO level and the HOMO level of a guest material is greater than the transition energy calculated from the absorption edge of the absorption spectrum of the guest material or the light emission energy of the guest material by 0.3 eV or more, a light-emitting element with high emission efficiency and low driving voltage can be obtained.

As described above, by employing the structure of one embodiment of the present invention, a light-emitting element having high emission efficiency can be fabricated. Furthermore, a light-emitting element with reduced power consumption can be fabricated.

The structures described in this example can be used in an appropriate combination with any of the other embodiments.

Example 4

Synthesis Example 1

In Example 4, a method of synthesizing N-(4-biphenyl)-N-(9,9-dimethyl-9H-fluoren-2-yl)-N-{4-[3-(dibenzo[f,h]quinoxalin-2-yl)phenyl]phenyl}amine (abbreviation: 2mFBiBPDBq) that is a compound of one embodiment of the present invention and represented by Structural Formula (500) in Embodiment 1 is described.

<<Step 1: Synthesis of 2mFBiBPDBq>>

A synthesis scheme of Step 1 is shown in (A-1).

Into a 200 mL three-neck flask were put 2.0 g (3.9 mmol) of N-(4-bromophenyl)-N-(4-biphenyl)-N-(9,9-dimethyl-9H-fluoren-2-yl)amine, 1.7 g (3.9 mmol) of 4,4,5,5-tetramethyl-2-[3-(dibenzo[f,h]quinoxalin-2-yl)phenyl]-1,3,2-dioxaborolane, 24 mg (0.078 mmol) of tris(2-methylphenyl) phosphine, and 1.1 g (7.8 mmol) of potassium carbonate, and the air in the flask was replaced with nitrogen. To this mixture, 15 mL of toluene, 4.5 mL of ethanol, and 4.5 mL of water were added. While the pressure was reduced, this mixture was stirred to be degassed. To this mixture, 8.8 mg (0.039 mmol) of palladium(II) acetate was added. This mixture was stirred under a nitrogen stream at 80° C. for 7 hours, whereby a solid was precipitated. Then, the precipitated solid was collected by suction filtration. The collected solid was dissolved in approximately 30 mL of hot toluene, and the obtained solution was purified by silica gel column chromatography (with a developing solvent of hexane and toluene in a ratio of 3:1) to give a solid. The solid was dissolved in chloroform, and purification was performed by HPLC to give a solid. The solid was washed with hexane, so that 1.7 g of a target pale yellow powder was obtained in 59% yield.

[Chemical Formula 32]

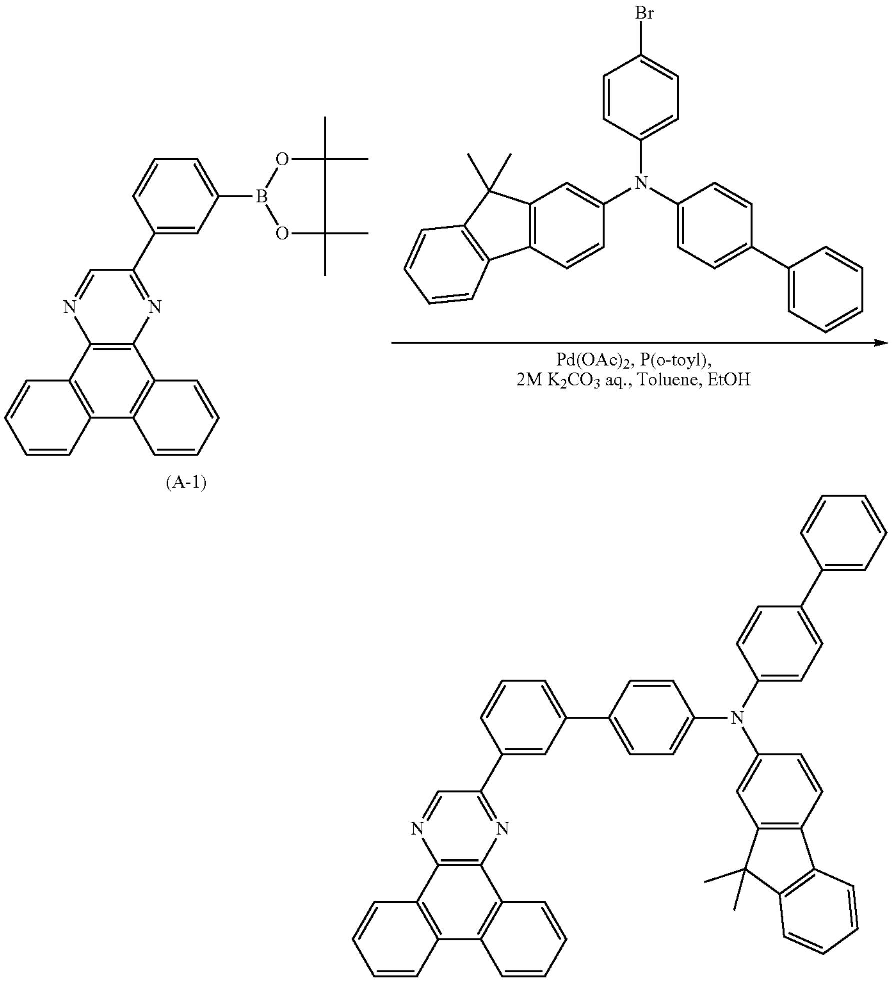

(A-1)

(500)

By a train sublimation method, 1.7 g of the obtained pale yellow powder was purified by sublimation. The pale yellow powder was heated at 330° C. with an argon flow rate of 5.0 mL/min under a pressure of 10 Pa. After the sublimation purification, 1.6 g of a pale yellow solid was obtained at a collection rate of 93%.

<$^1$H NMR Measurement Results>

The obtained substance was measured by $^1$H NMR. The measurement data are shown below.

$^1$H NMR ($CDCl_3$, 500 MHZ): δ=1.47, (s, 6H), 7.09 (dd, $J_1$=7.5 Hz, $J_2$=2.0 Hz, 1H), 7.27-7.35 (m, 8H), 7.41-7.46 (m, 3H), 7.55 (d, J=6.5 Hz, 2H), 7.62-7.69 (m, 7H), 7.76-7.84, (m, 5H), 8.28 (d, J=8.0 Hz, 1H), 8.60 (s, 1H), 8.66 (d, J=8.0 Hz, 2H), 9.25 (dd, $J_1$=8.0 Hz, $J_2$=2.0 Hz, 1H), 9.43 (dd, $J_1$=8.0 Hz, $J_2$=2.0 Hz, 1H), 9.46 (s, 1H).

Figure 60A:
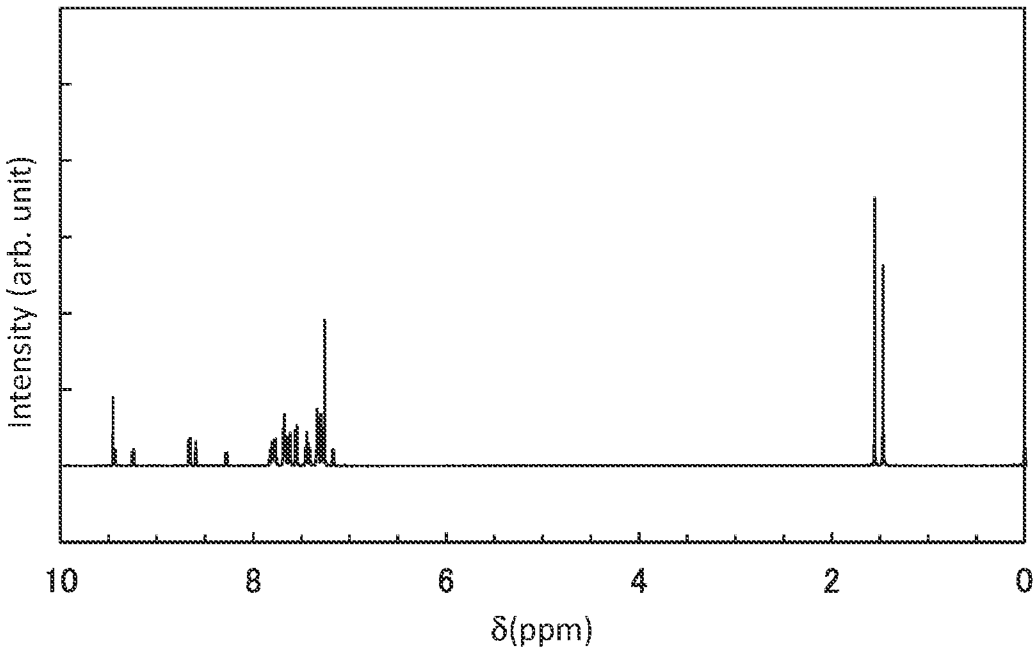
FIGS. 60A and 60B show $^1$H NMR charts of N-(4-biphenyl)-N-(9,9-dimethyl-9H-fluoren-2-yl)-N-{4-[3-(dibenzo[f,h]quinoxalin-2-yl)phenyl]phenyl}amine (abbreviation: 2mpFBiBPDBq).
Figure 60B:
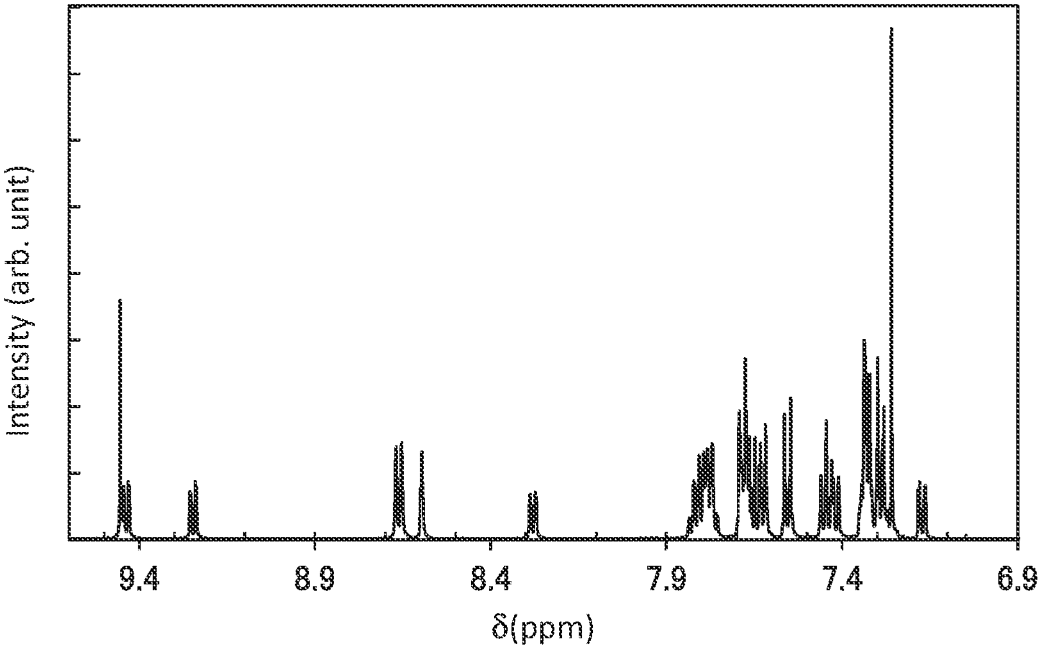

The $^1$H NMR charts are shown in FIGS. 60A and 60B. Note that FIG. 60B is a chart showing an enlarged part of FIG. 60A in the range of 6.90 ppm to 9.60 ppm. The charts reveal that 2mpFBiBPDBq that is a compound and represented by Structural Formula (500) was obtained.

<LC/MS Results>

Furthermore, liquid chromatography mass spectrometry (LC/MS) of 2mpFBiBPDBq was carried out.

The LC/MS analysis was carried out with Acquity UPLC (produced by Waters Corporation) and Xevo G2 Tof MS (produced by Waters Corporation). In the MS analysis, ionization was carried out by an electrospray ionization (ESI) method. At this time, the capillary voltage and the sample cone voltage were set to 3.0 kV and 30 V, respectively, and detection was performed in a positive mode. A component which underwent the ionization under the above-described conditions was collided with an argon gas in a collision cell to dissociate into product ions. Energy (collision energy) for the collision with argon was 50 eV. The mass range for the measurement was m/z=100 to 1200.

Figure 61:
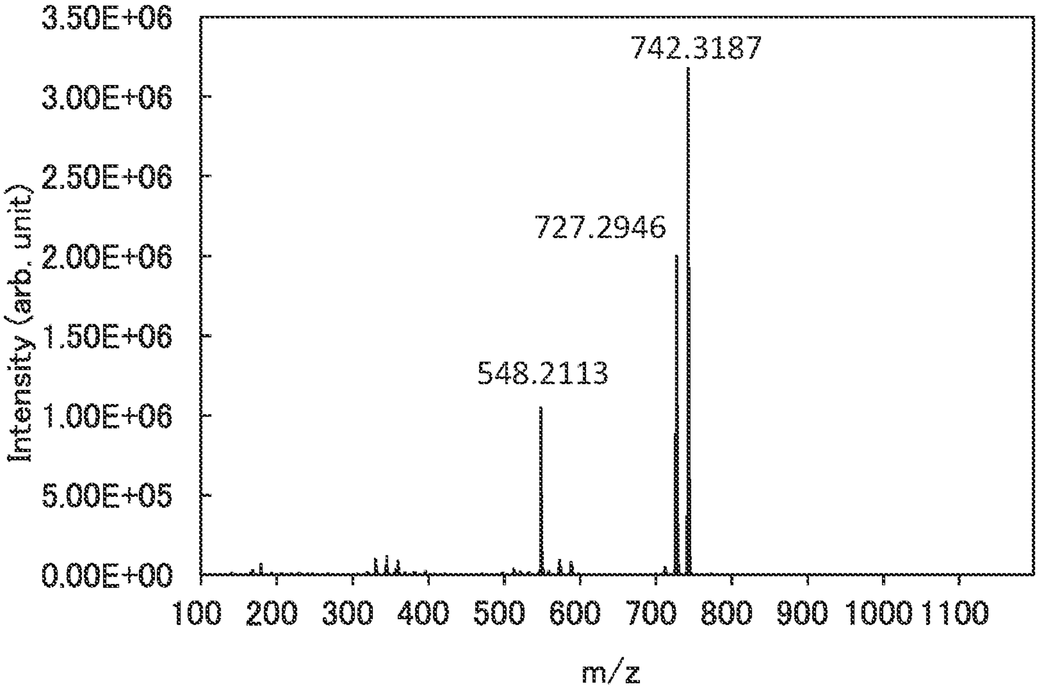
FIG. 61 shows LC/MS results of 2mpFBiBPDBq.

Measurement results are shown in FIG. 61. The results in FIG. 61 show that product ions of 2mpFBiBPDBq that is a compound of one embodiment of the present invention and represented by Structural Formula (500) are detected mainly around m/z=742, m/z=727, and m/z=548. Note that the result in FIG. 61 shows characteristics derived from 2mpFBiBPDBq and therefore can be regarded as important data for identifying 2mpFBiBPDBq contained in the mixture.

Note that a C—C bond between N-(4-biphenyl)-N-(9-methyl-9H-fluoren-2-yl)-N-{4-[3-(dibenzo[f,h]quinoxalin-2-yl)phenyl]phenyl}amine and methyl is cut and electric charge remains on the fluorene side. Therefore, the product ion observed at around m/z=727 is useful because the data is likely to indicate the state where the C—C bond between N-(4-biphenyl)-N-(9-methyl-9H-fluoren-2-yl)-N-{4-[3-(dibenzo[f,h]quinoxalin-2-yl)phenyl]phenyl}amine and methyl in the compound represented by Structural Formula (500) is cut. Furthermore, a C—N bond between N-(4-biphenyl)-N-{4-[3-(dibenzo[f,h]quinoxalin-2-yl)phenyl]phenyl}amine and 9,9-dimethylfluorene is cut and electric charge remains on the fluorene side. Therefore, the product ion observed at around m/z=548 is likely to indicate the state where the C—N bond between N-(4-biphenyl)-N-{4-[3-(dibenzo[f,h]quinoxalin-2-yl)phenyl]phenyl}amine and 9,9-dimethylfluorene in the compound represented by Structural Formula (500) is cut, suggesting that 2mpFBiBPDBq of a compound of one embodiment of the present invention includes N-(4-biphenyl)-N-{4-[3-(dibenzo[f,h]quinoxalin-2-yl)phenyl]phenyl}amine and 9,9-dimethylfluorene.

<TG-DTA Results>

Thermogravimetry-differential thermal analysis (TG-DTA) was performed on 2mpFBiBPDBq. The measurement was conducted by using a high vacuum differential type differential thermal balance (TG-DTA 2410SA, manufactured by Bruker AXS K.K.). The measurement was carried out under a nitrogen stream (a flow rate of 200 mL/min) and a normal pressure at a temperature rising rate of 10° C./min. It was found from the relationship between weight and temperature (thermogravimetry) that the 5% weight loss temperature of 2mpFBiBPDBq was higher than or equal to 500° C. This indicates that 2mpFBiBPDBq has high heat resistance.

<Measurement Results of Absorption Spectra and Emission Spectra>

Figure 62:
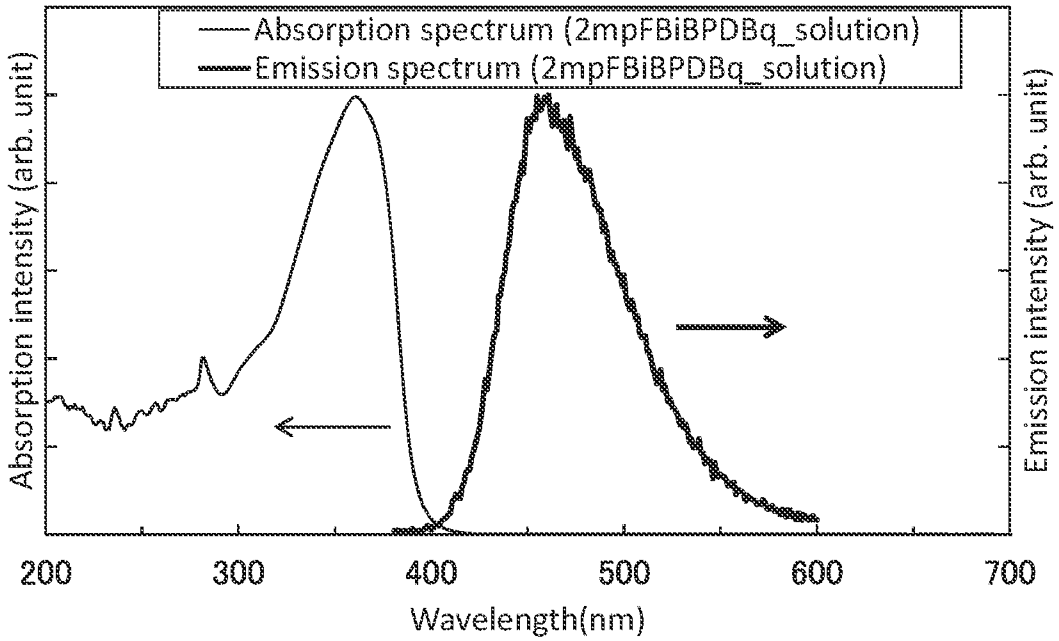
FIG. 62 shows an absorption spectrum and an emission spectrum of 2mpFBiBPDBq in a toluene solution of 2mpFBiBPDBq.
Figure 63:
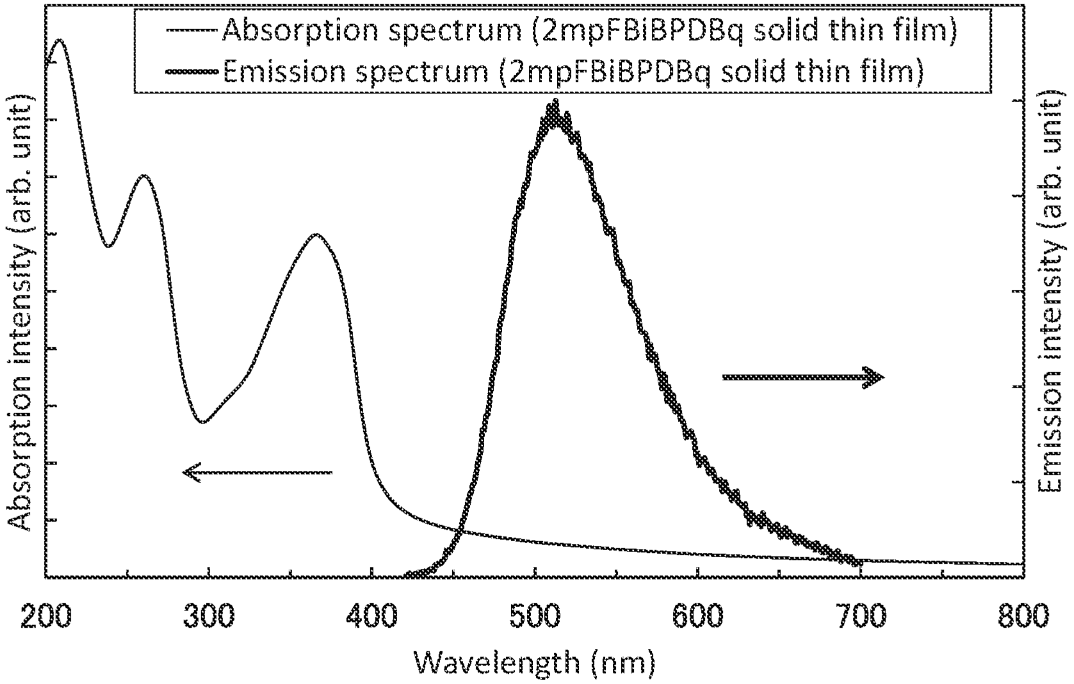
FIG. 63 shows an absorption spectrum and an emission spectrum of a solid thin film of 2mpFBiBPDBq.

Next, absorption spectra and emission spectra of 2mpFBiBPDBq in a toluene solution of 2mpFBiBPDBq and a solid thin film of 2mpFBiBPDBq were measured. The absorption spectra and emission spectra of 2mpFBiBPDBq in the toluene solution of 2mpFBiBPDBq were measured in a similar manner to Example 1. The solid thin film was formed over a quartz substrate by a vacuum evaporation method. The absorption spectrum was measured using an ultraviolet-visible light spectrophotometer (V550 type manufactured by JASCO Corporation). The absorption spectrum of the solid thin film was obtained by subtracting, from absorbance ($-\log_{10}$(% T/100)) calculated from transmittance, absorbance of the substrate. The emission spectrum was measured using a fluorescence spectrophotometer (FS920 manufactured by Hamamatsu Photonics K.K.). FIG. 62 shows the obtained absorption and emission spectra of 2mpFBiBPDBq in the toluene solution of 2mpFBiBPDBq. FIG. 63 shows the measurement results of the obtained absorption and emission spectra of the solid thin film.

In FIG. 62, the absorption peak of 2mpFBiBPDBq in the toluene solution of 2mpFBiBPDBq is observed at around 361 nm, and the emission wavelength peak is observed at 466 nm.

In FIG. 63, the absorption peaks of the solid thin film of 2mpFBiBPDBq are observed at around 211 nm, 260 nm, 311 nm, and 366 nm, and the emission wavelength peak is observed at 513 nm (excitation wavelength: 384 nm).

<Results of CV Measurement>

The electrochemical characteristics (oxidation reaction characteristics and reduction reaction characteristics) of the synthesized 2mpFBiBPDBq were measured by cyclic voltammetry (CV) measurement. The measurement method was similar to that used in Example 1.

On the assumption that the intermediate potential (the half-wave potential) between the oxidation peak potential $E_{pa}$ and the reduction peak potential $E_{pc}$ which are obtained in the CV measurement corresponds to the HOMO level, the HOMO level of 2mpFBiBPDBq was calculated to be −5.42 eV, and the LUMO level of 2mpFBiBPDBq was calculated to be −2.93 eV. Thus, the band gap (ΔE) of 2mpFBiBPDBq was found to be 2.49 eV.

Example 5

Synthesis Example 2

In Example 5, a method of synthesizing N-(4-biphenyl)-N-(4-{6-[3-(dibenzo[f,h]quinoxalin-2-yl)phenyl]dibenzofuran-4-yl}phenyl)-9,9-dimethyl-9H-fluoren-2-amine (abbreviation: 2mFBiPDBfPDBq) that is a compound of one embodiment of the present invention and represented by Structural Formula (501) in Embodiment 1 is described.

<<Step 1: Synthesis of 2mFBiPDBfPDBq>>

A synthesis scheme of Step 1 is shown in (A-2).

[Chemical Formula 33]

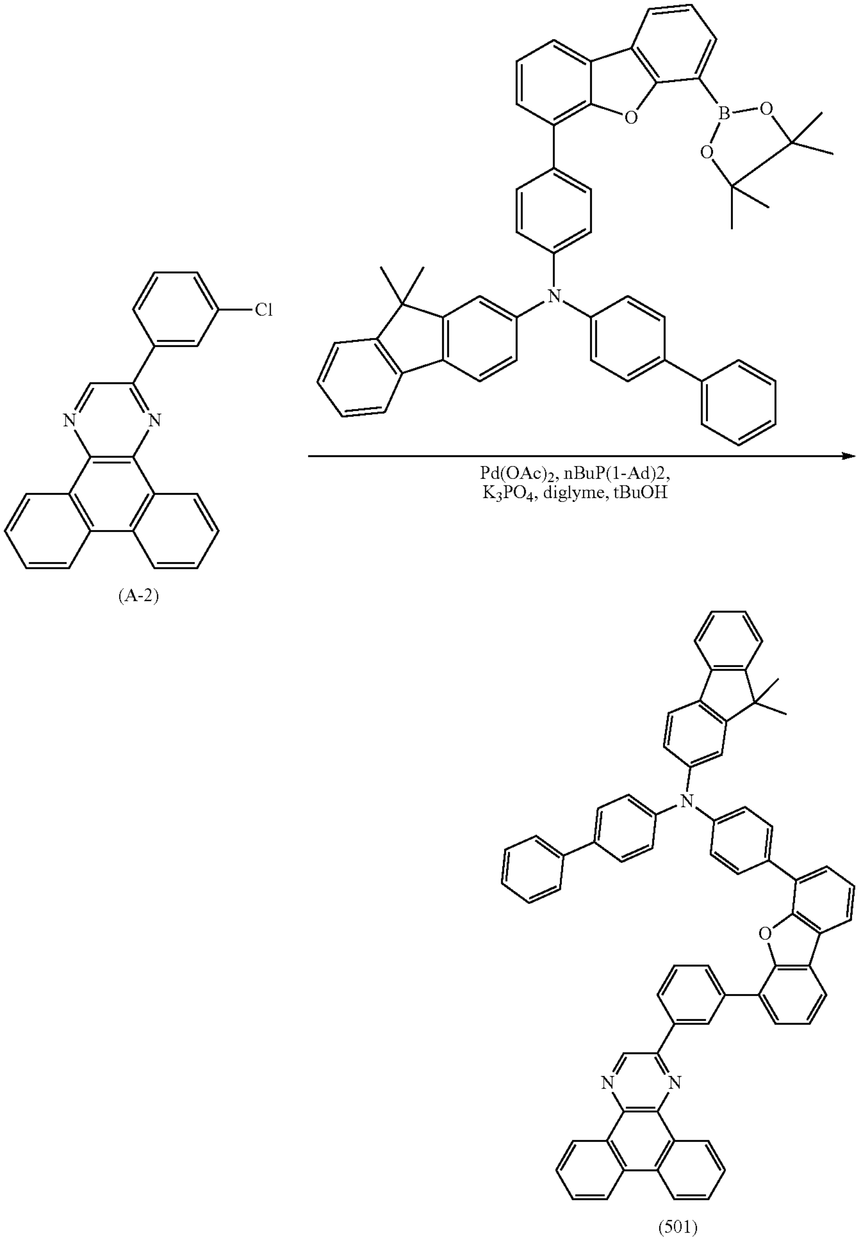

(A-2)

(501)

Into a 200 mL three-neck flask were put 2.5 g (3.4 mmol) of N-(4-biphenyl)-N-(4-{6-[4,4,5,5-tetramethyl-1,3,2-dioxaborolan-2-yl]dibenzofuran-4-yl}phenyl)-9,9-dimethy-9H-fluoren-2-amine, 1.1 (3.2 mmol) g of 2-(3-chlorophenyl) dibenzo[f,h]quinoxaline, 2.2 g (10 mmol) of tripotassium phosphate, and 24 mg (0.070 mmol) of di(1-adamantyl)-n-butylphosphine, and the air in the flask was replaced with nitrogen. To this mixture, 23 mL of 1,4-dioxane and 0.80 g (10 mmol) of tert-butyl alcohol were added. While the pressure was reduced, this mixture was stirred to be degassed. To this mixture, 8.0 mg (0.030 mmol) of palladium(II) acetate was added. This mixture was stirred under a nitrogen stream at 105° C. for 8 hours. After the stirring, water was added to this mixture, and an aqueous layer was subjected to extraction with toluene, and the extracted solution and the organic layer were combined and washed with saturated brine. After the washing, the organic layer was dried with magnesium sulfate, and then, this mixture was gravity-filtered. The filtrate was concentrated to give a solid. This solid was purified by silica gel column chromatography. As a developing solvent, a mixed solvent of toluene and hexane in a ratio of 1:2 was used. The obtained fraction was concentrated to give a solid. The solid was recrystallized with toluene:ethanol, so that 1.7 g of a pale yellow solid was obtained in 55% yield.

By a train sublimation method, 1.1 g of the pale yellow solid was purified by sublimation. In the purification by sublimation, the pale yellow powder was heated at 350° C.

under a pressure of 0.0089 Pa. After the purification by sublimation, 0.67 g of a yellow solid was obtained at a collection rate of 61%.

<$^1$H NMR Measurement Results>

The obtained substance was measured by $^1$H NMR. The measurement data are shown below.

$^1$H NMR ($CDCl_3$, 500 MHZ): δ=1.31 (s, 6H), 6.92 (dd, $J_1$=5.8 Hz, $J_2$=2.3 Hz, 1H), 7.02 (s, 1H), 7.04 (s, 1H), 7.14-7.17 (m, 3H), 7.22-7.40 (m, 9H), 7.44-7.60 m, 6H), 7.67-7.79 (m, 6H), 7.97-7.99 (m, 3H), 8.05 (dd, $J_1$=6.9 Hz, $J_2$=1.1 Hz, 1H), 8.08 (d, J=8.0 Hz, 1H), 8.40 (d, J=8.0 Hz, 1H), 8.56 (d, J=8.0 Hz, 1H), 8.59 (d, J=8.0 Hz, 1H), 8.97 (t, J=1.7 Hz, 1H), 9.15 (dd, J=1.2 Hz, J=6.8 Hz, 1H), 9.34 (d, J=8.0, 1H), 9.46 (s, 1H).

Figure 64A:
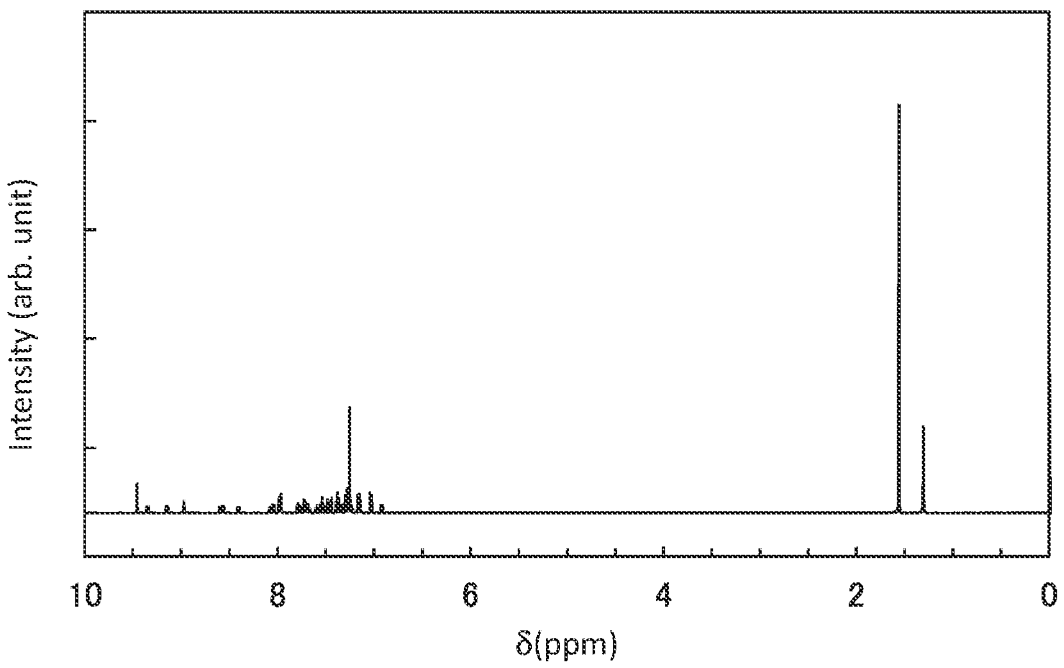
FIGS. 64A and 64B show $^1$H NMR charts of N-(4-biphenyl)-N-(4-{6-[3-(dibenzo[f,h]quinoxalin-2-yl)phenyl] dibenzofuran-4-yl}phenyl)-9,9-dimethyl-9H-fluoren-2-amine (abbreviation: 2mFBiPDBfPDBq).
Figure 64B:
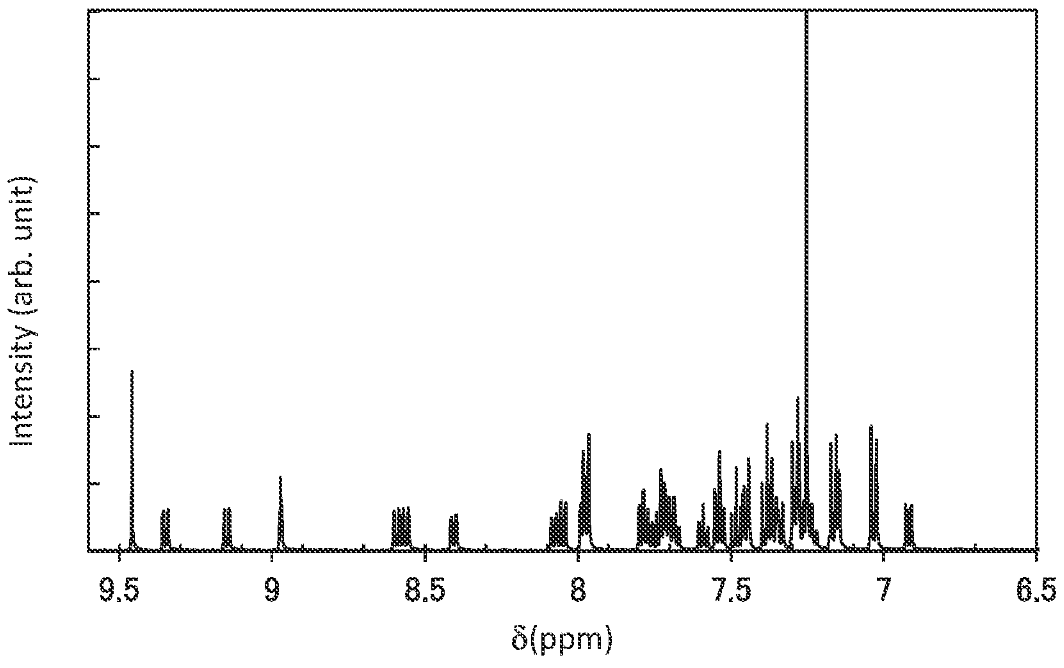

The $^1$H NMR charts are shown in FIGS. 64A and 64B. Note that FIG. 64B is a chart showing an enlarged part of FIG. 64A in the range of 6.50 ppm to 9.60 ppm. The charts reveal that 2mFBiPDBfPDBq, which is a compound represented by Structural Formula (501), was obtained.

<Measurement Results of Absorption Spectra and Emission Spectra>

Figure 65:
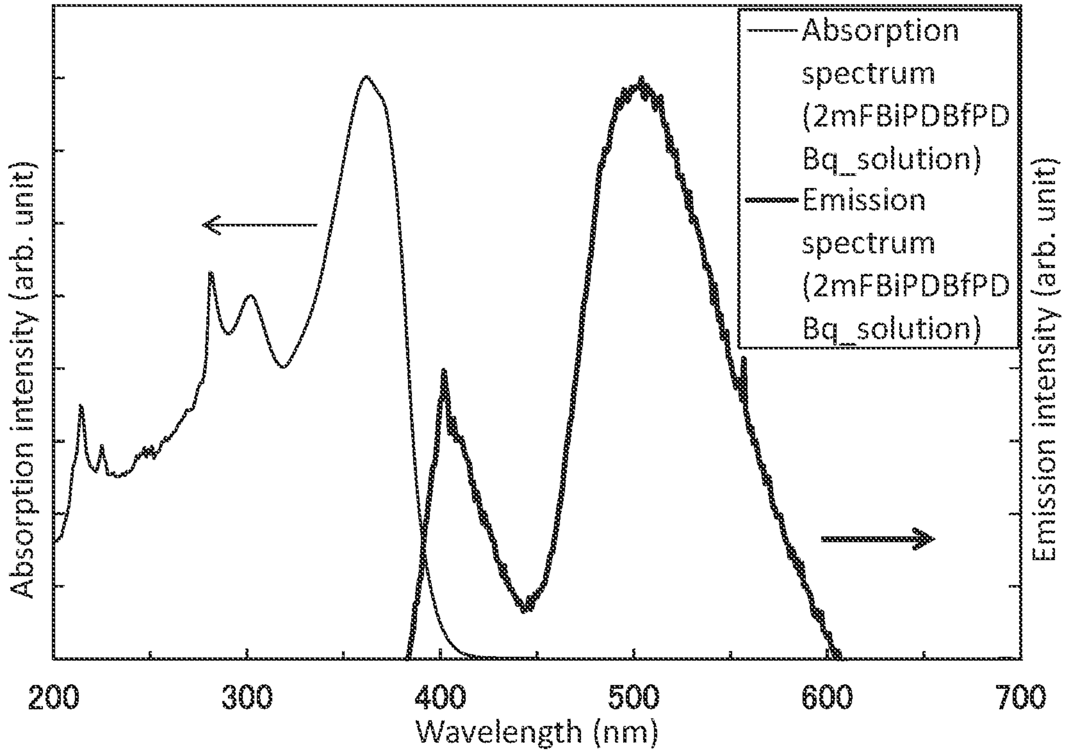
FIG. 65 shows an absorption spectrum and an emission spectrum of 2mFBiPDBfPDBq in a toluene solution of 2mFBiPDBfPDBq.
Figure 66:
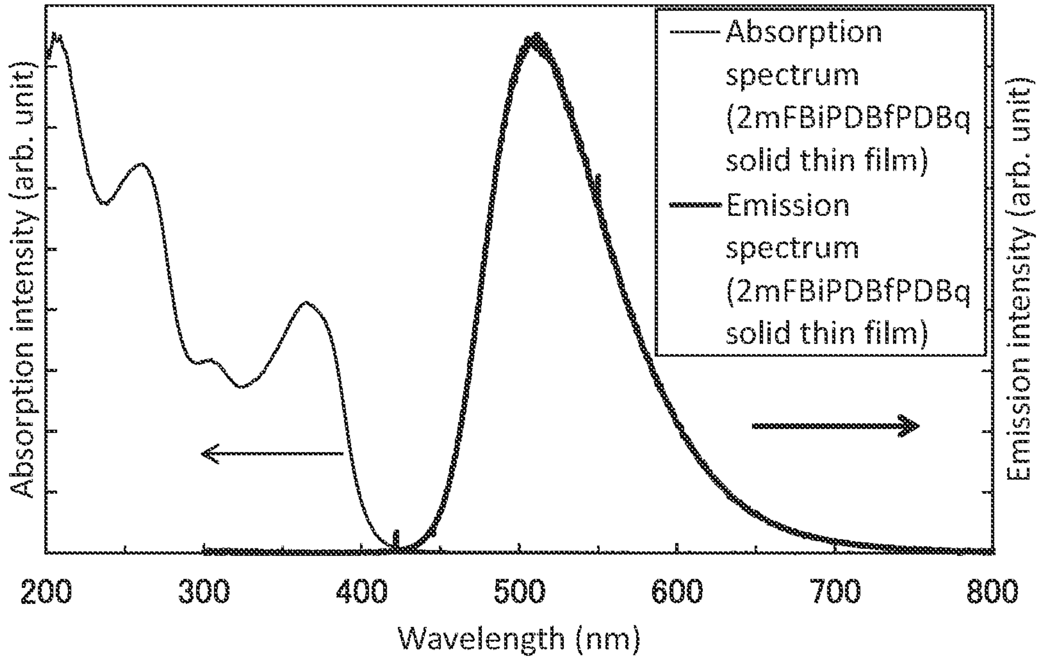
FIG. 66 shows an absorption spectrum and an emission spectrum of a solid thin film of 2mFBiPDBfPDBq.

Next, absorption spectra and emission spectra of 2mFBiPDBfPDBq in a toluene solution of 2mFBiPDBfPDBq and a solid thin film of 2mFBiPDBfPDBq were measured. The absorption spectra and emission spectra of 2mFBiPDBfPDBq in the toluene solution of 2mFBiPDBfPDBq were measured in a similar manner to Example 1. The absorption spectra and emission spectra of the solid thin film were measured in a similar manner to Example 4. FIG. 65 shows the obtained absorption and emission spectra of 2mFBiPDBfPDBq in the toluene solution of 2mFBiPDBfPDBq. FIG. 66 shows the measurement results of the obtained absorption and emission spectra of the solid thin film.

In FIG. 65, the absorption peak of 2mFBiPDBfPDBq in the toluene solution of 2mFBiPDBfPDBq is observed at around 361 nm, and the emission wavelength peaks are observed at around 402 nm and around 500 nm. In FIG. 66, the absorption peaks of the solid thin film of 2mFBiPDBfPDBq are observed at around 208 nm, 261 nm, 306 nm, and 364 nm, and the emission wavelength peak is observed at 516 nm.

<Results of CV Measurement>

The electrochemical characteristics (oxidation reaction characteristics and reduction reaction characteristics) of the synthesized 2mFBiPDBfPDBq were measured by cyclic voltammetry (CV) measurement. The measurement method was similar to that used in Example 1.

On the assumption that the intermediate potential (the half-wave potential) between the oxidation peak potential $E_{pa}$ and the reduction peak potential $E_{pc}$ which are obtained in the CV measurement corresponds to the HOMO level, the HOMO level of 2mFBiPDBfPDBq was calculated to be −5.42 eV, and the LUMO level of 2mFBiPDBfPDBq was calculated to be −2.93 eV. Thus, the band gap (ΔE) of 2mFBiPDBfPDBq was found to be 2.49 eV.

Example 6

Synthesis Example 3

In Example 6, method of synthesizing a 4-[3-(dibenzo[f, h]quinoxalin-2-yl)phenyl]-4'-(9-phenyl-9H-carbazol-3-yl)-triphenylamine (abbreviation: 2mpPCBABPDBq) that is a compound of one embodiment of the present invention and represented by Structural Formula (502) in Embodiment 1 is described.

<<Step 1: Synthesis of 2mpPCBABPDBq>>

A synthesis scheme of Step 1 is shown in (A-3).

[Chemical formula 34]

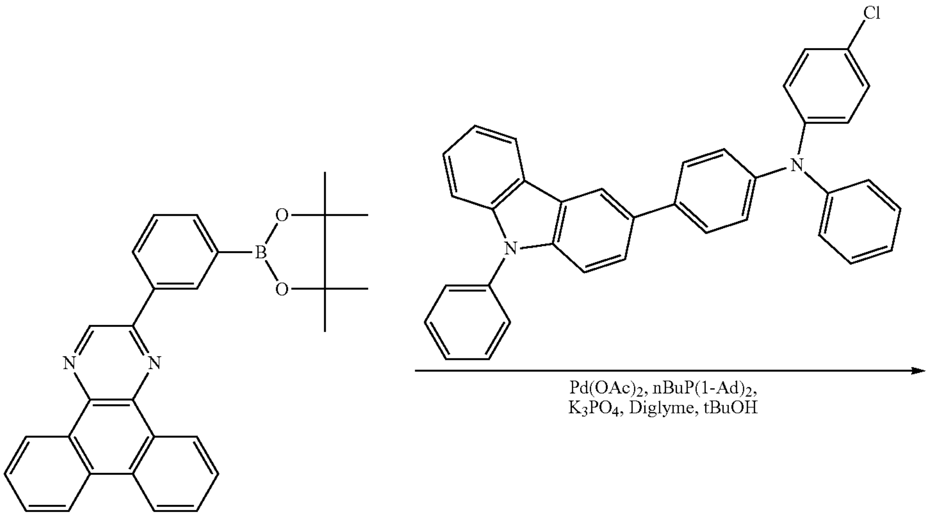

(A-3)

-continued

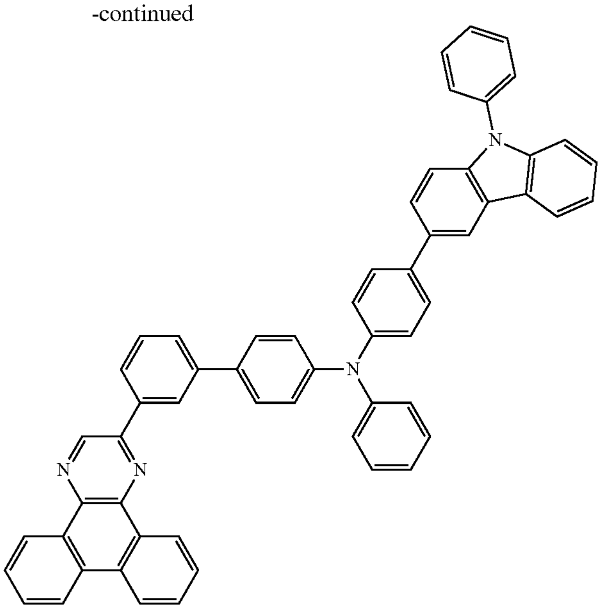

(502)

Into a 200 mL three-neck flask were put 2.0 g (3.8 mmol) of 4-chloro-4'-(9-phenyl-9H-carbazol-3-yl)-triphenylamine, 1.8 g (4.2 mmol) of 4,4,5,5-tetramethyl-2-[3-(dibenzo[f,h]quinoxalin-2-yl)phenyl]-1,3,2-dioxaborolane, 2.4 g (11 mmol) of tripotassium phosphate, and 27 mg (0.10 mmol) of di(1-adamantyl)-n-butylphosphine, and the air in the flask was replaced with nitrogen. To this mixture, 25 mL of diethylene glycol dimethyl ether and 0.84 g (11 mmol) of tert-butyl alcohol were added. While the pressure was reduced, this mixture was stirred to be degassed. To this mixture was added 8.5 mg (0.04 mmol) of palladium(II) acetate and stirring was performed under a nitrogen stream at 150° C. for 8 hours. After the stirring, water was added to this mixture, and an aqueous layer was subjected to extraction with toluene, and the extracted solution and the organic layer were combined and washed with saturated brine. After the washing, the organic layer was dried with magnesium sulfate. After the drying, the mixture was subjected to gravity filtration. The obtained filtrate was filtered through Celite, aluminum oxide, and Florisil and concentrated to give a solid. The solid was recrystallized with toluene, so that 1.5 g of a target pale yellow powder was obtained in 50% yield.

By a train sublimation method, 1.4 g of the pale yellow powder was purified by sublimation. In the purification by sublimation, the pale yellow powder was heated at 380° ° C. under a pressure of 2.4 Pa. After the purification by sublimation, 1.2 g of a pale yellow solid was obtained at a collection rate of 85%.

<$^1$H NMR Measurement Results>

The obtained substance was measured by $^1$H NMR. The measurement data are shown below.

$^1$H NMR ($CDCl_3$, 500 MHZ): δ=7.09 (t, J=7.4 Hz, 1H), 7.25-7.35 (m, 9H), 7.40-7.49 (m, 4H), 7.59-7.68 (m, 11H), 7.75-7.83 (m, 6H), 8.19 (d, J=8.0 Hz, 1H), 8.26, (d, J=8.0 Hz, 1H), 8.35 (d, J=1.8 Hz, 1H), 8.58 (s, 1H), 8.65 (d, J=8.1 Hz, 2H), 8.27 (d, J=7.5 Hz, 1H), 8.57 (s, 1H), 8.66 (d, J=8.0 Hz, 2H), 9.24 (dd, $J_1$=6.3 Hz, $J_2$=1.1 Hz, 1H), 9.44 (S, 1H).

Figure 67A:
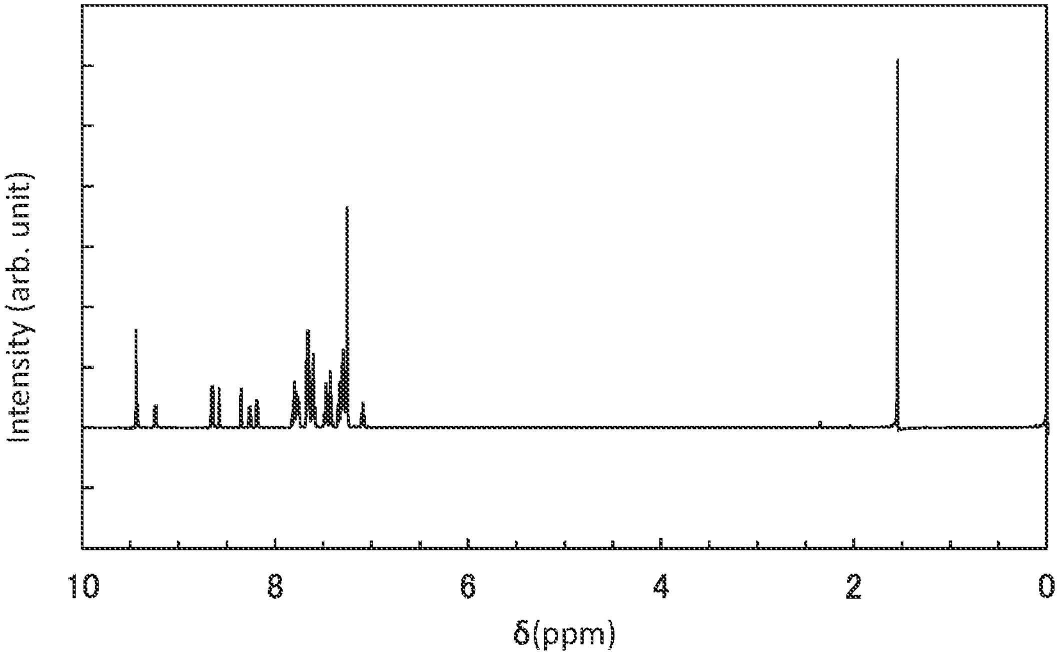
FIGS. 67A and 67B show $^1$H NMR charts of 4-[3-(dibenzo[f,h]quinoxalin-2-yl)phenyl]-4'-(9-phenyl-9H-carbazol-3-yl)-triphenylamine (abbreviation: 2mpPCBABPDBq).
Figure 67B:
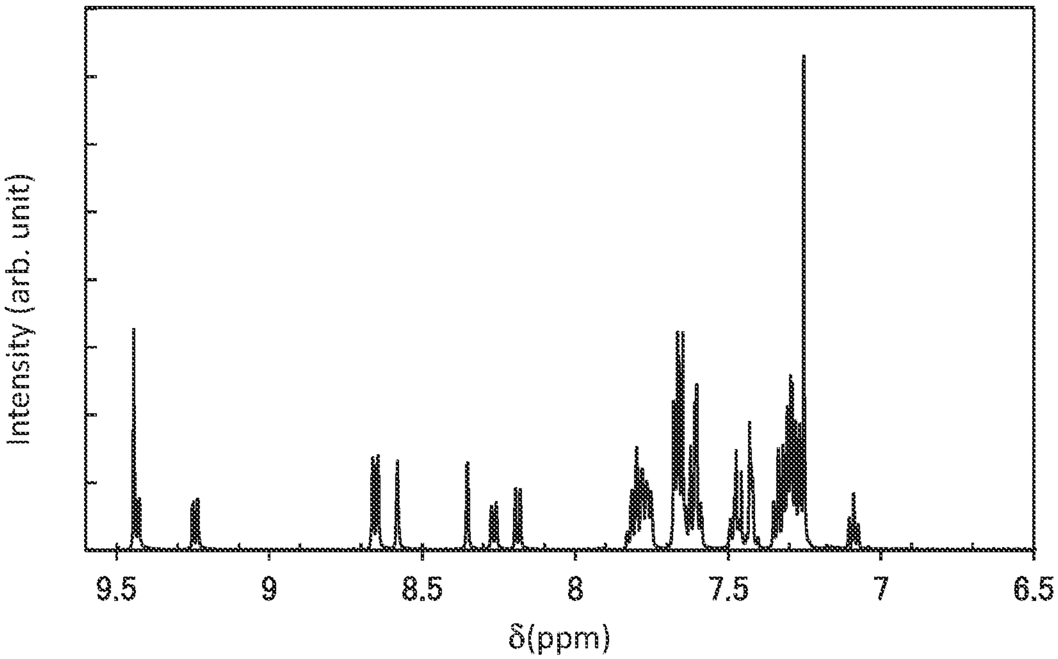

The $^1$H NMR charts are shown in FIGS. 67A and 67B. Note that FIG. 67B is a chart showing an enlarged part of FIG. 67A in the range of 6.50 ppm to 9.60 ppm. The charts reveal that 2mpPCBABPDBq, which is a compound represented by Structural Formula (502), was obtained.

<Measurement Results of Absorption Spectra and Emission Spectra>

Figure 68:
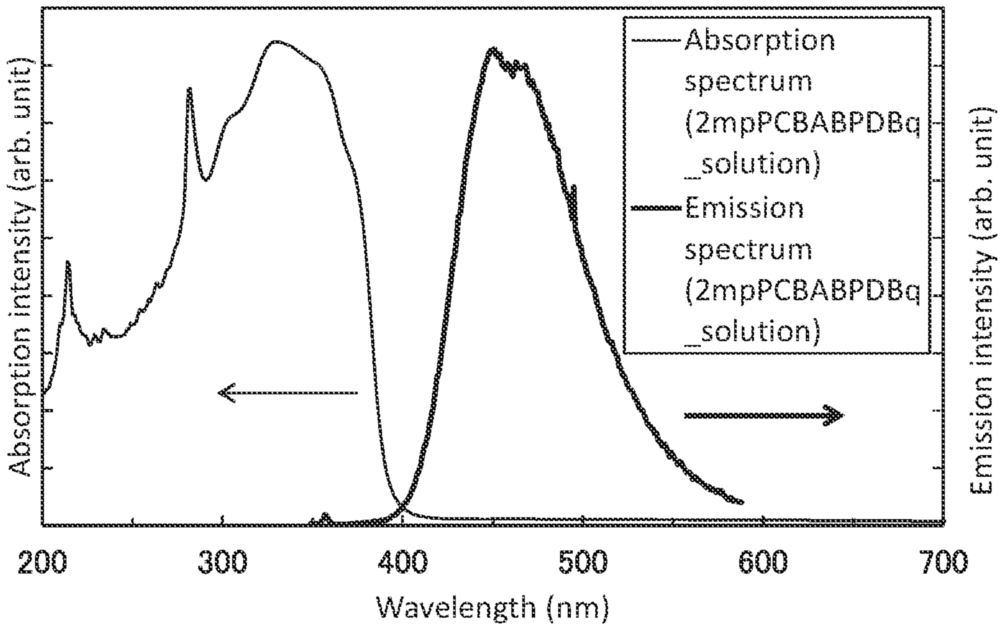
FIG. 68 shows an absorption spectrum and an emission spectrum of 2mpPCBABPDBq in a toluene solution of 2mpPCBABPDBq.
Figure 69:
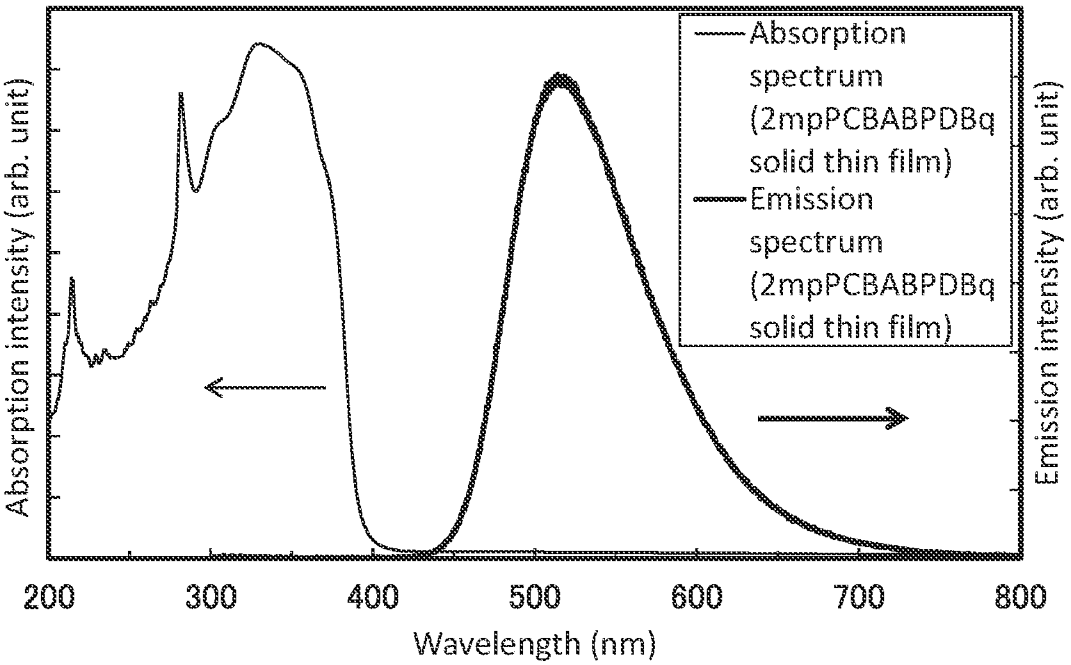
FIG. 69 shows an absorption spectrum and an emission spectrum of a solid thin film of 2mpPCBABPDBq.

Next, absorption spectra and emission spectra of 2mpPCBABPDBq in a toluene solution of 2mpPCBABPDBq and a solid thin film of 2mpPCBABPDBq were measured. The absorption spectra and emission spectra of 2mpPCBABPDBq in the toluene solution of 2mpPCBABPDBq were measured in a similar manner to Example 1. The absorption spectra and emission spectra of the solid thin film were measured in a similar manner to Example 4. FIG. 68 shows the obtained absorption and emission spectra of 2mpPCBABPDBq in the toluene solution of 2mpPCBABPDBq. FIG. 69 shows the measurement results of the obtained absorption and emission spectra of the solid thin film.

In FIG. 68, the absorption peak of 2mpPCBABPDBq in the toluene solution of 2mpPCBABPDBq is observed at around 330 nm, and the emission wavelength peak is observed at around 453 nm. In FIG. 69, the absorption peaks of the solid thin film of 2mpPCBABPDBq are observed at around 303 nm, 329 nm, and 371 nm, and the emission wavelength peak is observed at 516 nm.

<Results of CV Measurement>

The electrochemical characteristics (oxidation reaction characteristics and reduction reaction characteristics) of the synthesized 2mpPCBABPDBq were measured by cyclic voltammetry (CV) measurement. The measurement method was similar to that used in Example 1.

On the assumption that the intermediate potential (the half-wave potential) between the oxidation peak potential $E_{pa}$ and the reduction peak potential $E_{pc}$ which are obtained in the CV measurement corresponds to the HOMO level, the HOMO level of 2mpPCBABPDBq was calculated to be −5.43 eV, and the LUMO level of 2mpPCBABPDBq was calculated to be −2.94 eV. Thus, the band gap (ΔE) of 2mpPCBABPDBq was found to be 2.49 eV.

Example 7

Synthesis Example 4

In Example 7, a method of synthesizing N-phenyl-N-[(1,1'-biphenyl)-4-yl]-N-{4-[3-(dibenzo[f,h]quinoxalin-2-yl)phenyl]phenyl}amine (abbreviation: 2mpBPABPDBq) that is a compound of one embodiment of the present invention and represented by Structural Formula (503) in Embodiment 1 is described.

<<Step 1: Synthesis of 2mpBPABPDBq>>

A synthesis scheme of Step 1 is shown in (A-4).

[Chemical formula 35]

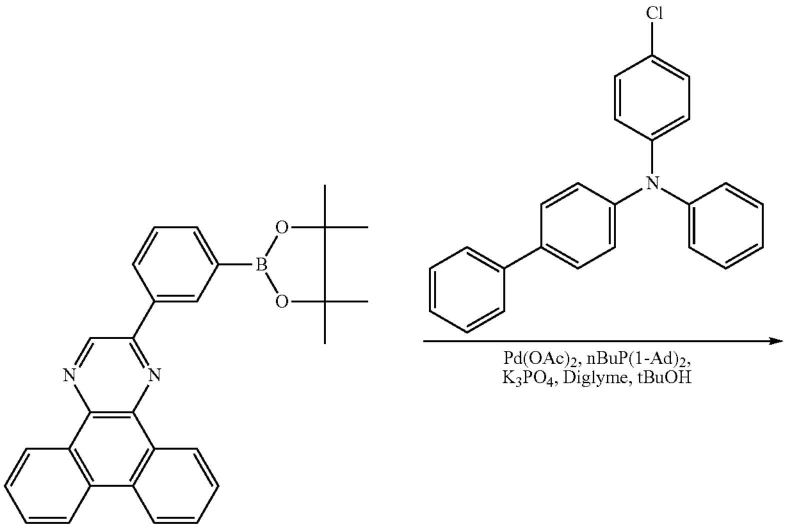

(A-4)

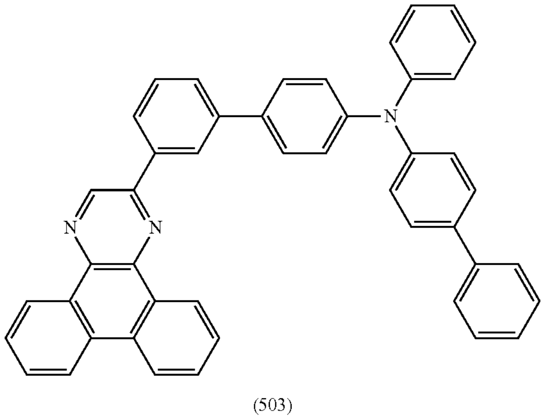

(503)

Into a 200 mL three-neck flask were put 3.5 g (10 mmol) of 4-chloro-4'-phenyltriphenylamine, 4.3 g (10 mmol) of 4,4,5,5-tetramethyl-2-[3-(dibenzo[f,h]quinoxalin-2-yl)phenyl]-1,3,2-dioxaborolane, 6.4 g (30 mmol) of tripotassium phosphate, and 71 mg (0.20 mmol) of di(1-adamantyl)-n-butylphosphine, and the air in the flask was replaced with nitrogen. To this mixture, 50 mL of diethylene glycol dimethyl ether and 2.2 g (30 mmol) of tert-butyl alcohol were added. While the pressure was reduced, this mixture was stirred to be degassed. To this mixture was added 27 mg (0.12 mmol) of palladium(II) acetate and stirring was performed under a nitrogen stream at 150° C. for 4 hours. After the stirring, water was added to this mixture, and an aqueous layer was subjected to extraction with toluene, and the extracted solution and the organic layer were combined and washed with saturated brine. After the washing, the organic layer was dried with magnesium sulfate. After the drying, the mixture was subjected to gravity filtration. The obtained filtrate was filtered through Celite, aluminum oxide, and Florisil and concentrated to give a solid. The solid was recrystallized with toluene, so that 3.3 g of a target pale yellow powder was obtained in 52% yield.

By a train sublimation method, 3.3 g of the obtained pale yellow powder was purified by sublimation. The pale yellow powder was heated at 320° C. under a pressure of 0.017 Pa. After the sublimation purification, 1.2 g of a pale yellow solid was obtained at a collection rate of 36%.

<$^1$H NMR Measurement Results>

The obtained substance was measured by $^1$H NMR. The measurement data are shown below.

$^1$H NMR ($CDCl_3$, 500 MHz): δ=7.09 (t, J=7.5 Hz, 1H), 7.23-7.25 (m, 4H), 7.28 (d, J=8.5 Hz, 2H), 7.31-7.35 (m, 3H), 7.44 (t, J=7.5 Hz, 2H), 7.54 (d, J=8.5 Hz, 2H), 7.60, (s, 1H), 7.61 (d, J=1.0 Hz, 1H), 7.65-7.68 (m, 3H), 7.75-7.83 (m, 5H), 8.27 (d, J=7.5 Hz, 1H), 8.57 (s, 1H), 8.66 (d, J=8.0 Hz, 2H), 9.25 (dd, $J_1$=8.0 Hz, $J_2$=1.0 Hz, 1H), 9.42-9.44 (m, 2H).

Figure 70A:
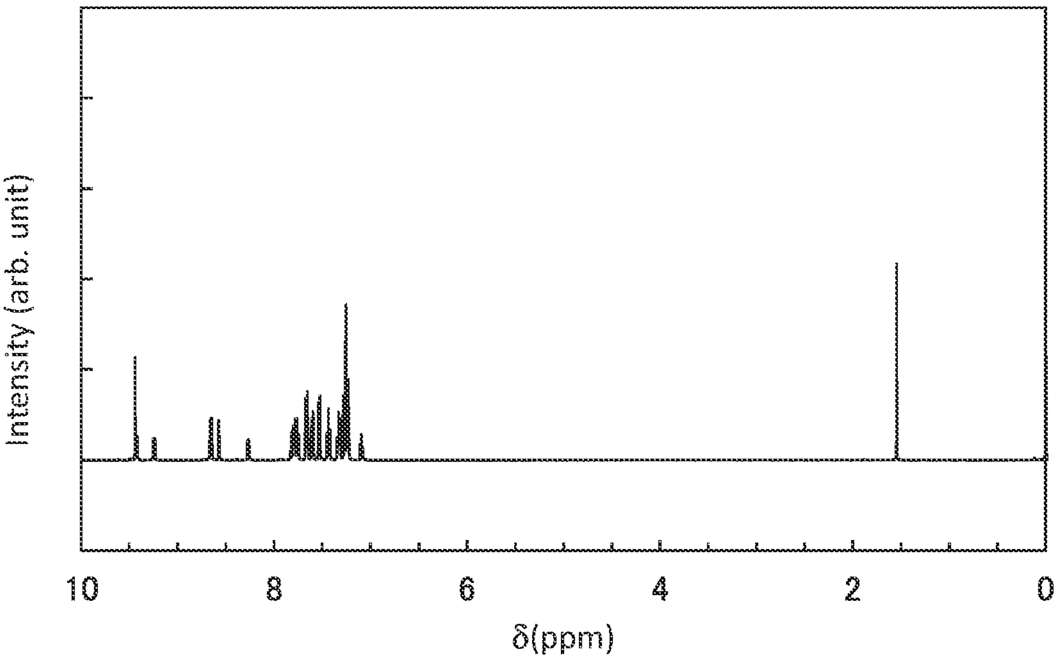
FIGS. 70A and 70B show $^1$H NMR charts of N-phenyl-N-[(1,1'-biphenyl)-4-yl]-N-{4-[3-(dibenzo[f,h]quinoxalin-2-yl)phenyl]phenyl}amine (abbreviation: 2mpBPABPDBq).
Figure 70B:
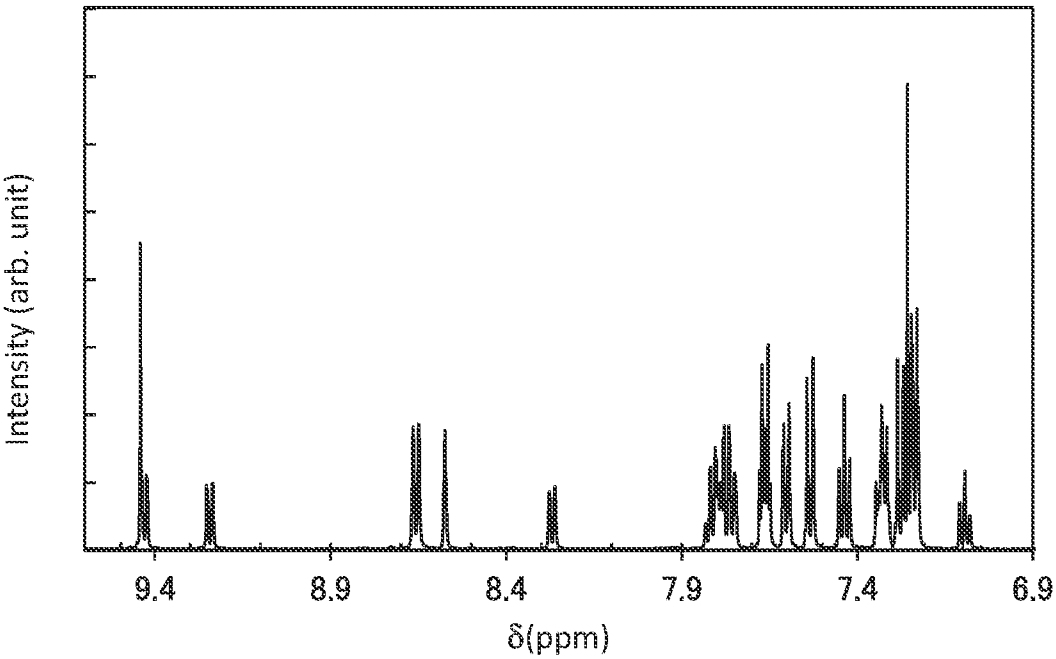

The $^1$H NMR charts are shown in FIGS. 70A and 70B. Note that FIG. 70B is a chart showing an enlarged part of FIG. 70A in the range of 6.90 ppm to 9.60 ppm. The charts reveal that 2mpBPABPDBq that is a compound and represented by Structural Formula (503) was obtained.

<LC/MS Results>

Furthermore, liquid chromatography mass spectrometry (LC/MS) of 2mpBPABPDBq was carried out. The measurement method is similar to that used in Example 4.

Figure 71:
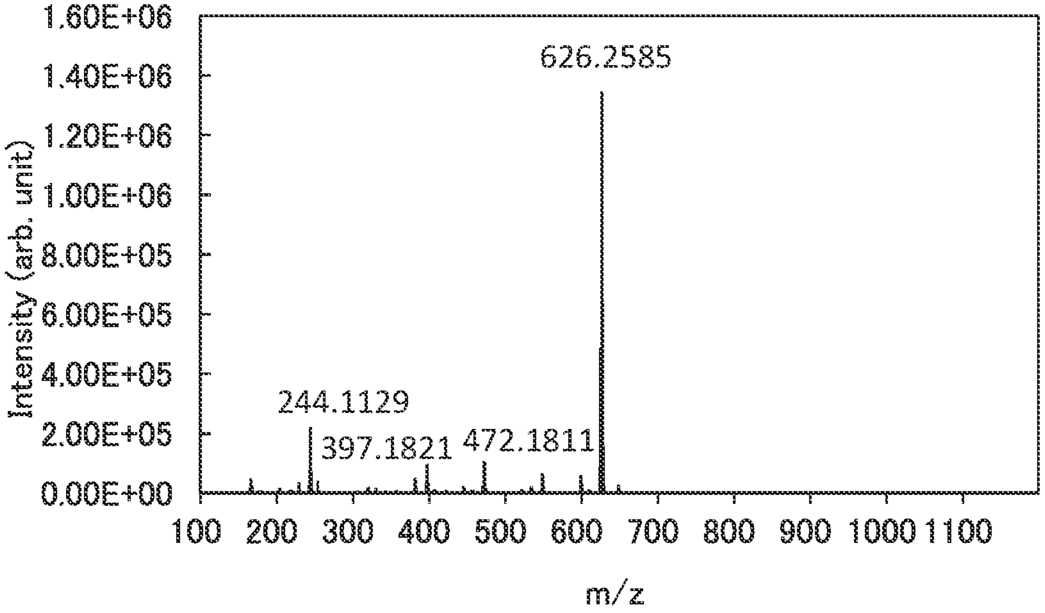
FIG. 71 shows LC/MS results of 2mpBPABPDBq.

Measurement results are shown in FIG. 71. The results in FIG. 71 show that product ions of 2mpBPABPDBq that is a compound of one embodiment of the present invention and represented by Structural Formula (503) are detected mainly around m/z=626, m/z=472, m/z=397, and m/z=244. Note that the result in FIG. 71 shows characteristics derived from 2mpBPABPDBq and therefore can be regarded as important data for identifying 2mpBPABPDBq contained in the mixture.

Note that a C—N bond between N-phenyl-N-{4-[3-(dibenzo[f,h]quinoxalin-2-yl)phenyl]phenyl}amine and 4-biphenyl is cut and electric charge remains on the amine side. Therefore, the product ion observed at around m/z=472 is useful because the data is likely to indicate the state where the C—N bond between N-phenyl-N-{4-[3-(dibenzo[f,h]quinoxalin-2-yl)phenyl]phenyl}amine and 4-biphenyl in the compound represented by Structural Formula (503) is cut. Furthermore, a C—N bond between 2-(3-phenyl)phenyldibenzo[f,h]quinoxaline and N-phenyl-N-[(1,1'-biphenyl)-4-yl]amine is cut and electric charge remains on the amine side. Therefore, the product ion observed at around m/z=244 is useful because the data is likely to indicate the state where the C—N bond between 2-(3-phenyl)phenyldibenzo[f,h]quinoxaline and N-phenyl-N-[(1,1'-biphenyl)-4-yl]amine in the compound represented by Structural Formula (503) is cut. Furthermore, a C—C bond between dibenzo[f,h]quinoxaline and N-phenyl-N,N'-bis[(1,1'-biphenyl)-4-yl]amine is cut and electric charge remains on the dibenzo[f,h]quinoxaline side. Therefore, the product ion observed at around m/z=397 is likely to indicate the state where the C—C bond between dibenzo[f,h]quinoxaline and 4,4'-diphenyltriphenylamine in the compound represented by Structural Formula (503) is cut, suggesting that 2mpBPABPDBq of a compound of one embodiment of the present invention includes dibenzo[f,h]quinoxaline and N-phenyl-N-[(1,1'-biphenyl)-4-yl]amine.

<TG-DTA Results>

TG-DTA was performed on 2mpBPABPDBq. The measurement method was similar to that used in Example 4. It was found from the relationship between weight and temperature (thermogravimetry) that the 5% weight loss temperature of 2mpBPABPDBq was 456° C. This indicates that 2mpBPABPDBq has high heat resistance.

<Measurement Results of Absorption Spectra and Emission Spectra>

Figure 72:
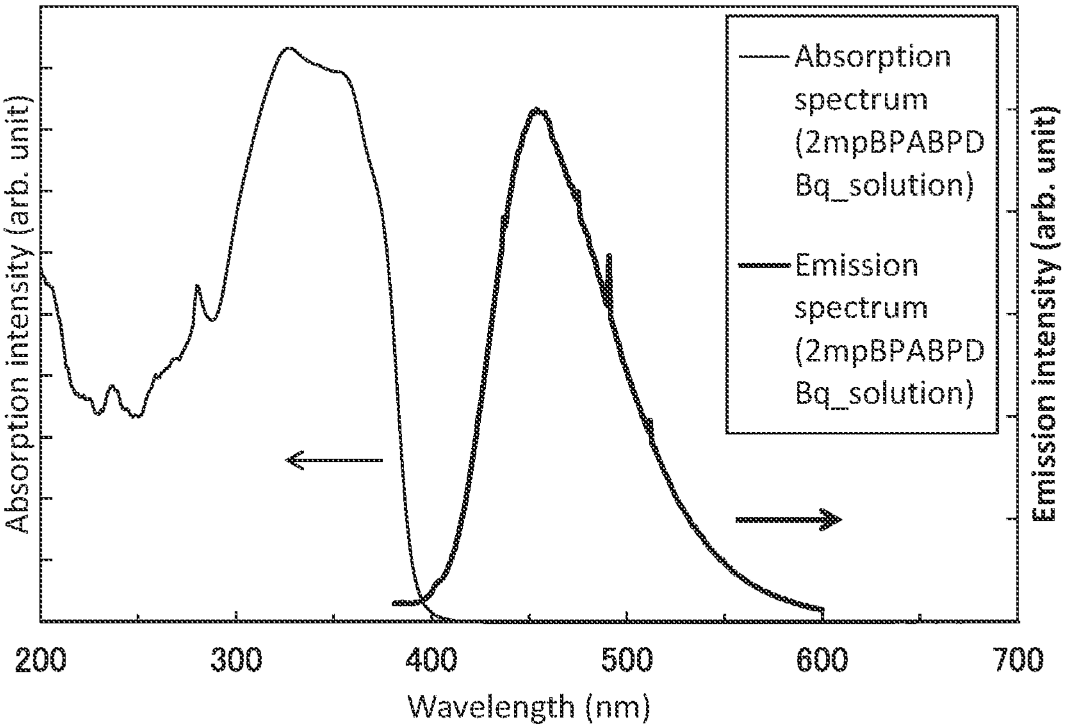
FIG. 72 shows an absorption spectrum and an emission spectrum of 2mpBPABPDBq in a toluene solution of 2mpBPABPDBq.
Figure 73:
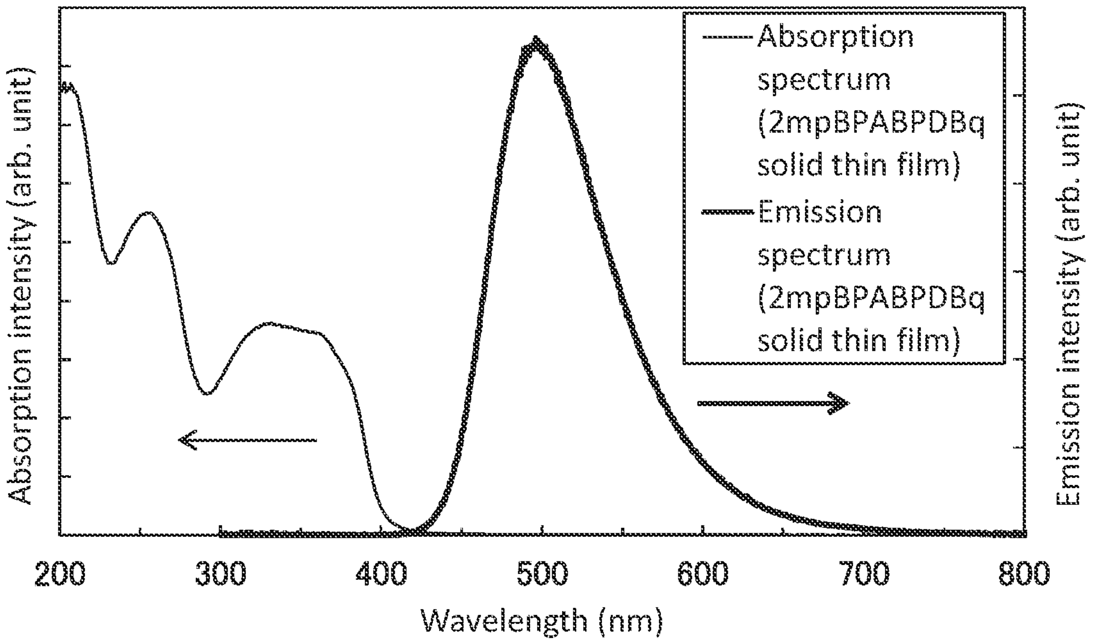
FIG. 73 shows an absorption spectrum and an emission spectrum of a solid thin film of 2mpBPABPDBq.

Next, absorption spectra and emission spectra of 2mpBPABPDBq in a toluene solution of 2mpBPABPDBq and a solid thin film of 2mpBPABPDBq were measured. The absorption spectra and emission spectra of 2mpBPABPDBq in the toluene solution of 2mpBPABPDBq were measured in a similar manner to Example 1. The absorption spectra and emission spectra of the solid thin film were measured in a similar manner to Example 4. FIG. 72 shows the obtained absorption and emission spectra of 2mpBPABPDBq in the toluene solution of 2mpBPABPDBq. FIG. 73 shows the measurement results of the obtained absorption and emission spectra of the solid thin film.

In FIG. 72, the absorption peak of 2mpBPABPDBq in the toluene solution of 2mpBPABPDBq is observed at around 361 nm, and the emission wavelength peaks are observed at around 402 nm and 500 nm. In FIG. 73, the absorption peaks of the solid thin film of 2mpBPABPDBq are observed at around 208 nm, 261 nm, 306 nm, and 364 nm, and the emission wavelength peak is observed at 516 nm.

<Results of CV Measurement>

The electrochemical characteristics (oxidation reaction characteristics and reduction reaction characteristics) of the synthesized 2mpBPABPDBq were measured by cyclic voltammetry (CV) measurement. The measurement method was similar to that used in Example 1.

On the assumption that the intermediate potential (the half-wave potential) between the oxidation peak potential $E_{pa}$ and the reduction peak potential $E_{pc}$ which are obtained in the CV measurement corresponds to the HOMO level, the HOMO level of 2mpBPABPDBq was calculated to be −5.52 eV, and the LUMO level of 2mpBPABPDBq was calculated to be −2.94 eV. Thus, the band gap ($\Delta E$) of 2mpBPABPDBq was found to be 2.58 eV.

This application is based on Japanese Patent Application serial No. 2015-194796 filed with Japan Patent Office on Sep. 30, 2015, the entire contents of which are hereby incorporated by reference.

What is claimed is:

1. A light-emitting element comprising:

a guest material; and a host material, wherein the host material comprises any of a pyrimidine skeleton, a pyridazine skeleton, and a triazine skeleton, wherein a LUMO level of the guest material is lower than a LUMO level of the host material, wherein an energy difference between the LUMO level of the guest material and a HOMO level of the guest material is larger than an energy difference between the LUMO level of the host material and a HOMO level of the host material, wherein the guest material is configured to convert triplet excitation energy into light emission, and wherein the energy difference between the LUMO level of the guest material and the HOMO level of the guest material is larger than transition energy calculated from an absorption edge of an absorption spectrum of the guest material by 0.4 eV or more.

2. The light-emitting element according to claim 1, wherein the energy difference between the LUMO level of the guest material and the HOMO level of the guest material is larger than light emission energy of the guest material by 0.4 eV or more.

3. The light-emitting element according to claim 1, wherein the host material has a difference between a singlet excitation energy level and a triplet excitation energy level of larger than 0 eV and smaller than or equal to 0.2 eV.

4. The light-emitting element according to claim 1, wherein the host material is configured to exhibit thermally activated delayed fluorescence at room temperature.

5. The light-emitting element according to claim 1, wherein the host material is configured to supply excitation energy to the guest material.

6. The light-emitting element according to claim 1, wherein a light emission spectrum of the host material comprises a wavelength region overlapping with an absorption band on the lowest energy side in the absorption spectrum of the guest material.

7. The light-emitting element according to claim 1, wherein the host material is configured to transport an electron, and wherein the host material is configured to transport a hole.

8. A light-emitting element comprising:

a guest material; and a host material, wherein the host material comprises any of a pyrimidine skeleton, a pyridazine skeleton, and a triazine skeleton, wherein a LUMO level of the guest material is lower than a LUMO level of the host material, wherein an energy difference between the LUMO level of the guest material and a HOMO level of the guest material is larger than an energy difference between the LUMO level of the host material and a HOMO level of the host material, wherein the guest material is configured to convert triplet excitation energy into light emission, wherein an energy difference between the LUMO level of the guest material and the HOMO level of the host material is larger than or equal to transition energy calculated from an absorption edge of an absorption spectrum of the guest material, and wherein the energy difference between the LUMO level of the guest material and the HOMO level of the guest material is larger than the transition energy calculated from the absorption edge of the absorption spectrum of the guest material by 0.4 eV or more.

9. The light-emitting element according to claim 8, wherein the energy difference between the LUMO level of the guest material and the HOMO level of the guest material is larger than light emission energy of the guest material by 0.4 eV or more.

10. The light-emitting element according to claim 8, wherein the host material has a difference between a singlet excitation energy level and a triplet excitation energy level of larger than 0 eV and smaller than or equal to 0.2 eV.

11. The light-emitting element according to claim 8, wherein the host material is configured to exhibit thermally activated delayed fluorescence at room temperature.

12. The light-emitting element according to claim 8, wherein the host material is configured to supply excitation energy to the guest material.

13. The light-emitting element according to claim 8, wherein a light emission spectrum of the host material comprises a wavelength region overlapping with an absorption band on the lowest energy side in the absorption spectrum of the guest material.

14. The light-emitting element according to claim 8, wherein the host material is configured to transport an electron, and wherein the host material is configured to transport a hole.

15. A light-emitting element comprising:

a guest material; and a host material, wherein the host material comprises any of a pyrimidine skeleton, a pyridazine skeleton, and a triazine skeleton, wherein a LUMO level of the guest material is lower than a LUMO level of the host material, wherein an energy difference between the LUMO level of the guest material and a HOMO level of the guest material is larger than an energy difference between the LUMO level of the host material and a HOMO level of the host material, wherein the guest material is configured to convert triplet excitation energy into light emission, wherein an energy difference between the LUMO level of the guest material and the HOMO level of the host material is larger than or equal to light emission energy of the guest material, wherein the energy difference between the LUMO level of the guest material and the HOMO level of the guest material is larger than transition energy calculated from an absorption edge of an absorption spectrum of the guest material by 0.4 eV or more.

16. The light-emitting element according to claim 15, wherein the energy difference between the LUMO level of the guest material and the HOMO level of the guest material is larger than light emission energy of the guest material by 0.4 eV or more.

17. The light-emitting element according to claim 15, wherein the host material has a difference between a singlet excitation energy level and a triplet excitation energy level of larger than 0 eV and smaller than or equal to 0.2 eV.

18. The light-emitting element according to claim 15, wherein the host material is configured to exhibit thermally activated delayed fluorescence at room temperature.

19. The light-emitting element according to claim 15, wherein the host material is configured to supply excitation energy to the guest material.

20. The light-emitting element according to claim 15, wherein a light emission spectrum of the host material comprises a wavelength region overlapping with an absorption band on the lowest energy side in the absorption spectrum of the guest material.

21. The light-emitting element according to claim 15, wherein the host material is configured to transport an electron, and wherein the host material is configured to transport a hole.

* * * * *